United States Patent [19]

Thompson

[11] Patent Number: 4,707,179

[45] Date of Patent: Nov. 17, 1987

[54] HERBICIDAL ORTHO-HETEROCYCLIC SULFONAMIDES

[75] Inventor: Mark E. Thompson, Wilmington, Del.

[73] Assignee: E. I. Du Pont de Nemours and Company, Wilmington, Del.

[21] Appl. No.: 944,814

[22] Filed: Feb. 17, 1987

Related U.S. Application Data

[60] Division of Ser. No. 753,118, Jul. 11, 1985, Pat. No. 4,657,578, which is a continuation-in-part of Ser. No. 671,851, Nov. 15, 1984, abandoned.

[51] Int. Cl.[4] .................. C07D 401/12; C07D 401/14; A01N 43/66; A01N 43/72

[52] U.S. Cl. .................................. 71/90; 71/93; 71/91; 544/113; 544/3; 544/54; 544/58.2; 544/219; 544/209; 544/207; 544/212; 544/198; 540/598

[58] Field of Search .............. 71/93, 90, 91; 544/198, 544/212, 207, 209, 113, 219, 3, 54, 58.2; 540/598

[56] References Cited

U.S. PATENT DOCUMENTS

| | | | |
|---|---|---|---|
| 4,522,645 | 6/1985 | Levitt | 71/93 |
| 4,579,583 | 4/1986 | Fory et al. | 71/93 |

*Primary Examiner*—John M. Ford

[57] ABSTRACT

Herbicidally active pyridinesulfonamide compounds having an ortho cyclic saturated or partially saturated group which includes a carbonyl or sulfonyl radical display utility as herbicides and plant growth regulants.

30 Claims, No Drawings

HERBICIDAL ORTHO-HETEROCYCLIC SULFONAMIDES

RELATED APPLICATION

This is a division of application Ser. No. 753,118, filed July 11, 1985, now U.S. Pat. No. 4,657,578 which, in turn, is a continuation-in-part of Ser. No. 671,851, filed Nov. 15, 1984, now abandoned.

BACKGROUND OF THE INVENTION

Herbicidal pyridinesulfonamides of the formula

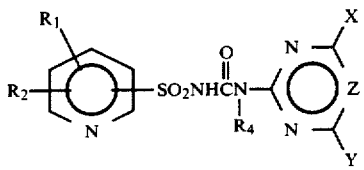

where
$R_1$ is H, Cl, Br, F, $C_1$–$C_4$ alkyl, $C_1$–$C_4$ alkoxy, $C_1$–$C_4$ alkylthio, $NO_2$ or $CO_2R_5$; and
$R_2$ is H, Cl, Br or $CH_3$,
are disclosed in European Patent Application (EP-A) 13,480.

No. EP-A-35,893 discloses herbicidal pyridinesulfonamides of formula

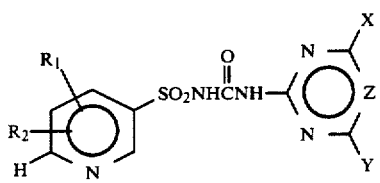

where
$R_1$ is $S(O)_nR_3$; and
$R_2$ is H, Cl, F, Br, $CH_3$, $OCH_3$, $CF_3$, $NO_2$, CN or $NH_2$.

No. EP-A-83,975 (published July 20, 1983) discloses herbicidal benzenesulfonamides of formula

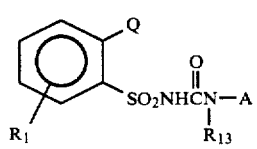

wherein
Q is selected from various saturated and unsaturated 5- and 6-membered aromatic or partially unsaturated heterocyclic rings containing 2 or 3 heteroatoms selected from O, S or NR.

No. EP-A-85,476 (published Aug. 10, 1983) discloses herbicidal benzenesulfonamides of formulae

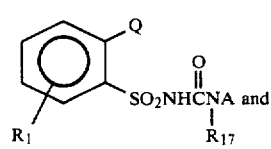

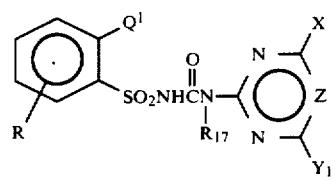

wherein
Q is selected from various 5-membered aromatic heterocycles, and their dihydro and tetrahydro analogs, which contain one heteroatom selected from O, S or NR, or Q is a saturated or partially unsaturated 6-membered ring containing one heteroatom selected from O or S; and
$Q^1$ is a 6-membered aromatic heterocycle containing one to three N atoms.

South African Patent Application No. 838,416 (published May 12, 1984) discloses herbicidal benzenesulfonamides of formula

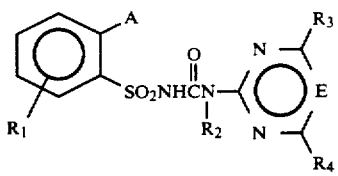

wherein
A is an unsaturated or only partially saturated 5- or 6-membered heterocyclic ring system which is bonded through a carbon atom and contains 1, 2 or 3 heteroatoms.

European Publication No. 116,518 (published Aug. 22, 1984; Swiss priority Feb. 4, 1983) discloses herbicidal sulfonylureas of the formula

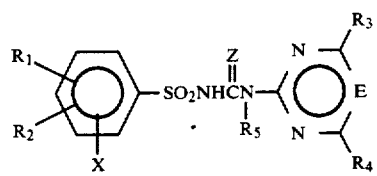

where, in part,
X is —$NR_6R_7$, —$N(SO_2R_9)_2$ or

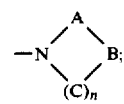

A is —CO—, —$SO_2$—, —$CONR_{23}$— or —$CO_2$—;
B is $C_1$–$C_4$ alkylene or $C_2$–$C_4$ alkenylene;
C is —CO—, $CR_{21}R_{22}$ or —$SO_2$—; and
n is 0 or 1.

SUMMARY OF THE INVENTION

This invention pertains to novel compounds of Formula I, agriculturally suitable compositions containing them and their method of use as general and/or selective preemergent and/or postemergent herbicides or plant growth regulants.

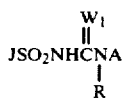

wherein
J is

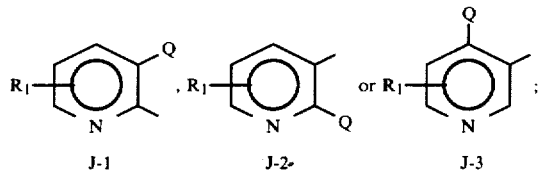

$W_1$ is O or S;

R is H or $CH_3$;

$R_1$ is H, $C_1$-$C_3$ alkyl, $C_1$-$C_3$ haloalkyl, halogen, nitro, $C_1$-$C_3$ alkoxy, $SO_2NR^I R^{II}$, $C_1$-$C_3$ alkylthio, $C_1$-$C_3$ alkylsulfinyl, $C_1$-$C_3$ alkylsulfonyl, $CO_2R^{III}$, $C_1$-$C_3$ haloalkoxy, amino, $C_1$-$C_3$ alkylamino, $C_1$-$C_3$ haloalkylthio, di($C_1$-$C_3$ alkyl)amino, $CH_2CN$, $CH_2OCH_3$ or $CH_2SCH_3$;

$R^I$ is H, $C_1$-$C_4$ alkyl, $C_2$-$C_3$ cyanoalkyl, methoxy or ethoxy;

$R^{II}$ is H, $C_1$-$C_4$ alkyl or $C_3$-$C_4$ alkenyl; or $R^I$ and $R^{II}$ may be taken together as —$(CH_2)_2$—, —$(CH_2)_4$—, —$(CH_2)_5$— or —$CH_2CH_2OCH_2CH_2$—;

$R^{III}$ is $C_1$-$C_4$ alkyl, $C_3$-$C_4$ alkenyl, $C_3$-$C_4$ alkynyl, $C_2$-$C_4$ haloalkyl, $C_2$-$C_3$ cyanoalkyl, $C_5$-$C_6$ cycloalkyl, $C_4$-$C_7$ cycloalkylalkyl or $C_2$-$C_4$ alkoxyalkyl;

Q is

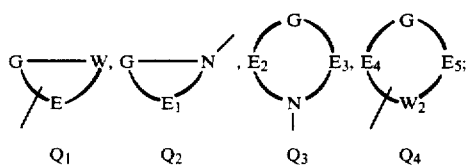

G is C=O or $SO_2$;

W is O, S, $CHR_2$ or $NR_3$;

$W_2$ is O, S, $SO_2$, $CHR_2$ or $NR_3$;

$R_2$ is H, $C_1$-$C_2$ alkyl, Cl, F or Br;

$R_3$ is H, $C_1$-$C_4$ alkyl, $C_1$-$C_4$ haloalkyl, $C_2$-$C_4$ alkoxyalkyl, $C_2$-$C_4$ cyanoalkyl, $C_3$-$C_4$ alkenyl or $C_3$-$C_4$ alkynyl;

E and $E_1$ independently are $C_3$-$C_4$ alkylene, $C_3$-$C_4$ alkenylene or $C_4$ alkenyldienyl;

$E_2$ and $E_4$ independently are $C_1$-$C_2$ alkylene or $C_2$ alkenylene;

$E_3$ and $E_5$ independently are $C_2$-$C_3$ alkylene or $C_2$-$C_3$ alkenylene; and E, $E_1$, $E_2$, $E_3$, $E_4$ and $E_5$ may optionally be substituted by 1-4 groups selected from $C_1$-$C_4$ alkyl, $C_1$-$C_4$ alkoxy, $C_1$-$C_4$ alkenyl, OH, halogen or $C_1$-$C_4$ haloalkoxy; further, when W is O, $CHR_2$ or $NR_3$, one of the carbon atoms of E may be in the form of a carbonyl group, and when $W_2$ is O, $CHR_2$ or $NR_3$, one of the carbon atoms of $E_4$ or $E_5$ may be in the form of a carbonyl group, provided that said carbonyl groups are not bonded directly to G;

A is

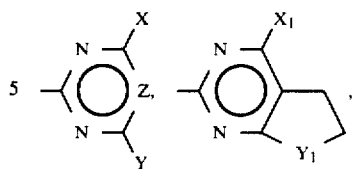

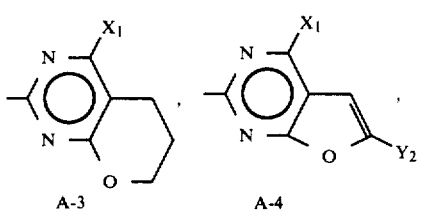

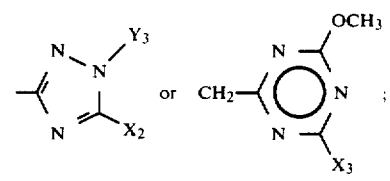

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_3$-$C_5$ cycloalkyl, $C_2$-$C_4$ alkynyl, $C(O)R_6$,

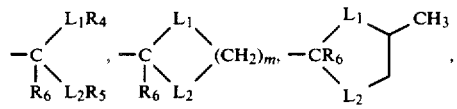

$N(OCH_3)CH_3$, $C_2$-$C_5$ alkylsulfinylalkyl or $C_2$-$C_5$ alkylsulfonylalkyl;

m is 2 or 3;

$L_1$ and $L_2$ are independently O or S;

$R_4$ and $R_5$ are independently $C_1$-$C_2$ alkyl;

$R_6$ is H or $CH_3$;

Z is CH or N;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $OCH_3$ or $SCH_3$;

$Y_3$ is $CH_3$, $CH_2CH_3$ or $CH_2CF_3$; and $X_3$ is $CH_3$ or $OCH_3$;

and their agriculturally suitable salts; provided that (a) when G is $SO_2$, then W is O, $CHR_2$ or $NR_3$;

(b) when $E_2$ or $E_4$ is $C_2$ alkylene or $C_2$ alkenylene, then $E_3$ or $E_5$ is $C_2$ alkylene or $C_2$ alkenylene;

(c) when X is Cl, F, Br or I, then Z is CH and Y is $OCH_3$, $OC_2H_5$, $N(OCH_3)CH_3$, $NHCH_3$, $N(CH_3)_2$ or $OCF_2H$;

(d) when X or Y is $OCF_2H$, then Z is CH;

(e) when the total number of carbon atoms of X and Y is greater than four, then the number of carbons of $R_1$ is less than or equal to two and the number of carbons of Q is less than or equal to eight; and (f) when $W_1$ is S, then R is H, A is A-1, and Y is $CH_3$, $OCH_3$, $OC_2H_5$, $CH_2OCH_3$, $C_2H_5$, $CF_3$, $SCH_3$, $OCH_2CH=CH_2$, $OCH_2C\equiv CH$, $OCH_2CH_2OCH_3$, $CH(OCH_3)_2$ or

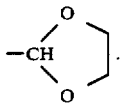

In the above definitions, the term "alkyl" used either alone or in compound words such as "alkylthio" or "haloalkyl", denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers. The term "$C_1$ alkenyl" denotes an exocyclic double bond.

Alkynyl denotes straight chain or branched alkynes, e.g., ethynyl, 1-propynyl, 2-propynyl and the different butynyl isomers.

The term "halogen", either alone or in compound words such as "haloalkyl", denotes fluorine, chlorine, bromine or iodine.

In terms such as $C_2$-$C_3$ alkylthioalkyl, the specified number of carbon atoms is meant to define the total number of carbon atoms in that substituent group. For example, $C_2$-$C_3$ alkylthioalkyl would designate $CH_2SCH_3$, $CH_2SC_2H_5$, $CH_2CH_2SCH_3$ or $CH(CH_3)SCH_3$, and $C_2$-$C_5$ alkoxyalkoxy would represent $OCH_2OCH_3$ through $O(CH_2)_4OCH_3$ or $OCH_2O(CH_2)_3CH_3$ and the various structural isomers embraced therein.

$C_4$-$C_7$ cycloalkylalkyl means cyclopropylmethyl through cyclopropylbutyl or cyclohexylmethyl.

Alkylsulfonyl denotes methylsulfonyl, ethylsulfonyl and the different propylsulfonyl isomers.

Alkylthio, alkylsulfinyl, alkylamino, etc. are defined in an analogous manner.

Alkylene denotes methylene (—$CH_2$—), ethylene (—$CH_2CH_2$—), propylene or butylene; alkenylene denotes —CH=CH—, —CH=CHCH_2—, —CH=CHCH_2CH_2— or —$CH_2$CH=CHCH_2—; and alkenyldienyl denotes —CH=CH—CH=CH—.

Preferred for reasons of increased ease of synthesis and/or greater herbicidal efficacy are:

(1) Compounds of Formula I where
$W_1$ is O; and
R is H;

(2) Compounds of Preferred 1 where
$R_1$ is H, Cl, $CH_3$, $OCH_3$ or $N(CH_3)_2$;
X is $CH_3$, $OCH_3$, $OCH_2CH_3$, Cl, F, Br, I, $OCF_2H$, $CH_2F$, $OCH_2CH_2F$, $OCH_2CHF_2$, $OCH_2CF_3$, $CF_3$, $CH_2Cl$ or $CH_2Br$; and
Y is H, $CH_3$, $OCH_3$, $OC_2H_5$, $CH_2OCH_3$, $NHCH_3$, $N(OCH_3)CH_3$, $N(CH_3)_2$, $CH_2CH_3$, $CF_3$, $SCH_3$, $OCH_2CH=CH_2$, $OCH_2C\equiv CH$, $CH_2OCH_2CH_3$, $OCF_2H$, $SCF_2H$, $OCH_2CH_2OCH_3$, $CH_2SCH_3$, $C(O)R_6$,

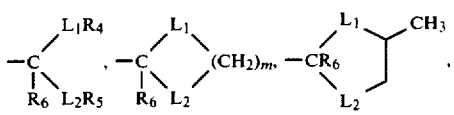

cyclopropyl, C≡CH or C≡CCH_3;

(3) Compounds of Preferred 2 where Q is $Q_1$;
(4) Compounds of Preferred 2 where Q is $Q_2$;
(5) Compounds of Preferred 2 where Q is $Q_3$;
(6) Compounds of Preferred 2 where Q is $Q_4$;
(7) Compounds of Preferred 2 where Q is

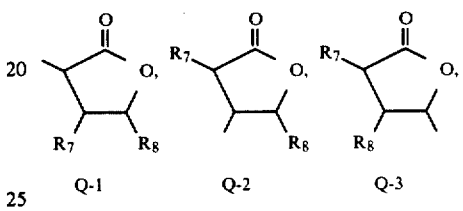

Q-1    Q-2    Q-3

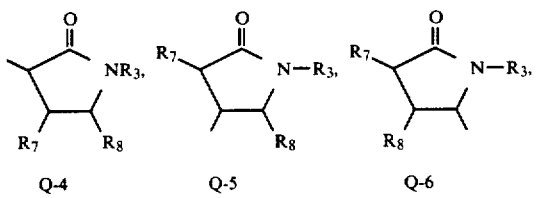

Q-4    Q-5    Q-6

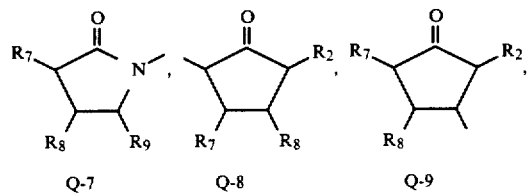

Q-7    Q-8    Q-9

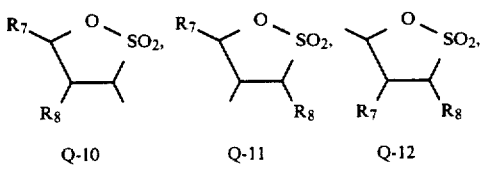

Q-10    Q-11    Q-12

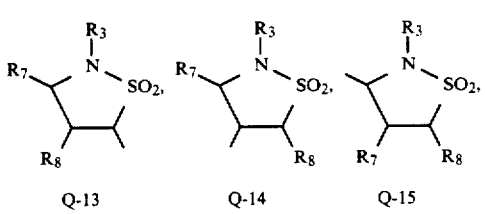

Q-13    Q-14    Q-15

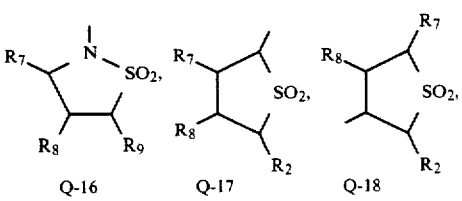

Q-16    Q-17    Q-18

-continued
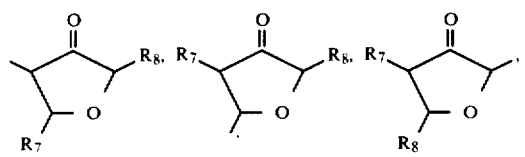
Q-19   Q-20   Q-21
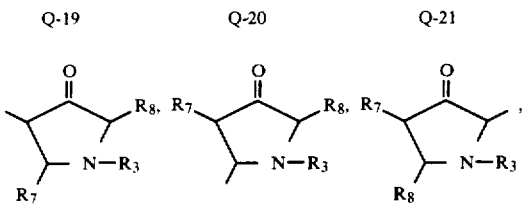
Q-22   Q-23   Q-24
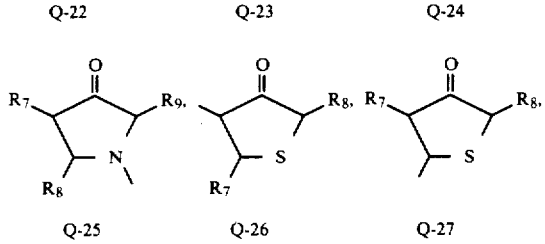
Q-25   Q-26   Q-27
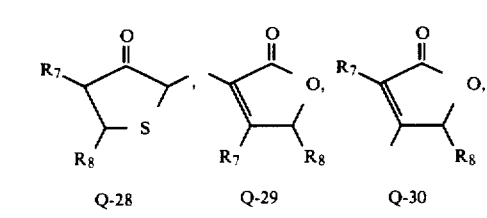
Q-28   Q-29   Q-30
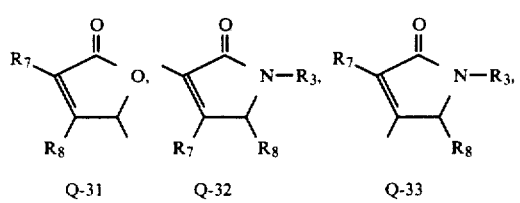
Q-31   Q-32   Q-33
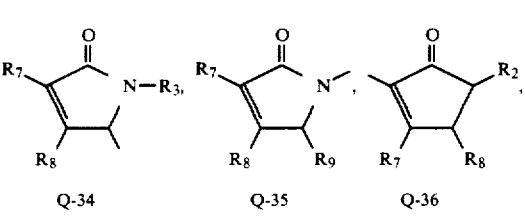
Q-34   Q-35   Q-36
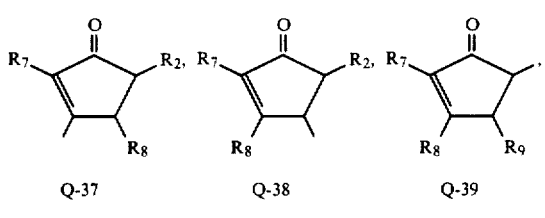
Q-37   Q-38   Q-39
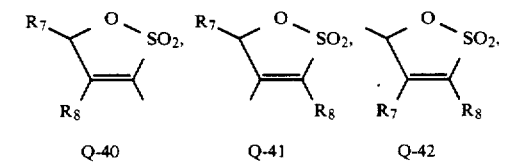
Q-40   Q-41   Q-42
-continued
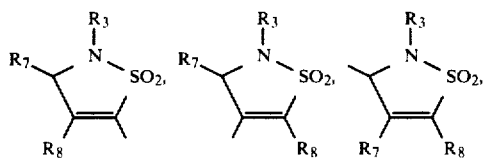
Q-43   Q-44   Q-45
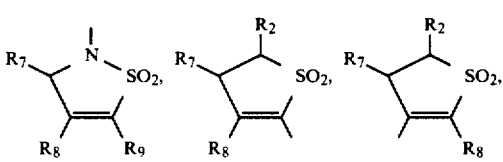
Q-46   Q-47   Q-48
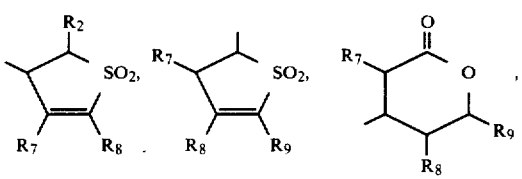
Q-49   Q-50   Q-51
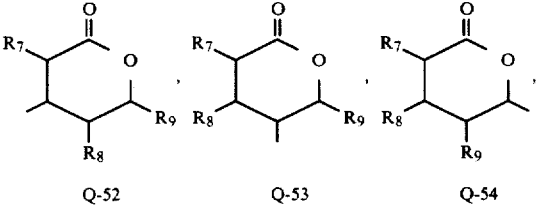
Q-52   Q-53   Q-54
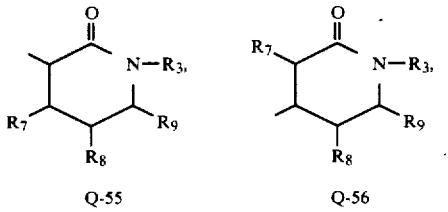
Q-55   Q-56
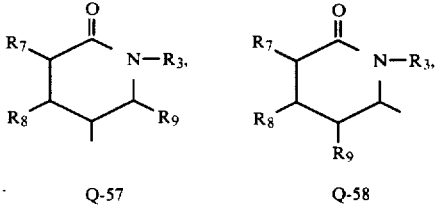
Q-57   Q-58
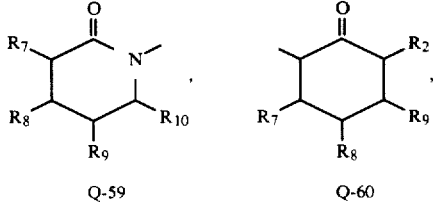
Q-59   Q-60

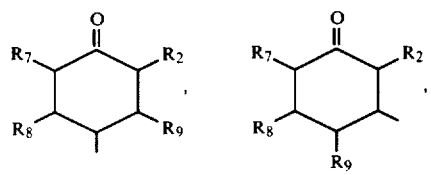
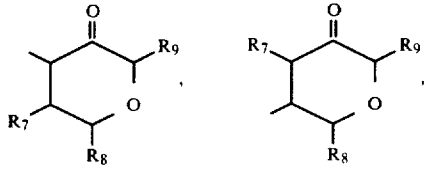
Q-61, Q-62, Q-75, Q-76
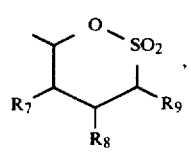
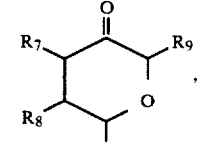
Q-63, Q-64, Q-77, Q-78
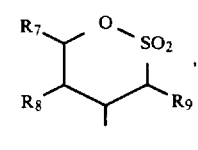
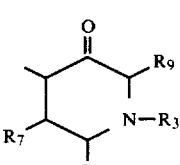
Q-65, Q-66, Q-79, Q-80
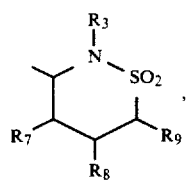
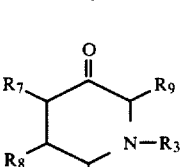
Q-67, Q-68, Q-81, Q-82
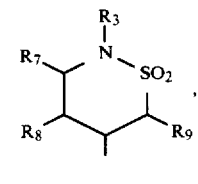
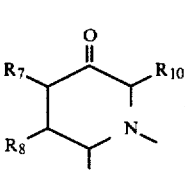
Q-69, Q-70, Q-83, Q-84
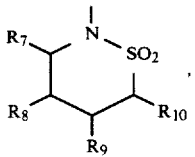
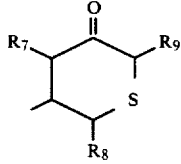
Q-71, Q-72, Q-85, Q-86
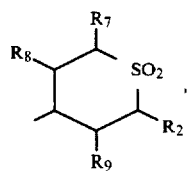
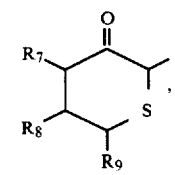
Q-73, Q-74, Q-87, Q-88

-continued

Q-89, Q-90, Q-91, Q-92, Q-93, Q-94, Q-95, Q-96, Q-97, Q-98, Q-99, Q-100, Q-101, Q-102

-continued

Q-103, Q-104, Q-105, Q-106, Q-107, Q-108, Q-109, Q-110, Q-111, Q-112, Q-113, Q-114, Q-115, Q-116

-continued
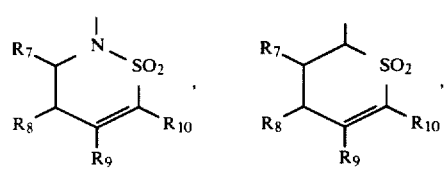 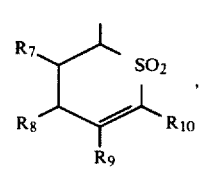
Q-117     Q-118
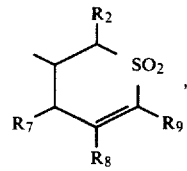 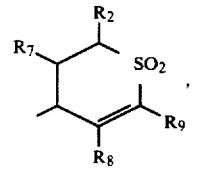
Q-119     Q-120
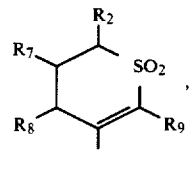 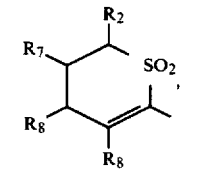
Q-121     Q-122
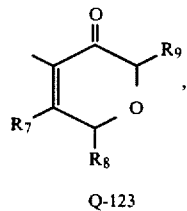 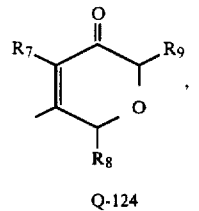
Q-123     Q-124
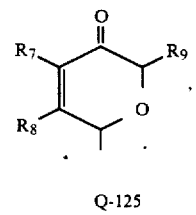 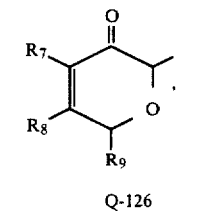
Q-125     Q-126
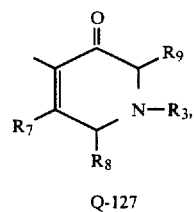 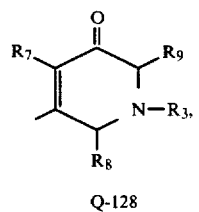
Q-127     Q-128
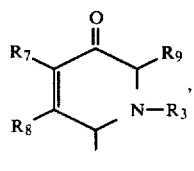 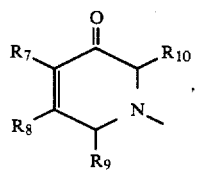
Q-129     Q-130
-continued
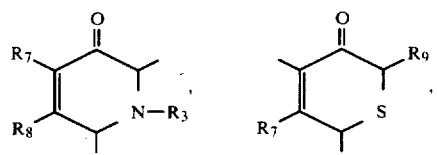
Q-131     Q-132
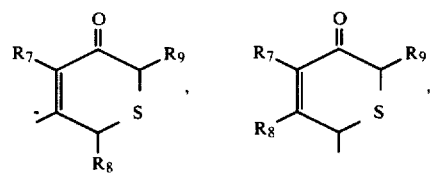
Q-133     Q-134

Q-135     Q-136
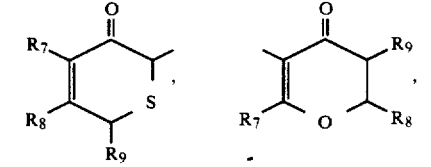
Q-137     Q-138
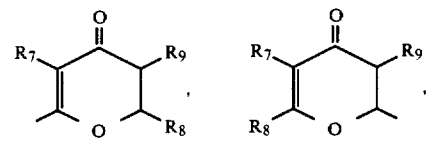
Q-139     Q-140
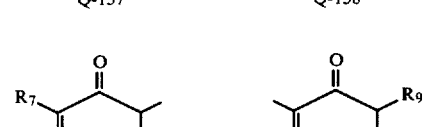

Q-141     Q-142

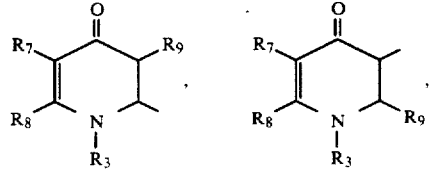
Q-143     Q-144

-continued

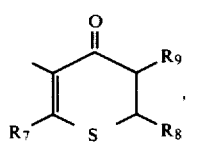 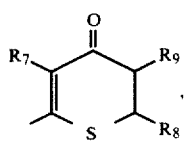
Q-145                    Q-146

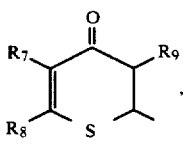 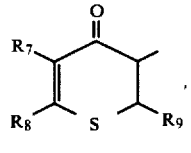
Q-147                    Q-148

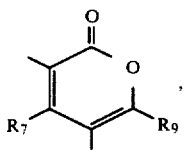 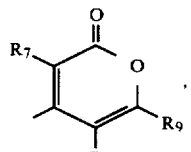
Q-149                    Q-150

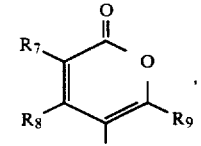 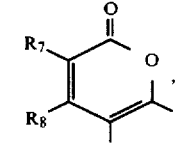
Q-151                    Q-152

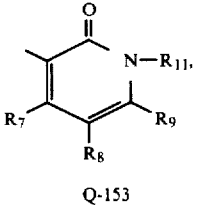 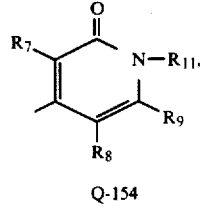
Q-153                    Q-154

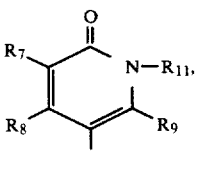 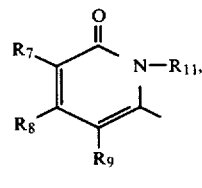
Q-155                    Q-156

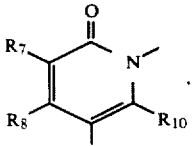 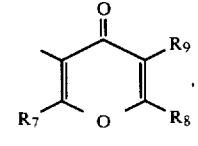
Q-157                    Q-158

-continued

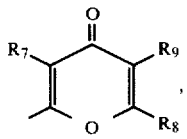 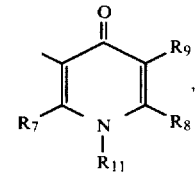
Q-159                    Q-160

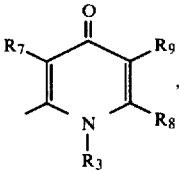 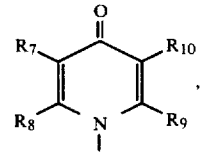
Q-161                    Q-162

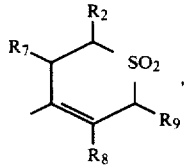 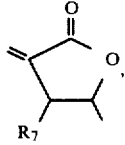
Q-163                    Q-164

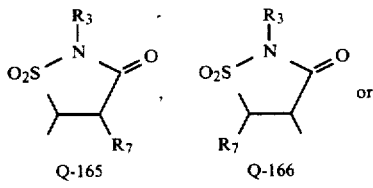
Q-165                    Q-166

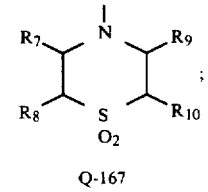
Q-167

$R_7$, $R_8$, $R_9$ and $R_{10}$ are independently H or $CH_3$; and $R_{11}$ is H, $CH_3$ or $CH_2CH_3$;

(8) Compounds of Preferred 7 where J is J-1 or J-2;
(9) Compounds of Preferred 8 where
$R_1$ is H; and
Y is $CH_3$, $OCH_3$, $C_2H_5$, $OC_2H_5$, $CH_2OCH_3$, $NHCH_3$, $CH(OCH_3)_2$ or cyclopropyl;
(10) Compounds of Preferred 9 where
$R_2$ is H or $CH_3$; and
$R_3$ is H, $CH_3$ or $C_2H_5$;
(11) Compounds of Preferred 10 where
A is A-1; and
X is $CH_3$, $OCH_3$, Cl or $OCF_2H$;
(12) Compounds of Preferred 11 where Q is Q-1;
(13) Compounds of Preferred 11 where Q is Q-2;
(14) Compounds of Preferred 11 where Q is Q-3;
(15) Compounds of Preferred 11 where Q is Q-4;
(16) Compounds of Preferred 11 where Q is Q-5;
(17) Compounds of Preferred 11 where Q is Q-6;
(18) Compounds of Preferred 11 where Q is Q-7;
(19) Compounds of Preferred 11 where Q is Q-8;
(20) Compounds of Preferred 11 where Q is Q-9;
(21) Compounds of Preferred 11 where Q is Q-10;

(22) Compounds of Preferred 11 where Q is Q-11;
(23) Compounds of Preferred 11 where Q is Q-12;
(24) Compounds of Preferred 11 where Q is Q-13;
(25) Compounds of Preferred 11 where Q is Q-14;
(26) Compounds of Preferred 11 where Q is Q-15;
(27) Compounds of Preferred 11 where Q is Q-16;
(28) Compounds of Preferred 11 where Q is Q-17;
(29) Compounds of Preferred 11 where Q is Q-18;
(30) Compounds of Preferred 11 where Q is Q-19;
(31) Compounds of Preferred 11 where Q is Q-20;
(32) Compounds of Preferred 11 where Q is Q-21;
(33) Compounds of Preferred 11 where Q is Q-22;
(34) Compounds of Preferred 11 where Q is Q-23;
(35) Compounds of Preferred 11 where Q is Q-24;
(36) Compounds of Preferred 11 where Q is Q-25;
(37) Compounds of Preferred 11 where Q is Q-26;
(38) Compounds of Preferred 11 where Q is Q-27;
(39) Compounds of Preferred 11 where Q is Q-28;
(40) Compounds of Preferred 11 where Q is Q-29;
(41) Compounds of Preferred 11 where Q is Q-30;
(42) Compounds of Preferred 11 where Q is Q-31;
(43) Compounds of Preferred 11 where Q is Q-32;
(44) Compounds of Preferred 11 where Q is Q-33;
(45) Compounds of Preferred 11 where Q is Q-34;
(46) Compounds of Preferred 11 where Q is Q-35;
(47) Compounds of Preferred 11 where Q is Q-36;
(48) Compounds of Preferred 11 where Q is Q-37;
(49) Compounds of Preferred 11 where Q is Q-38;
(50) Compounds of Preferred 11 where Q is Q-39;
(51) Compounds of Preferred 11 where Q is Q-40;
(52) Compounds of Preferred 11 where Q is Q-41;
(53) Compounds of Preferred 11 where Q is Q-42;
(54) Compounds of Preferred 11 where Q is Q-43;
(55) Compounds of Preferred 11 where Q is Q-44;
(56) Compounds of Preferred 11 where Q is Q-45;
(57) Compounds of Preferred 11 where Q is Q-46;
(58) Compounds of Preferred 11 where Q is Q-47;
(59) Compounds of Preferred 11 where Q is Q-48;
(60) Compounds of Preferred 11 where Q is Q-49;
(61) Compounds of Preferred 11 where Q is Q-50;
(62) Compounds of Preferred 11 where Q is Q-51;
(63) Compounds of Preferred 11 where Q is Q-52;
(64) Compounds of Preferred 11 where Q is Q-53;
(65) Compounds of Preferred 11 where Q is Q-54;
(66) Compounds of Preferred 11 where Q is Q-55;
(67) Compounds of Preferred 11 where Q is Q-56;
(68) Compounds of Preferred 11 where Q is Q-57;
(69) Compounds of Preferred 11 where Q is Q-58;
(70) Compounds of Preferred 11 where Q is Q-59;
(71) Compounds of Preferred 11 where Q is Q-60;
(72) Compounds of Preferred 11 where Q is Q-61;
(73) Compounds of Preferred 11 where Q is Q-62;
(74) Compounds of Preferred 11 where Q is Q-63;
(75) Compounds of Preferred 11 where Q is Q-64;
(76) Compounds of Preferred 11 where Q is Q-65;
(77) Compounds of Preferred 11 where Q is Q-66;
(78) Compounds of Preferred 11 where Q is Q-67;
(79) Compounds of Preferred 11 where Q is Q-68;
(80) Compounds of Preferred 11 where Q is Q-69;
(81) Compounds of Preferred 11 where Q is Q-70;
(82) Compounds of Preferred 11 where Q is Q-71;
(83) Compounds of Preferred 11 where Q is Q-72;
(84) Compounds of Preferred 11 where Q is Q-73;
(85) Compounds of Preferred 11 where Q is Q-74;
(86) Compounds of Preferred 11 where Q is Q-75;
(87) Compounds of Preferred 11 where Q is Q-76;
(88) Compounds of Preferred 11 where Q is Q-77;
(89) Compounds of Preferred 11 where Q is Q-78;
(90) Compounds of Preferred 11 where Q is Q-79;
(91) Compounds of Preferred 11 where Q is Q-80;
(92) Compounds of Preferred 11 where Q is Q-81;
(93) Compounds of Preferred 11 where Q is Q-82;
(94) Compounds of Preferred 11 where Q is Q-83;
(95) Compounds of Preferred 11 where Q is Q-84;
(96) Compounds of Preferred 11 where Q is Q-85;
(97) Compounds of Preferred 11 where Q is Q-86;
(98) Compounds of Preferred 11 where Q is Q-87;
(99) Compounds of Preferred 11 where Q is Q-88;
(100) Compounds of Preferred 11 where Q is Q-89;
(101) Compounds of Preferred 11 where Q is Q-90;
(102) Compounds of Preferred 11 where Q is Q-91;
(103) Compounds of Preferred 11 where Q is Q-92;
(104) Compounds of Preferred 11 where Q is Q-93;
(105) Compounds of Preferred 11 where Q is Q-94;
(106) Compounds of Preferred 11 where Q is Q-95;
(107) Compounds of Preferred 11 where Q is Q-96;
(108) Compounds of Preferred 11 where Q is Q-97;
(109) Compounds of Preferred 11 where Q is Q-98;
(110) Compounds of Preferred 11 where Q is Q-99;
(111) Compounds of Preferred 11 where Q is Q-100;
(112) Compounds of Preferred 11 where Q is Q-101;
(113) Compounds of Preferred 11 where Q is Q-102;
(114) Compounds of Preferred 11 where Q is Q-103;
(115) Compounds of Preferred 11 where Q is Q-104;
(116) Compounds of Preferred 11 where Q is Q-105;
(117) Compounds of Preferred 11 where Q is Q-106;
(118) Compounds of Preferred 11 where Q is Q-107;
(119) Compounds of Preferred 11 where Q is Q-108;
(120) Compounds of Preferred 11 where Q is Q-109;
(121) Compounds of Preferred 11 where Q is Q-110;
(122) Compounds of Preferred 11 where Q is Q-111;
(123) Compounds of Preferred 11 where Q is Q-112;
(124) Compounds of Preferred 11 where Q is Q-113;
(125) Compounds of Preferred 11 where Q is Q-114;
(126) Compounds of Preferred 11 where Q is Q-115;
(127) Compounds of Preferred 11 where Q is Q-116;
(128) Compounds of Preferred 11 where Q is Q-117;
(129) Compounds of Preferred 11 where Q is Q-118;
(130) Compounds of Preferred 11 where Q is Q-119;
(131) Compounds of Preferred 11 where Q is Q-120;
(132) Compounds of Preferred 11 where Q is Q-121;
(133) Compounds of Preferred 11 where Q is Q-122;
(134) Compounds of Preferred 11 where Q is Q-123;
(135) Compounds of Preferred 11 where Q is Q-124;
(136) Compounds of Preferred 11 where Q is Q-125;
(137) Compounds of Preferred 11 where Q is Q-126;
(138) Compounds of Preferred 11 where Q is Q-127;
(139) Compounds of Preferred 11 where Q is Q-128;
(140) Compounds of Preferred 11 where Q is Q-129;
(141) Compounds of Preferred 11 where Q is Q-130;
(142) Compounds of Preferred 11 where Q is Q-131;
(143) Compounds of Preferred 11 where Q is Q-132;
(144) Compounds of Preferred 11 where Q is Q-133;
(145) Compounds of Preferred 11 where Q is Q-134;
(146) Compounds of Preferred 11 where Q is Q-135;
(147) Compounds of Preferred 11 where Q is Q-136;
(148) Compounds of Preferred 11 where Q is Q-137;
(149) Compounds of Preferred 11 where Q is Q-138;
(150) Compounds of Preferred 11 where Q is Q-139;
(151) Compounds of Preferred 11 where Q is Q-140;
(152) Compounds of Preferred 11 where Q is Q-141;
(153) Compounds of Preferred 11 where Q is Q-142;
(154) Compounds of Preferred 11 where Q is Q-143;
(155) Compounds of Preferred 11 where Q is Q-144;
(156) Compounds of Preferred 11 where Q is Q-145;
(157) Compounds of Preferred 11 where Q is Q-146;

(158) Compounds of Preferred 11 where Q is Q-147;
(159) Compounds of Preferred 11 where Q is Q-148;
(160) Compounds of Preferred 11 where Q is Q-149;
(161) Compounds of Preferred 11 where Q is Q-150;
(162) Compounds of Preferred 11 where Q is Q-151;
(163) Compounds of Preferred 11 where Q is Q-152;
(164) Compounds of Preferred 11 where Q is Q-153;
(165) Compounds of Preferred 11 where Q is Q-154;
(166) Compounds of Preferred 11 where Q is Q-155;
(167) Compounds of Preferred 11 where Q is Q-156;
(168) Compounds of Preferred 11 where Q is Q-157;
(169) Compounds of Preferred 11 where Q is Q-158;
(170) Compounds of Preferred 11 where Q is Q-159;
(171) Compounds of Preferred 11 where Q is Q-160;
(172) Compounds of Preferred 11 where Q is Q-161;
(173) Compounds of Preferred 11 where Q is Q-162;
(174) Compounds of Preferred 11 where Q is Q-163;
(175) Compounds of Preferred 11 where Q is Q-164;
(176) Compounds of Preferred 11 where Q is Q-165;
(177) Compounds of Preferred 11 where Q is Q-166;
(178) Compounds of Preferred 11 where Q is Q-167.

Specifically preferred for reasons of greatest ease of synthesis and/or greatest herbicidal efficacy are:

N-[(4,6-dimethoxypyrimidin-2-yl)aminocarbonyl]-2-(tetrahydro-2-oxofuran-3-yl)-3-pyridinesulfonamide;

N-[(4-methoxy-6-methyltriazin-2-yl)aminocarbonyl]-2-(tetrahydro-2-oxofuran-3-yl)-3-pyridinesulfonamide; and N-[(4,6-dimethoxypyrimidin-2-yl)aminocarbonyl]-2-(4-thiomorpholinyl)-3-pyridinesulfonamide, S,S-dioxide, m.p. 204°-205° C.

DETAILED DESCRIPTION OF THE INVENTION

Synthesis

Compounds of Formula I may be synthesized by one or more of the methods shown below in Equations 1, 2 and 3.

Equation 1 depicts the reaction of sulfonyl isocyanates/isothiocyanates II with the appropriate heterocyclic amines of Formula III to give the desired sulfonylureas I.

Equation 1

$$JSO_2NCW_1 + A-NHR \longrightarrow I$$

II  III wherein

J, R, W$_1$ and A are as previously defined.

The reaction of Equation 1 may be carried out in an inert aprotic solvent such as methylene chloride, tetrahydrofuran or acetonitrile at a temperature between 0° and 82° C. A catalytic amount of 1,4-diazabicyclo[2.2.2]octane (DABCO) may be used to accelerate the reaction. In the cases in which the products are insoluble in the reaction solvent, they may be isolated by simple filtration. When the products are soluble, they may be isolated by evaporation of the solvent and trituration of the residue with solvents such as 1-chlorobutane, diethyl ether or ethyl acetate and filtration.

Compounds of Formula Ia may also be prepared as shown below in Equation 2 by treating sulfonamides of Formula IV with the methyl ester of a pyrimidine or triazine carbamic acid of Formula V in the presence of an equimolar quantity of trimethylaluminum.

Equation 2

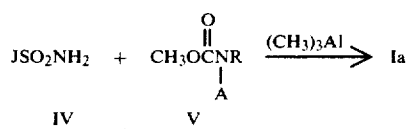

wherein

J, R and A are as previously defined.

The reaction of Equation 2 may be carried out at temperatures between 25° and 83° C. in a solvent such as methylene chloride or 1,2-dichloroethane for 12 to 96 hours under an inert atmosphere, as taught in European Patent Application (EP-A) No. 83,975 (published July 20, 1983). The products of Formula Ia may most conveniently be isolated by acidifying the reaction solution with dilute aqueous hydrochloric acid, and extraction with a suitable solvent such as methylene chloride or ethyl acetate. If necessary, purification may be achieved by recrystallization or column chromatography. The methyl carbamates V can be synthesized by treatment of the corresponding heterocyclic amines of Formula III with dimethyl carbonate or methyl chloroformate in the presence of a base such as sodium hydride or pyridine.

Alternatively, compounds of Formula Ia may be prepared as shown below in Equation 3 by the reaction of sulfonamides IV with the phenyl ester of the appropriate carbamic acid, VI, in the presence of an equimolar quantity of a tertiary amine base such as 1,8-diazabicyclo[5.4.0]undec-7-ene (DBU).

Equation 3

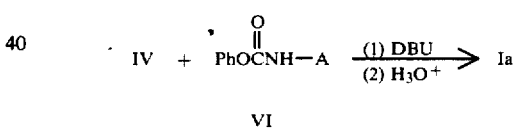

wherein

A, J and R are as previously defined.

The reaction shown in Equation 3 may be carried out at about 25° C. in a suitable solvent such as dioxane or acetonitrile for 1-2 hours under an inert atmosphere as described in European Patent Application No. 70,804 (published Jan. 26, 1983). The desired products of Formula Ia may be isolated by acidifying the reaction solution with dilute aqueous hydrochloric acid. In certain cases, the products may be insoluble and may be filtered. Alternatively, the aqueous layer may be extracted with a solvent such as methylene chloride or ethyl acetate. Drying and evaporation of the solvent should afford the desired products. The phenyl carbamates VI can be synthesized by treatment of the corresponding heterocyclic amines of Formula III with diphenyl carbonate or phenyl chloroformate in the presence of a base such as sodium hydride, pyridine, or potassium carbonate with a catalytic amount of 4-dimethylaminopyridine. The mixture is stirred at temperatures between 25° and 65° C. in a suitable solvent such as tetrahydrofuran for 12-36 hours.

A judicious choice of the appropriate methods for preparing compounds of Formula I must take into account the nature of the substituents Q and $R_1$, and their chemical compatibility with the reaction conditions of Equations 1–3.

Sulfonyl isocyanates of Formula II (wherein $W_1$ is O) may be prepared as shown in Equation 4 by the reaction of sulfonamides of general structure IV with phosgene in the presence of n-butyl isocyanate and a catalytic amount of 1,4-diazabicyclo[2.2.2]octane (DABCO).

Equation 4

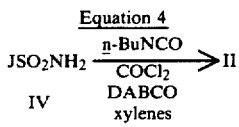

wherein

J is as previously defined.

The reaction shown in Equation 4 may be carried out according to the procedure described in U.S. Pat. No. 4,238,621.

Alternatively, sulfonyl isocyanates II may be prepared via phosgenation of the preferred n-butylureas of Formula VII as represented in Equation 5.

Equation 5

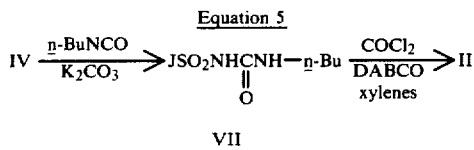

wherein

J is as previously defined.

The compounds of Formula VII may be conveniently prepared by stirring a mixture of the appropriate sulfonamides IV, anhydrous potassium carbonate, and n-butyl isocyanate in a suitable solvent such as acetone or methyl ethyl ketone at 25° to 80° C. until all of the isocyanate has reacted. The products may be isolated by quenching in dilute aqueous hydrochloric acid and recrystallizing the insoluble solid. The n-butylureas VII may then be treated with phosgene and a catalytic amount of DABCO in refluxing xylenes or chlorobenzene in a manner analogous to that described in Equation 4.

Another, somewhat milder, method for the preparation of sulfonyl isocyanates II is shown in Equation 6. Treatment of sulfonamides of Formula IV with thionyl chloride produces intermediate N-sulfinylsulfonamides VIII, which should afford sulfonyl isocyanates II upon exposure to phosgene in the presence of a catalytic amount of pyridine.

Equation 6

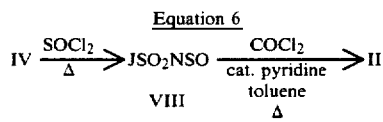

wherein

J is as previously defined.

The reaction of Equation 6 may be performed according to the procedure of H. Ulrich, B. Tucker and A. Sayigh, *J. Org. Chem.*, 34, 3200 (1969).

Sulfonyl isothiocyanates of Formula II (wherein $W_1$ is S) can be prepared by treatment of sulfonamides of Formula IV with carbon disulfide and potassium hydroxide followed by reaction of the dipotassium salt with phosgene according to K. Hartke, *Arch. Pharm.*, 299, 174 (1966).

A judicious choice of the appropriate method for preparing compounds of Formula II must take into account the nature of the substituents Q and $R_1$, and their chemical compatability with the reaction conditions of Equations 4–6.

The requisite sulfonamides of Formula IV may be synthesized by one or more of the methods shown below in Equations 7 and 8.

Equation 7 depicts the reaction of sulfonyl chlorides of Formula IX with ammonia to give sulfonamides of Formula IV.

Equation 7

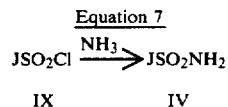

wherein

J is as previously defined.

The amination of Equation 7 may be effected by adding at least two molar equivalents of either anhydrous ammonia or concentrated ammonium hydroxide to a solution of the sulfonyl chloride IX in a suitable solvent such as diethyl ether, tetrahydrofuran, or methylene chloride at temperatures between −30° and 25° C. The desired sulfonamides of Formula IV may be isolated either by filtration, in which case the by-product ammonium chloride is removed by washing with water, or extraction into a suitable organic solvent such as methylene chloride or ethyl acetate. Drying and evaporation of the solvent should afford the products IV, which may be sufficiently pure to be carried directly on to the next step.

Sulfonamides of Formula IV may be prepared as shown in Equation 8 by treatment of the corresponding N-t-butylsulfonamides X with an appropriate acid such as trifluoroacetic (TFA), polyphosphoric (PPA), or p-toluenesulfonic acid (p-TSA).

Equation 8

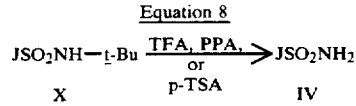

wherein

J is as previously defined.

The reaction of Equation 8 may be carried out by stirring a solution of the compound of Formula X in excess trifluoroacetic acid (approximately 0.3M) at about 25° C. for 1–24 hours. The desired sulfonamides of Formula IV may then be isolated by removal of the volatiles in vacuo and crystallization from a suitable solvent such as diethyl ether, 1-chlorobutane, or ethyl acetate. Alternatively, the N-t-butylsulfonamides of Formula IX may be treated with a catalytic amount of p-toluenesulfonic acid monohydrate in a solvent such as toluene or xylenes at reflux temperature for 1–6 hours. The desired products may then be isolated in a manner analogous to the one described above. For use of polyphosphoric acid in the deprotection of N-t-butylsulfonamides, see J. G. Lombardino, *J. Org. Chem.*, 36, 1843 (1971); for use of trifluoroacetic acid, see J. D. Catt and W. L. Matier, *J. Org. Chem.*, 39, 566 (1974).

Sulfonyl chlorides of Formula IX may be prepared by one or more of the methods shown below in Equations 9, 10 and 11.

Equation 9 depicts the diazotization of appropriately substituted aminopyridine derivatives of Formula XI and subsequent coupling with sulfur dioxide in the presence of either cupric or cuprous chloride to give the desired products of Formula IX.

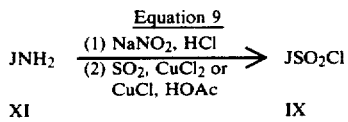

Equation 9

$$\text{JNH}_2 \xrightarrow[\text{(2) SO}_2, \text{CuCl}_2 \text{ or CuCl, HOAc}]{\text{(1) NaNO}_2, \text{HCl}} \text{JSO}_2\text{Cl}$$

XI → IX wherein

J is as previously defined.

The reaction of Equation 9 may be accomplished by treating a solution of the substituted aminopyridine XI in concentrated hydrochloric acid with a solution of sodium nitrite in water at $-5°$ to $5°$ C. After being stirred for 10–30 minutes at about $0°$ C., the solution can be added to a mixture of excess sulfur dioxide and a catalytic amount of cupric chloride or cuprous chloride in glacial acetic acid at about $10°$ C. The temperature is maintained at about $10°$ C. for $\frac{1}{4}$–1 hour, then raised to $25°$ C. and stirred for 2–24 hours. This solution can be poured into a large excess of ice-water. The desired sulfonyl chlorides IX may be isolated by filtration or by extraction into a solvent such as diethyl ether or methylene chloride, followed by drying and evaporation of the solvent.

Sulfonyl chlorides of Formula IX may also be prepared as shown below in Equation 10 by metal-halogen exchange of appropriately substituted pyridyl bromides XII, where K is Br, and trapping with sulfuryl chloride.

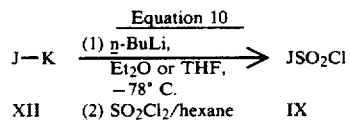

Equation 10

$$\text{J—K} \xrightarrow[\text{(2) SO}_2\text{Cl}_2/\text{hexane}]{\substack{\text{(1) n-BuLi,} \\ \text{Et}_2\text{O or THF,} \\ -78° \text{C.}}} \text{JSO}_2\text{Cl}$$

XII → IX wherein

J is as previously defined, and K is Br.

The lithiation shown in Equation 10 may be carried out according to the procedure of S. H. Bhattacharya, et al., *J. Chem. Soc.* (C), 1265 (1968).

Alternatively, compounds of Formula IX may be prepared via oxidative chlorination of the appropriate thioethers of Formula XIII, where K is SR$_{12}$, as represented in Equation 11.

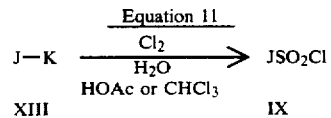

Equation 11

$$\text{J—K} \xrightarrow[\text{HOAc or CHCl}_3]{\text{Cl}_2/\text{H}_2\text{O}} \text{JSO}_2\text{Cl}$$

XIII → IX wherein

J is as previously defined, K is SR$_{12}$, and R$_{12}$ is C$_2$–C$_4$ alkyl or benzyl.

The reaction of Equation 11 may be accomplished by treating a solution of the thioether XIII with chlorine and water in a suitable solvent such as chloroform or methylene chloride; in some cases, it is advantageous to use acetic acid as solvent. The reaction is carried out in the presence of at least 2.5 equivalents of water and at least 3 molar equivalents of chlorine at $0°$–$30°$ C. for 1 to 5 hours. The products may be isolated by removal of the solvent in vacuo and may be sufficiently pure to be carried directly on to the next step.

The requisite aminopyridine derivatives of Formula XI may be prepared in a straightforward manner by reduction of the corresponding nitro compounds of Formula XIV, where K is NO$_2$, as shown in Equation 12.

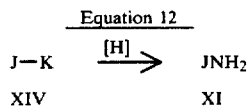

Equation 12

$$\text{J—K} \xrightarrow{[\text{H}]} \text{JNH}_2$$

XIV → XI wherein

J is as previously defined, and K is NO$_2$.

A wide variety of methods exists for effecting the reduction of aromatic nitro groups to the corresponding amine derivatives. One of the more common procedures involves treating the nitro compounds of Formula XIV with a slight excess of stannous chloride dihydrate in concentrated hydrochloric acid at temperatures between $25°$ and $80°$ C. Alternatively, reduction may be accomplished with iron powder in glacial acetic acid as described by Hazlet and Dornfeld, *J. Am. Chem. Soc.*, 66, 1781 (1944), and by West, *J. Chem. Soc.*, 127, 494 (1925). For a general review, see Groggins in "Unit Processes in Organic Synthesis", McGraw-Hill Book Co., New York, 1947, pp. 73–128.

A judicious choice of the appropriate method for preparing compounds of Formula IX must take into account the nature of the substituents Q and R$_1$, and their chemical compatability with the reaction conditions of Equations 9–12.

Sulfonamides of Formula XVII, where Q is Q-1, may be synthesized via the two-step procedure represented below in Equation 13(a) starting from compounds of Formula XV. In a similar fashion, sulfonamides of Formula XIX, where Q is Q-51, may be prepared via the two-step procedure shown in Equation 13(b) starting from the same compounds XV.

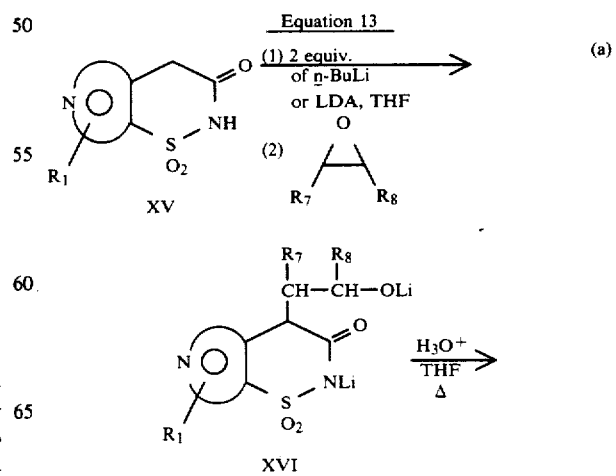

Equation 13 (a)

-continued
Equation 13

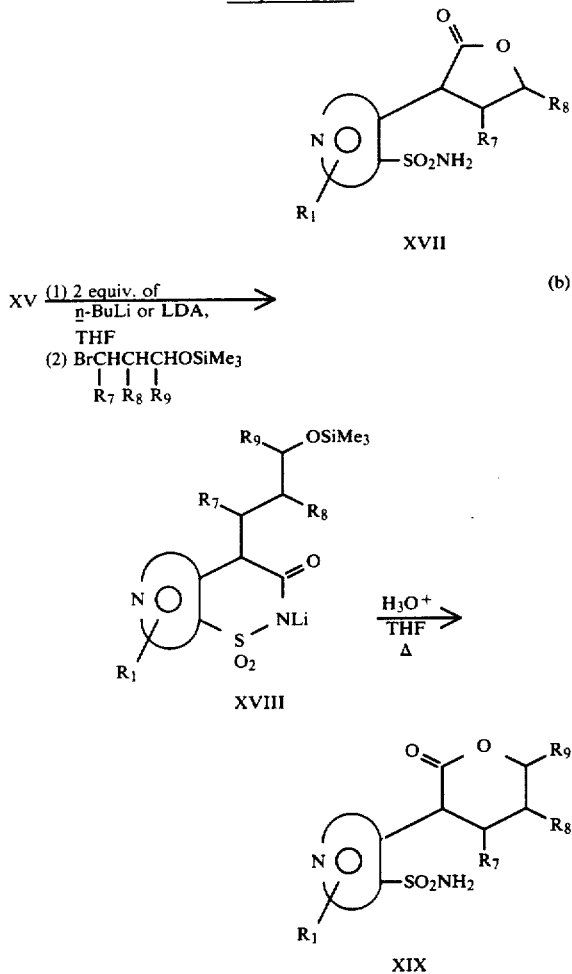

wherein
$R_1$, $R_7$, $R_8$, and $R_9$ are as previously defined.
The generalized structure:

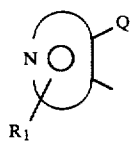

represents J-1, J-2, and J-3 which have been previously defined.

Equation 13(a)

The transformation shown above in Equation 13(a) may be conveniently carried out by adding a suitable base such as n-butyllithium (n-BuLi) or lithium diisopropylamide (LDA) to a solution of the compound of general structure XV in a solvent such as tetrahydrofuran, at −78° C., and under an inert atmosphere, such as nitrogen or argon. To ensure complete dianion formation, the reaction mixture is typically allowed to warm to about −30° C. over a period of 0.5 to 1 hour, and is then recooled and treated with the appropriate epoxide. After being stirred overnight at −78° to epoxide. After being stirred overnight at −78° to 25° C., the reaction solution is acidified with dilute aqueous hydrochloric acid and the water layer extracted with a suitable solvent such as diethyl ether or methylene chloride. Drying and evaporation of the organic extracts should afford a crude residue which may be immediately dissolved in an organic solvent such as tetrahydrofuran, and heated at reflux temperature in the presence of a mineral acid such as hydrochloric acid for 1 to 4 hours. The desired products of Formula XVII may be isolated by extraction into an organic solvent such as diethyl ether or methylene chloride. Drying and evaporation of the organic extracts should afford the crude sulfonamides XVII which may be purified by silica gel chromatography.

Equation 13(b)

The transformation depicted in Equation 13(b) may be carried out in a manner analogous to the one described for Equation 13(a), except that a protected bromoalkanol may be employed in the reaction with the dianions of compounds such as XV to give intermediates of Formula XVIII. These compounds may then be treated with aqueous acid as described above to afford the desired sulfonamides of Formula XIX, which may be purified by column chromatography if necessary.

The compounds of Formula XV may be prepared as shown below in Equation 14.

Equation 14

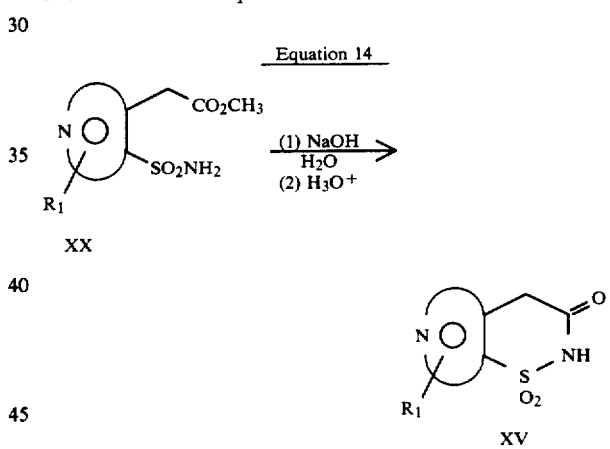

wherein
$R_1$ is as previously defined.

The ring-closure reaction shown in Equation 14 may be effected by stirring a solution of the compounds of Formula XX in excess 10% aqueous sodium hydroxide at about 25° C. for 1-12 hours. The products of Formula XV may then be isolated by acidifying the cooled (0°-10° C.) reaction mixture with concentrated HCl, and filtration. These compounds may be sufficiently pure to be carried directly on to the next step.

The requisite sulfonamides of Formula XX may be prepared by methods of modifications thereof described by Katrizky & Rees in "Comprehensive Heterocyclic Chemistry", Vol. 2, Pergamon Press, New York, N.Y., 1984, pp. 29–510.

Sulfonamides of Formulas XXIIa and XXIIb may be prepared as shown in Equations 15(a) and 15(b) by hydrogenolysis of the benzyl ethers XXIa and XXIb, followed by lactonization under acidic conditions.

Equation 15

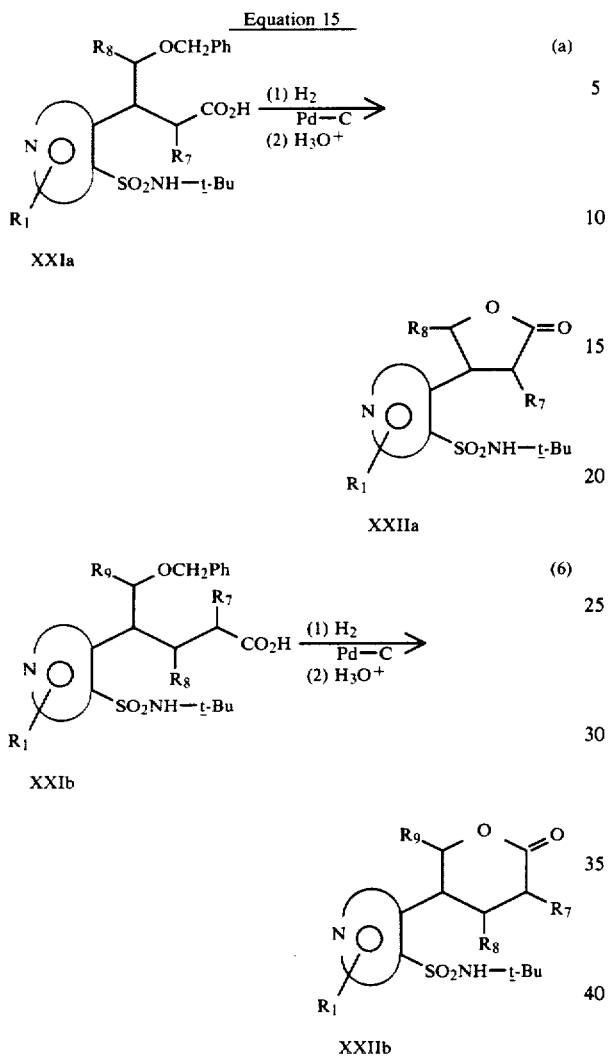

wherein $R_1$, $R_7$, $R_8$ and $R_9$ are as previously defined.

The hydrogenolysis of benzyl ether to generate alcohols as shown in the first step of Equations 15(a) and 15(b) is well precedented in the literature and may be accomplished by subjecting compounds of Formulas XXIa and XXIb to a hydrogen atmosphere in the presence of a suitable catalyst such as palladium-on-carbon. For relevant references, see C. H. Heathcock and R. Ratcliffe, *J. Am. Chem. Soc.*, 93, 1746 (1971), and A. M. Felix, et al. *J. Org. Chem.*, 43, 4194 (1978). The second step represented above in Equations 15(a) and 15(b) involves the formation of 5- or 6-membered ring lactones from the corresponding 5- or 6-hydroxy carboxylic acids, an extremely facile cyclization which often occurs spontaneously. This lactonization process may be aided by heating the hydroxy acids in the presence of a suitable acid such as hydrochloric or sulfuric acid. For a discussion of this reaction and useful references, see J. March, "Advanced Organic Chemistry", 2nd Ed., McGraw-Hill Book Co., New York, 1977, pp. 363-365.

Alternatively, sulfonamides of Formula XXIIa may be synthesized via iodolactonization of the appropriate unsaturated carboxylic acids of Formula XXIII, followed by reductive cleavage of the carbon-iodine bond as shown in Equation 16.

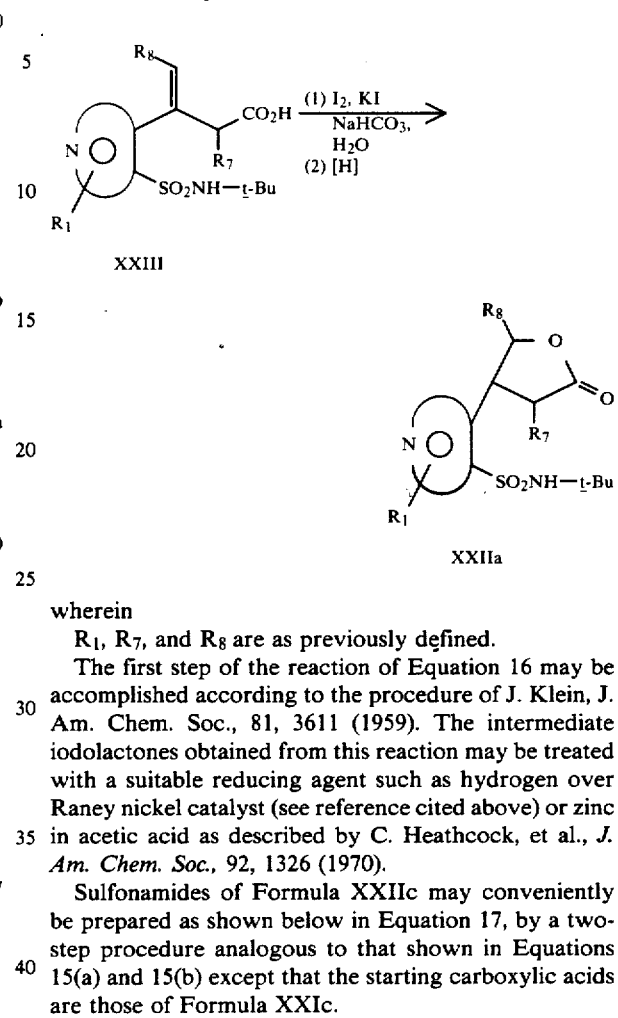

wherein $R_1$, $R_7$, and $R_8$ are as previously defined.

The first step of the reaction of Equation 16 may be accomplished according to the procedure of J. Klein, *J. Am. Chem. Soc.*, 81, 3611 (1959). The intermediate iodolactones obtained from this reaction may be treated with a suitable reducing agent such as hydrogen over Raney nickel catalyst (see reference cited above) or zinc in acetic acid as described by C. Heathcock, et al., *J. Am. Chem. Soc.*, 92, 1326 (1970).

Sulfonamides of Formula XXIIc may conveniently be prepared as shown below in Equation 17, by a two-step procedure analogous to that shown in Equations 15(a) and 15(b) except that the starting carboxylic acids are those of Formula XXIc.

Equation 17

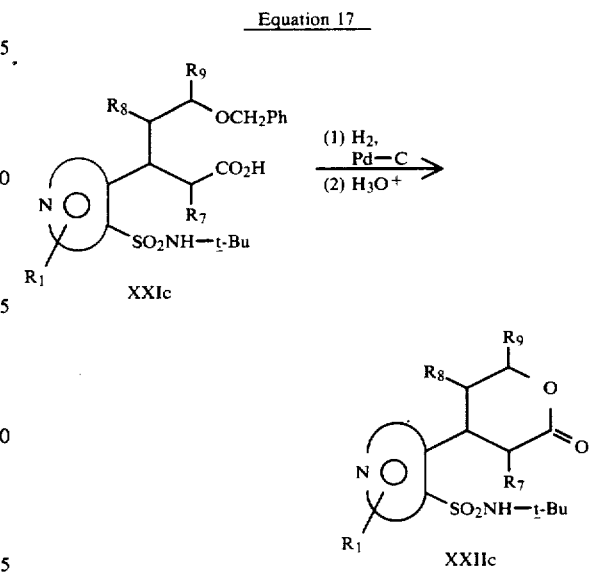

wherein $R_1$, $R_7$, $R_8$, and $R_9$ are as previously defined.

The transformation shown above in Equation 17 may be effected in a manner identical to that described for Equations 15(a) and 15(b).

Sulfonamides of Formulas XXIId and XXIIe may be synthesized by the three-step sequence of reactions outlined below in Equations 18(a) and 18(b) which involves: (1) addition of the dianions of suitable N-t-butyl pyridinesulfonamides of Formula XXIV to the appropriate β- or γ-formyl esters to give hydroxy esters XXVa and XXVb, (2) saponification of the esters XXVa and XXVb to afford the corresponding γ- or δ-hydroxy carboxylic acids, and (3) acid-induced lactonization.

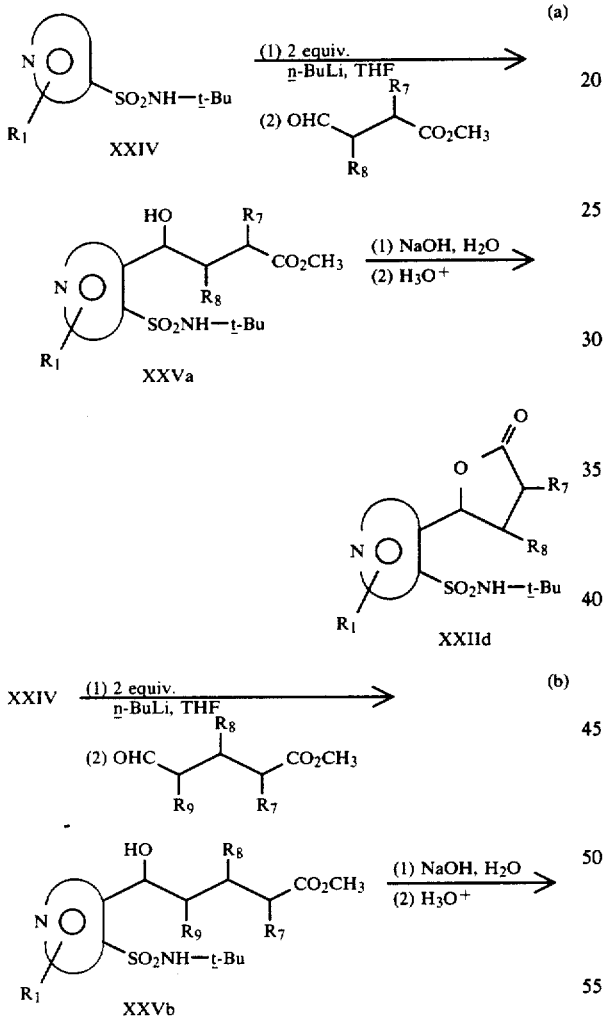

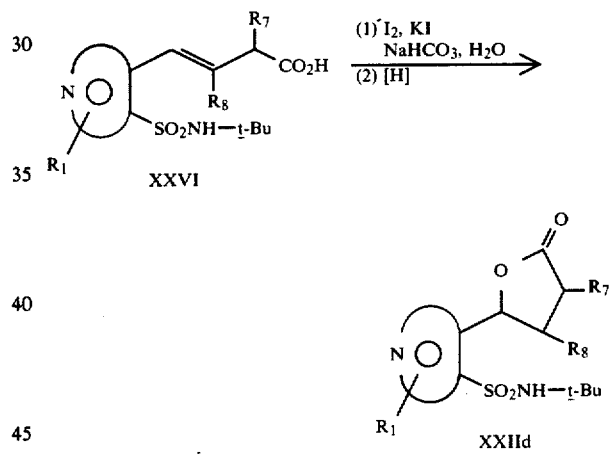

wherein $R_1$, $R_7$ and $R_8$ are as previously defined.

The transformation shown in Equation 19 above may be achieved in a manner identical to that described for Equation 16.

Sulfonamides of Formula XXIIe may also be synthesized by a Baeyer-Villiger reaction of the appropriately substituted cyclopentanones XXVII as depicted in Equation 20.

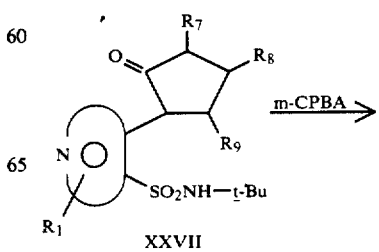

wherein $R_1$, $R_7$, $R_8$, and $R_9$ are as previously defined.

The first step of Equations 18(a) and 18(b) may be carried out by treating the appropriate N-t-butyl-pyridinesulfonamides XXIV with n-butyllithium in a solvent such as tetrahydrofuran at 0°–25° C. according to the procedure of J. G. Lombardino, *J. Org. Chem.*, 36, 1843 (1971). Addition of suitably substituted β- or γ-formyl esters to these should afford the hydroxy esters of Formula XXVa and XXVb. Saponification of these hydroxy esters may be accomplished by treatment with excess aqueous sodium hydroxide solution at about 25° C. for 1–6 hours. The desired products may be obtained by acidifying with concentrated hydrochloric acid (ice-water cooling) and either filtration or extraction into a suitable organic solvent such as methylene chloride, diethyl ether, or ethyl acetate. These γ- and δ hydroxy carboxylic acids may then spontaneously cyclize to give the desired products of Formulas XXIId and XXIIe; if not, lactonization may be achieved in a manner identical to that described for Equation 15.

Alternatively, sulfonamides of Formula XXIId may be prepared by iodolactonization of the appropriate unsaturated carboxylic acids of Formula XXVI, followed by reductive cleavage of the carbon-iodine bond as shown in Equation 19.

-continued
Equation 20

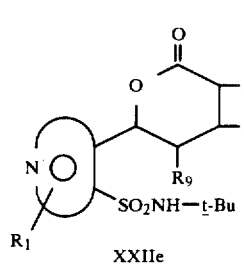
XXIIe wherein $R_1$, $R_7$, $R_8$, and $R_9$ are as previously defined.

The oxidation shown in Equation 20 may be carried out by treating a solution of the ketones XXVII in a suitable solvent such as chloroform or methylene chloride with m-chloroperoxybenzoic acid (m-CPBA) according to the methods described by S. L. Friess, *J. Am. Chem. Soc.*, 71, 2571 (1949), and S. L. Friess and P. E. Frankenburg, ibid., 74, 2679 (1952). For a review of the Baeyer Villiger reaction, refer to C. H. Hassall, *Org. Reactions*, 9, 73 (1957).

It should be recognized that removal of the tert-butyl protecting group from compunds of Formulas XXIIa–XXIIe by one of the methods described above in Equation 8 should furnish the primary sulfonamides of Formula IV, where Q is Q-2, Q-3, Q-52, Q-53 and Q-54, which may then be converted to compounds of Formula I with the corresponding Q substituents.

Compounds of Formula XXVIIIa–g may be prepared by treatment of the corresponding lactones XVII, XVIIa, XXIId, XIX, XXIIc, XXIIb and XXIIe, respectively, with ammonia of the appropriate primary amine, $R_3NH_2$, as shown below in Equation 21.

Equation 21

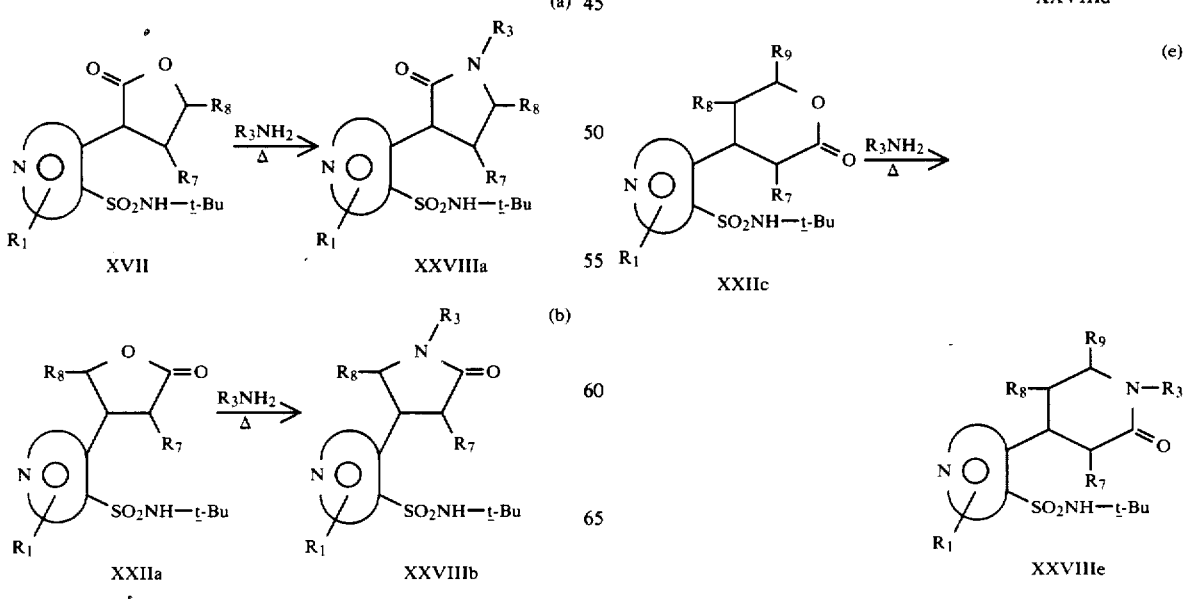

-continued
Equation 21

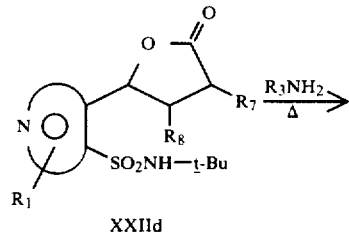

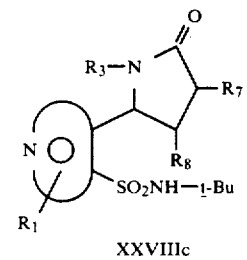

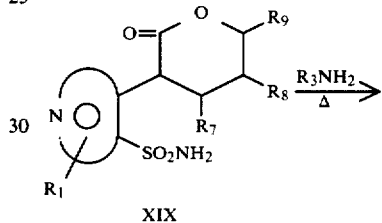

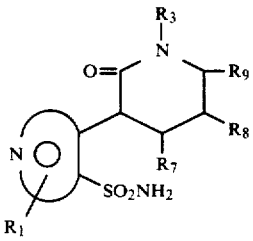

-continued
Equation 21

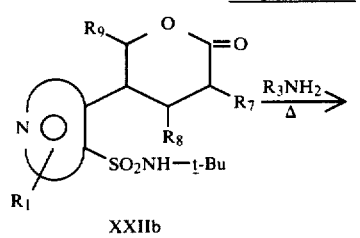
XXIIb
(f)

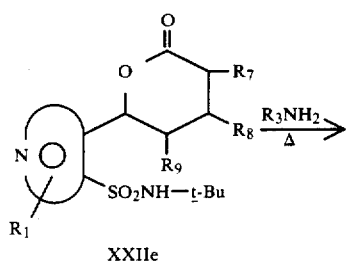
XXVIIIf

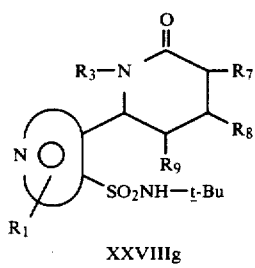
XXIIe
(g)

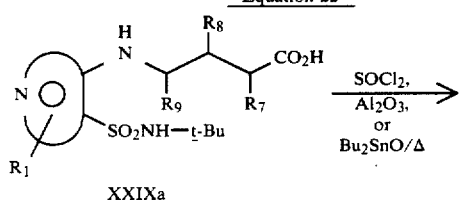
XXVIIIg wherein $R_1$, $R_3$, $R_7$, $R_8$ and $R_9$ are as previously defined.

The conversion of lactones to lactams as shown in Equations 21(a)–21(g) is a well-known process and may be effectively carried out according to the procedures of Scott and Kearse, *J. Org. Chem.*, 5, 598 (1940), and Jones, et al., *J. Am. Chem. Soc.*, 48, 181 (1926); 49, 2528 (1927).

Lactams of Formulas XXVIIIh and XXVIIIi may be prepared as shown below in Equation 22 by an intramolecular N-acylation reaction of amino pyridine derivatives of Formulas XXIXa and XXIXb.

Equation 22

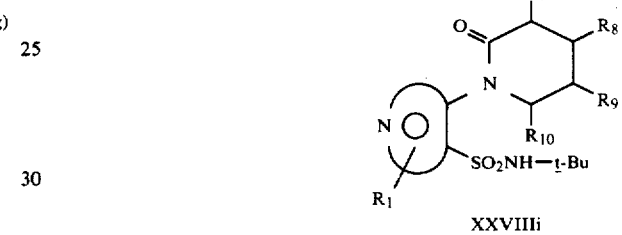
XXIXa
(a)

-continued
Equation 22

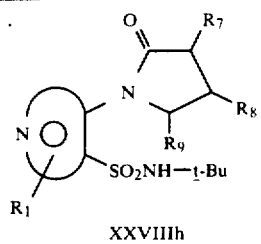
XXVIIIh

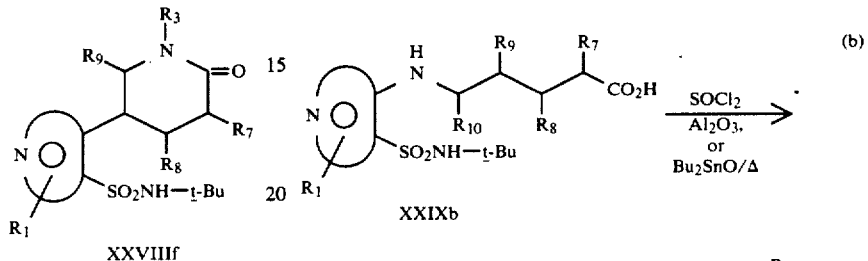
XXIXb
(b)

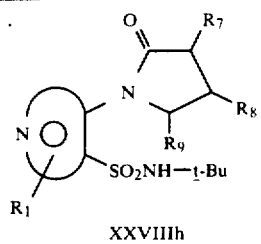
XXVIIIi wherein $R_1$, $R_7$, $R_8$, $R_9$ and $R_{10}$ are as previously defined.

The reaction represented in Equations 22(a) and 22(b) may be accomplished by one or more of the following procedures: (1) treatment of compounds of Formulas XXIXa and XXIXb with thionyl chloride at reflux temperature to give intermediate acid chlorides which should rapidly undergo cyclization (for related methods, see Kent and McElvain, *Org. Syntheses*, 25, 7 (1945); A. P. Martinez, et al., *J. Org. Chem.*, 26, 4501 (1961); W. B. Weaver and W. M. Whaley, *J. Am. Chem. Soc.*, 69, 515, 1144 (1947); and F. Falk, *J. Prakt. Chem.*, 15, 228 (1962)); (2) reaction of compounds of Formulas XXIXa and XXIXb with alumina or silica as described by A. Bladé-Font, *Tetrahedron Lett.*, 21, 2443 (1980); or (3) treatment of compounds XXIXa and XXIXb with dibutyltin oxide as described by K. Steliou, et al., *J. Am. Chem. Soc.*, 102, 7578 (1980).

Subsequent treatment of N-t-butylsulfonamides of Formulas XXVIIIa–i according to one of the methods described in Equation 8 should furnish the primary sulfonamides of Formula IV, where Q is Q-4, Q-5, Q-6, Q-7, Q-55, Q-56, Q-57, Q-58 and Q-59, which may then be converted to compounds of Formula I with the corresponding substituents.

Ketones of Formulas XXVIIa and XXVIIb may be prepared via the two-step sequence of reactions shown below in Equation 23, starting from the appropriate olefins of Formulas XXXa and XXXb.

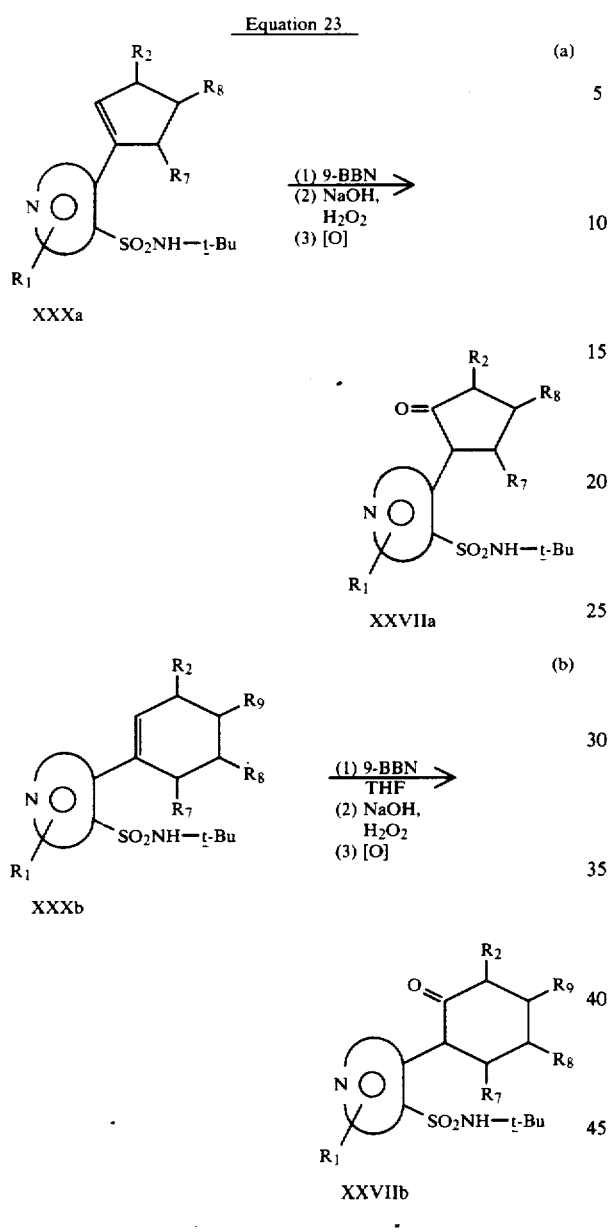

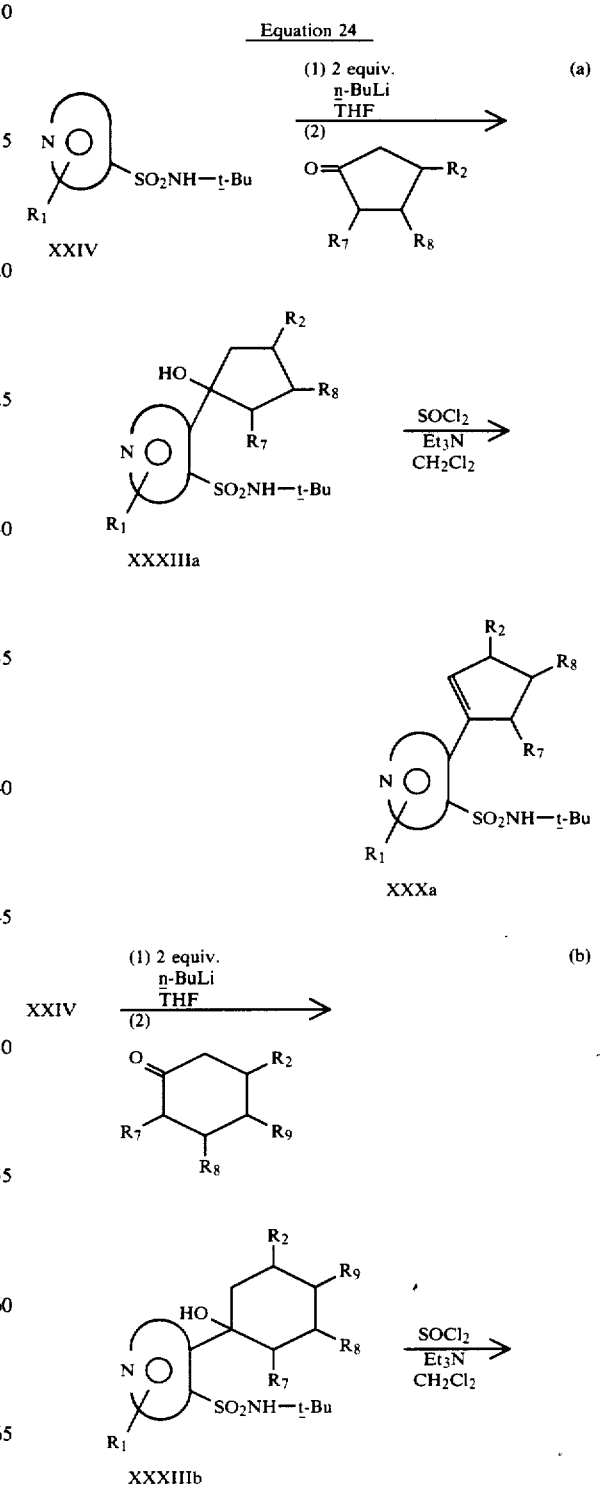

wherein
$R_1$, $R_2$, $R_7$, $R_8$ and $R_9$ are as previously defined.

The first step shown in Equations 23(a) and 23(b) above involves treating olefins of Formulas XXXa and XXXb with 9-borabicyclo[3.3.1]nonane (9-BBN) in a suitable solvent such as tetrahydrofuran, followed by an oxidative workup with basic hydrogen peroxide to generate intermediate secondary alcohols. For details of this procedure, see E. F. Knights and H. C. Brown, *J. Am. Chem. Soc.*, 90, 5280, 5281 (1968). The oxidation of these intermediate secondary alcohols to afford the desired products of Formulas XXXIa and XXXIb may be accomplished by any one of numerous methods; e.g., with chromium trioxide in aqueous sulfuric acid (E. R. H. Jones, et al., *J. Chem. Soc.*, 2548 (1953)), chromium trioxide-pyridine (G. I. Poos, G. E. Arth, R. E. Beyler and L. H. Sareff, *J. Am. Chem. Soc.*, 75, 422 (1953)), or pyridinium chlorochromate (E. J. Corey and T. L. Suggs, *Tetrahedron Lett.*, 2647 (1975)).

The requisite olefins of Formulas XXXa and XXXb may be synthesized by the two-step sequence of reactions represented in Equation 24, starting from the appropriate N-t-butylpyridinesulfonamides of Formula XXIV.

-continued
Equation 24

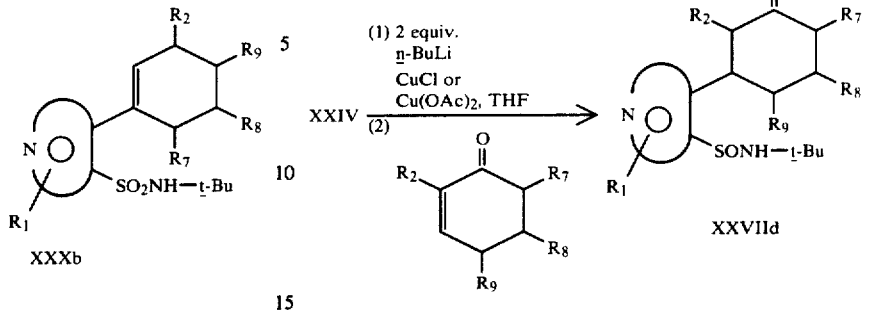

XXXb wherein $R_1$, $R_2$, $R_7$, $R_8$ and $R_9$ are as previously defined.

The first step of Equations 24(a) and 24(b) may be carried out as described for Equations 18. Addition of the appropriate cycloalkanone derivative to the dianions of sulfonamides XXXIV, and subsequent aqueous acid workup should give intermediate alcohols of Formulas XXXIIIa and XXXIIIb. The second step depicted in Equations 24(a) and 24(b) involves treatment of the alcohols XXXIIIa and XXXIIIb with thionyl chloride in the presence of a suitable acid scavenger such as triethylamine at 0°-25° C. to give the olefins of Formulas XXXa and XXXb, respectively. For a detailed description of this standard dehydration method refer to Linstead and Meade, *J. Chem. Soc.*, 942 (1934), or Cook and Lawrence, *J. Chem. Soc.*, 1637 (1935).

Ketones of Formulas XXVIIc and XXVIId may be conveniently synthesized by a process somewhat related to that of Equation 24, except that α, β-unsaturated cycloalkenones are employed in the reaction with dianions of N-t-butylpyridinesulfonamides XXIV instead of cycloalkanones. The result is a 1,4-addition to give the desired products of Formulas XXVIIc and XXVIId as shown below in Equation 25.

-continued

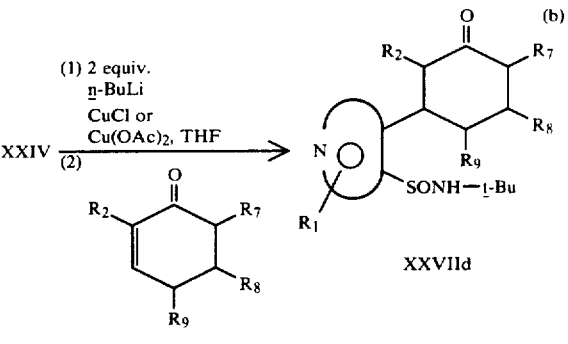

XXVIId wherein $R_1$, $R_2$, $R_7$, $R_8$ and $R_9$ are as previously defined.

The first step shown in Equations 25(a) and 25(b) involves the formation of N-t-butylpyridinesulfonamide dianions as described for Equation 18. However, in the case of the reactions shown above in Equation 25, a suitable copper ion catalyst such as cuprous chloride or cupric acetate is added to form aryl copper reagents which then undergo a conjugate addition to substituted cycloalkenones to generate the desired products of Formulas XXVIIc and XXVIId. Such a transformation is well precedented in the literature; for relevant examples, see Gorlier, Harmon, Levisalles and Wagnon, *Chem. Comm.*, 88 (1973), Posner, *Org. Reactions*, 19, 1 (1972), or House, *Acc. Chem. Res.*, 9, 59 (1976).

Ketones of Formula XXVIIe, may be synthesized in a straightforward manner via the three-step sequence of reactions shown in Equation 26 involving: (a) selective reduction of esters of Formula XXXIV to aldehydes of Formula XXXV, (b) base-induced aldol condensation and dehydration to give enones of Formula XXXVI, and (c) selective reduction of the olefinic bond of enones XXXVI to provide the desired products.

Equation 25

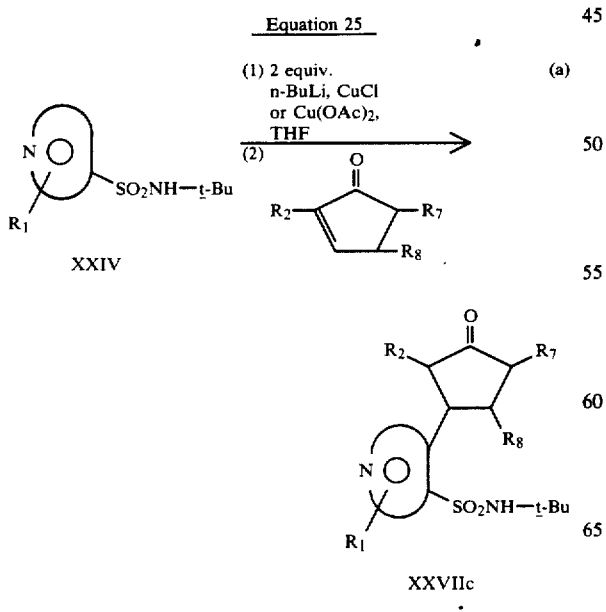

Equation 26

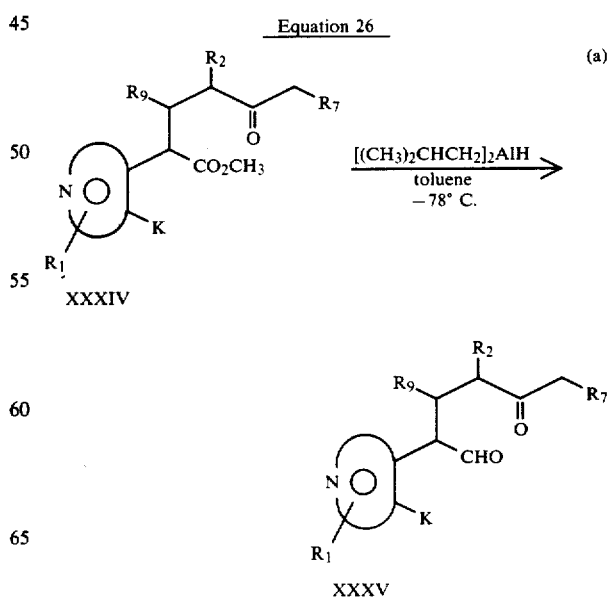

Equation 26
-continued

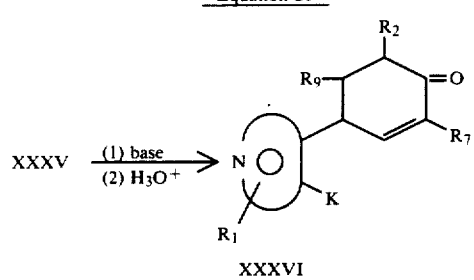

XXXV $\xrightarrow{\text{(1) base}}_{\text{(2) H}_3\text{O}^+}$ XXXVI   (b)

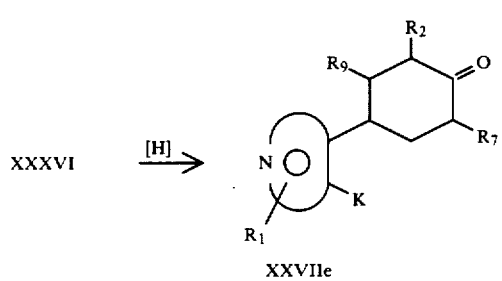

XXXVI $\xrightarrow{[H]}$ XXVIIe   (c)

wherein $R_1$, $R_2$, $R_7$ and $R_9$ are as previously defined,

K is Br, $SR_{12}$, or $NO_2$, and $R_{12}$ is $C_2$–$C_4$ alkyl or benzyl.

The selective reduction of carboxylic esters, such as those of Formula XXXIV, to the corresponding aldehydes of Formula XXXV as shown in Equation 26(a) may best be achieved with diisobutylaluminum hydride (DIBAL) at low temperatures as described by E. J. Corey, K. C. Nicolaou and T. Toru, *J. Am. Chem. Soc.*, 97, 2287 (1975). The intramolecular aldol condensation depicted in Equation 26(b) may be most effectively carried out by treating the compounds of Formula XXXV with a catalytic amount of a suitable base such as sodium methoxide or potassium tert-butoxide. Subsequent aqueous acid workup results in dehydration of the intermediate aldols to give the enones of Formula XXXVI. Alternatively, the aldol condensation may be achieved under conditions of acid catalysis, in which case the enones XXXVI may be obtained directly. For a comprehensive review of this well-known reaction, see A. T. Nielsen and W. J. Houlihan, *Org. Reactions*, 16, 1 (1968). Equation 26(c) represents a selective reduction of the olefinic bond of α,β-unsaturated ketones XXXVI, and may be accomplished by any one of several methods. Two such methods are catalytic hydrogenation (see H. O. House, "Modern Synthetic Methods", 2nd Ed., W. A. Benjamin, Inc., Menlo Park, 1972, pp. 26–28), and dissolving metal reduction with lithium in liquid ammonia (H. O. House, ibid., pp. 174–176).

Ketones of Formula XXVIIf may be synthesized by the 1,4-conjugate addition of appropriate cuprate reagents to enones of Formula XXXVI, as shown below in Equation 27.

Equation 27

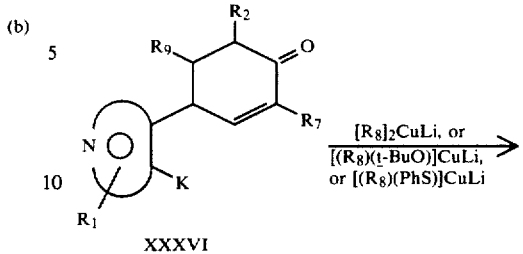

XXXVI $\xrightarrow{[R_8]_2\text{CuLi, or} \atop [(R_8)(\text{t-BuO})]\text{CuLi, or } [(R_8)(\text{PhS})]\text{CuLi}}$

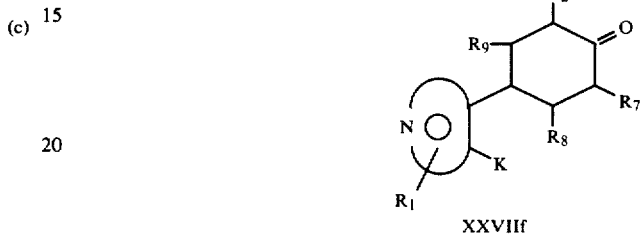

XXVIIf wherein $R_1$, $R_2$, $R_7$, $R_8$ and $R_9$ are as previously defined;

K is Br, $SR_{12}$, or $NO_2$; and $R_{12}$ is $C_2$–$C_4$ alkyl or benzyl.

The 1,4-conjugate addition reaction of Equation 27 may be carried out according to the procedure described by House, Respess and Whitesides, *J. Org. Chem.*, 31, 3128 (1966) when the copper reagent is of he form $[R_8]$CuLi. For use of "mixed" copper reagents, see Posner and Whitten, *Tetrahedron Lett.*, 1815 (1973) (for the reagent $[(R_8)(\text{t-Buo})]$CuLi), or Posner, Whitten and Sterling, *J. Am. Chem. Soc.*, 95, 7788 (1973) (for the reagent $[(R_8)(\text{PhS})]_2$CuLi).

It should be recognized that compounds of Formulas XXXe and XXXf may be treated according to one or both of the methods described in Equations 9, 11 and 12 to afford the corresponding sulfonyl chlorides of Formula IX, where Q is Q-61. Similarly, removal of the tert-butyl group from compounds of Formulas XXXa–d may be accomplished using one or more of the procedures outlined in Equation 8 and should furnish the primary sulfonamides of Formula IV, where Q is Q-8, Q-9, Q-60 or Q-62, which may then be converted to compounds of Formula I with the corresponding Q substituents.

The requisite aminopyridine derivatives of Formulas XXIXa and XXIXb may be prepared in a straight-forward fashion by N-alkylation of compounds of Formula XXXVII with the appropriate γ- or δ-bromo esters, followed by saponification of the intermediate compounds of Formulas XXXVIIIa and XXXVIIIb, as shown below in Equation 28.

Equation 28

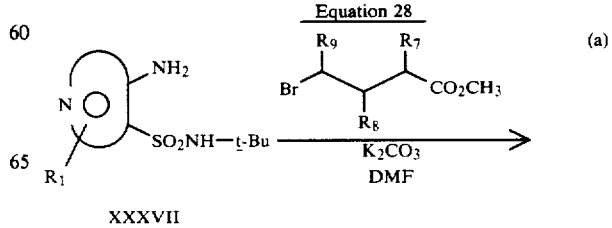

XXXVII   (a)

-continued

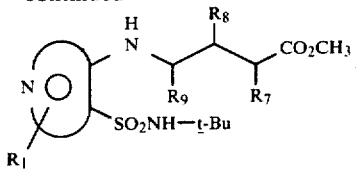
XXXVIIIa

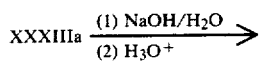

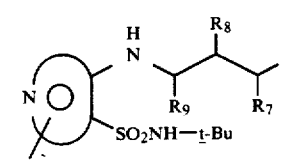
XXIXa (b)

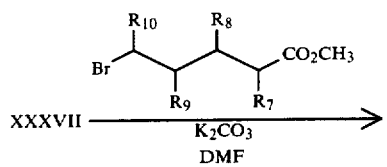

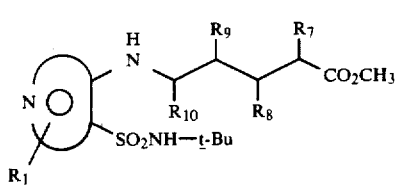
XXXVIIIb

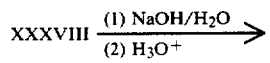

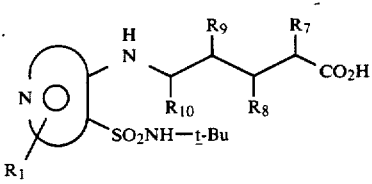
XXIXb wherein $R_1$, $R_7$, $R_8$, $R_9$ and $R_{10}$ are as previously defined.

The first step of Equations 28(a) and 28(b) may be most easily achieved by stirring a mixture of the aminopyridine derivative XXXVII and the appropriate γ- or δ-bromo ester together in the presence of an excess of a suitable base such as anhydrous potassium carbonate in a polar solvent such as N,N-dimethylformamide at temperatures of 25°-110° C. until all of the aminopyridine derivative has been consumed. The intermediate compounds of Formulas XXXVIIIa and XXXVIIIb may then be isolated by pouring the reaction mixture into ice-water, neutralizing by the addition of dilute aqueous mineral acid, and either filtration or extraction into a suitable organic solvent such as diethyl ether, methylene chloride, or ethyl acetate. These compounds of Formulas XXXVIIIa and XXXVIIIb may then be treated with excess dilute aqueous sodium hydroxide solution at about 25° C. for 1-6 hours. Acidification with concentrated hydrochloric acid (ice-water cooling) followed by either filtration or extraction as described above and removal of the solvent in vacuo should afford the desired amino pyridine derivatives of Formulas XXIXa and XXIXb.

The N-t-butylpyridinesulfonamides of Formula XXXVII may be prepared from the appropriate nitropyridinesulfonyl chlorides XXXIX by treatment with tert-butylamine, followed by reduction of the nitro group as depicted in Equation 29.

Equation 29

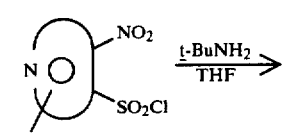

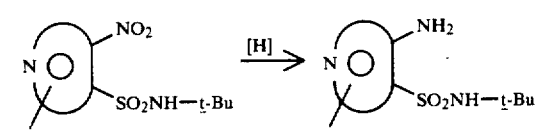

wherein $R_1$ is as previously defined.

The first step of Equation 29 may be effected by adding a solution of the appropriate nitropyridine sulfonyl chloride XXXIX in a suitable solvent such as tetrahydrofuran or methylene chloride to a solution of excess tert-butylamine in the same solvent at about 0° C. After being stirred at 0°-25° C. for 2 to 24 hours, the reaction mixture is washed with water, and the organic layer dried and evaporated to give the desired intermediates of Formula XL which may be sufficiently pure to be carried directly on to the next step. The reduction of nitro compounds of Formula XL to the corresponding aminopyridine derivatives XXXVII may be accomplished by one or more of the methods described for Equation 11.

Those sulfonyl chlorides of Formula XXXIX that are not known in the literature may be prepared by methods which are known to one skilled in the art.

The requisite unsaturated carboxylic acids of Formula XXVI may be synthesized by dehydration of the appropriate hydroxy esters of Formula XXVa, followed by saponification as shown in Equation 30.

Equation 30

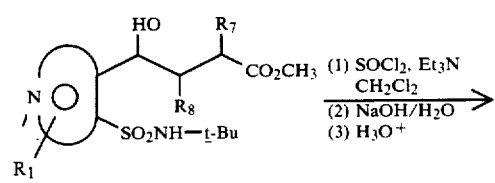
XXVa

-continued

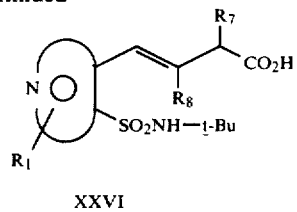

XXVI wherein
$R_1$, $R_7$ and $R_8$ are as previously defined.

The first step of Equation 30, dehydration of alcohols of Formula XXVa to give the corresponding olefins, may be carried out in a manner identical to that described for the second step in Equations 24(a) and 24(b). The saponification shown in Equation 30 (steps 2 and 3) may be accomplished as described for the second step in Equations 18(a) and 18(b).

The carboxylic esters of Formula XXXIV may be prepared by treatment of the anions derived from arylacetic esters of Formula XLI with the appropriate $\alpha,\beta$-unsaturated ketones as shown below in Equation 31.

Equation 31

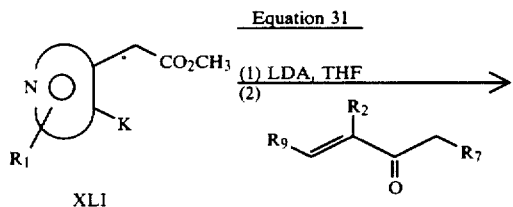

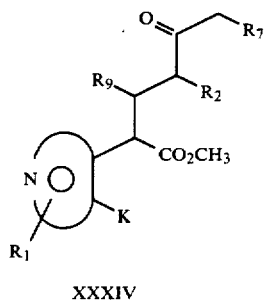

XXXIV wherein
$R_1$, $R_2$, $R_7$ and $R_9$ are as previously defined,
K is Br, $SR_{12}$, or $NO_2$, and $R_{12}$ is $C_2-C_4$ alkyl or benzyl.

The reaction of Equation 31 may be carried out by adding a solution of the pyridineacetic esters XLI in a suitable solvent such as tetrahydrofuran to a solution of a strong base such as lithium diisopropylamide (LDA) at $-78°$ to $0°$ C. under an inert atmosphere. The mixture is stirred at temperatures below $0°$ C. for 0.5–1 hour to ensure complete anion formation, and is then treated with an equimolar quantity of the appropriately substituted $\alpha,\beta$-unsaturated ketone, which is prone to undergo reaction in a 1,4-conjugate manner. For a compilation of references dealing with this type of reaction, see Bergmann, Ginsburg, and Pappo, Org. Reactions, 10, 179 (1959).

The requisite N-t-butylpyridinesulfonamides of Formulas XXIa, XXIb, XXIc, and XXIII, may all be synthesized from common pyridineacetic esters of Formula XLI via a sequence of reactions that entails the same seven basic processes. Equation 32 outlines this sequence of reactions leading to compounds of Formula XXIa (where $R_7$ is H): (a) alkylation of the anion derived from the appropriate pyridineacetic esters of Formula XLI with aldehydes of Formula $R_8CHO$ to give $\beta$-hydroxy arylacetic esters of Formula XLII, (b) protection of the alcohol with a suitable protecting group such as the benzyl ether of Formula XLIII, (c) reduction of the esters of Formula XLIII to afford primary alcohols of Formula XLIV, (d) conversion of the hydroxyl group to a good leaving group such as the alkyl bromide of Formula XLV, (e) conversion of the ortho substituent K to a N-t-butylsulfamoyl group by one of the methods described previously, (f) displacement of the bromides of Formula XLVI to give the corresponding nitriles of Formula XLVII, and (g) hydrolysis of the nitriles XLVII to afford the carboxylic acids of Formula XXIa.

Equation 32

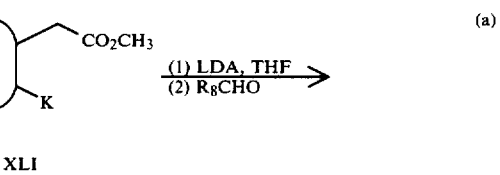

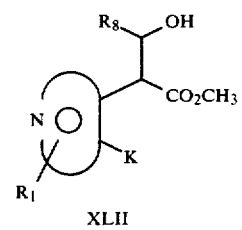

XLII

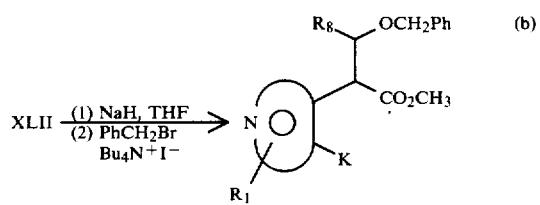

XLIII

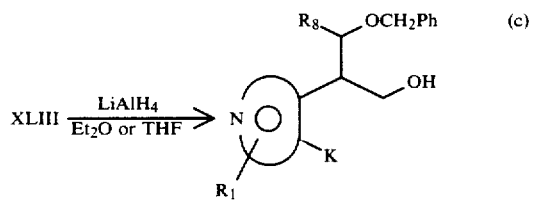

XLIV

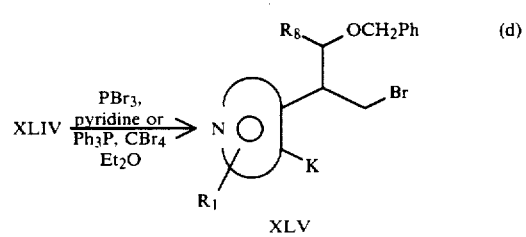

XLV

Equation 32 -continued

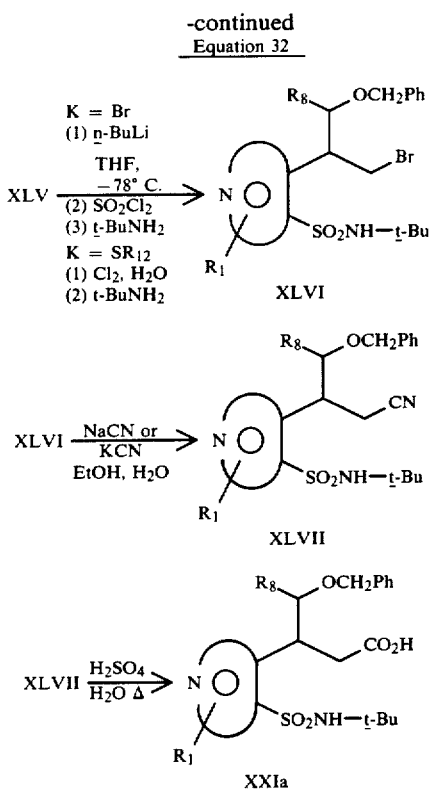

wherein $R_1$ and $R_8$ are as previously defined, K is Br or $SR_{12}$, and $R_{12}$ is $C_2$-$C_4$ alkyl or benzyl.

Equation 32(a)

Anions of pyridineacetic esters of Formula XLI may be formed as shown in Equation 32(a) by treatment with a suitable base such as lithium diisopropylamide (LDA). For a description of this procedure, see Equation 31. Other methods for the preparation and reaction of aliphatic ester enolates have been described by M. W. Rathke, *J. Am. Chem. Soc.*, 92, 3222 (1970), M. W. Rathke and D. F. Sullivan, ibid., 95, 3050 (1973), and M. W. Rathke and A. Lindert, ibid., 93, 2318 (1971). Addition of the appropriate aldehydes of structure $R_8$CHO to these anions should give the desired β-hydroxy esters XLII.

Equation 32(b)

The reaction of Equation 32(b) may be accomplished by formation of the sodium alkoxide of alcohols XLII with sodium hydride, and treatment with benzyl bromide in the presence of a phase-transfer catalyst such as tetrabutylammonium iodide. For a description of this procedure, see S. Czernecki, C. Georgoulis and C. Provelenghiou, *Tetrahedron Lett.*, 3535 (1976).

Equation 32(c)

The reduction of carboxylic esters such as those of Formula XLIII with lithium aluminum hydride as shown in Equation 32(c) is a well-known process and may be carried out according to the procedures described by Gaylord, "Reduction with Complex Metal Hydrides", Interscience Publishers, Inc., New York, 1956, pp. 391-531.

Equation 32(d)

The transformation shown in Equation 32(d) may be achieved by one or more of the following procedures: treatment of alcohols of Formula XLIV with phosphorus tribromide in pyridine (Shone, et al., *J. Am. Chem. Soc.*, 58, 585 (1936), or with triphenyl phosphinecarbon tetrabromide (Lee and Downie, *Tetrahedron*, 23, 2789 (1967); Hooz and Gilani, *Can. J. Chem.*, 46, 86 (1968)).

Equation 32(e)

Compounds of Formula XLV, where K is Br, may be converted to the corresponding sulfonyl chlorides as described for Equation 10. Compounds of Formula XLV, where K is $SR_{12}$, may be efficiently converted to the corresponding sulfonyl chlorides in a manner identical to that described in Equation 12. Treatment of these sulfonyl chlorides in a manner identical to that described in Equation 29 then should afford the desired products of Formula XLVI.

Equation 32(f)

The nucleophilic displacement reaction depicted in Equation 32(f) may be accomplished by treatment of bromides of Formula XLVI with sodium or potassium cyanide according to the procedure of J. R. Ruhoff, *Org. Syntheses*, Coll. Vol. II, 292 (1943).

Equation 32(g)

Nitriles of Formula XLVII may be converted to the corresponding acids of Formula XXIa, by treatment with sulfuric acid in the presence of water as described by Adams and Thal, *Org. Syntheses*, Coll. Vol. I 436 (1941), and Wenner, *J. Org. Chem.*, 15, 548 (1950).

Compounds of Formula XXIa, where $R_7$ is other than H, may be prepared from the corresponding unsubstituted acids of Formula XXIa, where $R_7$ is H, by formation of the O,α-dianion and subsequent trapping with the appropriate electrophile as shown in Equation 33.

Equation 33

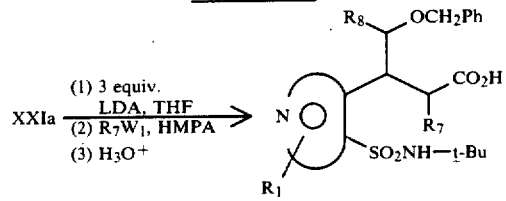

wherein $R_1$, $R_7$ and $R_8$ are as defined above, and $W_1$ is Cl, Br or I.

The alkylation of Equation 33 may be accomplished in a manner analogous to that described in Equation 32(a), except that 3 equivalents of a strong base such as LDA are required, and an electrophile of Formula $R_7W_1$, where $R_7$ is other than H and $W_1$ is Cl, Br, or I, is used to trap the enolate in lieu of an aldehyde. For relevant references, see J. C. Stowell, "Carbanions in Organic Synthesis", John Wiley and Sons, Inc., New York, 1979, pp 157-161.

As mentioned above, N-t-butylpyridinesulfonamides of Formulas XXIb, XXIc, and XXIII may all be synthesized from the appropriate arylacetic esters of Formula XLI in multi-step reaction schemes analogous to that described in Equation 32 for compounds of Formula XXIa. The minor modifications in reaction conditions necessary to achieve these syntheses would be obvious to one who is skilled in the art.

Butenolides of Formula XLIXa may be prepared as shown below in Equation 34 by oxidation of the α-phenylthioethers XLVIIIa and subsequent thermolytic elimination.

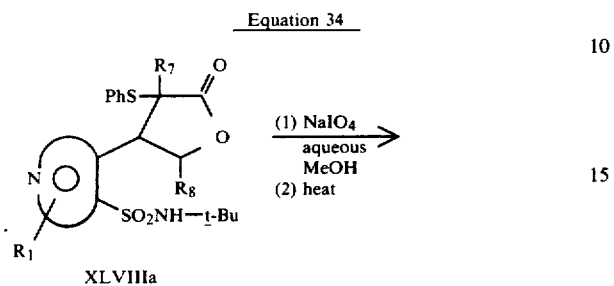

wherein $R_1$, $R_7$ and $R_8$ are as previously defined.

The reactions of Equation 34 may be carried out according to the procedure of B. M. Trost and T. N. Salzmann, *J. Am. Chem. Soc.*, 95, 6840 (1973).

The requisite α-phenylthioethers XLVIIIa may be readily obtained by treatment of the corresponding lactone of Formula XXIIa with a suitable base to generate the enolate, followed by trapping with diphenyl disulfide or phenylsulfenyl chloride as outlined in Equation 35.

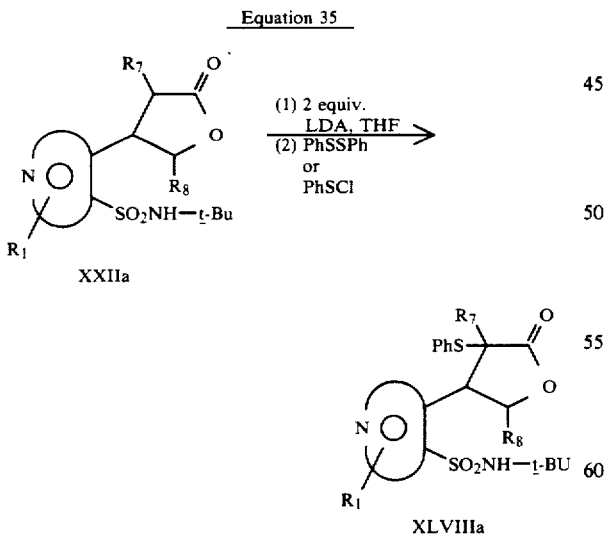

wherein $R_1$, $R_7$ and $R_8$ are as previously defined.

The α-alkylation of lactone enolates is a well-known process and may be successfully carried out according to G. H. Posner and G. L. Loomis, *Chem. Comm.*, 892 (1972), and K. Iwai, et al., *Chem. Letters*, 385 (1974). For use of diphenyl disulfide as the electrophile, see the reference cited for Equation 34. In the case of N-t-butylpyridinesulfonamides of Formula XXIIa, it is necessary to use two molar equivalents of base. The first equivalent of base removes the acidic N-H proton, and the second equivalent forms the lactone enolate.

By using processes analogous to those described above in Equations 34 and 35, or modifications thereof, it is possible for one skilled in the art to prepare α,β-unsaturated lactones of Formulas XLIXb–XLIXe from the appropriate saturated precursors of Formulas XXIIb–XXIIe as represented in Equations 36(a–d).

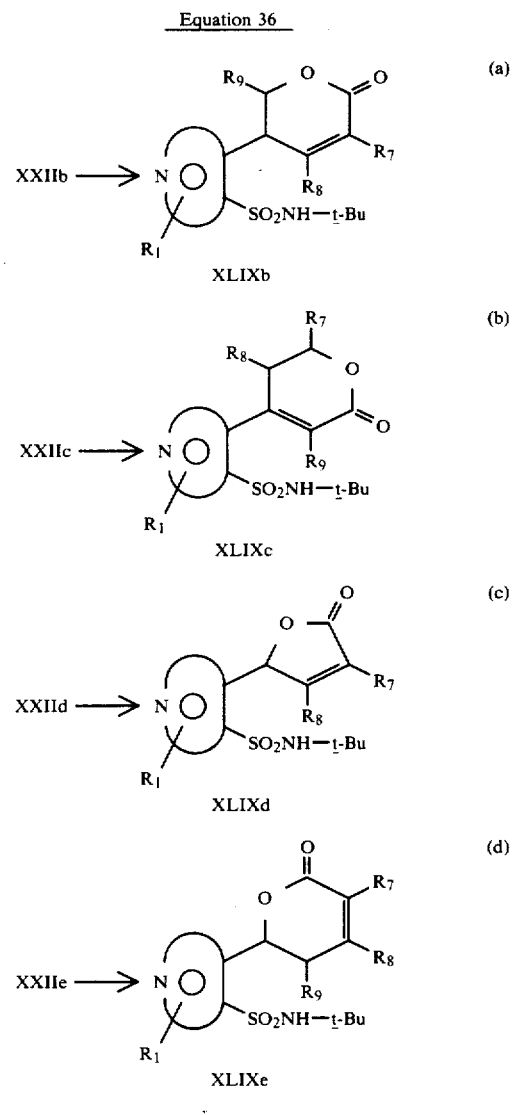

wherein $R_1$, $R_7$, $R_8$ and $R_9$ are as previously defined.

An alternative route to the lactones of Formula XLIXe above where $R_8$ is $C_1-C_4$ alkyl and $R_9$ is H involves the addition of the dienolates of the substituted crotonate esters of Formula XLIXf to the aldehyde XLIXg according to the procedure of R. W. Dugger and C. H. Heathcock, *J. Org. Chem.*, 45, 1181 (1980), as shown in Equation 36e. Aldehyde XLIXg, which exists mostly as its cyclized tautomer, can be synthesized by the addition of N,N-dimethylformamide (DMF) to the dianions of sulfonamides of Formula XXIV.

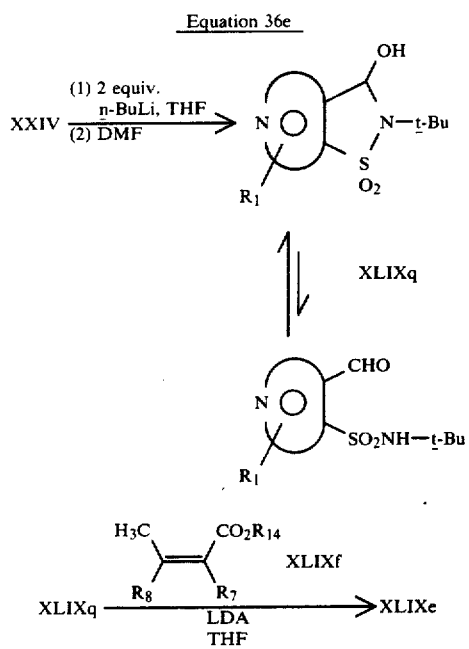

Equation 36e wherein $R_1$ and $R_7$ are as previously defined, $R_8$ and $R_{14}$ are $C_1$–$C_4$ alkyl, and $R_9$ is H.

In a similar fashion, the lactams of Formulas XXVIIIa–XXVIIIi, where $R_3$ is other than H, may be converted to the corresponding unsaturated lactams of Formulas La–Li as outlined in Equation 37(a-i).

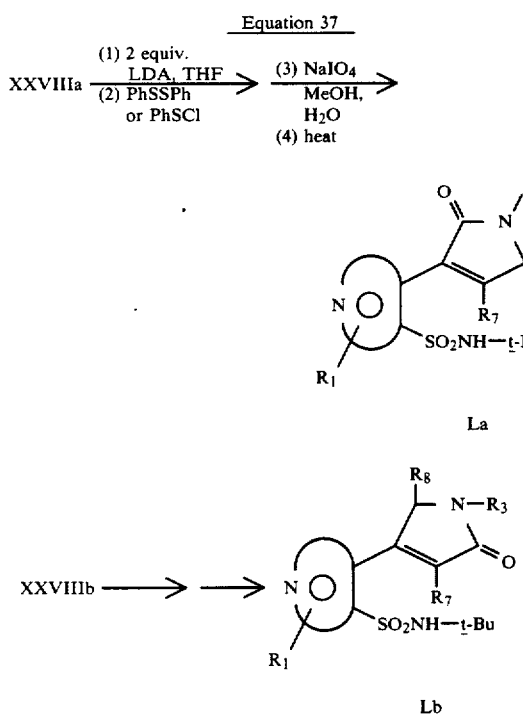

-continued

Equation 37

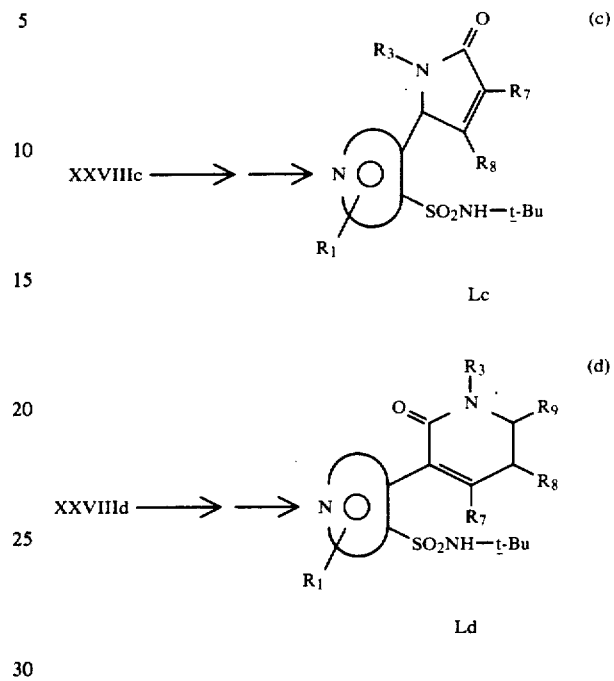

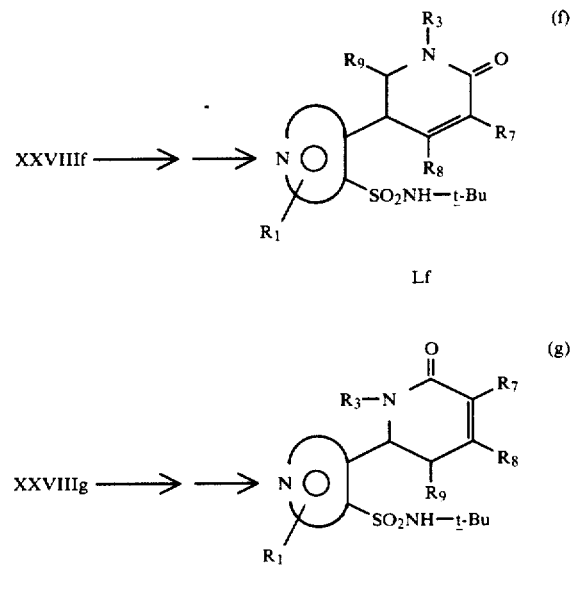

-continued
Equation 37

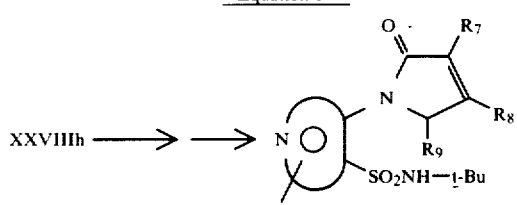

XXVIIIh ⟶ ⟶ Lh (h)

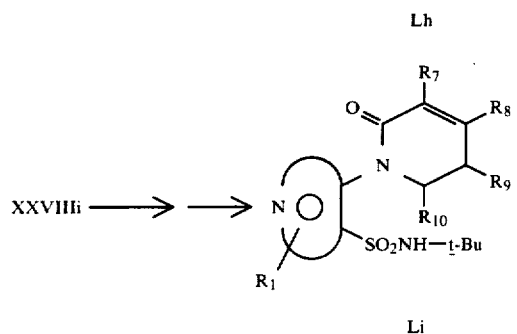

XXVIIIi ⟶ ⟶ Li (i)

wherein

R$_1$, R$_3$, R$_7$, R$_8$, R$_9$ and R$_{10}$ are as previously defined except R$_3$ is other than H.

Unsaturated lactams of Formulas La-Lg, where R$_3$ is H, may be prepared by methods similar to those described in Equation 37. However, it is necessary to use one extra equivalent of a base such as lithium diisopropylamide (LDA) to generate the N,α-dianions LI, which can then be treated with diphenyl disulfide or phenylsulfenyl chloride in a manner identical to that described above to afford the desired products of Formulas La-Lg. Equation 38 depicts this procedure as it applies to the preparation of lactams of Formula La from the appropriate saturated precursor of Formula XXVIIIa.

-continued
Equation 38

LII $\xrightarrow[(2) \text{ Heat}]{(1) \text{ NaIO}_4 \text{ MeOH, H}_2\text{O}}$ La wherein R$_1$, R$_7$ and R$_8$ are as previously defined.

For procedures dealing with the formation and alkylation of lactam α-anions such as those described in Equation 37, see P. A. Zoretic and F. Barcelos, *Tetrahedron Lett.*, 529 (1977), or B. M. Trost and R. A. Kunz, *J. Org. Chem.*, 39, 2475 (1974).

The method shown in Equation 38 may be applied to the synthesis of unsaturated lactams of Formulas Lb-Lg, where R$_3$ is H. For a relevant reference, see J-P. Depres, A. E. Greene and P. Crabbe, *Tetrahedron Lett.*, 2191 (1978).

Removal of the tert-butyl protecting group from compounds of Formula XLIXa-XLIXg and La-Li by one or more of the procedures described in Equation 8 should give the primary sulfonamides of Formula IV, where Q is Q-29, Q-30, Q-31, Q-32, Q-33, Q-34, Q-35, Q-95, Q-96, Q-97, Q-98, Q-99, Q-100, Q-101, Q-102, or Q-103. These sulfonamides may then be converted to compounds of Formula I with the corresponding substituents.

Enones of Formulas LIVa and LIVb may be prepared as shown below in Equation 34 by an intramolecular aldol condensation of the appropriate carbonyl compounds of Formulas LIIIa and LIIIb.

Equation 38

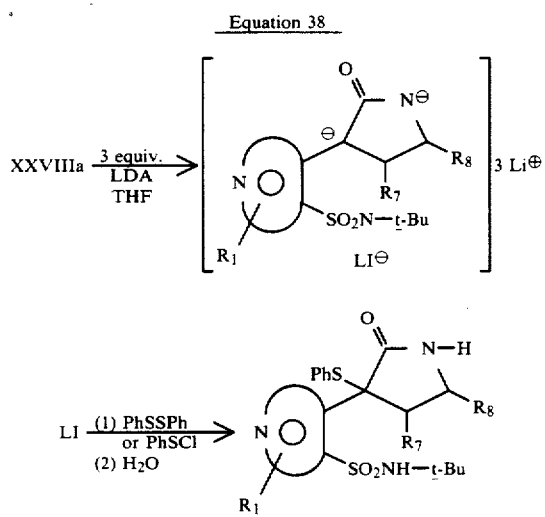

Equation 39

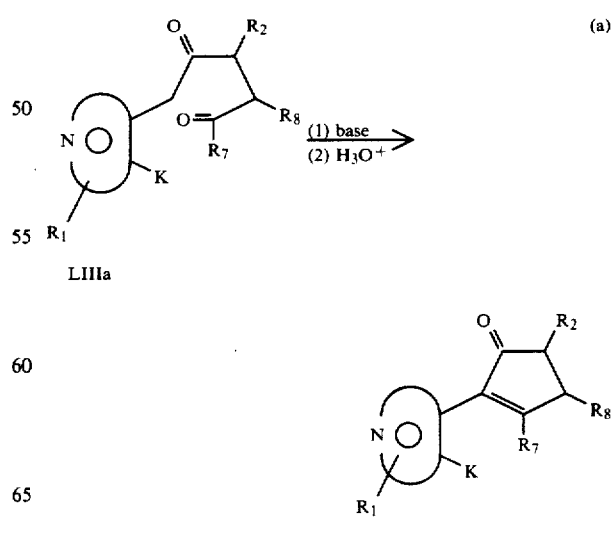

-continued
Equation 39

(b)
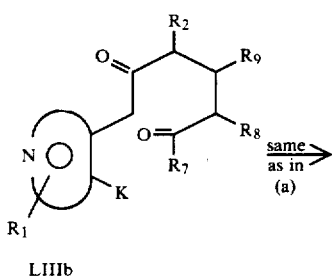
LIIIb

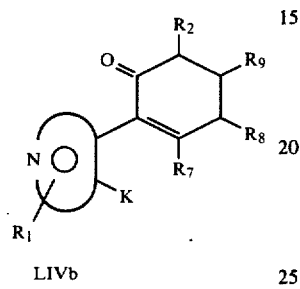
LIVb wherein
R₁, R₂, R₇, R₈ and R₉ are as previously defined,
K is Br, SR₁₂ or NO₂, and R₁₂ is C₂–C₄ alkyl or benzyl.

The aldol condensation depicted in Equations 39(a) and 39(b) may be carried out in a manner analogous to that described for Equation 26(b).

In a similar fashion, enones of Formulas LIVc–LIVi can be prepared from the appropriate carbonyl compounds of Formulas LIIIc–LIIIi as outlined below in Equation 40(a–g).

Equation 40

(a)
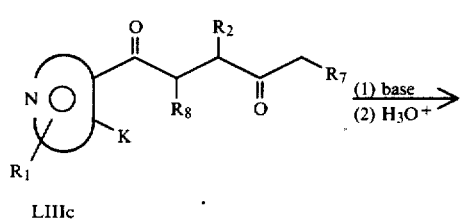
LIIIc

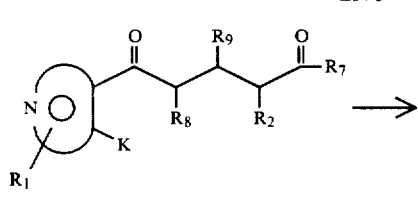
LIIId

-continued
Equation 40

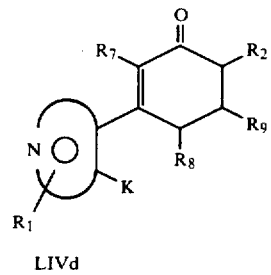
LIVd (c)
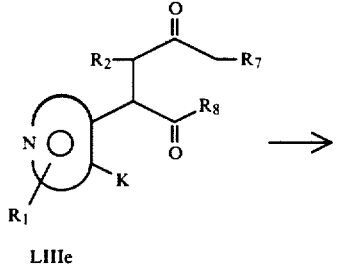
LIIIe

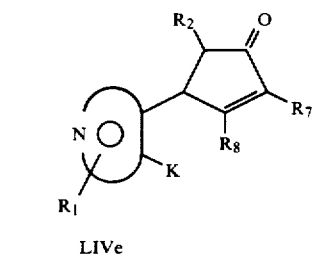
LIVe (d)
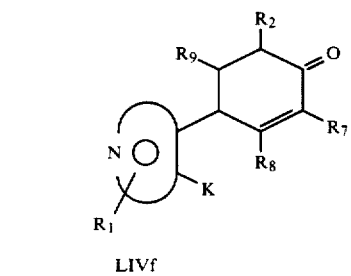
LIIIf

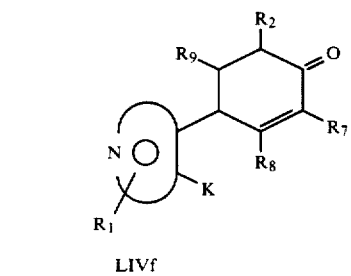
LIVf

-continued
Equation 40

(e)

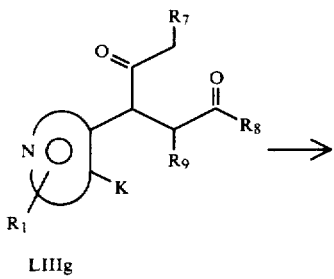
LIIIg

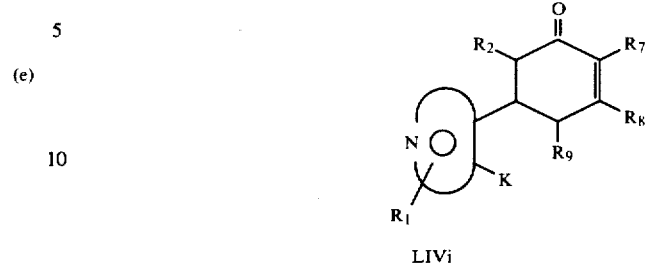
LIVi

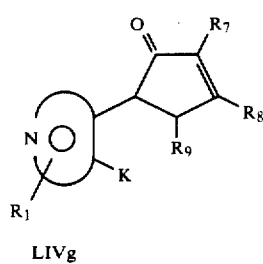
LIVg wherein $R_1$, $R_2$, $R_7$, $R_8$ and $R_9$ are as previously defined, K is Br, $SR_{12}$ or $NO_2$, and $R_{12}$ is $C_2$–$C_4$ alkyl or benzyl.

Another route to the enones of Formula LIVc and LIVd above is depicted in Equation 40h. The addition of 3-ethoxy-2-cyclohexenone or 3-ethoxy-2-cyclopentenone derivatives of Formula LIVs and LIVt respectively, to the dianions of sulfonamides of Formula XXIV followed by mild hydrolysis during workup affords the desired enones directly.

Equation 40h $$XXIV \xrightarrow[\substack{(1)\ 2\ \text{equiv.}\\ \underline{n\text{-BuLi, THF}}\\ (2)\ \text{LIVs or LIVt}\\ (3)\ H_3O^+}]{} \text{LIVd or LIVc}$$

(f)

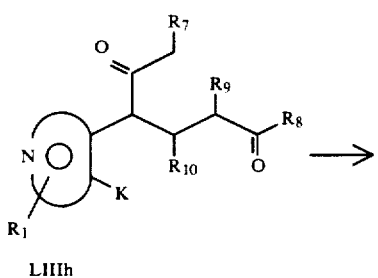
LIIIh

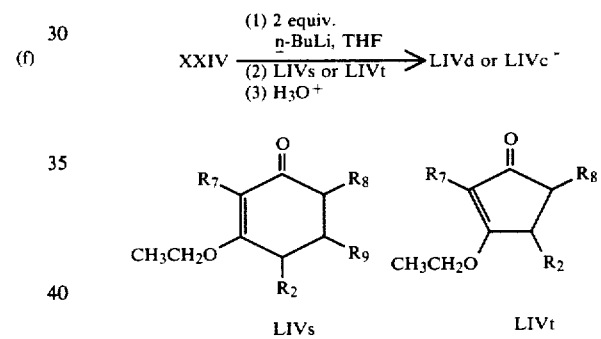

LIVs      LIVt

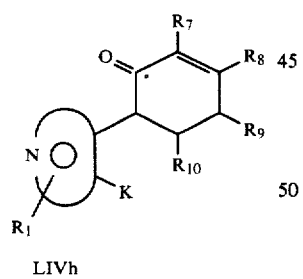
LIVh wherein $R_1$, $R_2$, $R_7$, $R_8$ and $R_9$ are as previously defined.

Alternatively, many of the enones of Formulas LIVj–LIVr may be prepared from the corresponding saturated ketones of Formulas XXVII–XXVII via treatment with the appropriate base to form the α-carbanions, trapping with diphenyl disulfide or phenylsulfenyl chloride, and subsequent oxidative elimination. This sequence is depicted below in Equation 41 for the preparation of enones LIVj and LIVp from ketones of Formula XXVII or XXVIIa.

Equation 41

(g)

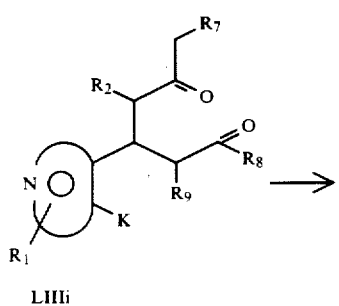
LIIIi

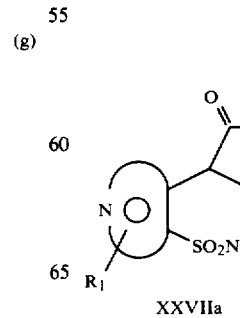
XXVIIa (1) 2 equiv.
t-BuOK
t-BuOH
(2) PhSSPh or PhSCl
(3) $NaIO_4$
MeOH/$H_2O$
(4) heat (a)

-continued
Equation 41

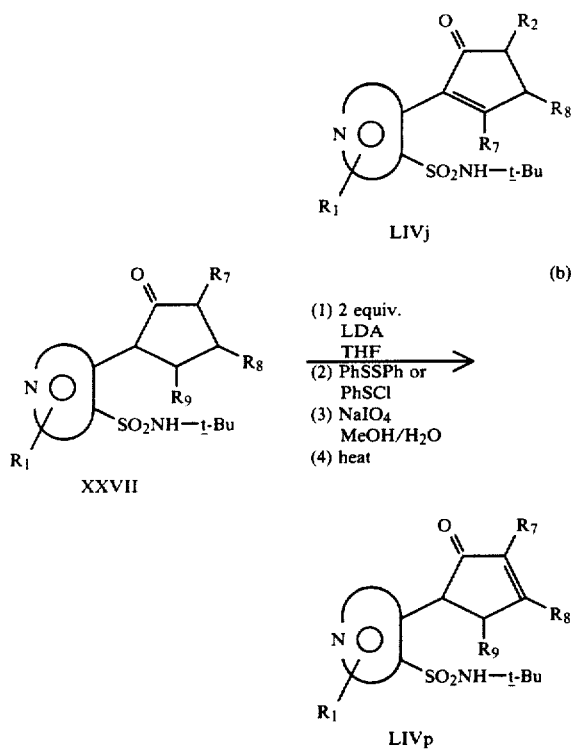

wherein $R_1$, $R_2$, $R_7$, $R_8$ and $R_9$ are as previously defined.

Equation 41(a)

The transformation shown above in Equation 41(a) may be carried out by treating ketones of Formula XXVIIa with two molar equivalents of a strong base such as potassium tert-butoxide (t-BuOK) in a suitable solvent such as t-butanol under an inert atmosphere at 0°–25° C. Such conditions are conducive to formation of the more stable, or thermodynamic, enolates. These anions may then be treated in a manner analogous to that described in Equations 34 and 35.

Equation 41(b)

The transformation shown above in Equation 41(b) may be carried out by treating ketones of Formula XXVII with two molar equivalents of a hindered base such a lithium diisopropylamide (LDA) in a suitable solvent such as tetrahydrofuran at low temperature (−78° C.) under an inert atmosphere. Such conditions are conducive to formation of the less stable, or kinetic, enolates. These anions may then be treated in a manner analogous to that described in Equations 34 and 35.

For a discussion of the optimal conditions required for selectively generating thermodynamic or kinetic enolates, see J. C. Stowell, "Carbanions in Organic Synthesis", John Wiley and Sons, Inc., New York, 1979, pp. 8–11, and references cited therein.

In a similar fashion, enones of Formulas LIVk, LIVl, LIVm, LIVn, LIVo, LIVq, and LIVr can be prepared from the corresponding ketones of Formulas XXVIIb-XXVIIf by selection of the appropriate conditions for enolate formation.

Many of the requisite carbonyl compounds of Formulas LIIIa–LIIIi are known in the literature or can be prepared from known intermediates by methods obvious to one skilled in the art. The appropriately substituted pyridinylacetic esters of Formulas XLI will serve as useful precursors for most of the desired compounds of Formulas LIIIa–LIIIi, and may be transformed by methods similar to those described in Equation 32 or modifications thereof. Such methods would be obvious to one skilled in the art.

Sulfonamides of Formulas LVIa and LVIb can be prepared as shown in Equation 42 by treatment of compounds of Formulas LVa and LVb with base.

Equation 42

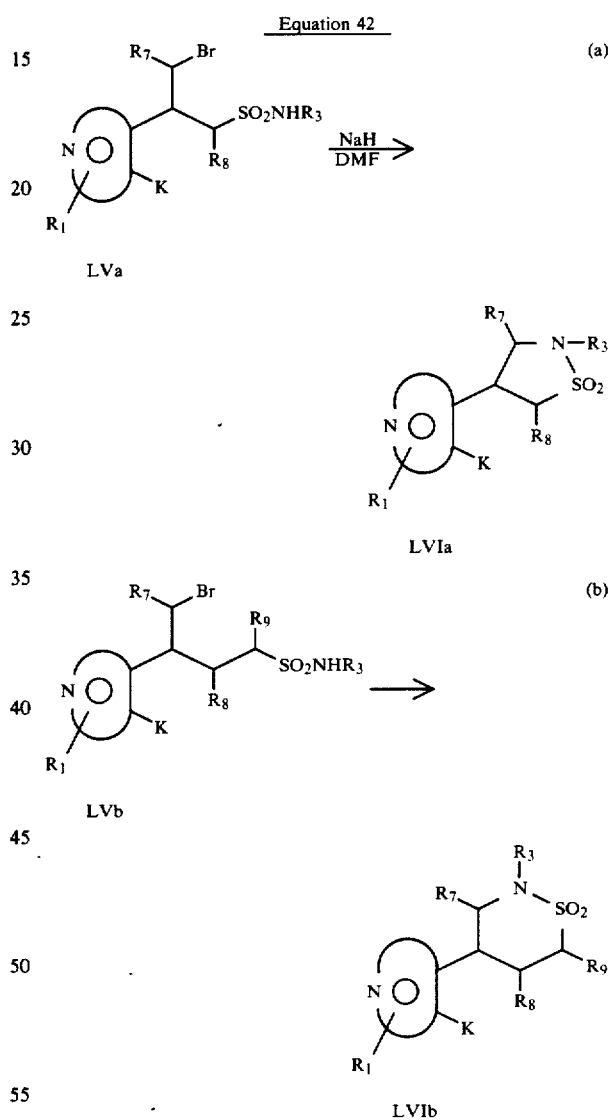

wherein $R_1$, $R_3$, $R_7$, $R_8$ and $R_9$ are as previously defined, K is Br, $SR_{12}$ or $NO_2$, and $R_{12}$ is $C_2$–$C_4$ alkyl or benzyl.

The reactions of Equations 42(a) and 42(b) may be accomplished by adding a solution of sulfonamide LVa or LVb in a suitable solvent such as N,N-dimethylformamide (DMF) to a stirred suspension of a base such as sodium hydride at 0°–25° C. under an inert atmosphere. After being stirred at 25°–100° C. for several hours, or until all of the starting material has disappeared, the reaction mixture is cooled and poured into ice-water.

The desired product of Formula LVIa or LVIb is then isolated by filtration or extraction with a suitable solvent such as diethyl ether, methylene chloride, or ethyl acetate, followed by drying and evaporation of the volatile components.

The sulfonamides of Formulas LVIc-LVIg may be synthesized in a manner identical to that described above in Equation 42 from the appropriate compounds of Formulas LVc-LVg as shown in Equation 43(a-a).

Equation 43

(a)
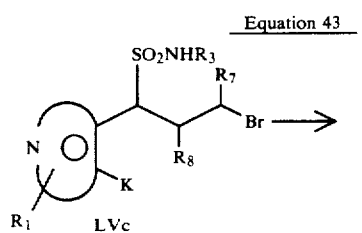
LVc

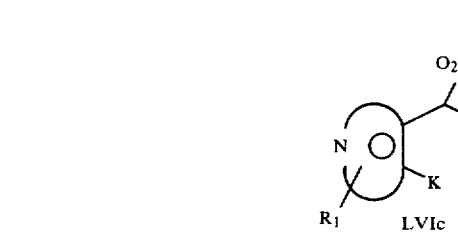
LVIc (b)
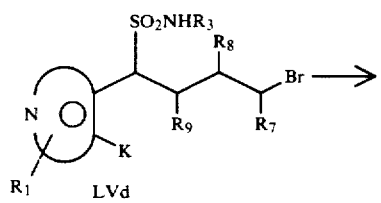
LVd

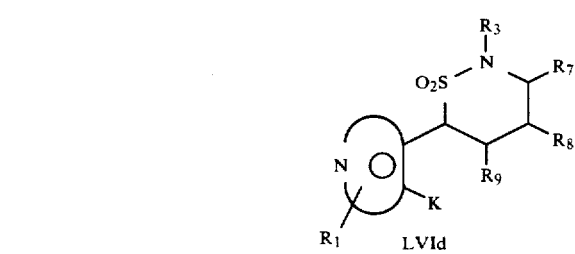
LVId (c)
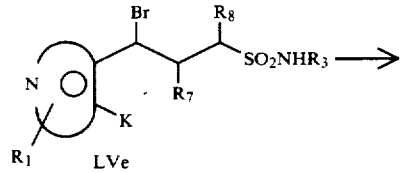
LVe

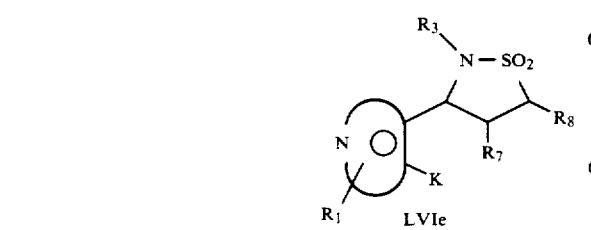
LVIe

-continued
Equation 43

(d)
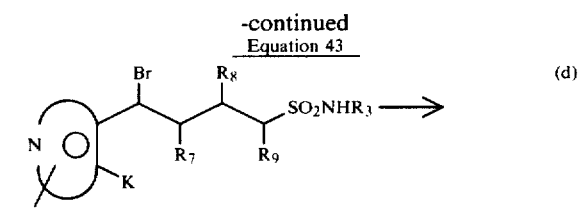
LVf

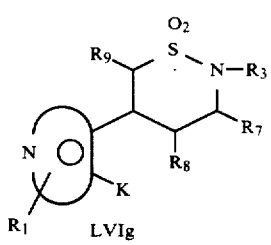
LVIf (e)
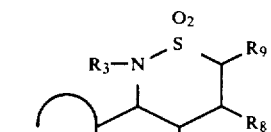
LVg

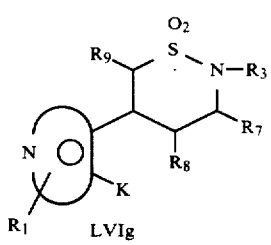
LVIg wherein
$R_1$, $R_3$, $R_7$, $R_8$ and $R_9$ are as previously defined, K is Br, $NO_2$, or $SR_{12}$, and $R_{12}$ is $C_2$–$C_4$ alkyl or benzyl.

Sulfonamides of Formulas LVIh and LVIi may be prepared by treatment of the appropriate compounds of Formulas LVIIa or LVIIb with base to generate anions of Formulas LVIIIa or LVIIIb, and subsequent reaction with suitably substituted nitropyridine compounds as shown in Equations 44(a) and 44(b).

Equation 44

(a)
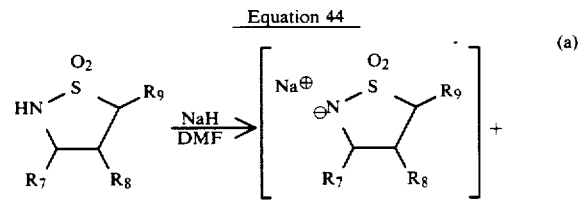
LVIIa     LVIIIa

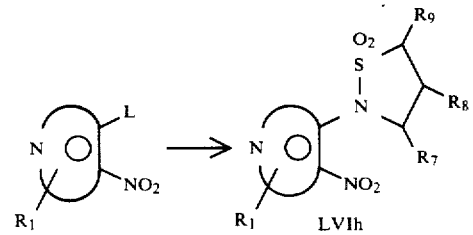
LVIh

-continued
Equation 44

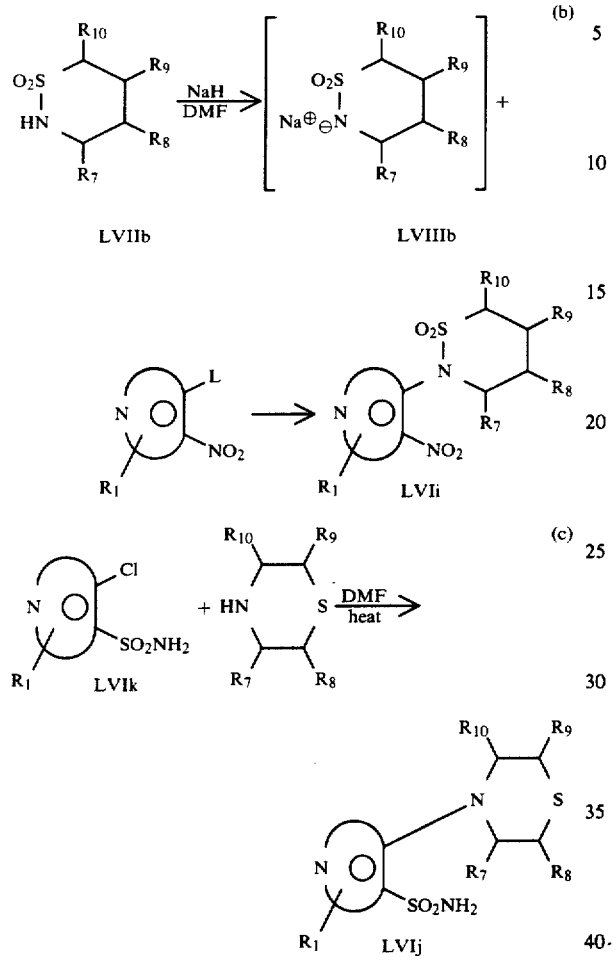

wherein $R_1$, $R_7$, $R_8$, $R_9$ and $R_{10}$ are as previously defined,
L is F, Cl or Br.

The reactions of Equation 44 may be carried out by adding a solution of the appropriate sulfonamide LVIIa or LVIIb in a suitable solvent such as N,N-dimethylformamide (DMF) to a suspension of a base such as sodium hydride in the same solvent at 0°–25° C. under an inert atmosphere. When anion formation is complete, as evidenced by the cessation of hydrogen gas evolution, the reaction mixture is treated with the appropriate nitropyridines, and stirring is continued at 25°–100° C. for 2 to 24 hours. In addition, direct displacement of the chlorine group in compounds such as LVIk with amine nucleophiles in a similar manner produces sulfonamides such as LVIj with ortho groups which can be converted into the desired Q substituents. The desired products of Formulas LVIh or LVIj may then be isolated in a manner similar to that described above for Equation 43.

The requisite compounds of Formula LVa–LVg may all be synthesized via the same basic four-step sequence of reactions. Equation 45 depicts this synthetic scheme for the preparation of sulfonamides LVa, starting from the appropriate alkyl bromides of Formula LIXa as a representative example.

Equation 45

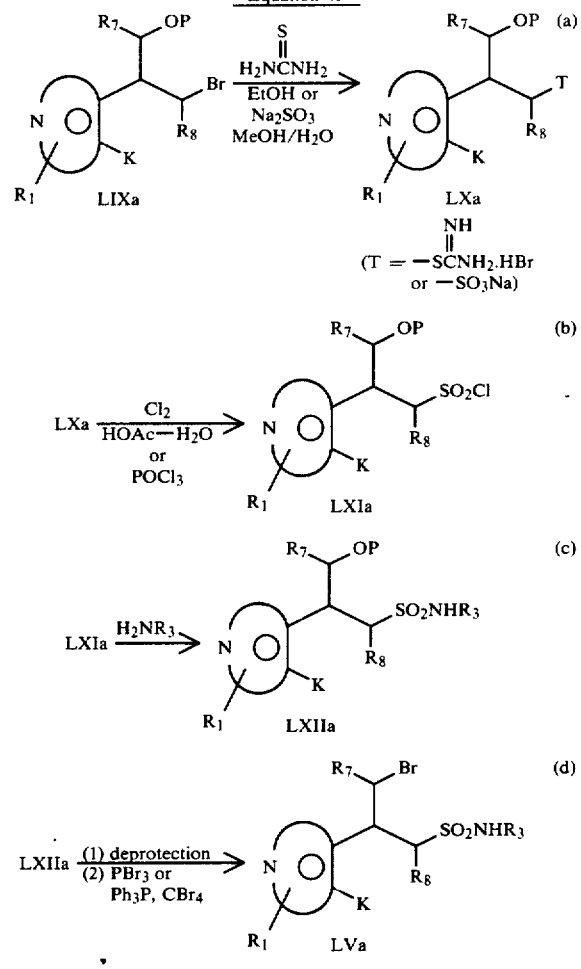

wherein $R_1$, $R_7$ and $R_8$ are as previously defined,
K is Br, $SR_{12}$ or $NO_2$, $R_{12}$ is $C_2$–$C_4$ alkyl or benzyl, and P is an appropriate alcohol protecting group such as $CH_2Ph$, t-butyl, $Si(CH_3)_2$(t-Bu), etc.

Equation 45(a)

The displacement reaction of Equation 45(a) may be effected by treating the alkyl bromides of Formula LIXa with either one molar equivalent of thiourea to give the corresponding isothiouronium salt LXa, where T is $-SC(NH_2)=NH \cdot HBr$, or with sodium sulfite to yield the sodium sulfonate salt LXa, where T is $-SO_3Na$. For detailed procedures relating to the preparation of isothiouronium salts, see Urguhart, Gates and Connor, Org. Syntheses, 21, 36 (1941), or Vogel, J. Chem. Soc., 1822 (1948). For the use of sodium sulfite in the preparation of sodium sulfonate salts, see Reed and Tarter, J. Am. Chem. Soc., 57, 571 (1935), or Latimer and Bost, J. Org. Chem., 5, 24 (1940).

Equation 45(b)

The choice of chlorination conditions to be employed in the reaction of Equation 45(b) depends upon the nature of the substituent T. When T is $-SC(NH_2)=NH \cdot HBr$, the process may best be effected with chlorine in an aqueous medium according to Johnson and Sprague, J. Am. Chem. Soc., 58, 1348

(1936); 59, 1837, 2439 (1937). When T is $-SO_3Na$, the reaction may be çarried out using phosphorous oxychloride according to the procedure of Westlake and Dougherty, *J. Am. Chem. Soc.*, 63, 658 (1941).

Equation 45(c)

The reaction shown in Equation 45(c) may be accomplished in a manner identical to that described for Equation 7. For useful references, see Huntress and Carter, *J. Am. Chem. Soc.*, 62, 511 (1940), or Huntress and Autenrieth, ibid., 63, 3446 (1941).

Equation 45(d)

The first step of Equation 45(d) involves removal of the hydroxyl protecting group to release an alcohol substituent. Selection of a suitable protecting group must take into account the nature of other substituents in the molecule and would be obvious to one skilled in the art. For a compilation of references describing the wide variety of protecting groups available for alcohols, see T. W. Greene, "Protective Groups in Organic Synthesis", John Wiley and Sons, Inc., New York, 1981, pp. 10–72. The second step shown in Equation 45(d) involves the preparation of the desired products of Formula LVa from the corresponding alcohols with either phosphorous tribromide or triphenylphosphine-carbon tetrabromide. For relevant procedures, see Equation 32(d).

The requisite alkyl bromides of Formula LIXa, where $R_8$ is H, may be synthesized in a manner analogous to that described in Equation 32 for compounds of Formula XLV. Alternatively, the alkyl bromides of Formula LIXa, where $R_8$ is other than H, may be obtained as shown in Equation 46, starting from the appropriate esters of Formula XLIIIa.

Equation 46

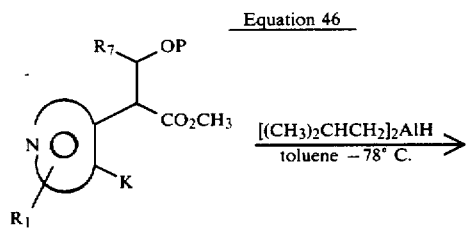

XLIIIa

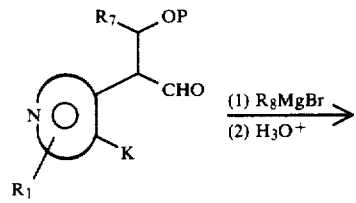

LXIVa

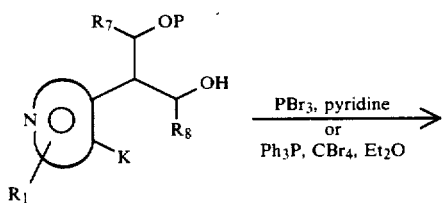

LXVa

-continued
Equation 46

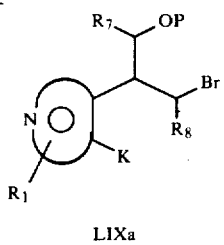

LIXa wherein
- $R_1$, $R_7$ and $R_8$ are as previously defined,
- K is Br, $SR_{12}$ or $NO_2$, $R_{12}$ is $C_2$–$C_4$ alkyl or benzyl, and P is a protecting group as defined above in Equation 45.

The reduction of carboxylic esters such as those of Formula XLIIIa to the corresponding aldehydes with diisobutylaluminum hydride may be carried out as described in Equation 26(a). The second step of Equation 46 involves the addition of appropriate Grignard reagents, $R_3MgBr$, to aldehydes of Formula LXIVa to afford the corresponding alcohols LXVa after aqueous workup. This is a well-known reaction and may be accomplished by following the procedures compiled in Patai, "The Chemistry of the Carbonyl Group", Vol. 1, Interscience Publishers, New York, 1969, pp. 621–693, or Kharasch and Reinmuth, "Grignard Reactions of Nonmetallic Substances", Prentice-Hall, Inc., Englewood Cliffs, N.J., 1954, pp. 138–528. The third step shown in Equation 46 involves the conversion of alcohols LXVa to the corresponding alky bromides LIXa, and has been described above in Equation 32(d).

Compounds of Formulas LVb–LVg may be prepared by methods analogous to those described in Equations 45 and 46 with suitable modifications which would be obvious to one skilled in the art.

Equation 47 depicts the intramolecular reactions of and γ- and δ-hydroxysulfonyl chlorides of Formula LXVIa and LXVIb which should afford the sulfonates of Formulas LXVIIa and LXVIIb.

Equation 47 (a)

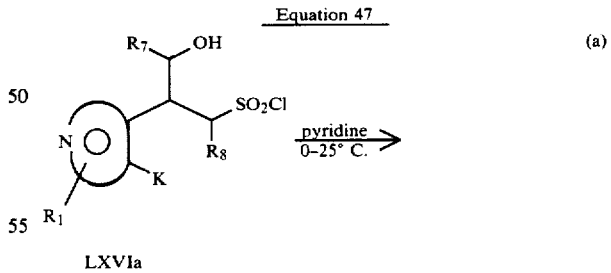

LXVIa

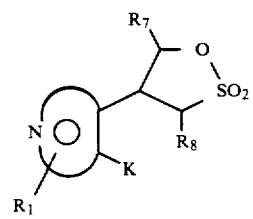

LXVIIa

-continued
Equation 47

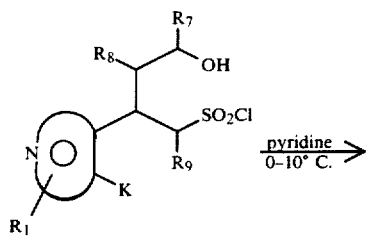

LXVIb

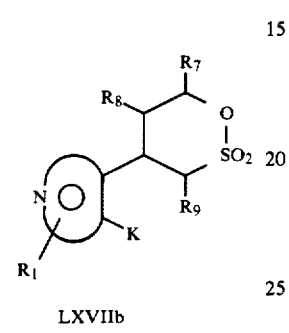

LXVIIb wherein
$R_1$, $R_7$, $R_8$ and $R_9$ are as previously defined,
K is Br, $NO_2$ or $SR_{12}$, and $R_{12}$ is $C_2$–$C_4$ alkyl or benzyl.

The cyclization shown in Equations 47(a) and 47(b) may be achieved according to the procedures of Tipson, *J. Org. Chem.*, 9, 235 (1944), Marvel and Sekera, *Org. Syntheses*, 20, 50 (1940), or Sekera and Marvel, *J. Am. Chem. Soc.*, 55, 346 (1933).

In a similar fashion, sulfonates of Formulas LXVIIc–LXVIIg may be prepared by base-induced cyclization of the appropriate or γ- or δ-hydroxysulfonyl chlorides of Formulas LXVIc–LXVIg, as shown below in Equations 48(a–e).

Equation 48

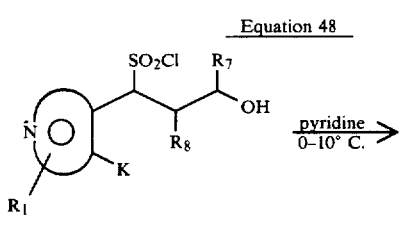

LXVIc

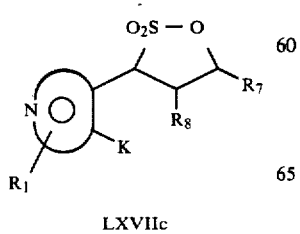

LXVIIc

-continued
Equation 48

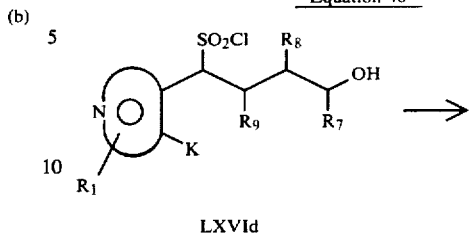

LXVId

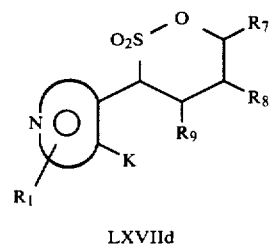

LXVIId (c)

LXVIe

LXVIIe (d)

LXVIf

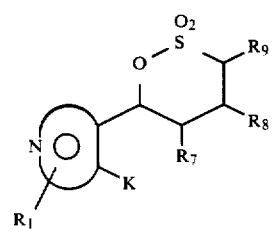

LXVIIf

-continued
Equation 48

(e)

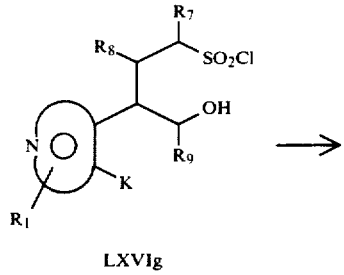

LXVIg

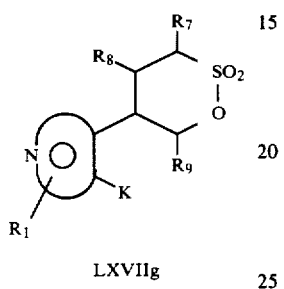

LXVIIg wherein
R₁, R₇, R₈ and R₉ are as previously defined,
K is Br, NO₂ or SR₁₂, and R₁₂ is C₂–C₄ alkyl or benzyl.

The synthesis of the requisite hydroxysulfonyl chlorides has been described previously. For example, γ-hydroxysulfonyl chlorides of Formula LXVIa may be obtained from the corresponding protected compounds of Formula LXIa (Equation 45). In a similar fashion, the requisite hydroxysulfonyl chlorides LXVIb–LXVIg can be prepared from the appropriate protected alcohols by methods which would be obvious to one skilled in the art.

Sulfones of Formulas LXIXa–LXIXe may be prepared as shown in Equation 49 by oxidation of the appropriate 5 and 6-membered ring thioethers of Formulas LXVIIIa–LXVIIIe.

Equation 49

(a)

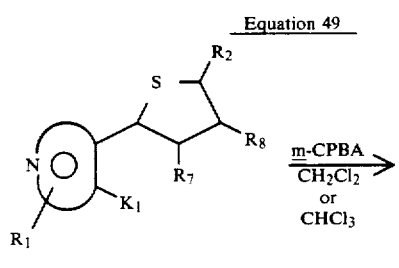

LXVIIIa

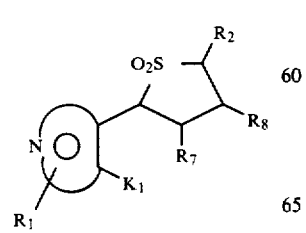

LXIXa

-continued
Equation 49

(b)

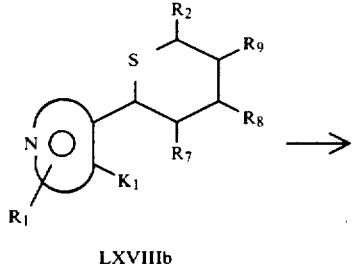

LXVIIIb

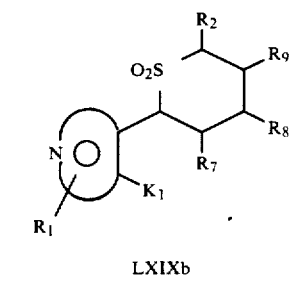

LXIXb (c)

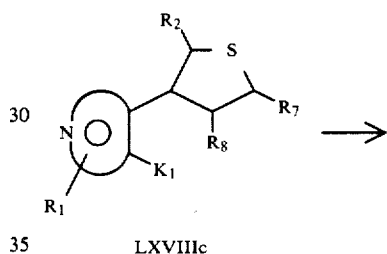

LXVIIIc

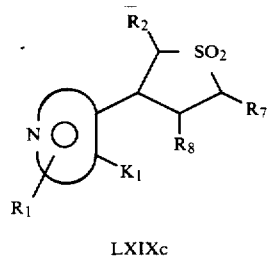

LXIXc (d)

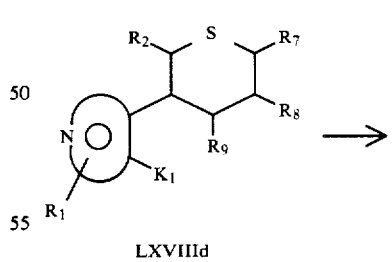

LXVIIId

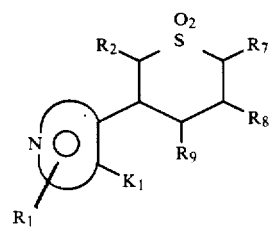

LXIXd

-continued
Equation 49

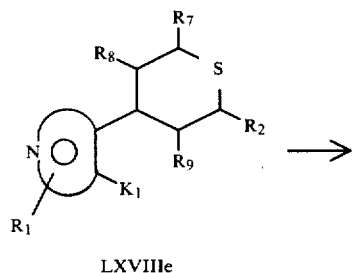

LXVIIIe

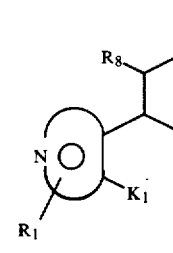

LXIXe wherein
$R_1$, $R_2$, $R_7$, $R_8$ and $R_9$ are as previously defined, and $K_1$ is $NO_2$ or $SO_2NH$-t-Bu.

The oxidation of Equation 49 may be carried out by adding a solution of at least two molar equivalents of m-chloroperoxybenzoic acid (m-CPBA) in a suitable solvent such as methylene chloride or chloroform to a solution of the sulfide LXVIII(a–e) in the same solvent at 0°–25° C. After the reaction mixture has been stirred at about 25° C. for 1–4 hours, excess oxidant is destroyed by the addition of saturated aqueous sodium bisulfite (ice-water cooling). The reaction mixture is then filtered to remove the by-product m-chlorobenzoic acid, and the filtrate is washed several times with portions of saturated aqueous sodium bicarbonate. The desired products of Formula LXIX(a–e) may be isolated by drying and evaporation of the organic layer, and may be sufficiently pure to be carried directly on to the next step.

The requisite sulfides of Formulas LXVIIIa and LXVIIIb may be prepared as shown in Equation 50, by conversion of the appropriate diols of Formulas LXXa and LXXb to the corresponding dibromides LXXIa and LXXIb, respectively, and subsequent treatment with sodium sulfide to effect cyclization.

Equation 50

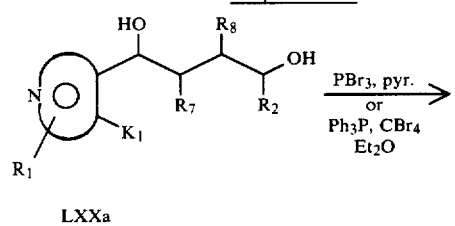

LXXa

-continued
Equation 50

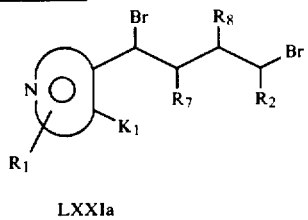

LXXIa

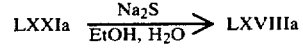

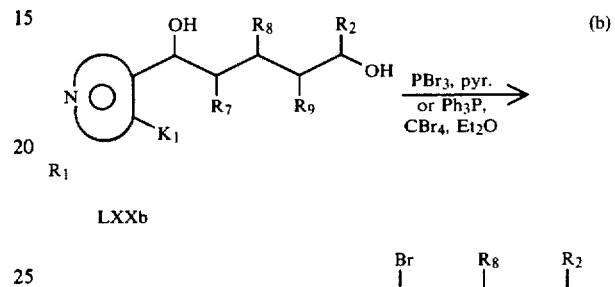

LXXb

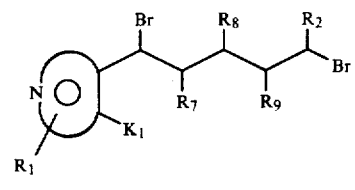

LXXIb

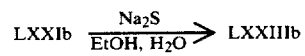

wherein
$R_1$, $R_2$, $R_7$, $R_8$ and $R_9$ are as previously defined, and $K_1$ is $NO_2$ or $SO_2NH$-t-Bu.

The first step of Equations 50(a) and 50(b) may be effected in a manner analogous to that described for Equation 32(d) except that two molar equivalents of the appropriate brominating agent are required. The second step shown above in Equations 50(a) and 50(b) may be carried out according to the method of Tarbell and Weaver, *J. Am. Chem. Soc.*, 63, 2940 (1941), or Naylor, *J. Chem. Soc.*, 1107 (1947).

In a similar manner, the requisite sulfides of Formulas LXVIIIc–LXVIIIe may be prepared via conversion of the appropriate diols to the corresponding dibromides, and subsequent cyclization by treatment with sodium sulfide.

Diols such as those of Formulas LXXa and LXXb may be prepared from the appropriately substituted intermediates, many of which have already been described. Methods needed to effect these transformations would be obvious to one skilled in the art.

The $\alpha,\beta$-unsaturated sulfonamides, represented by Formula LXXIIIa, may be prepared by a procedure identical to that described for the synthesis of $\alpha,\beta$-unsaturated lactams of Formulas La–Li as shown in Equations 37 and 38. For example, treatment of sulfonamides of Formula LVIa with base, addition of diphenyl disulfide or phenylsulfenyl chloride, and subsequent oxidative elimination should give the unsaturated compounds of Formula LXXIIIa as shown in Equation. 51.

Equation 51

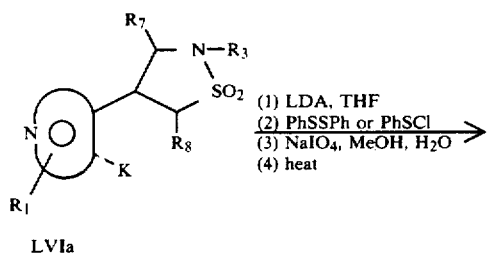

LVIa

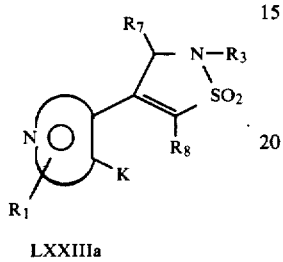

LXXIIIa wherein
$R_1$, $R_3$, $R_7$ and $R_8$ are as previously defined,
and K is Br or $NO_2$.

The transformation depicted in Equation 51 may be carried out in a manner analogous to that described in Equations 37 and 38. When $R_3$ is H, in Equation 51, it is necessary to use one extra molar equivalent of lithium diisopropylamide (LDA) to form the N,α-dianions of sulfonamides LVIa–LVIi. This procedure may be applied to the preparation of the remaining α,β-unsaturated analogues of sulfonamides LVIb–LVIi.

The α,β-unsaturated sulfonates of Formulas LXXIVa–LXXIVg may be synthesized via the four-step sequence of reactions shown below in Equation 52(a–g), starting from the saturated compounds of Formulas LXVIIa–LXVIIg.

Equation 52

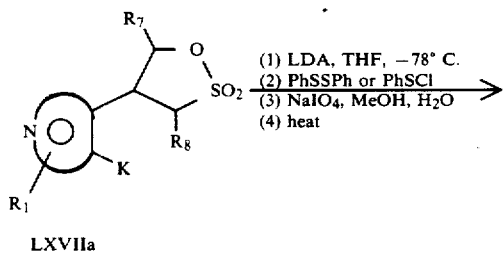

LXVIIa

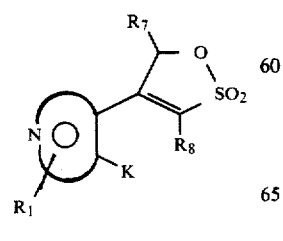

LXXIVa

-continued
Equation 52

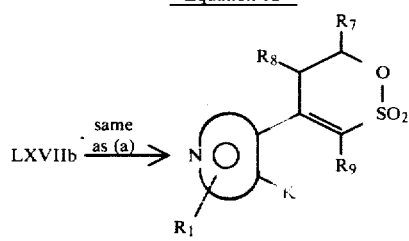

LXXIVb

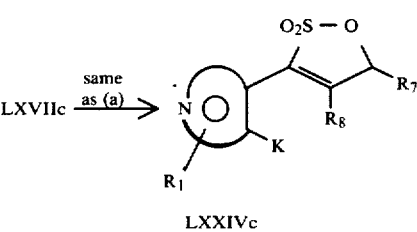

LXXIVc

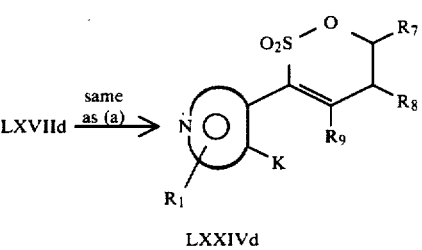

LXXIVd

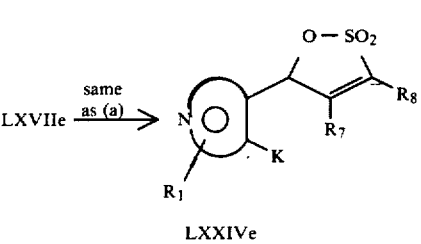

LXXIVe

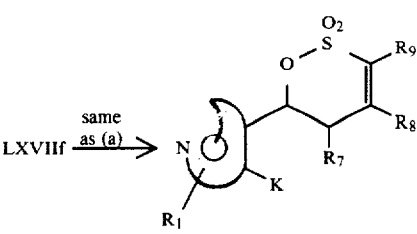

LXXIVf

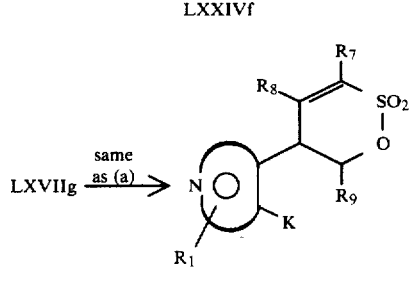

LXXIVg wherein
$R_1$, $R_7$, $R_8$ and $R_9$ are as previously defined and K is Br, or $NO_2$.

The formation of anions alpha to the sulfonyl group of alkyl sulfonates such as those of Formulas LXVIIa-LXVIIg is a process with considerable precedent in the literature. For related examples, refer to Truce, Hollister, Lindy and Parr, *J. Org. Chem.*, 33, 43 (1968); Truce and Vrencur, *Can. J. Chem.*, 47, 860 (1969), *J. Org. Chem.*, 35, 1226 (1970); Julia and Arnould, *Bull. Soc. Chim. Fr.*, 743, 746 (1973); and Bird and Stirling, *J. Chem. Soc. (B)*, 111 (1968). Reaction of these sulfonate anions with diphenyl disulfide or phenylsulfenyl chloride and subsequent oxidative elimination may be effected as described for Equations 37 and 38.

Compounds of Formulas LXXVIa-LXXVId may be synthesized as shown in Equation 53 by the reaction of appropriate α,β-unsaturated carbonyl compounds LXXVa-LXXVd with α-chloroketene acetals of Formulas LXXVIIa or LXXVIIb.

Equation 53

(a)

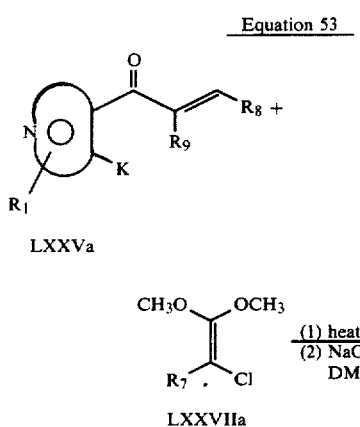

(b)

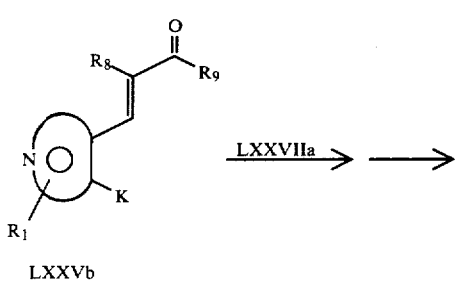

-continued
Equation 53

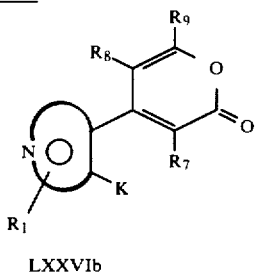

(c)

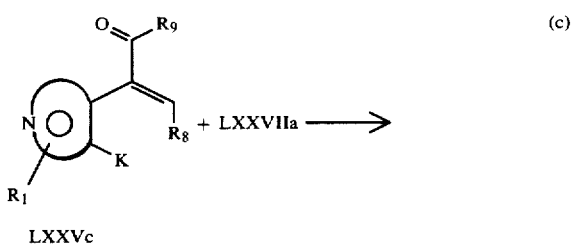

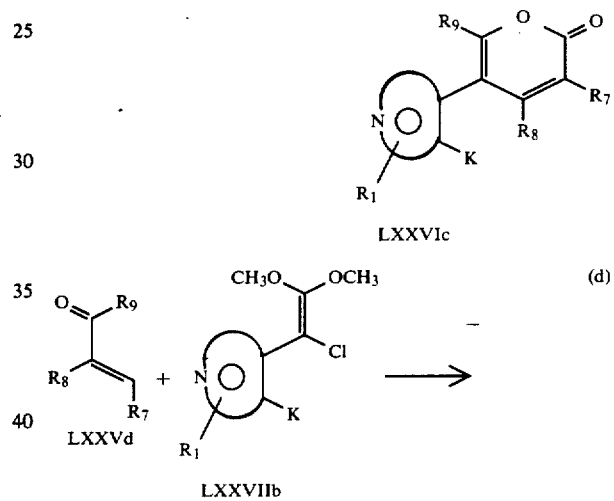

(d)

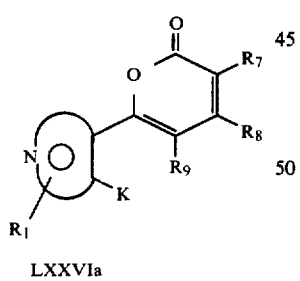

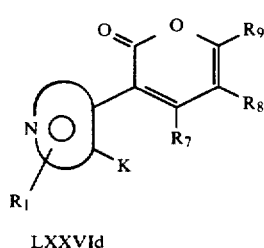

wherein
$R_1$, $R_7$, $R_8$ and $R_9$ are as previously defined,
K is Br, $NO_2$, or $SR_{12}$, and $R_{12}$ is $C_2$-$C_4$ alkyl or benzyl.

The transformations outlined in Equation 53 may be carried out by the procedure of A. Belanger and P. Brassard, *Chem. Comm.*, 863 (1972). Other syntheses of α-pyrones are known in the literature and have been reviewed by J. Fried in "Heterocyclic Compounds", ed. R. C. Elderfield, Wiley, New York, 1950, Vol. I, pp. 358-370, and L. F. Cavalieri, *Chem. Rev.*, 41, 525 (1947).

The requisite olefinic compounds of Formulas LXXVa-d and the α-chloro ketene acetals of Formula LXXVIIa and LXXVIIb may be prepared by methods known to one skilled in the art.

The γ-pyrones of Formulas LXXXIa and LXXXIb may be prepared by one or more of several methods which have been reviewed by J. Fried in "Heterocyclic Compounds", ed. R. C. Eldeffield, Wiley, New York, Vol. I, pp. 379-391. A more recent procedure involves the reaction of suitable potassium enolates of Formulas LXXIXa and LXXIXb with the appropriate acid chlorides of Formulas LXXXa and LXXXb, as shown in Equation 54.

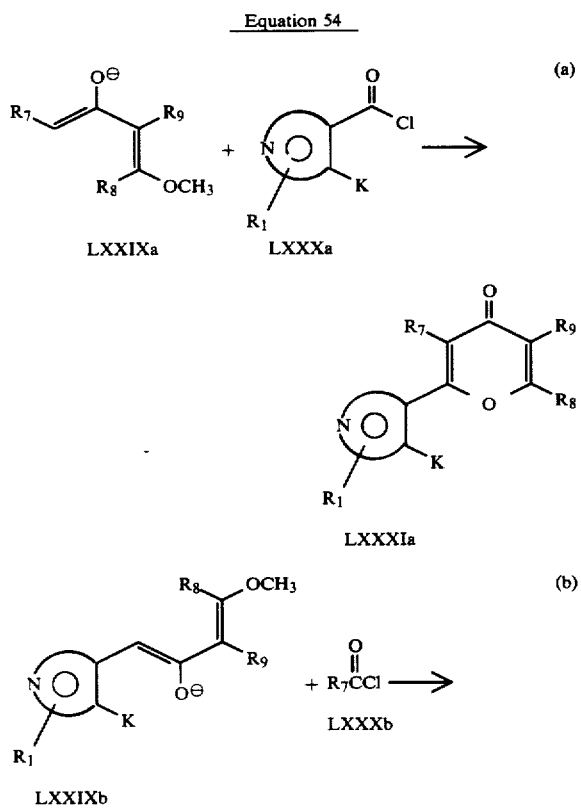

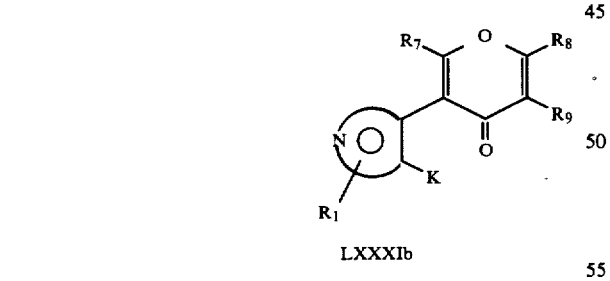

wherein

R$_1$, R$_7$, R$_8$ and R$_9$ are as previously defined,

K is Br, NO$_2$ or SR$_{12}$, and R$_{12}$ is C$_2$-C$_4$ alkyl or benzyl.

The reactions shown above in Equations 54(a) and 54(b) can be carried out according to the procedures described by T. A. Morgan and B. Ganem, Tetrahedron Lett., 21, 2773 (1980).

The requisite potassium enolates of Formulas LXXIXa and LXXIXb can be most conveniently prepared by treatment of the appropriate unsaturated ketones of Formulas LXXXIIa and LXXXIIb with a suitable base such as potassium tert-butoxide as shown in Equation 55.

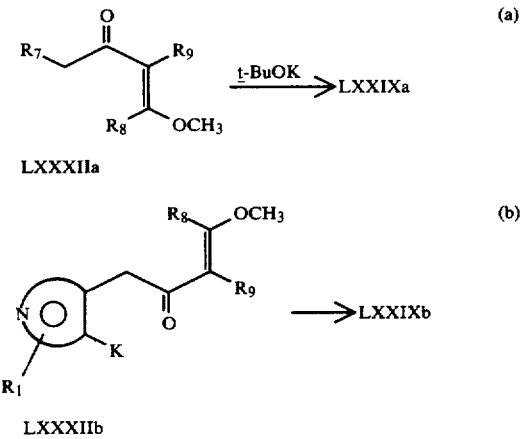

wherein

R$_1$, R$_7$, R$_8$ and R$_9$ are as previously defined,

K is Br, NO$_2$ or SR$_{12}$, and R$_{12}$ is C$_2$-C$_4$ alkyl or benzyl.

The reaction shown in Equation 55 may best be carried out according to the method described in Morgan and Ganem, Tetrahedron Lett., 21, 2773 (footnote 6) (1980).

The requisite unsaturated ketones of Formulas LXXXIIa and LXXXIIb, as well as the acid chlorides of Formula LXXXa and LXXXb, may be synthesized by methods known to one skilled in the art.

α-Pyridones of Formulas LXXXIVa-d may be prepared in a straightforward manner by treatment of the appropriate α-pyrones of Formulas LXXXVIa-d with suitable amines, H$_2$NR$_{11}$, as represented below in Equations 56(a-d).

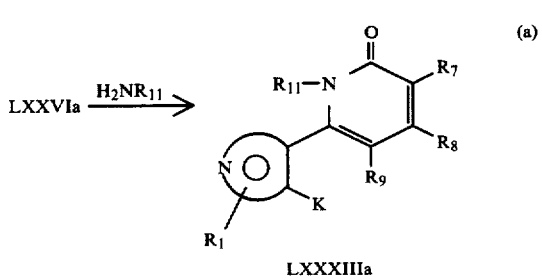

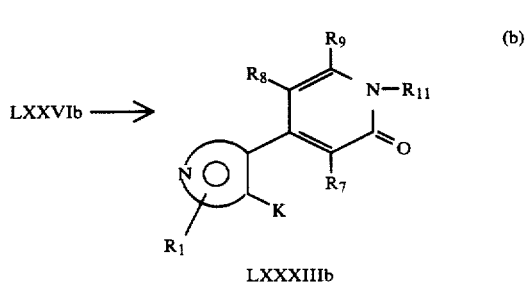

-continued
Equation 56

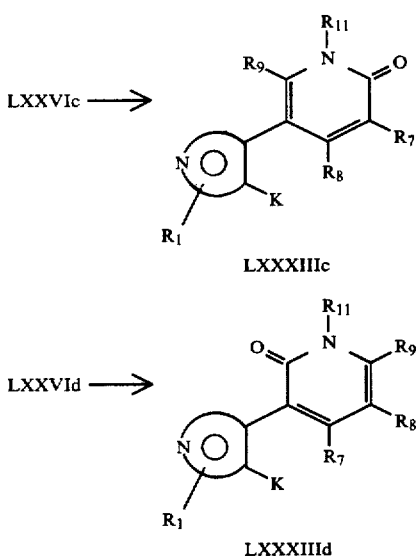

wherein
R₁, R₇, R₈, R₉ and R₁₁ are as previously defined, K is Br, NO₂ or SR₁₂, and R₁₂ is C₂–C₄ alkyl or benzyl.

The conversion of α-pyrones to the corresponding pyridones as shown in Equation 56 is a well-precedented process in the literature. For detailed descriptions of the procedure, see the following references: J. A. Leben, Ber., 29, 1673, (1896); von Pechmann and W. Welsh, Ber., 17, 2351 (1884); and J. H. Boyer and W. Schoen, Org. Syntheses, Coll. Vol. IV, 532 (1963).

Compounds of Formula LXXXIIIe may be prepared as shown in Equation 57 by the reaction of α-pyrones of Formula LXXXVI with the anions of the appropriate amino pyridine derivatives of Formula LXXXV.

Equation 57

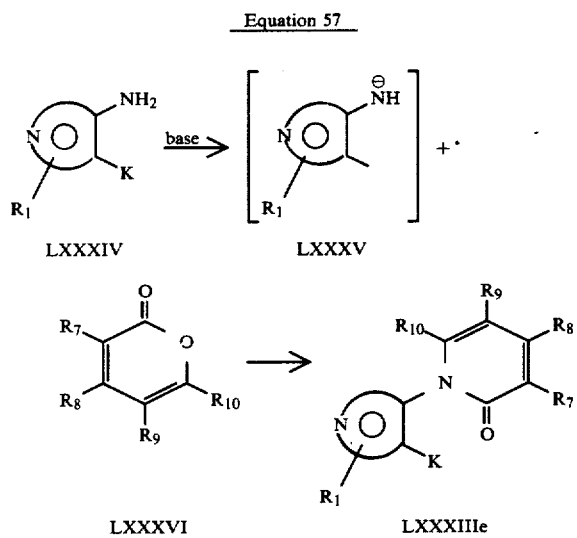

wherein
R₁, R₇, R₈, R₉ and R₁₀ are as previously defined, K is Br, NO₂ or SR₁₂ and R₁₂ is C₂–C₄ alkyl or benzyl.

The first step of Equation 57, formulation of the anions LXXXV of amino pyridine derivatives LXXXIV by treatment with a suitable base such as ethoxide ion, may be carried out according to the methods described by DeFeo and Strickler, J. Org. Chem., 28, 2915 (1963), Yang, Cannon and Rose. Tetrahedron Lett., 1791 (1970), or Singh, Tetrahedron Lett., 321 (1971). The second step of Equation 57 may be effected in a manner analogous to that described in Equation 56.

γ-Pyridones of Formulas LXXXVIIa and LXXXVIIb may be synthesized from the corresponding γ-pyrones of Formulas LXXXIa and LXXXIb by treatment with the appropriate amines, H₂NR₁₁. This transformation is depicted in Equation 58.

Equation 58

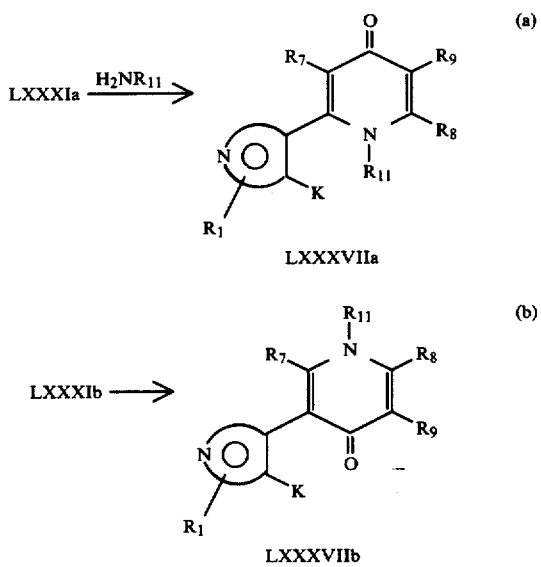

wherein
R₁, R₇, R₈, R₉ and R₁₁ are as previously defined, K is Br, NO₂ or SR₁₂, and R₁₂ is C₂–C₄ alkyl or benzyl.

The reactions of Equations 58(a) and 58(b) may be carried out as described by C. F. Rassweiler and R. Adams, J. Am. Chem. Soc., 46, 2758 (1924).

γ-Pyridones of Formula LXXXVIIc may be prepared in a manner analogous to that outlined in Equation 57. Thus, addition of the anions of Formula LXXXV to γ-pyrones of Formula LXXXVIII, as shown in Equation 59, should afford the desired products of Formula LXXXVIIc.

Equation 59

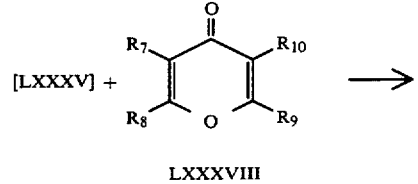

Equation 59

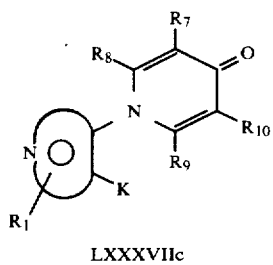

LXXXVIIc wherein $R_1$, $R_7$, $R_8$, $R_9$ and $R_{10}$ are as previously defined, K is Br, $NO_2$ or $SR_{12}$ and $R_2$ is $C_2$–$C_4$ alkyl or benzyl.

Compounds of Formula XCIIa, where $R_8$ is H, may be prepared as shown in Equation 60 by the three-step sequence of reactions involving: (a) conversion of suitably protected carboxylic acids of Formula LXXXIX to the acid chlorides XC, (b) treatment with diazomethane to give diazoketones of Formula XCI, and (c) acid-induced cyclization.

Equation 60

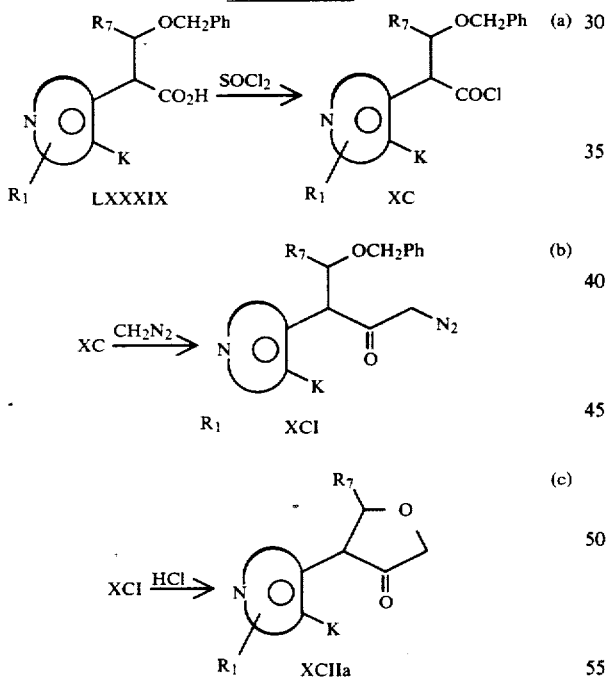

wherein $R_1$ and $R_7$ are as previously defined, K is Br, $NO_2$ or $SR_{12}$, and $R_{12}$ is $C_2$–$C_4$ alkyl or benzyl.

The transformations outlined in Equation 60(a–c) may be achieved according to the procedure of V. Luhmann and W. Luttke, *Chem. Ber.*, 105, 1350 (1972).

Compounds of Formula XCIIb may be prepared via an intramolecular epoxide opening reaction followed by oxidation of the resulting alcohol as depicted in Equation 61.

Equation 61

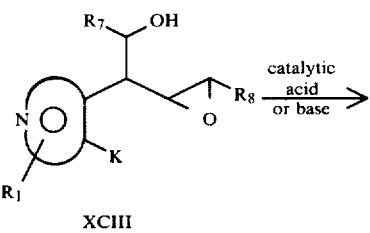

XCIII

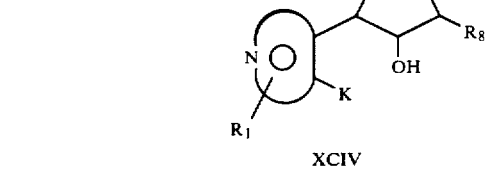

XCIV

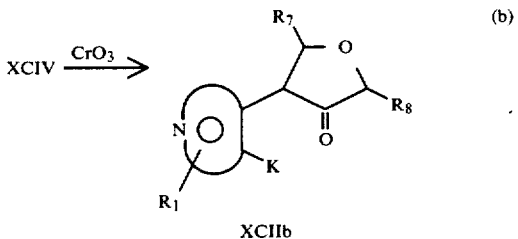

XCIIb wherein $R_1$, $R_7$ and $R_8$ are as previously defined, K is Br, $NO_2$ or $SR_{12}$, and $R_{12}$ is $C_2$–$C_4$ alkyl or benzyl.

Equation 61(a)

The reaction of Equation 61(a) involves the intramolecular alcoholysis of epoxides of Formula XCIII, and may be accomplished by treatment with either a catalytic amount of a suitable base such as potassium tert-butoxide, or with a catalytic amount of a suitable acid such as sulfuric acid. For relevant procedures, refer to Chitwood and Freure, *J. Am. Chem. Soc.*, 68, 680 (1946), Sexton and Britton, ibid., 70 3606 (1948), or Winstein and Henderson, ibid., 65, 2196 (1943).

Equation 61(b)

The oxidation of 3-hydroxy tetrahydrofurans, such as those of Formula XCIV, to the corresponding furanones of Formula XCIIb, may be accomplished with chromium trioxide as described by V. Luhmann and W. Luttke, *Chem. Ber.*, 105, 1350 (1972).

Furanones of Formula XCIIc may be synthesized as depicted in Equation 62 via a three-step process involving: (a) o-alkylation of the appropriate alcohols of Formula XCV, (b) Dieckmann cyclization to give α-carboethoxy furanones XCVII, and (c) hydrolysis and decarboxylation of esters XCVII with sulfuric acid.

Equation 62

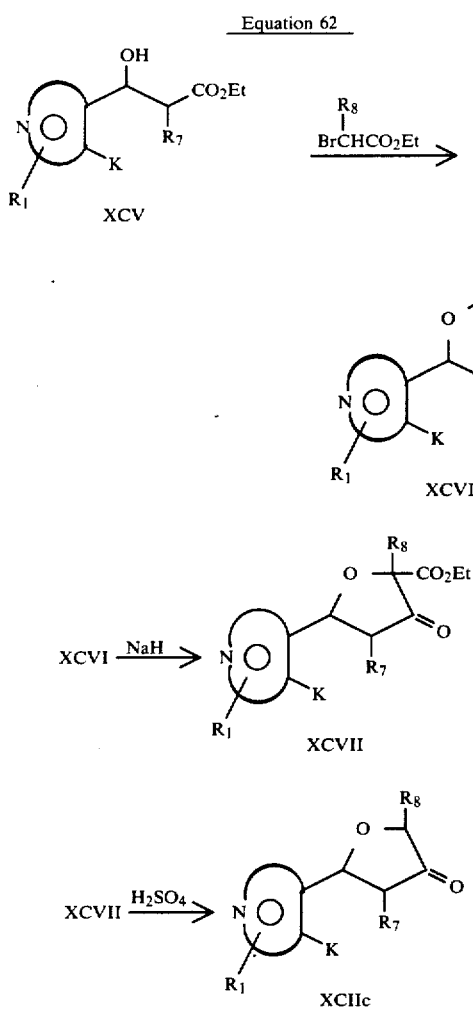

wherein $R_1$, $R_7$ and $R_8$ are as previously defined, K is Br, $NO_2$ or $SR_{12}$, and $R_{12}$ is $C_2$-$C_4$ alkyl or benzyl.

The transformation outlined above in Equations 62(a–c) may be accomplished by the procedure of V. Luhmann and W. Luttke, *Chem. Ber.*, 105, 1350 (1972).

Furanones of Formula XCIId may be prepared as shown in Equation 63 by addition of anions of Formula XCIX to the appropriate aldehydes XCVIII, and subsequent acid-induced cyclization of the resultant α-hydroxyenones of Formula C.

Equation 63

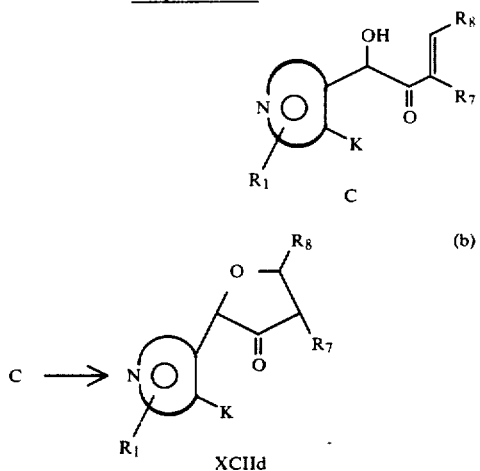

wherein $R_1$, $R_7$ and $R_8$ are as previously defined, K is Br, $NO_2$ or $SR_{12}$, and $R_{12}$ is $C_2$-$C_4$ alkyl or benzyl.

Equation 63(a)

The addition of protected cyanohydrin anions of Formula XCIX to aldehydes of Formula XCVIII and subsequent hydrolysis to afford α-hydroxyenones of Formula C may best be carried out according to the procedure of G. Stork and L. Maldonado, *J. Am. Chem. Soc.*, 93, 5286 (1971). Also, refer to Stork and Maldonado, ibid., 96, 5272 (1974).

Equation 63(b)

The cyclizations of Equation 63(b) may be carried out by heating a solution of the hydroxyenones of Formula C in a suitable solvent such as tetrahydrofuran in the presence of a catalytic amount of an appropriate acid such as hydrochloric or sulfuric acid. Alternatively, compounds of Formula C may be heated in a suitable solvent such as toluene at reflux temperature in the presence of a catalytic amount of p-toluenesulfonic acid.

Compounds of Formulas XCIIe–XCIIh, which are homologs of furanones XCIIa–XCIId, may be prepared by methods analogous to those described above in Equations 60, 61, 62 and 63. The minor modifications needed to implement these syntheses would be obvious to one skilled in the art. Equations 64(a)–64(d) depict the procedures for the preparation of compounds XCIIe–XCIIh.

Equation 63

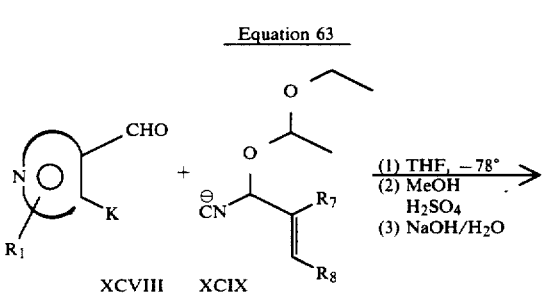

Equation 64

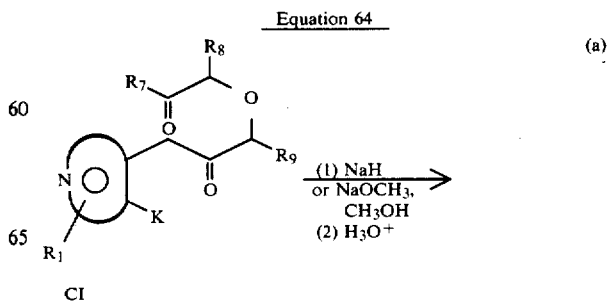

-continued
Equation 64

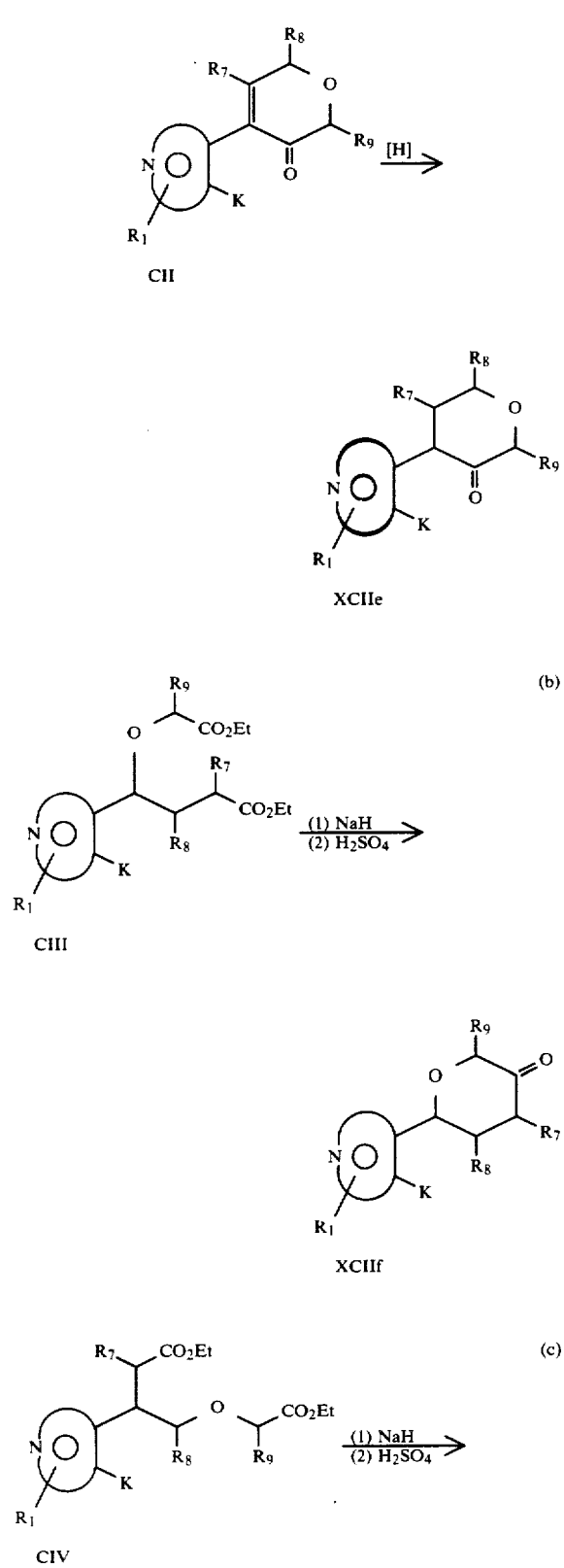

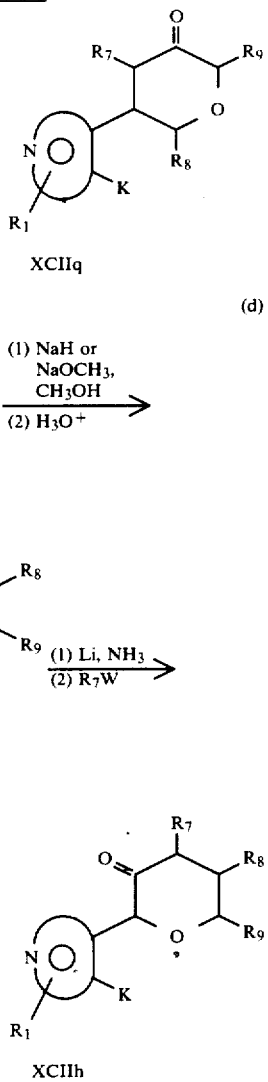

wherein
$R_1$, $R_7$, $R_8$ and $R_9$ are as previously defined, K is Br, $NO_2$ or $SR_{12}$, $R_2$ is $C_2$–$C_4$ alkyl or benzyl, and W is Cl, Br, or I.

Equation 64(a)

The first step of Equation 64(a) is an intramolecular aldol condensation and may be carried out in a manner analogous to that described for Equation 26(b). The second step of Equation 64(a) involves a selective 1,4 reduction of an $\alpha,\beta$-unsaturated ketone and may be achieved by methods described in Equation 26(c).

Equations 64(b)–64(d)

For a description of the procedures for carrying out the reactions of Equations 64(b)–64(d), see the reference cited for Equation 62. The reductive alkylation process shown in the second step of Equation 64d, whereby unsaturated ketones of Formula CVI are converted to the desired products of Formula XCIIh, may conveniently be effected according to the to the method of V. I. Mel'nikova and K. K. Pivnitskii, *J. Org. Chem. USSR (Engl. Trans.)*, 6, 2635 (1970).

The pyrrolidones of Formulas CVa–CVd may be synthesized as shown in Equation 65 via hydroboration-/oxidation of the appropriate Δ²-pyrrolines of Formulas CIVa–CIVd.

Equation 65

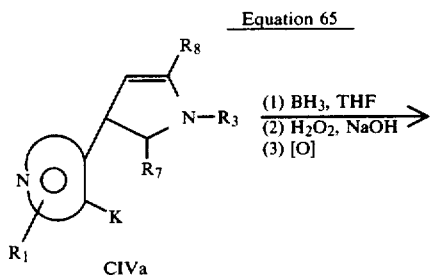

(a)

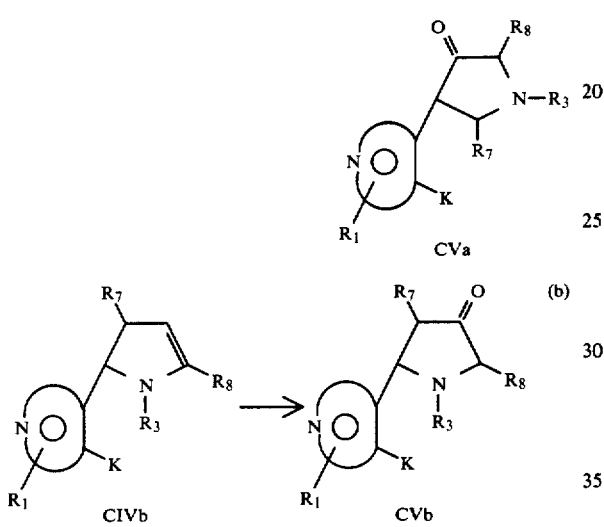

(b)

(c)

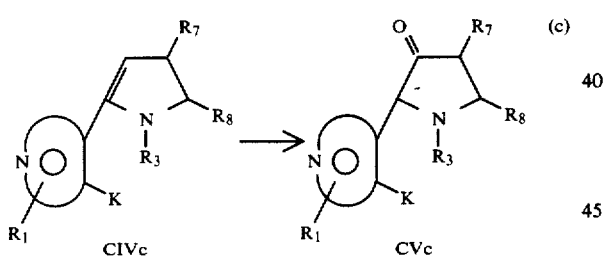

(d)

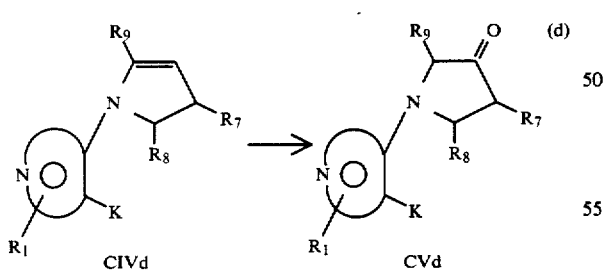

wherein
R₁, R₃, R₇, R₈ and R₉ are as previously defined, and K is Br or NO₂.

The reactions of Equations 65(a)–(d) may be carried out according to the method of I. J. Borowitz and G. J. Williams, *J. Org. Chem.*, 32, 4157 (1967).

In a similar fashion, the compounds of Formulas CVe–CVi may be prepared from the appropriate enamines of Formulas CIVe–CIVi as represented in Equation 66(a–e).

Equation 66

(a)

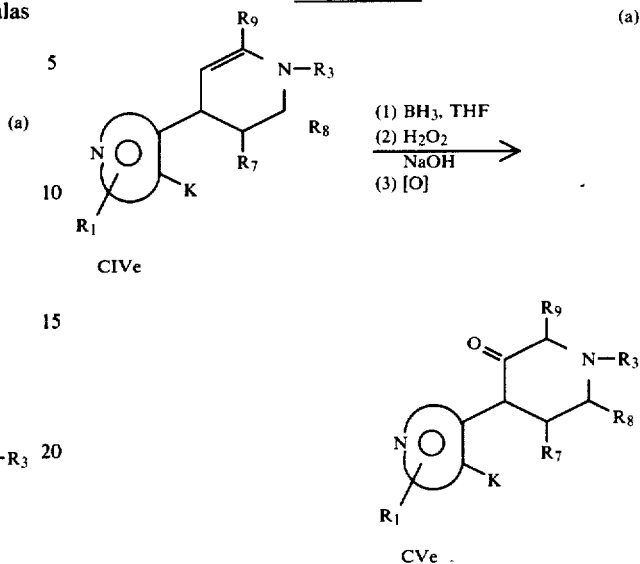

(b)

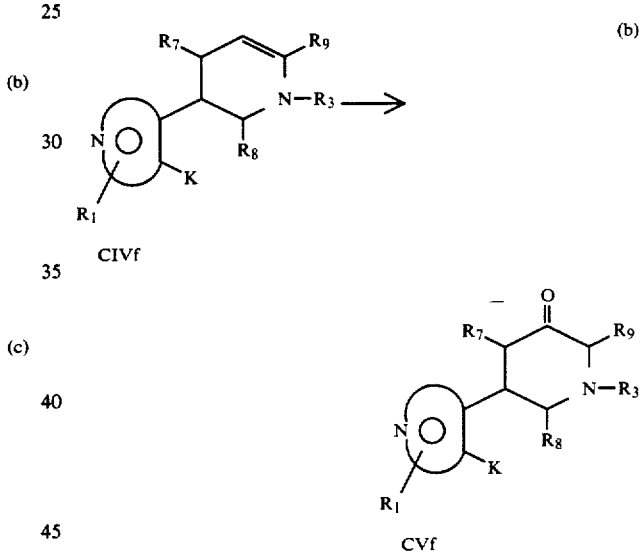

(c)

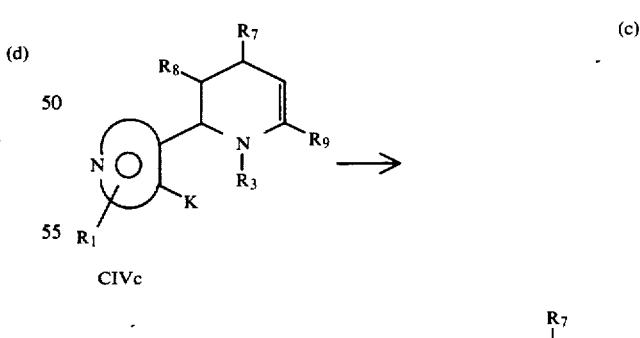

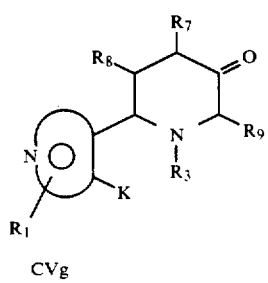

-continued
Equation 66

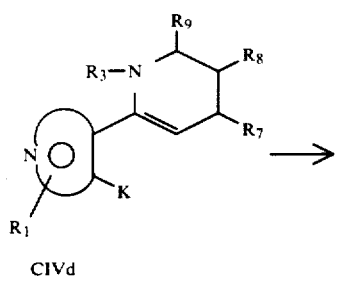
CIVd

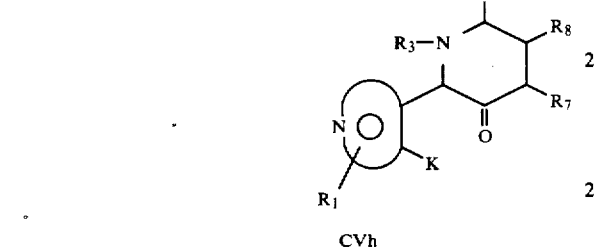
CVh

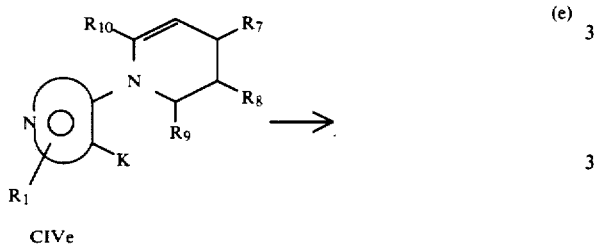
CIVe

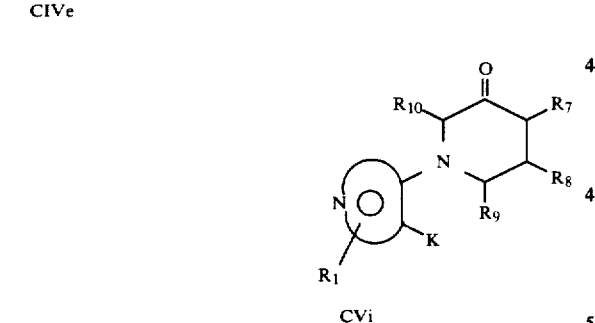
CVi wherein

R₁, R₃, R₇, R₈, R₉ and R₁₀ are as previously defined, and K is Br or NO₂.

The requisite compounds of Formulas CIVa–CIVi may be prepared by the method shown in Equation 67. For example, treatment of the appropriate compounds of Formulas CVIIa or CVIIb with suitable amines, H₂NR₃, should afford the desired pyrrolines or tetrahydropyridines of Formulas CIVa and CIVe, respectively.

Equation 67

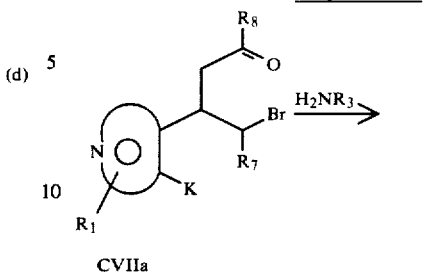
CVIIa

CIVa

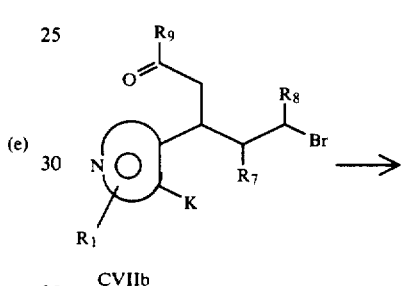
CVIIb

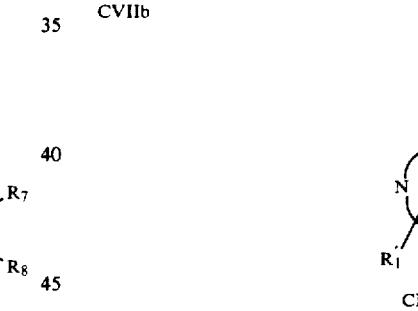
CIVe wherein

R₁, R₃, R₇, R₈ and R₉ are as previously defined, and K is Br or NO₂.

The reactions of Equations 67(a) and 67(b) may be carried out according to procedures described in the following references: J. Cloke, *J. Am. Chem. Soc.*, 51, 1174 (1929); A. Wohl, *Ber.*, 34, 1914 (1901); A. Kipp. *Ber.*, 18, 3284 (1895), and 25, 2190 (1892); and S. Gabriel, *Ber.*, 41, 210 (1908).

The transformations depicted above in Equation 67 may be applied in a straightforward manner to the synthesis of the related compounds of Formulas CIVa–CIVi.

The α,β-unsaturated compounds of Formulas CIXa may be prepared by the same type of process described in Equations 34 and 35 used to synthesize unsaturated lactones of Formulas XLIXa. Thus, treatment of compounds CVe with a kinetic base such as lithium diisopropylamide (LDA) should generate the corresponding enolates of Formula CVIIIa. Trapping with diphenyl disulfide or phenylsulfenyl chloride, and subsequent oxidative elimination should give the desired compounds of Formulas CIXa, as shown in Equation 68.

Equation 68

$$CVe \xrightarrow[\text{THF} \\ -78°\text{C.}]{\text{LDA}}$$

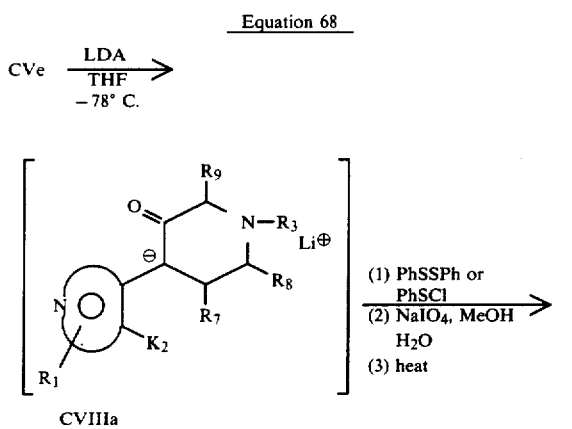

CVIIIa (1) PhSSPh or PhSCl
(2) NaIO$_4$, MeOH H$_2$O
(3) heat

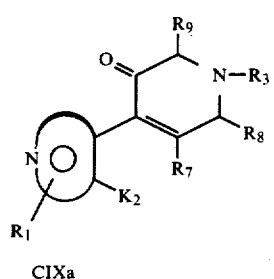

CIXa wherein

R$_1$, R$_3$, R$_7$, R$_8$ and R$_9$ are as previously defined, and K$_2$ is Br, NO$_2$, or SO$_2$NH-t-Bu.

It should be noted in Equation 68 that for compounds of Formula CVe, where R$_3$ is H, one extra molar equivalent of base must be employed to generate the dianions. For a procedure describing the formation of enolates of 3-piperidones such as those of Formula CVe-CVi, see McElvain, *J. Am. Chem. Soc.*, 55, 1233 (1933), and McElvain and Vozza, ibid., 71, 896 (1949).

The procedure shown in Equation 68 may be applied to compounds of Formulas CVf-CVi. In this manner, the corresponding α,β-unsaturated derivatives may be synthesized and further transformed into the appropriate sulfonamides of Formula IV, where Q is Q-128, Q-129, Q-131, and Q-130.

In an analogous fashion, compounds of Formulas XCIIe-XCIIh may be treated according to the procedures described in Equations 34 and 35 to give the corresponding α,β-unsaturated derivatives. Further elaborations of these compounds then should afford the primary sulfonamides of Formula IVa or IVb, where Q is Q-123, Q-125, Q-124, and Q-126.

Compounds of Formulas CXIa an CXIb may be prepared as shown in Equation 69(a and b) by a Dieckmann cyclization of the appropriate sulfides of Formulas CXa and CXb, followed by hydrolysis and decarboxylation.

Equation 69

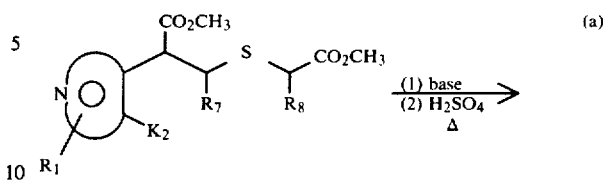

(a)

CXa (1) base
(2) H$_2$SO$_4$
Δ

CXIa

(b)

CXb same as (a)

CXIb wherein

R$_1$, R$_7$, R$_8$ and R$_9$ are as previously defined, and K$_2$ is Br, NO$_2$ or SO$_2$NH-t-Bu.

The reactions of Equations 69(a) and 69(b) may be carried out according to the procedure of Woodward and Eastman, *J. Am. Chem. Soc.*, 68, 2229 (1946), and Woodward and Eastman, ibid., 66, 849 (1944). For a review of synthesis of these ring systems, see Wolf and Folkers, *Org. Reactions*, Vol. 6, 1951, pp. 443–468.

In a similar fashion, the 2-ketothiolanes of Formulas CXIc-CXIg may be prepared via Dieckmann cyclization of the appropriate sulfides of Formulas CXb-CXg as outlined below in Equation 70(a-e).

Equation 70

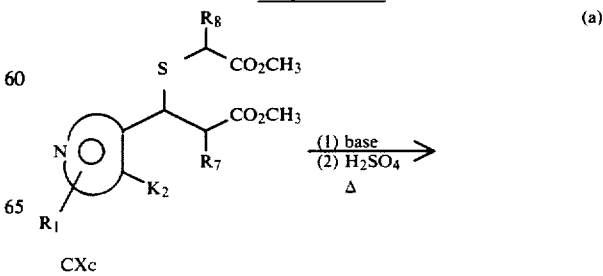

(a)

CXc (1) base
(2) H$_2$SO$_4$
Δ

-continued
Equation 70

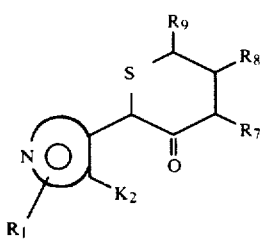
CXIc (b)

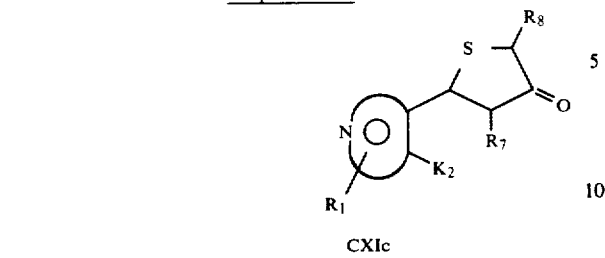
CXd →

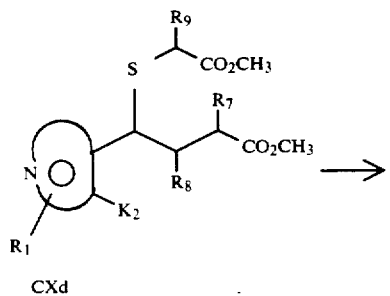
CXId (c)

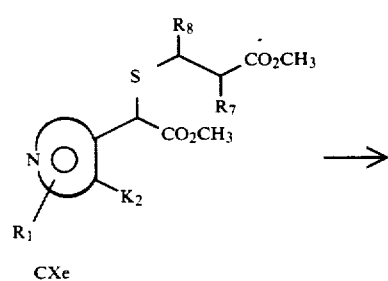
CXe

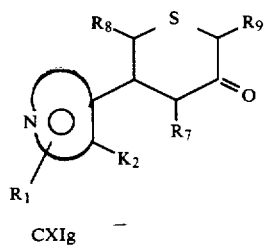
CXIe (d)

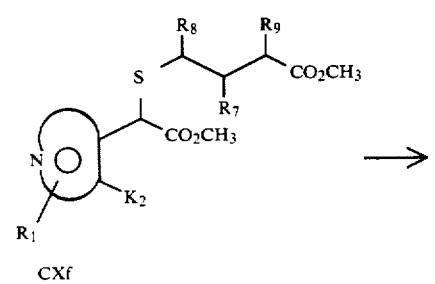
CXf →

-continued
Equation 70

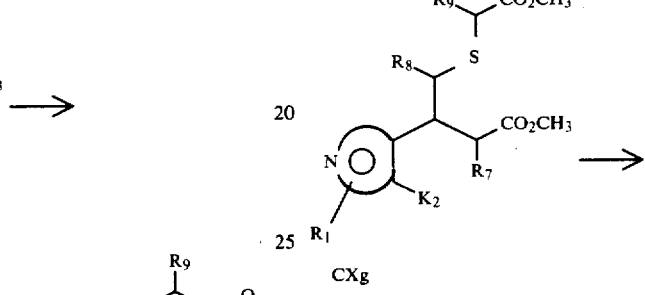
CXIf (e)

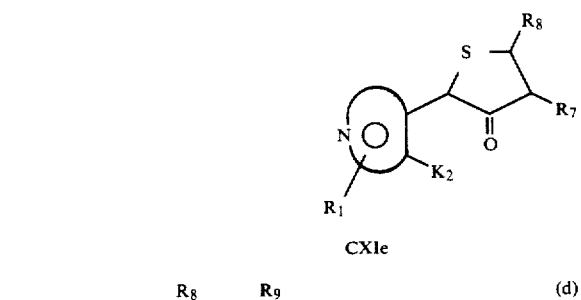
CXg →

CXIg wherein
$R_1$, $R_7$, $R_8$ and $R_9$ are as previously defined, and $K_2$ is Br, $NO_2$, or $SO_2NH$-t-Bu.

The requisite sulfides of Formulas CXa–CXg may be prepared by the reaction of appropriate alkyl bromides of Formula CXII with substituted mercaptans of Formula CXIII. Equation 71 shows this reaction for the example CXa.

Equation 71

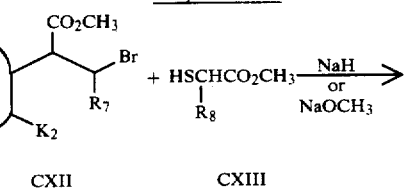
CXII    CXIII

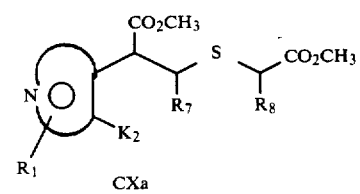
CXa wherein
$R_1$, $R_7$ and $R_8$ are as previously defined, and $K_2$ is Br, $NO_2$, or $SO_2NH$-t-Bu.

The alkylations of mercaptans such as those of Formula CXII with alkyl halides is a well-known process with considerable precedent in the literature. For relevant references, see Shriner, Struck and Jorison, *J. Am. Chem. Soc.*, 52, 2066 (1930); Kirner and Richter, ibid., 51, 3135 (1929); Kipnis and Ornfelt, ibid., 71, 3571 (1949); and Fehnel and Carmack, ibid., 71, 92 (1949).

By applying the procedures described above in Equation 71, one skilled in the art may prepare the requisite sulfides of Formulas CXb–CXg from the appropriate alkyl bromides and mercaptans.

In an analogous manner, the requisite ethers of Formulas CI, CII, CIV and CVI may be prepared via treatment of the appropriate alkyl bromides of Formula CXIV with the sodium salt of the appropriate alcohols of Formula CXV. This reaction is shown below in Equation 72 for the synthesis of compounds CI as a representative example.

Equation 72

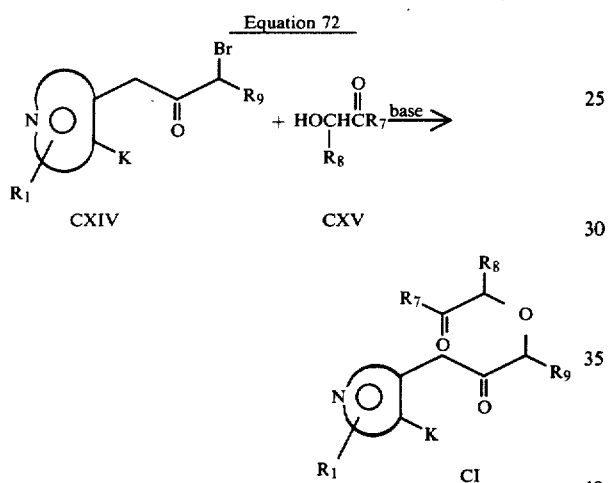

wherein
$R_1$, $R_7$, $R_8$ and $R_9$ are as previously defined,
K is Br, $NO_2$ or $SR_{12}$ and $R_2$ is $C_2$–$C_4$ alkyl or benzyl.

For a compilation of references dealing with the reaction of Equation 72, see R. B. Wagnmer and H. D. Zook, "Synthetic Organic Chemistry", John Wiley and Sons, Inc., New York, 1953, pp. 226–228.

Unsaturated sulfones of Formulas CXIXa and CXIXb may be prepared as shown in Equation 73 by a three step sequence of reactions involving: (1) addition of the appropriate organometallic reagents, $R_8M$ or $R_7M$, to compounds of Formula CXVIa or CXVIb, (2) dehydration of the adducts of Formula CXVIIa or CXVIIb, and (3) oxidation of the unsaturated sulfides CXVIIIa or CXVIIIb to the corresponding products of Formula CXIXa or CXIXb.

Equation 73

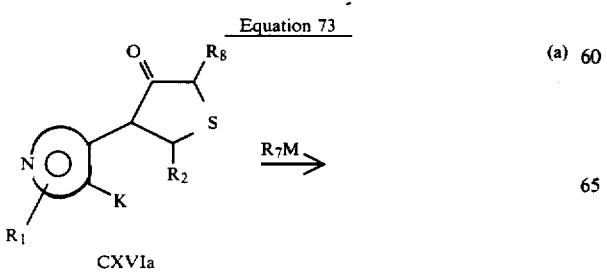

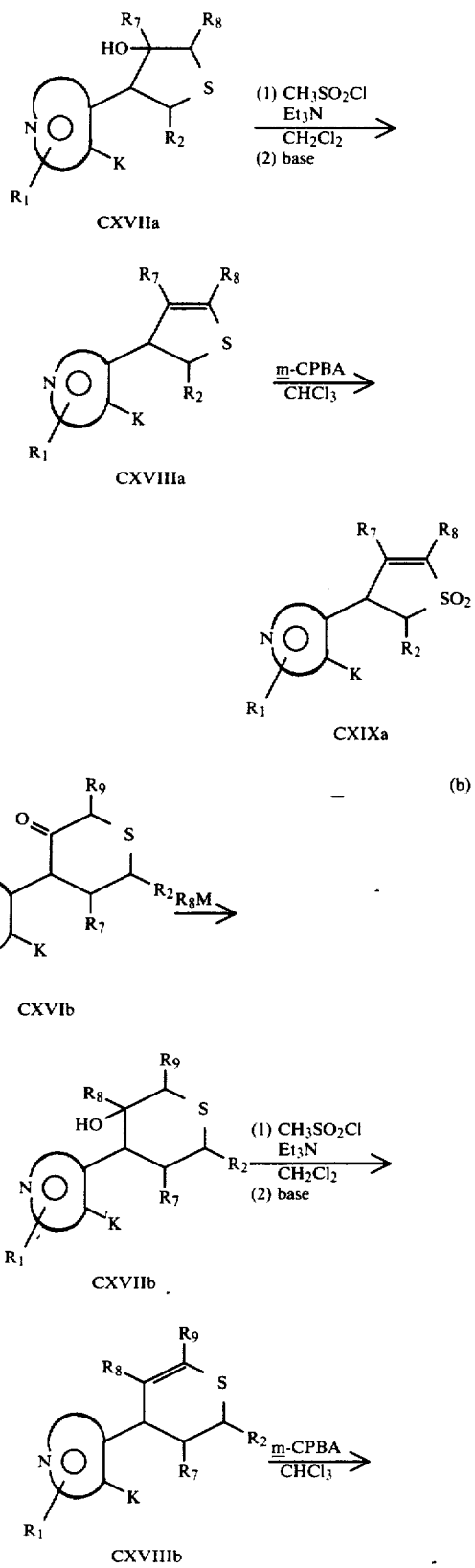

-continued
Equation 73

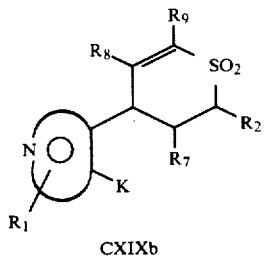

CXIXb wherein
$R_1$, $R_2$, $R_7$, $R_8$ and $R_9$ are as previously defined, K is Br or $NO_2$, and M is MgBr, or Li.

The transformations shown above in Equations 73(a) and 73(b) may best be effected according to the method of T. Takaya, et al., *Bull. Chem. Soc. Japan*, 41, 2086 (1968).

In a similar fashion, compounds of Formulas CXIc–g may be treated according to the procedures described above in Equations 73(a) and 73(b) to afford the corresponding unsaturated sulfones. Further elaboration of these compounds by methods described previously should yield the primary sulfonamides of Formula IV, where Q is Q-49, Q-120, Q-84, Q-50, Q-118, Q-47, Q-122, and Q-119.

The unsaturated sulfones of Formulas CXIXh and CXIXi may be prepared as shown in Equation 74 by: (1) addition of the dianions of N-t-butylpyridine sulfonamides CXX to the appropriately substituted compounds of Formulas CXXIa and CXXIb, and (2) dehydration and oxidation of the resultant adducts of Formulas CXXIIa and CXXIIb.

Equation 74

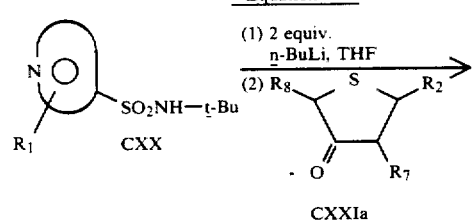

CXXIa

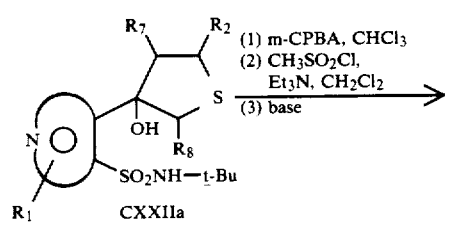

CXXIIa

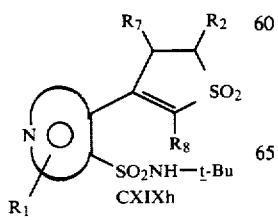

CXIXh

-continued
Equation 74

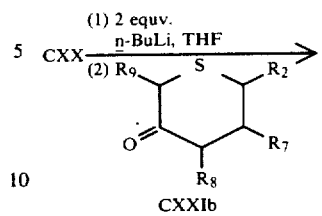

CXXIb

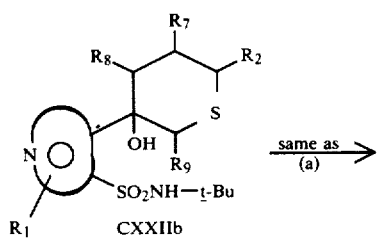

CXXIIb

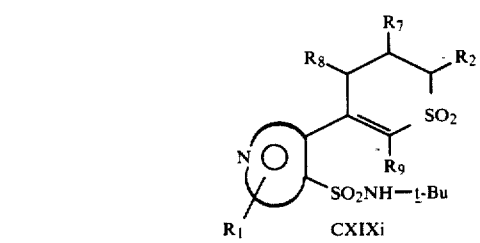

CXIXi wherein
$R_1$, $R_2$, $R_7$, $R_8$ and $R_9$ are as previously defined.

The first step of the reactions of Equations 74(a) and 74(b) may be carried out according to the procedure of J. G. Lombardino, *J. Org. Chem.*, 36, 1843 (1971). The second step shown in Equations 73(a) and 73(b) may be accomplished by the method described in Equation 73.

Dihydrothiopyran-3-ones of Formulas CXXIVa–CXXIVd may be synthesized as depicted below in Equation 75 by a Dieckmann-type cyclization of the appropriate sulfides of Formulas CXXIIIa–CXXIIId and subsequent acid-induced hydrolysis and decarboxylation.

Equation 75

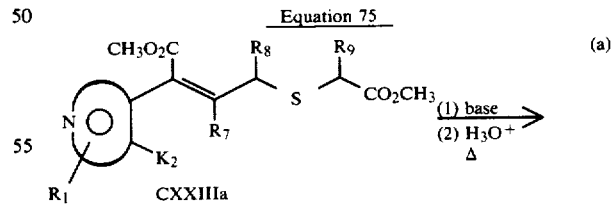

CXXIIIa

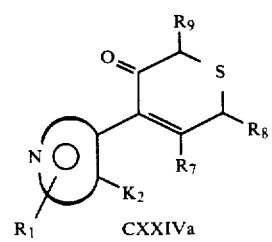

CXXIVa

-continued

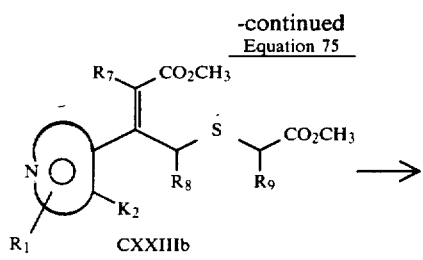

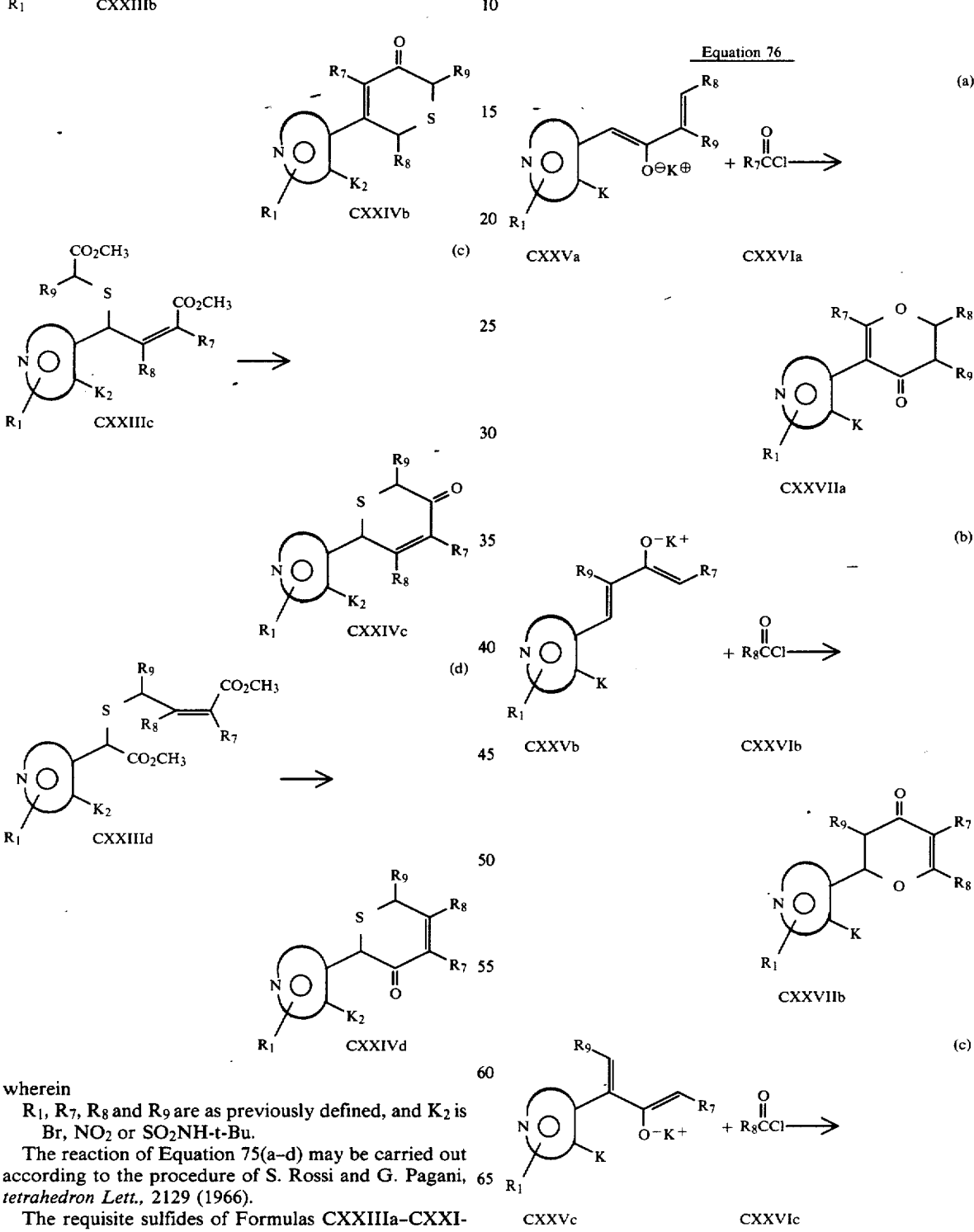

wherein $R_1$, $R_7$, $R_8$ and $R_9$ are as previously defined, and $K_2$ is Br, $NO_2$ or $SO_2NH$-t-Bu.

The reaction of Equation 75(a–d) may be carried out according to the procedure of S. Rossi and G. Pagani, tetrahedron Lett., 2129 (1966).

The requisite sulfides of Formulas CXXIIIa–CXXIIId may be prepared in a manner analogous to that described in Equation 71 for the preparation of compounds CXa.

Dihydropyrones of Formulas CXXVIIa–CXXVIId may be prepared as shown in Equation 76 by reaction of the appropriate potassium enolates of Formulas CXXVa–CXXVd with suitable acid chlorides of Formulas CXXVIa–CXXVId.

-continued

Equation 76

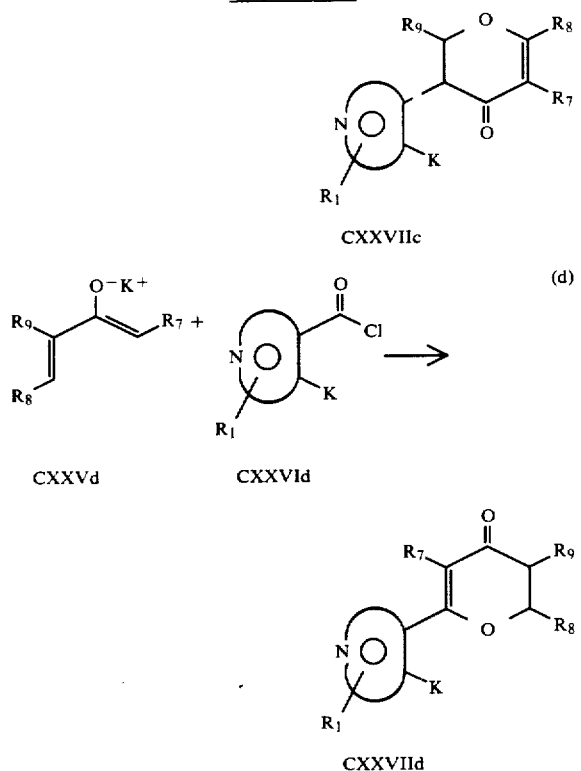

wherein
$R_1$, $R_7$, $R_8$ and $R_9$ are as previously defined.
K is Br, $NO_2$ or $SR_{12}$, and $R_{12}$ is $C_2$–$C_4$ alkyl or benzyl.

The reactions of Equation 76 may be carried out in a manner analogous to that described for Equation 54.

An alternative method for the preparation of dihydropyrones of Formula CXXVIIb above where $R_8$ is H involves the Lewis acid catalyzed hetero-Diels-Alder reaction of sulfonamide XCVIII with dienes of Formula CXXVIIe followed by mild hydrolysis as depicted in Equation 76e. Suitable Lewis acids include magnesium bromide, zinc chloride, and (6,6,7,7,8,8,8-heptafluoro-2,2-dimethyl-3,5-octanedionato)europium [Eu(fod)$_3$]. For typical procedures for carrying out the cyclocondensations, see M. Bednarski and S. Danishefsky, *J. Am. Chem. Soc.*, 105, 5716 (1983).

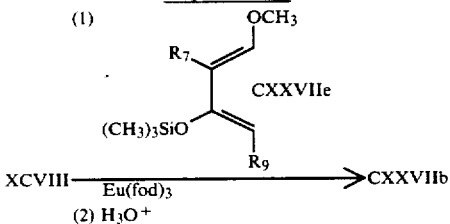

wherein
$R_1$, $R_7$ and $R_9$ are as previously defined, $R_8$ is H,
K is Br, $NO_2$, $SR_{12}$ or $SO_2NH$-t-Bu, and $R_{12}$ is $C_2$–$C_4$ alkyl or benzyl.

Reduction of dihydropyrones of Formulas CXXVIIa-CXXVIId should give the corresponding tetrahydropyrones as shown in Equation 77 for the specific example of CXXVIIa.

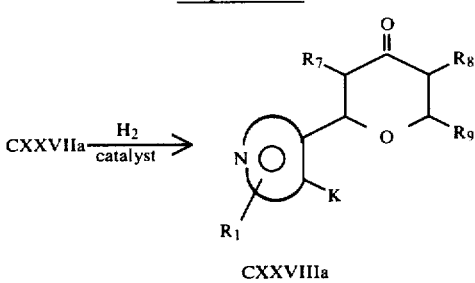

wherein
$R_1$, $R_7$, $R_8$ and $R_9$ are as previously defined,
K is Br, $NO_2$ or $SR_{12}$, and $R_{12}$ is $C_2$–$C_4$ alkyl or benzyl.

The reduction of Equation 77 may be carried out in the presence of a suitable catalyst such as colloidal palladium (cf., Borsche, *Ber.*, 48, 682 (1915); 56, 2012, 2132 (1923); 59, 237 (1926)) or palladized strontium carbonate (see Cawley and Plant, *J. Chem. Soc.*, 1214 (1938); Attenburrow, et al., ibid., 571 (1945)).

In a similar fashion, compounds of Formulas CXXVIIa-CXXVIId may be reduced to afford the corresponding tetrahydropyrones. Further elaboration of the compounds by methods described previously should yield the primary sulfonamides IV, where Q is Q-88 or Q-89.

Compounds of Formulas CXXXIIa-CXXXIIe may be synthesized as shown in Equation 78 by condensation of 1,3-diketones of Formulas CXXXa-CXXXe with the appropriate imines of Formulas CXXXIa-CXXXId.

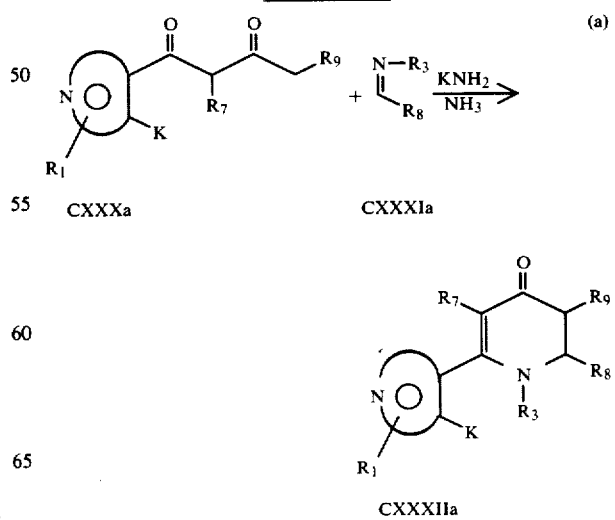

-continued
Equation 78

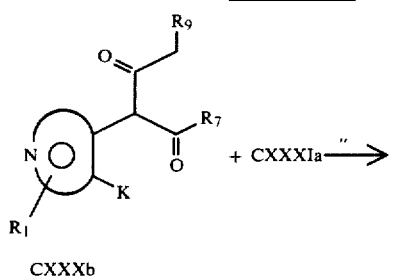

CXXXb + CXXXIa →

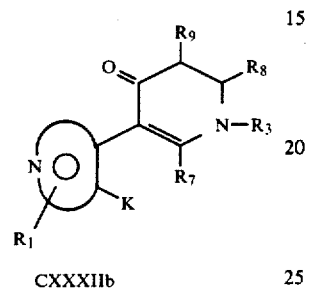

CXXXIIb

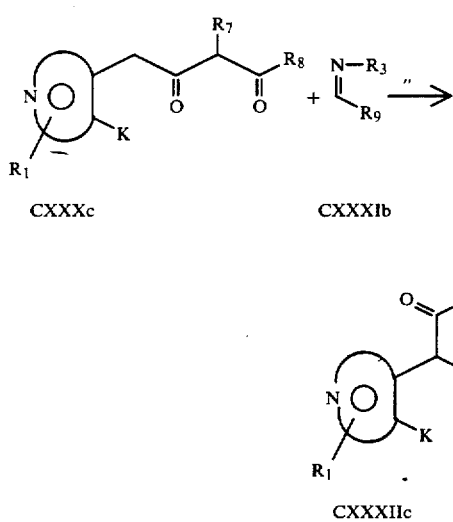

CXXXc  CXXXIb

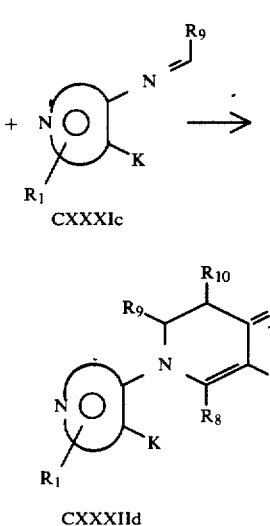

CXXXd  CXXXIc

-continued
Equation 78

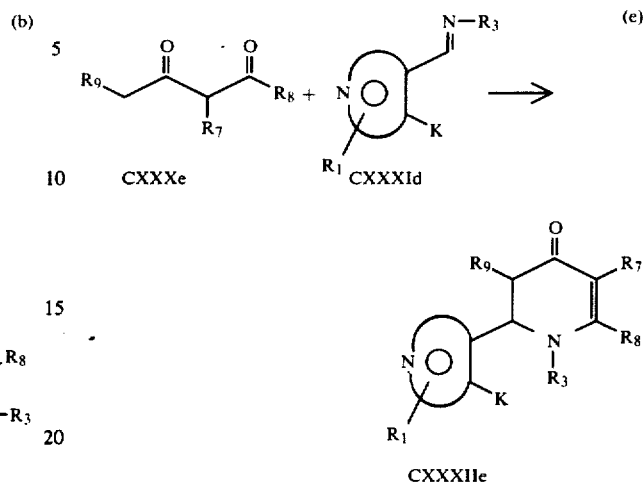

CXXXe  CXXXId →

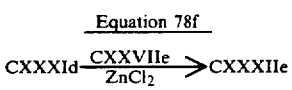

CXXXIIe wherein
$R_1$, $R_3$, $R_7$, $R_8$, $R_9$ and $R_{10}$ are as previously defined, K is Br, $NO_2$ or $SR_{12}$, and $R_{12}$ is $C_2$–$C_4$ alkyl or benzyl.

The reactions of Equation 78 may be carried out by the procedure described by N. Sugiyama, M. Yamamoto and C. Kashima, *Bull. Chem. Soc. Japan*, 42, 1357 (1969).

Dihydropyridone CXXXIIe above (when $R_8$ is H) may also be prepared in an analogous manner to Equation 76 as depicted in Equation 78f. The Lewis acid catalyzed Diels-Alder reaction of imines of Formula CXXXId with dienes CXXVIIe results in the desired dihydropyridones.

Equation 78f $$CXXXId \xrightarrow[ZnCl_2]{CXXVIIe} CXXXIIe$$

wherein
$R_1$, $R_3$, $R_7$, $R_9$ and $R_{10}$ are as previously defined, $R_8$ is H, K is Br, $NO_2$, $SR_{12}$ or $SO_2NH$-t-Bu, and $R_{12}$ is $C_2$–$C_4$ alkyl or benzyl.

Dihydropyridones such as those of Formulas CXXXIIa-CXXXIIe have also been prepared by reduction of the appropriate pyridones of Formulas LXXXVIIa and LXXXVIIb with lithium aluminum hydride (E. Winterfeldt, *Ber. deutsch Chem. Ges.*, 97, 2463 (1964)), lithium triethoxyaluminum hydride (Y., Tamura, et al., *Chem. and Ind.*, 168 (1972)), and catalytic hydrogenation (see J. Hebky and J. Kejha, CA, 50, 15532c).

Piperidones of Formulas CXXXIIIa-CXXXIIIc may be prepared in a straightforward manner via reduction of the appropriate dihydropyridones of Formulas CXXXIIa-CXXXIIe. Equation 79 depicts the reduction of compounds of Formula CXXXIIa with lithium aluminum hydride which yields piperidones of Formula CXXXIIIa.

Equation 79

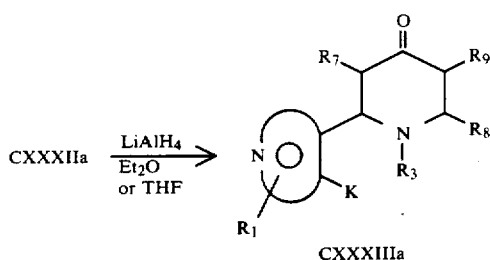

CXXXIIa $\xrightarrow[\text{Et}_2\text{O}]{\text{LiAlH}_4}$ CXXXIIIa
or THF wherein $R_1$, $R_3$, $R_7$, $R_8$ and $R_9$ are as previously defined, K is Br, $NO_2$ or $SR_{12}$, and $R_{12}$ is $C_2-C_4$ alkyl or benzyl.

The 1,4-reduction of enaminones such as those of Formula CXXXIIa may be achieved with lithium aluminum hydride and a variety of other reagents. For a review of these methods, see J. V. Greenhill, *Chem. Soc. Rev.* 6, 277 (1977).

The tetrahydrothiopyrones of Formulas CXXXVa and CXXXVb may be prepared as shown in Equation 80 by a Dieckmann-type cyclization of the appropriate sulfides of Formulas CXXXIVa and CXXXIVb, followed by acid- or base-induced ester cleavage and decarboxylation.

Equation 80

CXXXIVa (a)

CXXXVa (b)

CXXXIVb

Equation 80 -continued

CXXXVb wherein $R_1$, $R_7$, $R_8$ and $R_9$ are as previously defined, and K is Br, $NO_2$ or $SO_2NH$-t-Bu.

The reactions of Equations 80(a) and 80(b) may be accomplished by the procedure of G. M. Bennett and L. V. D. Scorah, *J. Chem. Soc.*, 194 (1927).

The requisite sulfides of Formulas CXXXIVa and CXXXIVb may be synthesized by either of the methods shown in Equation 81. Thus, treatment of the mercaptide salts of Formula CXXXVI with either (a) α,β-unsaturated esters of Formula CXXXVIIa, or (b) alkyl halides of Formula CXXXVIIb should afford the desired products of Formula CXXXIVa.

Equation 81

(a)

CXXXVI

CXXXVIIa → CXXXIVa (b)

CXXXVI + CXXXVIIIb → CXXIVa wherein $R_1$, $R_7$, $R_8$ and $R_9$ are as previously defined, and K is Br, $NO_2$ or $SO_2NH$-t-Bu.

The reaction of Equation 81 may be carried out according to the procedures discussed by Bruson, *Org. Reactions*, 5 (1949), pp. 95-97 and 129-130.

The dihydrothiopyrones of Formulas CXLa-CXLd may be prepared from the appropriate tetrahydropyrones of Formulas CXXXIXa and CXXXIXb by oxidation with N-chlorosuccinimide (NCS) as shown in Equations 82(a) and 82(b).

Equation 82

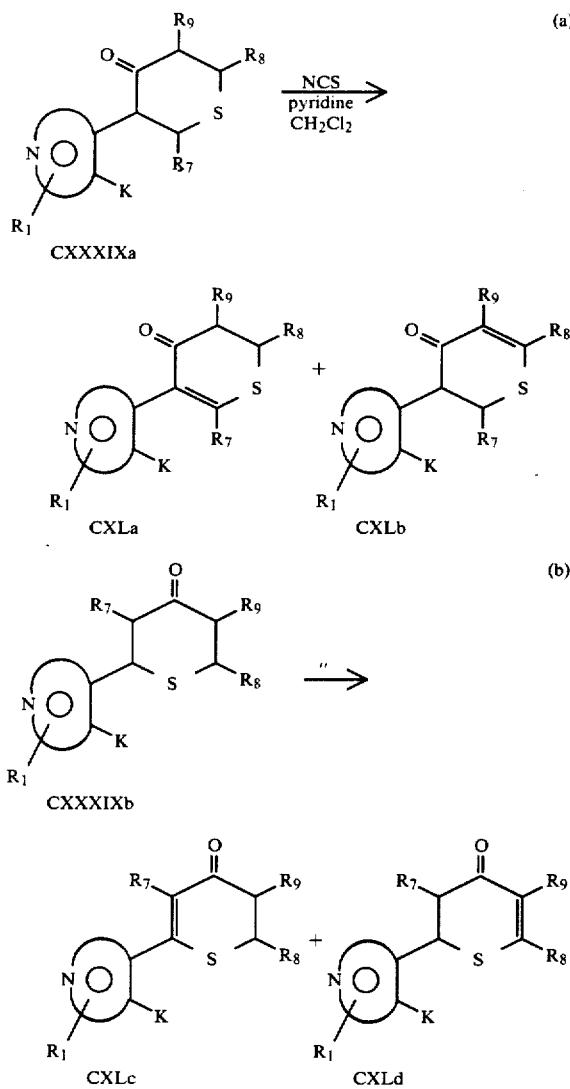

wherein

R$_1$, R$_7$, R$_8$ and R$_9$ are as previously defined,
and K is Br, NO$_2$ or SO$_2$NH-t-Bu.

The reaction of Equation 82 may be carried out according to the procedure of C. H. Chen. G. A. Reynolds and J. A. VanAllan, *J. Org. Chem.*, 42 2777 (1977). It should be noted that the reaction shown in Equation 82, when applied to unsymmetrical tetrahydropyrones such as those of Formulas CXXXIXa and CXXXIXb, should give mixtures of isomers. These compounds may be separated by recrystallization from a suitable solvent such as diethyl ether, benzene, or ethyl acetate, or by column chromatography.

The synthesis of heterocyclic amines such as those represented by Formula III has been reviewed in "The Chemistry of Heterocyclic Compounds," a series published by Interscience Publ., New York and London. Aminopyrimidines are described by D. J. Brown in "The Pyrimidines", Vol. XVI of the series mentioned above which is herein incorporated by reference. The 2-amino-1,3,5-triazines of Formula III, where A is A-1 and Z is N, can be prepared according to methods described by E. M. Smolin and L. Rapaport in "s-Triazines and Derivatives," Vol. XIII.

Pyrimidines of Formula III, where A is A-1 and Y is an acetal or thioacetal substituent, can be prepared by methods taught in European Patent Application No. 84,224 (published July 27, 1983).

Pyridimidines of Formula III, where A is A-1 and Y is cyclopropyl or OCF$_2$H, can be synthesized according to the methods taught in South African Patent Application No. 837,434 and South African Publication No. 82/5045, respectively.

Compounds of Formula III, where A is A-2 or A-3, can be prepared by procedures disclosed in U.S. Pat. No. 4,339,267.

Compounds of Formula III, where A is A-4, can be prepared by methods taught in European Patent Application No. 46,677 (published Mar. 3, 1982).

Additional references dealing with the synthesis of bicyclic pyrimidines of Formula III, where A is A-2, A-3, or A-4 are Braker, Sheehan, Spitzmiller and Lott. *J. Am. Chem. Soc.*, 69, 3072 (1947); Mitler and Bhattachanya, *Quart. J. Indian Chem. Soc.*, 4, 152 (1927); Shrage and Hitchings, *J. Org. Chem.*, 16, 1153 (1951); Caldwell, Kornfeld and Donnell, *J. Am. Chem. Soc.*, 63, 2188 (1941); and Fissekis, Myles and Brown, *J. Org. Chem.*, 29, 2670 (1964).

Compounds of Formula III, where A is A-5, can be prepared by methods taught in U.S. Pat. No. 4,421,550.

Compounds of Formula III, where A is A-6, can be prepared by methods taught in European Patent Application No. 94,260 (published Nov. 16, 1983).

Agriculturally suitable salts of compounds of Formula I are also useful herbicides and can be prepared in a number of ways known to the art. For example, metal salts can be made by treating compounds of Formula I with a solution of an alkali or alkaline earth metal salt having a sufficiently basic anion (e.g., hydroxide, alkoxide, carbonate or hydride). Quaternary amine salts can be made by similar techniques. Detailed examples of such techniques are given in U.S. Pat. No. 4,127,405, the disclosure of which is herein incorporated by reference.

The compounds of this invention and their preparation are further illustrated by the following examples.

EXAMPLE 1

2-Chloro-3-pyridinesulfonamide

A solution of 50.4 g of sodium nitrite in 112 mL of water was added to 93.8 g of 3-amino-2-chloropyridine suspended at 0° C. in 112 mL of acetic acid, 56 mL of water and 280 mL of concentrated HCl. After the addition was complete, the mixture was stirred at 0° to 5° C. for 45 minutes. The resulting slurry was added dropwise to a suspension of 7.5 g of cuprous chloride in acetic acid (280 mL), concentrated HCl (140 mL), and sulfur dioxide (75 mL) at 0° to 5° C. The mixture was stirred for 1 hour at 0° C., then 1 hour at 25° C., was poured into water, and the resultant solution was extracted with methylene chloride. The organic layer was washed and then dried (Na$_2$SO$_4$).

This methylene chloride solution was cooled to 0° C. and an excess of ammonia was added in a dropwise manner. The suspension was stirred at 10°-15° C. for 1 hour and was then allowed to warm to 25° C. for an additional hour. The solid was collected and washed with water to furnish 55 g of the desired sulfonamide, m.p. 184°-186° C.

EXAMPLE 2

2-(4-Thiomorpholinyl)-3-pyridinesulfonamide

In a dry flask under an inert nitrogen atmosphere was mixed 2.5 g of 2-chloro-3-pyridinesulfonamide, 100 mL of dry N,N-dimethylformamide (DMF), and 2.7 mL of thiomorpholine. The mixture was heated at 80° C. overnight at which time an additional 0.3 mL of thiomorpholine was added and the heating was continued. After 24 hours the mixture was concentrated and the residue was taken up in THF. The solids were filtered and the filtrate was concentrated and chromatographed on silica gel using 1:1 ethyl acetate/hexane as eluent. The pure subject compound was isolated as a solid, which melted at 176°–177° C.; NMR (200 MHz, CDCl$_3$): δ 2.89 (m, CH$_2$S, 4H), 3.45 (m, CH$_2$N, 4H), 5.52 (s, NH$_2$, 2H), 7.26 (t, ArH, 1H), 8.2–8.6 (m, ArH, 2H).

EXAMPLE 3

2-(4-Thiomorpholinyl)-3-pyridinesulfonamide, S,S-dioxide

To a solution of 2-(4-thiomorpholinyl)-3-pyridinesulfonamide in 50 mL of trifluoroacetic acid was added 0.23 mL of methanesulfonic acid. Hydrogen peroxide (0.79 mL) was added dropwise and the resultant mixture was stirred at 25° C. for 4 hours. An additional 0.3 mL of hydrogen peroxide was added and the mixture was stirred for 72 hours. The volatiles were removed and the residue was partitioned between a saturated aqueous sodium bicarbonate solution and ethyl acetate. The organic layer was dried over magnesium sulfate, filtered and concentrated. The residue was chromatographed on silica gel using 40% ethyl acetate in hexane as eluent. The desired subject compound was isolated and crystallized from chloroform to give 0.6 g of a solid, m.p. 210°–211° C.; NMR (90 MHz, DMSO-d$_6$): δ 3.3–3.5 (m, CH$_2$, 4H), 3.55–3.75 (m, CH$_2$, 4H), 7.2–7.5 (m, ArH & SO$_2$NH$_2$, 3H), 8.2–8.4 & 8.5–8.7 (m, ArH, 2H).

EXAMPLE 4

N-[(4,6-Dimethoxypyrimidin-2-yl)aminocarbonyl]-2-(4-thiomorpholinyl)-3-pyridinesulfonamide, S,S-dioxide In a dry flask under an inert nitrogen atmosphere was mixed 0.13 g of 2-(4-thiomorpholine, S,S-dioxide)-3-pyridinesulfonamide and 0.132 g of phenyl 4,6-dimethoxy-1,3-pyrimidin-2-ylcarbamate. To this mixture was added 0.072 mL of 1,8-diazabicyclo[5.4.0]undec-7-ene and the resultant mixture was stirred for 0.5 hour. Water (50 mL) was added followed by 1N HCl dropwise until a pH of 5 was obtained. The solid was filtered and washed with water and then 1:1 ether-hexane to furnish 0.1 g of the title compound as a solid, mp 204°–205° C.; IR (nujol) 1700 cm$^{-1}$; NMR (200 MHz, DMSO-d$_6$): δ 3.19 (m, 4H), 3.54 (m, 4H), 3.8 (s, OCH$_3$, 6H), 6.06 (s, CH, 1H), 7.4–8.7 (m, ArH, 3H), 10.6 and 12.9 (bs, NH, 2H).

By applying the procedures of Examples 1–4 and Equations 1 through 82, the compounds shown in Tables 1 through 7 can be prepared by one skilled in the art.

| General Formulas for Tables | |
|---|---|
| General Formula 1<br>W$_1$ is O unless indicated by *, wherein W$_1$ is S. | 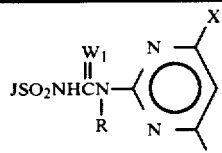 |
| General Formula 2<br>W$_1$ is O unless indicated by *, wherein W$_1$ is S. | 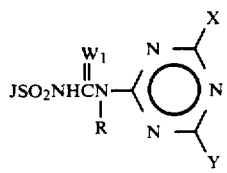 |
| General Formula 3 | 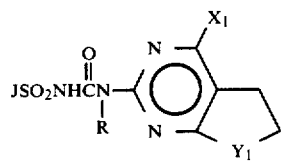 |
| General Formula 4 | 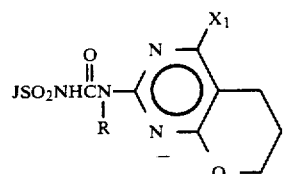 |
| General Formula 5 | 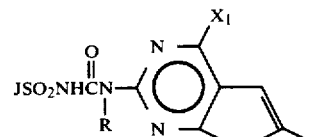 |
| General Formula 6 | 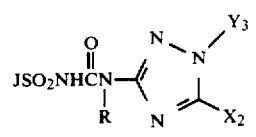 |
| General Formula 7 | 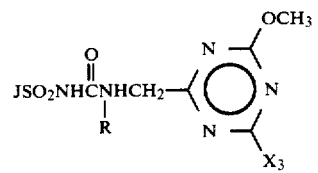 |

TABLE 1

General Formula 1

| J | Q | R | R₁ | X | Y | m.p. (°C.) |
|---|---|---|---|---|---|---|
| J-1 | Q-1 (R₇=H, R₈=H) | H | H | CH₃ | CH₃ | |
| J-1 | Q-1 (R₇=H, R₈=H) | H | H | OCH₃ | CH₃ | |
| J-1 | Q-1 (R₇=H, R₈=H) | H | H | OCH₃ | OCH₃ | |
| J-1 | Q-1 (R₇=H, R₈=H) | H | 5-CH₃ | OCH₃ | OCH₃ | |
| J-1 | Q-1 (R₇=H, R₈=H) | H | 5-OCH₃ | OCH₃ | OCH₃ | |
| J-1 | Q-1 (R₇=H, R₈=H) | H | 6-OCH₂CH₂Br | OCH₃ | OCH₃ | |
| J-1 | Q-1 (R₇=H, R₈=H) | H | 5-CH₂F | OCH₃ | OCH₃ | |
| J-1 | Q-1 (R₇=H, R₈=H) | H | 5-SCH₃ | OCH₃ | OCH₃ | |
| J-1 | Q-1 (R₇=H, R₈=H) | H | 5-SCH₂F | OCH₃ | OCH₃ | |
| J-1 | Q-1 (R₇=H, R₈=H) | H | 5-NHCH₃ | OCH₃ | OCH₃ | |
| J-1 | Q-1 (R₇=H, R₈=H) | H | 5-Cl | OCH₃ | OCH₃ | |
| J-1 | Q-1 (R₇=H, R₈=H) | H | 4-NO₂ | OCH₃ | OCH₃ | |
| J-1 | Q-1 (R₇=H, R₈=H) | H | 5-CF₃ | OCH₃ | OCH₃ | |
| J-1 | Q-1 (R₇=H, R₈=H) | H | H | OCH₃ | CH₂CH₃ | |
| J-1 | Q-1 (R₇=H, R₈=H) | H | H | OCF₂H | OCH₂CH₃ | |
| J-1 | Q-1 (R₇=H, R₈=H) | H | H | OCH₂CF₃ | OCH₃ | |
| J-1 | Q-1 (R₇=H, R₈=H) | H | H | CF₃ | OCH₃ | |
| J-1 | Q-1 (R₇=H, R₈=H) | H | H | SCH₃ | OCH₃ | |
| J-1 | Q-1 (R₇=H, R₈=H) | H | H | SCHF₂ | OCH₃ | |
| J-1 | Q-1 (R₇=H, R₈=H) | H | H | Cl | OCH₃ | |
| J-1 | Q-1 (R₇=H, R₈=H) | H | H | OCH₃ | CH₂OCH₃ | |
| J-1 | Q-1 (R₇=H, R₈=H) | H | H | OCH₃ | NH₂ | |
| J-1 | Q-1 (R₇=H, R₈=H) | H | H | OCH₃ | NHCH₃ | |
| J-1 | Q-1 (R₇=H, R₈=H) | H | H | H | OCH₃ | |
| J-1 | Q-1 (R₇=H, R₈=H) | H | H | OCH₃ | OCH₂C≡CH | |
| J-1 | Q-1 (R₇=H, R₈=H) | H | H | OCH₃ | CH₂S(CH₂)₃CH₃ | |
| J-1 | Q-1 (R₇=H, R₈=H) | H | H | OCH₃ | cyclopropyl | |
| J-1 | Q-1 (R₇=H, R₈=H) | H | H | OCH₃ | C≡CH | |
| J-1 | Q-1 (R₇=H, R₈=H) | H | H | OCH₃ | —CH(OCH₃)₂ | |
| J-1 | Q-2 (R₇=H, R₈=H) | H | H | OCH₃ | OCH₃ | |
| J-1 | Q-3 (R₇=H, R₈=H) | H | H | OCH₃ | OCH₃ | |
| J-1 | Q-4 (R₇=H, R₈=H, R₃=CH₃) | H | H | CH₃ | OCH₃ | |
| J-1 | Q-5 (R₇=H, R₈=H, R₃=H) | H | H | OCH₃ | OCH₃ | |
| J-1 | Q-6 (R₇=CH₃, R₈=H, R₃=CH₃) | H | H | CH₃ | OCH₃ | |
| J-1 | Q-7 (R₇=H, R₈=H, R₉=H) | H | H | CH₃ | OCH₃ | |
| J-1 | Q-8 (R₇=H, R₈=H, R₂=H) | H | H | OCH₃ | OCH₃ | |
| J-1 | Q-9 (R₇=H, R₈=H, R₂=H) | H | H | OCH₃ | OCH₃ | |
| J-1 | Q-10 (R₇=H, R₈=H, R₂=H) | H | H | OCH₃ | OCH₃ | |
| J-1 | Q-11 (R₇=H, R₈=H) | H | H | OCH₃ | OCH₃ | |
| J-1 | Q-12 (R₇=H, R₈=H) | H | H | OCH₃ | OCH₃ | |
| J-1 | Q-13 (R₇=H, R₈=H, R₃=H) | H | H | OCH₃ | OCH₃ | |
| J-1 | Q-14 (R₇=H, R₈=H, R₃=CH₃) | H | H | OCH₃ | OCH₃ | |
| J-1 | Q-15 (R₇=CH, R₈=H, R₃=H) | H | H | OCH₃ | OCH₃ | |
| J-1 | Q-16 (R₇=H, R₈=H, R₉=H) | H | H | OCH₃ | OCH₃ | |
| J-1 | Q-17 (R₇=H, R₈=H, R₂=H) | H | H | OCH₃ | OCH₃ | |
| J-1 | Q-18 (R₇=H, R₈=H, R₂=H) | H | H | OCH₃ | OCH₃ | |
| J-1 | Q-19 (R₇=H, R₈=H) | H | H | CH₃ | OCH₃ | |
| J-1 | Q-20 (R₇=H, R₈=H) | H | H | OCH₃ | OCH₃ | |
| J-1 | Q-21 (R₇=H, R₈=H) | H | H | CH₃ | OCH₃ | |
| J-1 | Q-22 (R₇=H, R₈=H, R₃=H) | H | H | OCH₃ | OCH₃ | |

TABLE 1-continued

General Formula 1

| J | Q | R | $R_1$ | X | Y | m.p. (°C.) |
|---|---|---|---|---|---|---|
| J-1 | Q-23 ($R_7$=H, $R_8$=H, $R_3$=H) | H | H | $OCH_3$ | $OCH_3$ | |
| J-1 | Q-24 ($R_7$=H, $R_8$=H, $R_3$=$CH_3$) | H | H | $OCH_3$ | $OCH_3$ | |
| J-1 | Q-25 ($R_7$=H, $R_8$=H, $R_9$=H) | H | H | $CH_3$ | $OCH_3$ | |
| J-1 | Q-26 ($R_7$=H, $R_8$=H) | H | H | $OCH_3$ | $OCH_3$ | |
| J-1 | Q-27 ($R_7$=H, $R_8$=H) | H | H | $CH_3$ | $OCH_3$ | |
| J-1 | Q-28 ($R_7$=H, $R_8$=H) | H | H | $OCH_3$ | $OCH_3$ | |
| J-1 | Q-29 ($R_7$=H, $R_8$=H) | H | H | $OCH_3$ | $OCH_3$ | |
| J-1 | Q-30 ($R_7$=H, $R_8$=H) | H | H | $OCH_3$ | $OCH_3$ | |
| J-1 | Q-31 ($R_7$=H, $R_8$=H) | H | H | $CH_3$ | $OCH_3$ | |
| J-1 | Q-32 ($R_7$=H, $R_8$=H, $R_3$=H) | H | H | $OCH_3$ | $OCH_3$ | |
| J-1 | Q-33 ($R_7$=H, $R_8$=H, $R_8$=$CH_3$) | H | H | $CH_3$ | $OCH_3$ | |
| J-1 | Q-34 ($R_7$=H, $R_8$=H, $R_3$=H) | H | H | $OCH_3$ | $OCH_3$ | |
| J-1 | Q-35 ($R_7$=H, $R_8$=H, $R_9$=H) | H | H | $OCH_3$ | $OCH_3$ | |
| J-1 | Q-36 ($R_7$=H, $R_8$=H, $R_2$=H) | H | H | $CH_3$ | $OCH_3$ | |
| J-1 | Q-37 ($R_7$=H, $R_8$=H, $R_2$=H) | H | H | $OCH_3$ | $OCH_3$ | |
| J-1 | Q-38 ($R_7$=H, $R_8$=H, $R_2$=H) | H | H | $OCH_3$ | $OCH_3$ | |
| J-1 | Q-39 ($R_7$=H, $R_8$=H, $R_9$=H) | H | H | $OCH_3$ | $OCH_3$ | |
| J-1 | Q-40 ($R_7$=H, $R_8$=H) | H | H | $CH_3$ | $OCH_3$ | |
| J-1 | Q-41 ($R_7$=H, $R_8$=H) | H | H | $OCH_3$ | $OCH_3$ | |
| J-1 | Q-42 ($R_7$=H, $R_8$=H) | H | H | $CH_3$ | $OCH_3$ | |
| J-1 | Q-43 ($R_7$=H, $R_8$=H, $R_3$=H) | H | H | $OCH_3$ | $OCH_3$ | |
| J-1 | Q-44 ($R_7$=H, $R_8$=H, $R_3$=$CH_3$) | H | H | $OCH_3$ | $OCH_3$ | |
| J-1 | Q-45 ($R_7$=H, $R_8$=H, $R_9$=H) | H | H | $CH_3$ | $OCH_3$ | |
| J-1 | Q-46 ($R_7$=H, $R_8$=H, $R_9$=H) | H | H | $OCH_3$ | $OCH_3$ | |
| J-1 | Q-47 ($R_7$=H, $R_8$=H, $R_2$=H) | H | H | $OCH_3$ | $OCH_3$ | |
| J-1 | Q-48 ($R_7$=H, $R_8$=H, $R_2$=H) | H | H | $CH_3$ | $OCH_3$ | |
| J-1 | Q-49 ($R_7$=H, $R_8$=H, $R_2$=H) | H | H | $OCH_3$ | $OCH_3$ | |
| J-1 | Q-50 ($R_7$=H, $R_8$=H, $R_9$=H) | H | H | $OCH_3$ | $OCH_3$ | |
| J-1 | Q-51 ($R_7$=H, $R_8$=H, $R_9$=H) | H | H | $OCH_3$ | $OCH_3$ | |
| J-1 | Q-52 ($R_7$=H, $R_8$=H, $R_9$=H) | H | H | $CH_3$ | $OCH_3$ | |
| J-1 | Q-53 ($R_7$=H, $R_8$=H, $R_9$=H) | H | H | $OCH_3$ | $OCH_3$ | |
| J-1 | Q-54 ($R_7$=H, $R_8$=H, $R_9$=H) | H | H | $CH_3$ | $OCH_3$ | |
| J-1 | Q-55 ($R_7$=H, $R_8$=H, $R_9$=H, $R_3$=H) | H | H | $CH_3$ | $OCH_3$ | |
| J-1 | Q-56 ($R_7$=H, $R_8$=H, $R_9$=H, $R_3$=$C_2H_5$) | H | H | $CH_3$ | $OCH_3$ | |
| J-1 | Q-57 ($R_7$=H, $R_8$=H, $R_9$=H, $R_3$=i-$C_3H_7$) | H | H | $OCH_3$ | $OCH_3$ | |
| J-1 | Q-58 ($R_7$=H, $R_8$=H, $R_9$=H, $R_3$=H) | H | H | $OCH_3$ | $OCH_3$ | |
| J-1 | Q-59 ($R_7$=H, $R_8$=H, $R_9$=H, $R_{10}$=H) | H | H | $CH_3$ | $OCH_3$ | |
| J-1 | Q-60 ($R_7$=H, $R_8$=H, $R_9$=H, $R_2$=H) | H | H | $OCH_3$ | $OCH_3$ | |
| J-1 | Q-61 ($R_7$=H, $R_8$=H, $R_9$=H, $R_2$=H) | H | H | $CH_3$ | $OCH_3$ | |
| J-1 | Q-62 ($R_7$=H, $R_8$=H, $R_9$=H, $R_2$=H) | H | H | $OCH_3$ | $OCH_3$ | |
| J-1 | Q-63 ($R_7$=H, $R_8$=H, $R_9$=H) | H | H | $OCH_3$ | $OCH_3$ | |
| J-1 | Q-64 ($R_7$=H, $R_8$=H, $R_9$=H) | H | H | $OCH_3$ | $OCH_3$ | |
| J-1 | Q-65 ($R_7$=H, $R_8$=H, $R_9$=H) | H | H | $CH_3$ | $OCH_3$ | |
| J-1 | Q-66 ($R_7$=H, $R_8$=H, $R_9$=H) | H | H | $OCH_3$ | $OCH_3$ | |
| J-1 | Q-67 ($R_7$=H, $R_8$=H, $R_9$=H, $R_3$=H) | H | H | $OCH_3$ | $OCH_3$ | |
| J-1 | Q-68 ($R_7$=H, $R_8$=H, $R_9$=H, $R_3$=$CH_3$) | H | H | $CH_3$ | $OCH_3$ | |
| J-1 | Q-69 ($R_7$=H, $R_8$=H, $R_9$=H, $R_3$=$CH_3$) | H | H | $OCH_3$ | $OCH_3$ | |
| J-1 | Q-70 ($R_7$=H, $R_8$=H, $R_9$=H, $R_3$=$CH_3$) | H | H | $CH_3$ | $OCH_3$ | |
| J-1 | Q-71 ($R_7$=H, $R_8$=H, $R_9$=H, $R_{10}$=H) | H | H | $OCH_3$ | $OCH_3$ | |
| J-1 | Q-72 ($R_7$=H, $R_8$=H, $R_9$=H, $R_2$=H) | H | H | $OCH_3$ | $OCH_3$ | |
| J-1 | Q-73 ($R_7$=H, $R_8$=H, $R_9$=H, $R_2$=H) | H | H | $OCH_3$ | $OCH_3$ | |

TABLE 1-continued

General Formula 1

| J | Q | R | $R_1$ | X | Y | m.p. (°C.) |
|---|---|---|---|---|---|---|
| J-1 | Q-74 ($R_7$=H, $R_8$=H, $R_9$=H, $R_2$=H) | H | H | $CH_3$ | $OCH_3$ | |
| J-1 | Q-75 ($R_7$=H, $R_8$=H, $R_9$=H) | H | H | $OCH_3$ | $OCH_3$ | |
| J-1 | Q-76 ($R_7$=H, $R_8$=H, $R_9$=H) | H | H | $CH_3$ | $OCH_3$ | |
| J-1 | Q-77 ($R_7$=H, $R_8$=H, $R_9$=H) | H | H | $OCH_3$ | $OCH_3$ | |
| J-1 | Q-78 ($R_7$=H, $R_8$=H, $R_9$=H) | H | H | $OCH_3$ | $OCH_3$ | |
| J-1 | Q-79 ($R_7$=H, $R_8$=H, $R_9$=H, $R_3$=H) | H | H | $OCH_3$ | $OCH_3$ | |
| J-1 | Q-80 ($R_7$=H, $R_8$=H, $R_9$=H, $R_3$=$CH_3$) | H | H | $OCH_3$ | $OCH_3$ | |
| J-1 | Q-81 ($R_7$=H, $R_8$=H, $R_9$=H, $R_3$=$CH_3$) | H | H | $CH_3$ | $OCH_3$ | |
| J-1 | Q-82 ($R_7$=H, $R_8$=H, $R_9$=H, $R_3$=$CH_3$) | H | H | $OCH_3$ | $OCH_3$ | |
| J-1 | Q-83 ($R_7$=H, $R_8$=H, $R_9$=H, $R_{10}$=H) | H | H | $OCH_3$ | $OCH_3$ | |
| J-1 | Q-84 ($R_7$=H, $R_8$=H, $R_9$=H) | H | H | $CH_3$ | $OCH_3$ | |
| J-1 | Q-85 ($R_7$=H, $R_8$=H, $R_9$=H) | H | H | $OCH_3$ | $OCH_3$ | |
| J-1 | Q-86 ($R_7$=H, $R_8$=H, $R_9$=H) | H | H | $OCH_3$ | $OCH_3$ | |
| J-1 | Q-87 ($R_7$=H, $R_8$=H, $R_9$=H) | H | H | $OCH_3$ | $OCH_3$ | |
| J-1 | Q-88 ($R_7$=H, $R_8$=H, $R_9$=H) | H | H | $CH_3$ | $OCH_3$ | |
| J-1 | Q-89 ($R_7$=H, $R_8$=H, $R_9$=H) | H | H | $OCH_3$ | $OCH_3$ | |
| J-1 | Q-90 ($R_7$=H, $R_8$=H, $R_9$=H, $R_3$=$CH_3$) | H | H | $CH_3$ | $OCH_3$ | |
| J-1 | Q-91 ($R_7$=H, $R_8$=H, $R_9$=H, $R_3$=$CH_3$) | H | H | $OCH_3$ | $OCH_3$ | |
| J-1 | Q-92 ($R_7$=H, $R_8$=H, $R_9$=H, $R_{10}$=H) | H | H | $OCH_3$ | $OCH_3$ | |
| J-1 | Q-93 ($R_7$=H, $R_8$=H, $R_9$=H) | H | H | $CH_3$ | $OCH_3$ | |
| J-1 | Q-94 ($R_7$=H, $R_8$=H, $R_9$=H) | H | H | $OCH_3$ | $OCH_3$ | |
| J-1 | Q-95 ($R_7$=H, $R_8$=H, $R_9$=H) | H | H | $OCH_3$ | $OCH_3$ | |
| J-1 | Q-96 ($R_7$=H, $R_8$=H, $R_9$=H) | H | H | $OCH_3$ | $OCH_3$ | |
| J-1 | Q-97 ($R_7$=H, $R_8$=H, $R_9$=H) | H | H | $CH_3$ | $OCH_3$ | |
| J-1 | Q-98 ($R_7$=H, $R_8$=H, $R_9$=H) | H | H | $OCH_3$ | $OCH_3$ | |
| J-1 | Q-99 ($R_7$=H, $R_8$=H, $R_9$=H, $R_3$=H) | H | H | $OCH_3$ | $OCH_3$ | |
| J-1 | Q-100 ($R_7$=H, $R_8$=H, $R_9$=H, $R_3$=$C_2H_5$) | H | H | $OCH_3$ | $OCH_3$ | |
| J-1 | Q-101 ($R_7$=H, $R_8$=H, $R_9$=H, $R_3$=i-$C_2H_5$) | H | H | $OCH_3$ | $OCH_3$ | |
| J-1 | Q-102 ($R_7$=H, $R_8$=H, $R_9$=H, $R_3$=H) | H | H | $CH_3$ | $OCH_3$ | |
| J-1 | Q-103 ($R_7$=H, $R_8$=H, $R_9$=H, $R_{10}$=H) | H | H | $OCH_3$ | $OCH_3$ | |
| J-1 | Q-104 ($R_7$=H, $R_8$=H, $R_9$=H, $R_2$=H) | H | H | $OCH_3$ | $OCH_3$ | |
| J-1 | Q-105 ($R_7$=H, $R_8$=H, $R_9$=H, $R_2$=H) | H | H | $CH_3$ | $OCH_3$ | |
| J-1 | Q-106 ($R_7$=H, $R_8$=H, $R_9$=H, $R_2$=H) | H | H | $OCH_3$ | $OCH_3$ | |
| J-1 | Q-107 ($R_7$=H, $R_8$=H, $R_9$=H, $R_2$=H) | H | H | $OCH_3$ | $OCH_3$ | |
| J-1 | Q-108 ($R_7$=H, $R_8$=H, $R_9$=H) | H | H | $OCH_3$ | $OCH_3$ | |
| J-1 | Q-109 ($R_7$=H, $R_8$=H, $R_9$=H) | H | H | $CH_3$ | $OCH_3$ | |
| J-1 | Q-110 ($R_7$=H, $R_8$=H, $R_9$=H) | H | H | $OCH_3$ | $OCH_3$ | |
| J-1 | Q-111 ($R_7$=H, $R_8$=H, $R_9$=H) | H | H | $CH_3$ | $OCH_3$ | |
| J-1 | Q-112 ($R_7$=H, $R_8$=H, $R_9$=H) | H | H | $CH_3$ | $OCH_3$ | |
| J-1 | Q-113 ($R_7$=H, $R_8$=H, $R_9$=H, $R_3$=$CH_3$) | H | H | $OCH_3$ | $OCH_3$ | |
| J-1 | Q-114 ($R_7$=H, $R_8$=H, $R_9$=H, $R_3$=$CH_3$) | H | H | $OCH_3$ | $OCH_3$ | |
| J-1 | Q-115 ($R_7$=H, $R_8$=H, $R_9$=H, $R_3$=$CH_3$) | H | H | $OCH_3$ | $OCH_3$ | |
| J-1 | Q-116 ($R_7$=H, $R_8$=H, $R_9$=H, $R_{10}$=H) | H | H | $CH_3$ | $OCH_3$ | |
| J-1 | Q-117 ($R_7$=H, $R_8$=H, $R_9$=H, $R_2$=H) | H | H | $OCH_3$ | $OCH_3$ | |
| J-1 | Q-118 ($R_7$=H, $R_8$=H, $R_9$=H, $R_{10}$=H) | H | H | $OCH_3$ | $OCH_3$ | |
| J-1 | Q-119 ($R_7$=H, $R_8$=H, $R_9$=H, $R_2$=H) | H | H | $OCH_3$ | $OCH_3$ | |
| J-1 | Q-120 ($R_7$=H, $R_8$=H, $R_9$=H, $R_2$=H) | H | H | $CH_3$ | $OCH_3$ | |
| J-1 | Q-121 ($R_7$=H, $R_8$=H, $R_9$=H, $R_2$=H) | H | H | $OCH_3$ | $OCH_3$ | |
| J-1 | Q-122 ($R_7$=H, $R_8$=H, $R_9$=H, $R_2$=H) | H | H | $OCH_3$ | $OCH_3$ | |
| J-1 | Q-123 ($R_7$=H, $R_8$=H, $R_9$=H) | H | H | $CH_3$ | $OCH_3$ | |
| J-1 | Q-124 ($R_7$=H, $R_8$=H, $R_9$=H) | H | H | $OCH_3$ | $OCH_3$ | |

TABLE 1-continued

General Formula 1

| J | Q | R | R₁ | X | Y | m.p. (°C.) |
|---|---|---|----|---|---|------------|
| J-1 | Q-125 (R₇=H, R₈=H, R₉=H) | H | H | CH₃ | OCH₃ | |
| J-1 | Q-126 (R₇=H, R₈=H, R₉=H) | H | H | OCH₃ | OCH₃ | |
| J-1 | Q-127 (R₇=H, R₈=H, R₉=H, R₃=H) | H | H | OCH₃ | OCH₃ | |
| J-1 | Q-128 (R₇=H, R₈=H, R₉=H, R₃=CH₃) | H | H | OCH₃ | OCH₃ | |
| J-1 | Q-129 (R₇=H, R₈=H, R₉=H, R₃=CH₃) | H | H | CH₃ | OCH₃ | |
| J-1 | Q-130 (R₇=H, R₈=H, R₉=H, R₃=CH₃) | H | H | OCH₃ | OCH₃ | |
| J-1 | Q-131 (R₇=H, R₈=H, R₉=H, R₁₀=H) | H | H | CH₃ | OCH₃ | |
| J-1 | Q-132 (R₇=H, R₈=H, R₉=H) | H | H | OCH₃ | OCH₃ | |
| J-1 | Q-133 (R₇=H, R₈=H, R₉=H) | H | H | OCH₃ | OCH₃ | |
| J-1 | Q-134 (R₇=H, R₈=H, R₉=H) | H | H | OCH₃ | OCH₃ | |
| J-1 | Q-135 (R₇=H, R₈=H, R₉=H) | H | H | OCH₃ | OCH₃ | |
| J-1 | Q-136 (R₇=H, R₈=H, R₉=H) | H | H | CH₃ | OCH₃ | |
| J-1 | Q-137 (R₇=H, R₈=H, R₉=H) | H | H | OCH₃ | OCH₃ | |
| J-1 | Q-138 (R₇=H, R₈=H, R₉=H) | H | H | CH₃ | OCH₃ | |
| J-1 | Q-139 (R₇=H, R₈=H, R₉=H) | H | H | OCH₃ | OCH₃ | |
| J-1 | Q-140 (R₇=H, R₈=H, R₉=H, R₃=CH₃) | H | H | OCH₃ | OCH₃ | |
| J-1 | Q-141 (R₇=H, R₈=H, R₉=H, R₃=CH₃) | H | H | OCH₃ | OCH₃ | |
| J-1 | Q-142 (R₇=H, R₈=H, R₉=H, R₁₀=H) | H | H | OCH₃ | OCH₃ | |
| J-1 | Q-143 (R₇=H, R₈=H, R₉=H, R₃=CH₃) | H | H | CH₃ | OCH₃ | |
| J-1 | Q-144 (R₇=H, R₈=H, R₉=H) | H | H | OCH₃ | OCH₃ | |
| J-1 | Q-145 (R₇=H, R₈=H, R₉=H) | H | H | CH₃ | OCH₃ | |
| J-1 | Q-146 (R₇=H, R₈=H, R₉=H) | H | H | OCH₃ | OCH₃ | |
| J-1 | Q-147 (R₇=H, R₈=H, R₉=H) | H | H | CH₃ | OCH₃ | |
| J-1 | Q-148 (R₇=H, R₈=H, R₉=H, R₃=CH₃) | H | H | OCH₃ | OCH₃ | |
| J-1 | Q-149 (R₇=H, R₈=H, R₉=H, R₁₀=H) | H | H | OCH₃ | OCH₃ | |
| J-1 | Q-150 (R₇=H, R₈=H, R₉=H) | H | H | OCH₃ | OCH₃ | |
| J-1 | Q-151 (R₇=H, R₈=H, R₉=H) | H | H | CH₃ | OCH₃ | |
| J-1 | Q-152 (R₇=H, R₈=H, R₉=H, R₁₁=CH₃) | H | H | OCH₃ | OCH₃ | |
| J-1 | Q-153 (R₇=H, R₈=H, R₉=H, R₁₁=CH₃) | H | H | CH₃ | OCH₃ | |
| J-1 | Q-154 (R₇=H, R₈=H, R₉=H, R₁₁=CH₃) | H | H | OCH₃ | OCH₃ | |
| J-1 | Q-155 (R₇=H, R₈=H, R₉=H) | H | H | OCH₃ | OCH₃ | |
| J-1 | Q-156 (R₇=H, R₈=H, R₉=H) | H | H | OCH₃ | OCH₃ | |
| J-1 | Q-157 (R₇=H, R₈=H, R₉=H, R₁₀=H) | H | H | OCH₃ | OCH₃ | |
| J-1 | Q-158 (R₇=H, R₈=H, R₉=H) | H | H | CH₃ | OCH₃ | |
| J-1 | Q-159 (R₇=H, R₈=H, R₉=H, R₁₁=CH₃) | H | H | OCH₃ | OCH₃ | |
| J-1 | Q-160 (R₇=H, R₈=H, R₉=H, R₁₁=CH₃) | H | H | CH₃ | OCH₃ | |
| J-1 | Q-161 (R₇=H, R₈=H, R₉=H, R₁₁=CH₃) | H | H | OCH₃ | OCH₃ | |
| J-1 | Q-162 (R₇=H, R₈=H, R₉=H, R₁₀=H) | H | H | CH₃ | OCH₃ | |
| J-1 | Q-163 (R₂=H, R₈=H, R₉=H) | H | H | OCH₃ | OCH₃ | |
| J-1 | Q-164 (R₇=H) | H | H | OCH₃ | OCH₃ | |
| J-1 | Q-165 (R₃=H, R₇=H) | H | 5-SOCH₃ | OCH₃ | OCH₃ | |
| J-1 | Q-166 (R₃=H, R₇=H) | H | 5-SO₂CH₃ | OCH₃ | OCH₃ | |
| J-2 | Q-1 (R₇=H, R₈=H) | H | 5-CO₂CH₃ | OCH₃ | OCH₃ | |
| J-2 | Q-1 (R₇=H, R₈=H) | H | 4-SO₂N(CH₃)₂ | OCH₃ | OCH₃ | |
| J-2 | Q-1 (R₇=H, R₈=H) | H | 6-Cl | OCH₃ | OCH₃ | |
| J-2 | Q-1 (R₇=H, R₈=H) | H | 6-COOCH₃ | OCH₃ | OCH₃ | |
| J-2 | Q-1 (R₇=H, R₈=H) | H | 4-SO₂CH₃ | OCH₃ | OCH₃ | |
| J-2 | Q-1 (R₇=H, R₈=H) | H | H | CH₃ | CH₃ | |
| J-2 | Q-1 (R₇=H, R₈=H) | H | H | OCH₃ | CH₃ | |

TABLE 1-continued

General Formula 1

| J | Q | R | R₁ | X | Y | m.p. (°C.) |
|---|---|---|----|----|----|-----------|
| J-2 | Q-1 (R₇=H, R₈=H) | H | H | OCH₃ | OCH₃ | |
| J-2 | Q-1 (R₇=H, R₈=H) | CH₃ | H | OCH₃ | OCH₃ | |
| J-2 | Q-1 (R₇=H, R₈=H) | CH₃ | H | CH₃ | CH₃ | |
| J-2 | Q-1 (R₇=H, R₈=H) | H | 5-CH₃ | OCH₃ | OCH₃ | |
| J-2 | Q-1 (R₇=H, R₈=H) | H | 6-CH₂CH₃ | OCH₃ | OCH₃ | |
| J-2 | Q-1 (R₇=H, R₈=H) | H | 5-CH(CH₃)₂ | OCH₃ | OCH₃ | |
| J-2 | Q-1 (R₇=H, R₈=H) | H | 5-OCH₃ | OCH₃ | OCH₃ | |
| J-2 | Q-1 (R₇=H, R₈=H) | H | 5-OCH₂CH₃ | OCH₃ | OCH₃ | |
| J-2 | Q-1 (R₇=H, R₈=H) | H | 5-OCH(CH₃)₂ | OCH₃ | OCH₃ | |
| J-2 | Q-1 (R₇=H, R₈=H) | H | 5-OCF₂H | OCH₃ | OCH₃ | |
| J-2 | Q-1 (R₇=H, R₈=H) | H | 6-OCH₂CH₂Br | OCH₃ | OCH₃ | |
| J-2 | Q-1 (R₇=H, R₈=H) | H | 5-OCH(CH₃)(CH₂Cl) | OCH₃ | OCH₃ | |
| J-2 | Q-1 (R₇=H, R₈=H) | H | 5-CH₂F | OCH₃ | OCH₃ | |
| J-2 | Q-1 (R₇=H, R₈=H) | H | 5-CH₂CH₂Br | OCH₃ | OCH₃ | |
| J-2 | Q-1 (R₇=H, R₈=H) | H | 5-CH(CH₃)(CH₂Cl) | OCH₃ | OCH₃ | |
| J-2 | Q-1 (R₇=H, R₈=H) | H | 5-SCH₃ | OCH₃ | OCH₃ | |
| J-2 | Q-1 (R₇=H, R₈=H) | H | 6-SCH₂CH₃ | OCH₃ | OCH₃ | |
| J-2 | Q-1 (R₇=H, R₈=H) | H | 5-SCH(CH₃)₂ | OCH₃ | OCH₃ | |
| J-2 | Q-1 (R₇=H, R₈=H) | H | 5-SCH₂F | OCH₃ | OCH₃ | |
| J-2 | Q-1 (R₇=H, R₈=H) | H | 5-SCH₂CH₂Br | OCH₃ | OCH₃ | |
| J-2 | Q-1 (R₇=H, R₈=H) | H | 5-SCH(CH₃)(CH₂Cl) | OCH₃ | OCH₃ | |
| J-2 | Q-1 (R₇=H, R₈=H) | H | 4-NH₂ | OCH₃ | OCH₃ | |
| J-2 | Q-1 (R₇=H, R₈=H) | H | 5-NHCH₃ | OCH₃ | OCH₃ | |
| J-2 | Q-1 (R₇=H, R₈=H) | H | 6-NHCH₂CH₃ | OCH₃ | OCH₃ | |
| J-2 | Q-1 (R₇=H, R₈=H) | H | 5-NHCH(CH₃)₂ | OCH₃ | OCH₃ | |
| J-2 | Q-1 (R₇=H, R₈=H) | H | 4-N(CH₃)₂ | OCH₃ | OCH₃ | |
| J-2 | Q-1 (R₇=H, R₈=H) | H | 6-N(CH₃)(CH₂CH₃) | OCH₃ | OCH₃ | |
| J-2 | Q-1 (R₇=H, R₈=H) | H | 5-N(CH₃)(CH(CH₃)₂) | OCH₃ | OCH₃ | |
| J-2 | Q-1 (R₇=H, R₈=H) | H | 5-Cl | OCH₃ | OCH₃ | |
| J-2 | Q-1 (R₇=H, R₈=H) | H | 5-Br | OCH₃ | OCH₃ | |
| J-2 | Q-1 (R₇=H, R₈=H) | H | 4-F | OCH₃ | OCH₃ | |
| J-2 | Q-1 (R₇=H, R₈=H) | H | 5-I | OCH₃ | OCH₃ | |
| J-2 | Q-1 (R₇=H, R₈=H) | H | 4-NO₂ | OCH₃ | OCH₃ | |
| J-2 | Q-1 (R₇=H, R₈=H) | H | 5-CF₃ | OCH₃ | OCH₃ | |
| J-2 | Q-1 (R₇=H, R₈=H) | H | 5-OCF₂H | OCH₃ | OCH₃ | |
| J-2 | Q-1 (R₇=H, R₈=H) | H | H | OCH₃ | CH₂CH₃ | |
| J-2 | Q-1 (R₇=H, R₈=H) | H | H | OCH₃ | CH(CH₃)₂ | |
| J-2 | Q-1 (R₇=H, R₈=H) | H | H | OCH₃ | (CH₂)₃CH₃ | |
| J-2 | Q-1 (R₇=H, R₈=H) | H | H | OCH₃ | OCH₂CH₃ | |
| J-2 | Q-1 (R₇=H, R₈=H) | H | H | OCH₃ | OCH(CH₃)₂ | |
| J-2 | Q-1 (R₇=H, R₈=H) | H | H | OCH₃ | O(CH₂)₃CH₃ | |
| J-2 | Q-1 (R₇=H, R₈=H) | H | H | OCF₂H | OCH₃ | |
| J-2 | Q-1 (R₇=H, R₈=H) | H | H | OCH₂CH₂F | OCH₃ | |
| J-2 | Q-1 (R₇=H, R₈=H) | H | H | OCH₂CHF₂ | OCH₃ | |
| J-2 | Q-1 (R₇=H, R₈=H) | H | H | OCH₂CF₃ | OCH₃ | |
| J-2 | Q-1 (R₇=H, R₈=H) | H | H | OCH(CH₃)(CH₂Cl) | OCH₃ | |
| J-2 | Q-1 (R₇=H, R₈=H) | H | H | O(CH₂)₃CH₂Br | OCH₃ | |
| J-2 | Q-1 (R₇=H, R₈=H) | H | H | CH₂F | OCH₃ | |
| J-2 | Q-1 (R₇=H, R₈=H) | H | H | CH₂Cl | OCH₃ | |
| J-2 | Q-1 (R₇=H, R₈=H) | H | H | CH₂Br | OCH₃ | |
| J-2 | Q-1 (R₇=H, R₈=H) | H | H | CF₃ | OCH₃ | |

TABLE 1-continued
General Formula 1

| J | Q | R | R₁ | X | Y | m.p. (°C.) |
|---|---|---|----|---|---|-----------|
| J-2 | Q-1 (R₇=H, R₈=H) | H | H | CH₂CH₂Br | OCH₃ | |
| J-2 | Q-1 (R₇=H, R₈=H) | H | H | CH(CH₃)(CH₂Cl) | OCH₃ | |
| J-2 | Q-1 (R₇=H, R₈=H) | H | H | (CH₂)₃CH₂I | OCH₃ | |
| J-2 | Q-1 (R₇=H, R₈=H) | H | H | SCH₃ | OCH₃ | |
| J-2 | Q-1 (R₇=H, R₈=H) | H | H | SCH₂CH₃ | OCH₃ | |
| J-2 | Q-1 (R₇=H, R₈=H) | H | H | SCH(CH₃)₂ | OCH₃ | |
| J-2 | Q-1 (R₇=H, R₈=H) | H | H | S(CH₂)₃CH₃ | OCH₃ | |
| J-2 | Q-1 (R₇=H, R₈=H) | H | H | SCHF₂ | OCH₃ | |
| J-2 | Q-1 (R₇=H, R₈=H) | H | H | SCH₂CH₂Br | OCH₃ | |
| J-2 | Q-1 (R₇=H, R₈=H) | H | H | SCH(CH₃)(CH₂Cl) | OCH₃ | |
| J-2 | Q-1 (R₇=H, R₈=H) | H | H | S(CH₂)₃CH₂F | OCH₃ | |
| J-2 | Q-1 (R₇=H, R₈=H) | H | H | Cl | OCH₃ | |
| J-2 | Q-1 (R₇=H, R₈=H) | H | H | Br | OCH₃ | |
| J-2 | Q-1 (R₇=H, R₈=H) | H | H | F | OCH₃ | |
| J-2 | Q-1 (R₇=H, R₈=H) | H | H | I | OCH₃ | |
| J-2 | Q-1 (R₇=H, R₈=H) | H | H | OCH₃ | CH₂OCH₃ | |
| J-2 | Q-1 (R₇=H, R₈=H) | H | H | OCH₂O(CH₂)₃CH₃ | CH₂CH₂OCH(CH₃)₂ | |
| J-2 | Q-1 (R₇=H, R₈=H) | H | H | OCH₂CH₂OCH(CH₃)₂ | CH(CH₃)(CH₂OCH₃) | |
| J-2 | Q-1 (R₇=H, R₈=H) | H | H | OCH(CH₃)(CH₂OCH₃) | (CH₂)₄CH₂OCH₂CH₃ | |
| J-2 | Q-1 (R₇=H, R₈=H) | H | H | O(CH₂)₄CH₂OCH₂CH₃ | OCH₃ | |
| J-2 | Q-1 (R₇=H, R₈=H) | H | H | OCH₃ | OCH₃ | |
| J-2 | Q-1 (R₇=H, R₈=H) | H | H | OCH₃ | OCH₃ | |
| J-2 | Q-1 (R₇=H, R₈=H) | H | H | OCH₃ | NH₂ | |
| J-2 | Q-1 (R₇=H, R₈=H) | H | H | OCH₃ | NHCH₃ | |
| J-2 | Q-1 (R₇=H, R₈=H) | H | H | OCH₃ | NHCH₂CH₃ | |
| J-2 | Q-1 (R₇=H, R₈=H) | H | H | OCH₃ | NHCH(CH₃)₂ | |
| J-2 | Q-1 (R₇=H, R₈=H) | H | H | OCH₃ | N(CH₃)₂ | |
| J-2 | Q-1 (R₇=H, R₈=H) | H | H | OCH₃ | N(CH₃)(CH₂CH₃) | |
| J-2 | Q-1 (R₇=H, R₈=H) | H | H | OCH₃ | N(CH₃)(CH(CH₃)₂) | |
| J-2 | Q-1 (R₇=H, R₈=H) | H | H | OCH₃ | N(CH₃)(CH₂SCH₃) | |
| J-2 | Q-1 (R₇=H, R₈=H) | H | H | OCH₃ | (CH₂)₄CH₂OCH₂CH₃ | |
| J-2 | Q-1 (R₇=H, R₈=H) | H | H | H | OCH₃ | |
| J-2 | Q-1 (R₇=H, R₈=H) | H | H | OCH₃ | OCH₂CH=CH₂ | |
| J-2 | Q-1 (R₇=H, R₈=H) | H | H | OCH₃ | OCH₂C(CH₃)=CH₂ | |
| J-2 | Q-1 (R₇=H, R₈=H) | H | H | OCH₃ | OCH₂C≡CH | |
| J-2 | Q-1 (R₇=H, R₈=H) | H | H | OCH₃ | OCH₂C≡CCH₃ | |
| J-2 | Q-1 (R₇=H, R₈=H) | H | H | OCH₃ | CH₃S(CH₂)₃CH₃ | |
| J-2 | Q-1 (R₇=H, R₈=H) | H | H | OCH₃ | CH₂CH₂SCH(CH₃)₂ | |
| J-2 | Q-1 (R₇=H, R₈=H) | H | H | OCH₃ | CH(CH₃)(CH₂SCH₃) | |
| J-2 | Q-1 (R₇=H, R₈=H) | H | H | OCH₃ | (CH₂)₄CH₂SCH₂CH₃ | |
| J-2 | Q-1 (R₇=H, R₈=H) | H | H | OCH₃ | cyclopropyl | |
| J-2 | Q-1 (R₇=H, R₈=H) | H | H | OCH₃ | 2-methylcyclopropyl | |
| J-2 | Q-1 (R₇=H, R₈=H) | H | H | OCH₃ | cyclopentyl | |
| J-2 | Q-1 (R₇=H, R₈=H) | H | H | OCH₃ | C≡CH | |
| J-2 | Q-1 (R₇=H, R₈=H) | H | H | OCH₃ | C≡CCH₃ | |
| J-2 | Q-1 (R₇=H, R₈=H) | H | H | OCH₃ | —CHO | |
| J-2 | Q-1 (R₇=H, R₈=H) | H | H | OCH₃ | —COCH₃ | |
| J-2 | Q-1 (R₇=H, R₈=H) | H | H | OCH₃ | —CH(OCH₃)₂ | |
| J-2 | Q-1 (R₇=H, R₈=H) | H | H | OCH₃ | —CH(SCH₃)(OCH₂CH₃) | |
| J-2 | Q-1 (R₇=H, R₈=H) | H | H | OCH₃ | —C(CH₃)(SCH₃)₂ | |
| J-2 | Q-1 (R₇=H, R₈=H) | H | H | OCH₃ | —CH(SCH₂CH₃)₂ | |

TABLE 1-continued

General Formula 1

| J | Q | R | R$_1$ | X | Y | m.p. (°C.) |
|---|---|---|---|---|---|---|
| J-2 | Q-1 (R$_7$=H, R$_8$=H) | H | H | OCH$_3$ | 1,3-dioxolan-2-yl | |
| J-2 | Q-1 (R$_7$=H, R$_8$=H) | H | H | OCH$_3$ | 2-methyl-1,3-oxa-thiolan-2-yl | |
| J-2 | Q-1 (R$_7$=H, R$_8$=H) | H | H | OCH$_3$ | 1,3-oxathian-2-yl | |
| J-2 | Q-1 (R$_7$=H, R$_8$=H) | H | H | OCH$_3$ | 2-methyl-1,3-dithian-2-yl | |
| J-2 | Q-1 (R$_7$=H, R$_8$=H) | H | H | OCH$_3$ | 4-methyl-1,3-dioxolan-2-yl | |
| J-2 | Q-1 (R$_7$=H, R$_8$=H) | H | H | OCH$_3$ | 4-methyl-1,3-oxathiolan-2-yl | |
| J-2 | Q-1 (R$_7$=H, R$_8$=H) | H | H | OCH$_3$ | 2,4-dimethyl-1,3-dithiolan-2-yl | |
| J-2 | Q-1 (R$_7$=H, R$_8$=H) | H | H | OCH$_3$ | N(OCH$_3$)(CH$_3$)$_2$ | |
| J-2 | Q-1 (R$_7$=H, R$_8$=CH$_3$) | H | H | OCH$_3$ | OCH$_3$ | |
| J-2 | Q-1 (R$_7$=H, R$_8$=CH$_3$) | H | H | CH$_3$ | CH$_3$ | |
| J-2 | Q-1 (R$_7$=H, R$_8$=CH$_3$) | H | H | CH$_3$ | OCH$_3$ | |
| J-2 | Q-1 (R$_7$=H, R$_8$=CH$_2$CH$_3$) | H | H | OCH$_3$ | OCH$_3$ | |
| J-2 | Q-1 (R$_7$=H, R$_8$=CH(CH$_3$)$_2$) | H | H | OCH$_3$ | OCH$_3$ | |
| J-2 | Q-1 (R$_7$=H, R$_8$=(CH$_2$)$_3$CH$_3$) | H | H | OCH$_3$ | OCH$_3$ | |
| J-2 | Q-1 (R$_7$=CH$_3$, R$_8$=CH$_3$) | H | H | OCH$_3$ | OCH$_3$ | |
| J-2 | Q-2 (R$_7$=H, R$_8$=H) | CH$_3$ | H | OCH$_3$ | OCH$_3$ | |
| J-2 | Q-2 (R$_7$=H, R$_8$=H) | H | 5-OCH$_3$ | OCH$_3$ | OCH$_3$ | |
| J-2 | Q-2 (R$_7$=H, R$_8$=CH$_3$) | H | H | OCH$_3$ | OCH$_3$ | |
| J-2 | Q-3 (R$_7$=H, R$_8$=H) | H | H | OCH$_3$ | OCH$_3$ | |
| J-2 | Q-3 (R$_7$=C$_2$H$_5$, R$_8$=H) | H | H | OCF$_2$H | OCH$_3$ | |
| J-2 | Q-3 (R$_7$=CH$_3$, R$_8$=H) | H | 5-Cl | OCH$_3$ | OCH$_3$ | |
| J-2 | Q-4 (R$_7$=H, R$_8$=H, R$_3$=CH$_3$) | H | H | CH$_3$ | CH$_3$ | |
| J-2 | Q-4 (R$_7$=H, R$_8$=H, R$_3$=C$_2$H$_5$) | H | H | CH$_3$ | OCH$_3$ | |
| J-2 | Q-4 (R$_7$=H, R$_8$=H, R$_3$=i-C$_3$H$_7$) | H | 5-CH$_3$ | OCH$_3$ | OCH$_3$ | |
| J-2 | Q-5 (R$_7$=H, R$_8$=H, R$_3$=H) | H | H | CH$_3$ | CH$_3$ | |
| J-2 | Q-5 (R$_7$=H, R$_8$=CH$_3$, R$_3$=CH$_3$) | H | H | Cl | OCH$_3$ | |
| J-2 | Q-5 (R$_7$=CH$_3$, R$_8$=CH$_3$, R$_3$=CH$_3$) | H | H | CH$_3$ | OCH$_3$ | |
| J-2 | Q-6 (R$_7$=H, R$_8$=H, R$_3$=C$_2$H$_5$) | H | H | CH$_3$ | OCH$_3$ | |
| J-2 | Q-6 (R$_7$=C$_2$H$_5$, R$_8$=H, R$_3$=H) | H | H | CH$_3$ | OCH$_3$ | |
| J-2 | Q-7 (R$_7$=H, R$_8$=H, R$_9$=H) | H | H | OCH$_3$ | OCH$_3$ | |
| J-2 | Q-7 (R$_7$=H, R$_8$=C$_2$H$_5$, R$_9$=H) | H | 5-OCH$_3$ | OCH$_3$ | OCH$_3$ | |
| J-2 | Q-7 (R$_7$=i-C$_3$H$_7$, R$_8$=H, R$_9$=CH$_3$) | H | H | OCH$_3$ | OCH$_3$ | |
| J-2 | Q-8 (R$_7$=H, R$_8$=H, R$_2$=H) | H | H | OCH$_3$ | OCH$_3$ | |
| J-2 | Q-8 (R$_7$=CH$_3$, R$_8$=H, R$_2$=OCH$_3$) | H | 5-Cl | OCH$_3$ | OCF$_2$H | |
| J-2 | Q-8 (R$_7$=H, R$_8$=H, R$_2$=OCH(CH$_3$)CH$_2$CH$_3$) | H | H | OCH$_3$ | OCH$_3$ | |
| J-2 | Q-9 (R$_7$=H, R$_8$=H, R$_2$=H) | H | 5-OCH$_3$ | OCH$_3$ | OCH$_3$ | |
| J-2 | Q-9 (R$_7$=CH$_3$, R$_8$=H, R$_2$=CH$_3$) | CH$_3$ | H | OCH$_3$ | OCH$_3$ | |
| J-2 | Q-9 (R$_7$=H, R$_8$=H, R$_2$=Cl) | H | 5-Cl | OCH$_3$ | CH$_3$ | |
| J-2 | Q-10 (R$_7$=H, R$_8$=H) | H | H | OCF$_2$H | CH$_3$ | |
| J-2 | Q-10 (R$_7$=H, R$_8$=CH$_3$) | H | 5-OCH$_3$ | OCH$_3$ | CH$_3$ | |
| J-2 | Q-11 (R$_7$=H, R$_8$=H) | H | H | CH$_3$ | OCH$_3$ | |
| J-2 | Q-11 (R$_7$=n-C$_4$H$_9$, R$_8$=H) | H | H | OCH$_3$ | OCH$_3$ | |
| J-2 | Q-11 (R$_7$=CH$_3$, R$_8$=CH$_3$) | H | 5-CH$_3$ | OCH$_3$ | OCH$_3$ | |
| J-2 | Q-12 (R$_7$=H, R$_8$=H) | H | H | OCH$_3$ | OCH$_3$ | |

TABLE 1-continued

General Formula 1

| J | Q | R | R$_1$ | X | Y | m.p. (°C.) |
|---|---|---|---|---|---|---|
| J-2 | Q-12 (R$_7$=CH$_3$, R$_8$=H) | H | H | Cl | OCH$_3$ | |
| J-2 | Q-12 (R$_7$=H, R$_8$=C$_2$H$_5$) | H | H | CH$_3$ | OCH$_3$ | |
| J-2 | Q-13 (R$_7$=H, R$_8$=H, R$_3$=H) | H | H | CH$_3$ | OCH$_3$ | |
| J-2 | Q-13 (R$_7$=H, R$_8$=H, R$_3$=CH$_3$) | CH$_3$ | H | CH$_3$ | OCH$_3$ | |
| J-2 | Q-13 (R$_7$=CH$_3$, R$_8$=H, R$_3$=CH$_3$) | H | H | OCH$_3$ | OCH$_3$ | |
| J-2 | Q-14 (R$_7$=H, R$_8$=H, R$_3$=CH$_3$) | H | H | OCH$_3$ | OCH$_3$ | |
| J-2 | Q-14 (R$_7$=CH$_3$, R$_8$=H, R$_3$=C$_2$H$_5$) | H | 5-OCH$_3$ | OCH$_3$ | OCH$_3$ | |
| J-2 | Q-14 (R$_7$=H, R$_8$=CH$_3$, R$_3$=CH$_3$) | H | H | OCH$_3$ | OCH$_3$ | |
| J-2 | Q-15 (R$_7$=H, R$_8$=H, R$_3$=H) | H | H | OCH$_3$ | OCH$_3$ | |
| J-2 | Q-15 (R$_7$=C$_2$H$_5$, R$_8$=H, R$_3$=CH$_3$) | H | 5-Cl | OCH$_3$ | OCF$_2$H | |
| J-2 | Q-15 (R$_7$=CH$_3$, R$_8$=CH$_3$, R$_3$=CH$_3$) | H | H | OCH$_3$ | OCH$_3$ | |
| J-2 | Q-16 (R$_7$=H, R$_8$=H, R$_9$=H) | CH$_3$ | H | OCH$_3$ | OCH$_3$ | |
| J-2 | Q-16 (R$_7$=CH$_3$, R$_8$=H, R$_9$=H) | H | 5-OCH$_3$ | OCH$_3$ | OCH$_3$ | |
| J-2 | Q-16 (R$_7$=CH$_3$, R$_8$=CH$_3$, R$_9$=H) | H | H | OCH$_3$ | OCH$_3$ | |
| J-2 | Q-17 (R$_7$=H, R$_8$=H, R$_2$=H) | H | H | CH$_3$ | CH$_3$ | |
| J-2 | Q-17 (R$_7$=CH$_3$, R$_8$=H, R$_2$=CH$_3$) | H | 5-Cl | OCF$_2$H | CH$_3$ | |
| J-2 | Q-17 (R$_7$=H, R$_8$=CH$_3$, R$_2$=C$_2$H$_5$) | H | H | OCH$_3$ | OCH$_3$ | |
| J-2 | Q-18 (R$_7$=H, R$_8$=H, R$_2$=H) | H | 5-CH$_3$ | CH$_3$ | CH$_3$ | |
| J-2 | Q-18 (R$_7$=H, R$_8$=OC$_2$H$_5$, R$_2$=H) | H | H | OCH$_3$ | OCH$_3$ | |
| J-2 | Q-18 (R$_7$=CH$_3$, R$_8$=OCH(CH$_3$)$_2$, R$_2$=CH$_3$) | H | H | OCH$_3$ | OCH$_3$ | |
| J-2 | Q-19 (R$_7$=H, R$_8$=H) | H | H | Cl | OCH$_3$ | |
| J-2 | Q-19 (R$_7$=CH$_3$, R$_8$=H) | H | H | CH$_3$ | OCH$_3$ | |
| J-2 | Q-19 (R$_7$=CH$_3$, R$_8$CH$_3$) | H | H | CH$_3$ | OCH$_3$ | |
| J-2 | Q-20 (R$_7$=H, R$_8$=H) | H | H | OCH$_3$ | OCH$_3$ | |
| J-2 | Q-20 (R$_7$=CH$_3$, R$_8$=H) | H | H | OCH$_3$ | OCH$_3$ | |
| J-2 | Q-20 (R$_7$=H, R$_8$=CH$_3$) | H | H | OCH$_3$ | OCH$_3$ | |
| J-2 | Q-21 (R$_7$=H, R$_8$=H) | H | H | OCH$_3$ | OCH$_3$ | |
| J-2 | Q-21 (R$_7$=CH$_3$, R$_8$=CH$_3$) | H | 5-OCH$_3$ | OCH$_3$ | OCH$_3$ | |
| J-2 | Q-22 (R$_7$=H, R$_8$=H, R$_3$=H) | H | H | OCH$_3$ | OCH$_3$ | |
| J-2 | Q-22 (R$_7$=H, R$_8$=H, R$_3$=CH$_3$) | H | 5-Cl | OCH$_3$ | OCF$_2$H | |
| J-2 | Q-22 (R$_7$=CH$_3$, R$_8$=H, R$_3$=C$_2$H$_5$) | H | H | OCH$_3$ | OCH$_3$ | |
| J-2 | Q-23 (R$_7$=H, R$_8$=H, R$_1$=CH$_3$) | CH$_3$ | H | OCH$_3$ | OCH$_3$ | |
| J-2 | Q-23 (R$_7$=CH$_3$, R$_8$=H, R$_3$=n-C$_4$H$_9$) | H | 5-OCH$_3$ | OCH$_3$ | OCH$_3$ | |
| J-2 | Q-24 (R$_7$=CH$_3$, R$_8$=H, R$_3$=C$_2$H$_5$) | H | H | OCF$_2$H | OCH$_3$ | |
| J-2 | Q-24 (R$_7$=CH$_3$, R$_8$=CH$_3$, R$_3$=i-C$_3$H$_7$) | H | 5-Cl | CH$_3$ | CH$_3$ | |
| J-2 | Q-25 (R$_7$=H, R$_8$=H, R$_9$=H) | H | H | CH$_3$ | CH$_3$ | |
| J-2 | Q-25 (R$_7$=H, R$_8$=H, R$_9$=C$_2$H$_5$) | H | 5-CH$_3$ | OCH$_3$ | OCH$_3$ | |
| J-2 | Q-26 (R$_7$=H, R$_8$=H) | H | H | Cl | OCH$_3$ | |
| J-2 | Q-26 (R$_7$=CH$_3$, R$_8$=H) | H | H | CH$_3$ | OCH$_3$ | |
| J-2 | Q-27 (R$_7$=H, R$_8$=H) | H | H | CH$_3$ | OCH$_3$ | |
| J-2 | Q-27 (R$_7$=CH$_3$, R$_8$=CH$_3$) | CH$_3$ | H | OCH$_3$ | OCH$_3$ | |
| J-2 | Q-28 (R$_7$=H, R$_8$=H) | H | H | OCH$_3$ | OCH$_3$ | |
| J-2 | Q-28 (R$_7$=CH$_3$, R$_8$=H) | H | H | OCH$_3$ | OCH$_3$ | |
| J-2 | Q-28 (R$_7$=H, R$_8$=CH$_3$) | H | 5-OCH$_3$ | OCH$_3$ | OCH$_3$ | |
| J-2 | Q-29 (R$_7$=H, R$_8$=H) | H | H | OCH$_3$ | OCH$_3$ | |

TABLE 1-continued

| | | | General Formula 1 | | | | |
|---|---|---|---|---|---|---|---|
| J | Q | | R | $R_1$ | X | Y | m.p. (°C.) |
| J-2 | Q-29 ($R_7$=CH$_3$, $R_8$=H) | | H | H | OCH$_3$ | OCF$_2$H | |
| J-2 | Q-29 ($R_7$=H, $R_8$=CH$_3$) | | H | 5-Cl | OCH$_3$ | OCH$_3$ | |
| J-2 | Q-30 ($R_7$=H, $R_8$=H) | | CH$_3$ | H | OCH$_3$ | OCH$_3$ | |
| J-2 | Q-30 ($R_7$=CH$_3$, $R_8$=CH$_3$) | | H | H | OCH$_3$ | CH$_3$ | |
| J-2 | Q-30 ($R_7$=C$_2$H$_5$, $R_8$=H) | | H | 5-OCH$_3$ | OCH$_3$ | OCH$_3$ | |
| J-2 | Q-31 ($R_7$=H, $R_8$=H) | | H | H | OCF$_2$H | OCH$_3$ | |
| J-2 | Q-31 ($R_7$=i-C$_3$H$_7$, R=H) | | H | H | OCH$_3$ | CH$_3$ | |
| J-2 | Q-31 ($R_7$=H, $R_8$=n-C$_4$H$_9$) | | H | 5-Cl | CH$_3$ | CH$_3$ | |
| J-2 | Q-32 ($R_7$=H, $R_8$=H, $R_3$=CH$_3$) | | H | H | CH$_3$ | OCH$_3$ | |
| J-2 | Q-32 ($R_7$=CH$_3$, $R_8$=H, $R_3$=CH$_3$) | | H | H | CH$_3$ | OCH$_3$ | |
| J-2 | Q-32 ($R_7$=H, $R_8$=CH$_3$, $R_3$=C$_2$H$_5$) | | H | 5-CH$_3$ | OCH$_3$ | OCH$_3$ | |
| J-2 | Q-33 ($R_7$=H, $R_8$=H, $R_8$=CH$_3$) | | H | H | OCH$_3$ | OCH$_3$ | |
| J-2 | Q-33 ($R_7$=CH$_3$, $R_8$=CH$_3$, $R_3$=i-C$_3$H$_7$) | | H | H | Cl | OCH$_3$ | |
| J-2 | Q-33 ($R_7$=C$_2$H$_5$, $R_8$=H, $R_3$=n-C$_4$H$_9$) | | H | H | CH$_3$ | OCH$_3$ | |
| J-2 | Q-34 ($R_7$=H, $R_8$=H, $R_3$=CH$_3$) | | CH$_3$ | H | CH$_3$ | OCH$_3$ | |
| J-2 | Q-34 ($R_7$=i-C$_3$H$_7$, $R_8$=H, $R_3$=CH$_3$) | | H | H | CH$_3$ | OCH$_3$ | |
| J-2 | Q-34 ($R_7$=H, $R_8$=n-C$_4$H$_9$, $R_3$=CH$_3$) | | H | H | OCH$_3$ | OCH$_3$ | |
| J-2 | Q-35 ($R_7$=H, $R_8$=H, $R_9$=H) | | H | H | OCH$_3$ | OCH$_3$ | |
| J-2 | Q-35 ($R_7$=CH$_3$, $R_8$=CH$_3$, $R_9$=H) | | H | 5-OCH$_3$ | OCH$_3$ | OCH$_3$ | |
| J-2 | Q-35 ($R_7$=H, $R_8$=H, $R_2$=H) | | H | H | OCH$_3$ | OCH$_3$ | |
| J-2 | Q-36 ($R_7$=CH$_3$, $R_8$=H, $R_2$=CH$_3$) | | H | H | OCH$_3$ | OCF$_2$H | |
| J-2 | Q-36 ($R_7$=H, $R_8$=H, $R_2$=C$_2$H$_5$) | | H | 5-Cl | OCH$_3$ | OCH$_3$ | |
| J-2 | Q-37 ($R_7$=H, $R_8$=H, $R_2$=H) | | CH$_3$ | H | OCH$_3$ | OCH$_3$ | |
| J-2 | Q-37 ($R_7$=H, $R_8$=H, $R_2$=i-C$_3$H$_7$) | | H | H | OCH$_3$ | OCH$_3$ | |
| J-2 | Q-37 ($R_7$=H, $R_8$=H, $R_2$=n-C$_4$H$_9$) | | H | 5-OCH$_3$ | OCH$_3$ | OCH$_3$ | |
| J-2 | Q-38 ($R_7$=CH$_3$, $R_8$=H, $R_2$=OCH$_2$CH$_2$F) | | H | H | OCF$_2$H | CH$_3$ | |
| J-2 | Q-38 ($R_7$=H, $R_8$=H, $R_2$=Cl) | | H | 5-Cl | OCH$_3$ | CH$_3$ | |
| J-2 | Q-39 ($R_7$=H, $R_8$=H, $R_9$=H) | | H | H | CH$_3$ | CH$_3$ | |
| J-2 | Q-39 ($R_7$=C$_2$H$_5$, $R_8$=H, $R_9$=H) | | H | 5-CH$_3$ | CH$_3$ | OCH$_3$ | |
| J-2 | Q-39 ($R_7$=H, $R_8$=H, $R_9$=CH$_3$) | | H | H | OCH$_3$ | OCH$_3$ | |
| J-2 | Q-40 ($R_7$=H, $R_8$=H) | | H | H | OCH$_3$ | OCH$_3$ | |
| J-2 | Q-40 ($R_7$=CH$_3$, $R_8$=H) | | CH$_3$ | H | OCH$_3$ | OCH$_3$ | |
| J-2 | Q-40 ($R_7$=H, $R_8$=CH$_3$) | | H | H | OCH$_3$ | OCH$_3$ | |
| J-2 | Q-41 ($R_7$=H, $R_8$=H) | | H | H | Cl | OCH$_3$ | |
| J-2 | Q-41 ($R_7$=CH$_3$, $R_8$=CH$_3$) | | H | H | CH$_3$ | OCH$_3$ | |
| J-2 | Q-41 ($R_7$=H, $R_8$=C$_2$H$_5$) | | H | H | CH$_3$ | OCH$_3$ | |
| J-2 | Q-42 ($R_7$=H, $R_8$=H) | | H | H | CH$_3$ | OCH$_3$ | |
| J-2 | Q-42 ($R_7$=CH$_3$, $R_8$=CH$_3$) | | CH$_3$ | H | OCH$_3$ | OCH$_3$ | |
| J-2 | Q-42 ($R_7$=C$_2$H$_5$, $R_8$=H, $R_3$=C$_2$H$_5$) | | H | 5-OCH$_3$ | OCH$_3$ | OCH$_3$ | |
| J-2 | Q-43 ($R_7$=H, $R_8$=H, $R_3$=H) | | H | H | OCH$_3$ | OCH$_3$ | |
| J-2 | Q-43 ($R_7$=H, $R_8$=H, $R_3$=CH$_3$) | | H | H | OCH$_3$ | OCH$_3$ | |
| J-2 | Q-43 ($R_7$=CH$_3$, $R_8$=H, $R_3$=CH$_3$) | | H | 5-Cl | OCH$_3$ | OCF$_2$H | |
| J-2 | Q-44 ($R_7$=H, $R_8$=H, $R_3$=CH$_3$) | | H | H | OCH$_3$ | OCH$_3$ | |
| J-2 | Q-44 ($R_7$=CH$_3$, $R_8$=H, $R_3$=C$_2$H$_5$) | | CH$_3$ | H | OCH$_3$ | OCH$_3$ | |
| J-2 | Q-45 ($R_7$=H, $R_8$=H, $R_3$=H) | | H | 5-OCH$_3$ | OCH$_3$ | OCH$_3$ | |
| J-2 | Q-45 ($R_7$=C$_2$H$_5$, $R_8$=H, $R_3$=CH$_3$) | | H | H | CH$_3$ | CH$_3$ | |
| J-2 | Q-45 ($R_7$=CH$_3$, $R_8$=CH$_3$, $R_3$=CH$_3$) | | H | 5-Cl | OCH$_3$ | CH$_3$ | |
| J-2 | Q-46 ($R_7$=H, $R_8$=H, $R_9$=H) | | H | H | CH$_3$ | OCH$_3$ | |

TABLE 1-continued

General Formula 1

| J | Q | R | R₁ | X | Y | m.p. (°C.) |
|---|---|---|----|---|---|------------|
| J-2 | Q-46 (R₇=CH₃, R₈=H, R₉=H) | H | H | CH₃ | OCH₃ | |
| J-2 | Q-46 (R₇=CH₃, R₈=CH₃, R₉=H) | H | 5-CH₃ | OCH₃ | OCH₃ | |
| J-2 | Q-47 (R₇=H, R₈=CH₃, R₂=H) | H | H | OCH₃ | OCH₃ | |
| J-2 | Q-47 (R₇=H, R₈=CH₃, R₂=CH₃) | H | H | Cl | OCH₃ | |
| J-2 | Q-47 (R₇=H, R₈=H, R₂=C₂H₅) | H | H | CH₃ | OCH₃ | |
| J-2 | Q-48 (R₇=H, R₈=H, R₂=H) | CH₃ | H | CH₃ | OCH₃ | |
| J-2 | Q-48 (R₇=CH₃, R₈=CH₃, R₂=CH₃) | H | H | CH₃ | OCH₃ | |
| J-2 | Q-48 (R₇=H, R₈=C₂H₅, R₂=C₂H₅) | H | H | OCH₃ | OCH₃ | |
| J-2 | Q-49 (R₇=H, R₈=H, R₂=H) | H | H | OCH₃ | OCH₃ | |
| J-2 | Q-49 (R₇=CH₃, R₈=CH₃, R₂=H) | H | 5-OCH₃ | OCH₃ | OCH₃ | |
| J-2 | Q-49 (R₇=CH₃, R₈=CH₃, R₂=CH₃) | H | H | OCH₃ | OCH₃ | |
| J-2 | Q-50 (R₇=H, R₈=H, R₂=H) | H | H | OCH₃ | OCF₂H | |
| J-2 | Q-50 (R₇=CH₃, R₈=CH₃, R₂=CH₃) | H | 5-Cl | OCH₃ | OCH₃ | |
| J-2 | Q-50 (R₇=CH₃, R₈=CH₃, R₂=CH₃) | H | H | OCH₃ | OCH₃ | |
| J-2 | Q-51 (R₇=H, R₈=H, R₉=H) | CH₃ | H | OCH₃ | OCH₃ | |
| J-2 | Q-51 (R₇=H, R₈=H, R₉=CH₃) | H | 5-OCH₃ | OCH₃ | OCH₃ | |
| J-2 | Q-51 (R₇=H, R₈=H, R₉=s-C₄H₉) | H | H | OCH₃ | OCH₃ | |
| J-2 | Q-52 (R₇=H, R₈=H, R₉=H) | H | H | OCH₃ | CH₃ | |
| J-2 | Q-52 (R₇=CH₃, R₈=H, R₉=H) | H | 5-Cl | OCF₂H | CH₃ | |
| J-2 | Q-52 (R₇=H, R₈=H, R₉=H) | H | H | OCH₃ | OCH₃ | |
| J-2 | Q-53 (R₇=CH₃, R₈=CH₃, R₉=CH₃) | H | 5-CH₃ | CH₃ | OCH₃ | |
| J-2 | Q-53 (R₇=H, R₈=H, R₉=CH₃) | H | H | OCH₃ | OCH₃ | |
| J-2 | Q-54 (R₇=CH₃, R₈=H, R₉=H) | H | H | OCH₃ | OCH₃ | |
| J-2 | Q-54 (R₇=H, R₈=H, R₉=i-C₃H₇) | H | H | Cl | OCH₃ | |
| J-2 | Q-55 (R₇=H, R₈=H, R₉=H, R₃=H) | H | H | CH₃ | OCH₃ | |
| J-2 | Q-55 (R₇=H, R₈=H, R₉=CH₃, R₃=CH₃) | H | H | CH₃ | OCH₃ | |
| J-2 | Q-55 (R₇=H, R₈=H, R₉=s-C₄H₉, R₃=H) | H | H | OCH₃ | OCH₃ | |
| J-2 | Q-56 (R₇=H, R₈=H, R₉=H, R₃=C₂H₅) | H | H | OCH₃ | OCH₃ | |
| J-2 | Q-56 (R₇=CH₃, R₈=H, R₉=H, R₃=H) | H | 5-OCH₃ | CH₃ | OCH₃ | |
| J-2 | Q-56 (R₇=H, R₈=H, R₉=CH₃, R₃=CH₃) | H | H | CH₃ | OCH₃ | |
| J-2 | Q-57 (R₇=H, R₈=H, R₉=H, R₃=i-C₃H₇) | H | H | CH₃ | OCH₃ | |
| J-2 | Q-57 (R₇=CH₃, R₈=CH₃, R₉=CH₃, R₃=H) | H | 5-Cl | OCH₃ | OCF₂H | |
| J-2 | Q-57 (R₇=H, R₈=H, R₉=CH₃, R₃=H) | H | H | OCH₃ | OCH₃ | |
| J-2 | Q-58 (R₇=H, R₈=H, R₉=CH₃, R₃=CH₃) | H | H | OCH₃ | CH₃ | |
| J-2 | Q-58 (R₇=CH₃, R₈=H, R₉=H, R₃=CH₃) | H | 5-OCH₃ | OCH₃ | OCH₃ | |
| J-2 | Q-58 (R₇=H, R₈=H, R₉=i-C₃H₇, R₃=CH₃) | H | H | OCH₃ | OCH₃ | |
| J-2 | Q-59 (R₇=H, R₈=H, R₉=H, R₁₀=H) | H | H | OCH₃ | OCH₃ | |
| J-2 | Q-59 (R₇=H, R₈=H, R₉=H, R₁₀=CH₃) | H | H | OCF₂H | CH₃ | |
| J-2 | Q-59 (R₇=H, R₈=H, R₉=H, R₁₀=s-C₄H₉) | H | 5-Cl | CH₃ | CH₃ | |
| J-2 | Q-60 (R₇=H, R₈=H, R₉=H, R₂=H) | H | H | CH₃ | CH₃ | |
| J-2 | Q-60 (R₇=H, R₈=H, R₉=H, R₂=O(CH₂)₃Br) | H | 5-CH₃ | CH₃ | OCH₃ | |
| J-2 | Q-60 (R₇=H, R₈=H, R₉=H, R₂=Br) | H | H | OCH₃ | OCH₃ | |
| J-2 | Q-61 (R₇=H, R₈=H, R₉=H, R₂=H) | H | H | OCH₃ | OCH₃ | |
| J-2 | Q-61 (R₇=CH₃, R₈=H, R₉=H, R₂=OCH₂F) | H | H | OCH₃ | OCH₃ | |
| J-2 | Q-61 (R₇=H, R₈=CH₃, R₉=H, R₂=O(CH₂)₃CH₃) | H | H | OCH₃ | OCH₃ | |
| J-2 | Q-62 (R₇=H, R₈=H, R₉=H, R₂=CH₃) | H | H | OCH₃ | OCH₃ | |
| J-2 | Q-62 (R₇=CH₃, R₈=H, R₉=H, R₂=H) | H | H | Cl | OCH₃ | |
| J-2 | Q-62 (R₇=Cl, R₈=H, R₉=H) | H | H | CH₃ | OCH₃ | |
| J-2 | Q-63 (R₇=H, R₈=H, R₉=H) | H | H | OCH₃ | OCH₃ | |
| J-2 | Q-63 | H | H | OCH₃ | OCH₃ | |

TABLE 1-continued

| | | | General Formula 1 | | | |
|---|---|---|---|---|---|---|
| J | Q | R | R₁ | X | Y | m.p. (°C.) |
| J-2 | Q-63 (R₇=CH₃, R₈=H, R₉=H) | H | H | OCH₃ | OCH₃ | |
| J-2 | Q-63 (R₇=H, R₈=H, R₉=CH₃) | H | 5-OCH₃ | OCH₃ | OCH₃ | |
| J-2 | Q-64 (R₇=H, R₈=H, R₉=H) | H | H | OCH₃ | OCF₂H | |
| J-2 | Q-64 (R₇=C₂H₅, R₈=H, R₉=H) | H | 5-Cl | OCH₃ | OCH₃ | |
| J-2 | Q-64 (R₇=H, R₈=H, R₉=C₂H₅) | H | H | OCH₃ | OCH₃ | |
| J-2 | Q-65 (R₇=n-C₄H₉, R₈=H, R₉=H) | CH₃ | H | OCH₃ | CH₃ | |
| J-2 | Q-65 (R₇=H, R₈=CH₃, R₉=i-C₃H₇) | H | 5-OCH₃ | OCH₃ | OCH₃ | |
| J-2 | Q-66 (R₇=H, R₈=H, R₉=H) | H | H | OCH₃ | OCH₃ | |
| J-2 | Q-66 (R₇=i-C₃H₇, R₈=H, R₉=H) | H | 5-Cl | CH₃ | CH₃ | |
| J-2 | Q-66 (R₇=H, R₈=C₂H₅, R₉=CH₃) | H | H | OCF₂H | CH₃ | |
| J-2 | Q-67 (R₇=H, R₈=H, R₉=H, R₃=H) | H | H | OCH₃ | OCH₃ | |
| J-2 | Q-67 (R₇=CH₃R₈=H, R₉=H, R₃=CH₃) | H | 5-CH₃ | CH₃ | OCH₃ | |
| J-2 | Q-67 (R₇=H, R₈=H, R₉=CH₃, R₃=C₂H₅) | H | H | CH₃ | OCH₃ | |
| J-2 | Q-68 (R₇=H, R₈=H, R₉=H, R₃=CH₃) | H | H | OCH₃ | OCH₃ | |
| J-2 | Q-68 (R₇=C₂H₅, R₈=H, R₉=H, R₃=i-C₃H₇) | H | H | Cl | OCH₃ | |
| J-2 | Q-68 (R₇=H, R₈=H, R₉=C₂H₅, R₃=n-C₄H₉) | H | H | CH₃ | OCH₃ | |
| J-2 | Q-69 (R₇=H, R₈=H, R₉=H, R₃=CH₃) | H | H | CH₃ | OCH₃ | |
| J-2 | Q-69 (R₇=n-C₄H₉, R₈=H, R₉=H, R₃=C₂H₅) | H | H | OCH₃ | OCH₃ | |
| J-2 | Q-69 (R₇=H, R₈=CH₃, R₉=i-C₃H₇, R₃=H) | H | H | OCH₃ | OCH₃ | |
| J-2 | Q-70 (R₇=H, R₈=H, R₉=H, R₃=CH₃) | H | H | OCH₃ | OCH₃ | |
| J-2 | Q-70 (R₇=i-C₃H₇, R₈=H, R₉=H, R₃=CH₃) | H | H | OCH₃ | OCH₃ | |
| J-2 | Q-70 (R₇=H, R₈=C₂H₅, R₉=CH₃, R₃=H) | H | H | OCH₃ | OCH₃ | |
| J-2 | Q-71 (R₇=H, R₈=H, R₉=H, R₁₀=H) | H | H | OCH₃ | OCF₂H | |
| J-2 | Q-71 (R₇=CH₃, R₈=H, R₉=H, R₁₀=H) | H | 5-OCH₃ | OCH₃ | OCH₃ | |
| J-2 | Q-71 (R₇=H, R₈=H, R₉=H, R₁₀=CH₃) | H | H | OCH₃ | OCH₃ | |
| J-2 | Q-72 (R₇=H, R₈=H, R₉=H, R₂=H) | H | 5-Cl | OCH₃ | OCH₃ | |
| J-2 | Q-72 (R₇=H, R₈=H, R₉=H, R₂=CH₃) | CH₃ | H | OCH₃ | CH₃ | |
| J-2 | Q-72 (R₇=CH₃, R₈=H, R₉=H, R₂=H) | H | 5-OCH₃ | OCH₃ | OCH₃ | |
| J-2 | Q-73 (R₇=H, R₈=H, R₉=H, R₂=H) | H | H | OCH₃ | CH₃ | |
| J-2 | Q-73 (R₇=CH₃, R₈=H, R₉=CH₃, R₂=C₂H₅) | H | 5-Cl | OCH₃ | CH₃ | |
| J-2 | Q-74 (R₇=H, R₈=H, R₉=H, R₂=H) | H | H | OCF₂H | CH₃ | |
| J-2 | Q-74 (R₇=CH₃, R₈=H, R₉=CH₃, R₂=H) | H | 5-CH₃ | OCH₃ | OCH₃ | |
| J-2 | Q-74 (R₇=H, R₈=H, R₉=H, R₂=C₂H₅) | H | H | OCH₃ | OCH₃ | |
| J-2 | Q-75 (R₇=H, R₈=H, R₉=H) | H | H | OCH₃ | OCH₃ | |
| J-2 | Q-75 (R₇=CH₃, R₈=H, R₉=CH₃) | H | 5-OCH₃ | OCH₃ | OCH₃ | |
| J-2 | Q-76 (R₇=H, R₈=H, R₉=H) | H | H | OCH₃ | OCH₃ | |
| J-2 | Q-76 (R₇=H, R₈=H, R₉=CH₃) | H | 5-Cl | OCH₃ | OCH₃ | |
| J-2 | Q-76 (R₇=C₂H₅, R₈=H, R₉=C₂H₅) | H | H | OCH₃ | OCH₃ | |
| J-2 | Q-77 (R₇=H, R₈=H, R₉=H) | H | 5-CH₃ | OCH₃ | OCH₃ | |
| J-2 | Q-77 (R₇=H, R₈=H, R₉=n-C₃H₇) | H | H | OCH₃ | OCH | |
| J-2 | Q-77 (R₇=H, R₈=CH₃, R₉=H) | CH₃ | H | OCH₃ | OCH₃ | |
| J-2 | Q-78 (R₇=H, R₈=H, R₉=H) | H | 5-OCH₃ | OCH₃ | OCF₂H | |
| J-2 | Q-78 (R₇=H, R₈=H, R₉=s-C₄H₉) | H | H | OCH₃ | OCH₃ | |
| J-2 | Q-78 (R₇=n-C₃H₇, R₈=H, R₉=H) | H | 5-Cl | OCH₃ | OCH₃ | |
| J-2 | Q-79 (R₇=H, R₈=H, R₉=H, R₃=H) | H | H | OCH₃ | OCH₃ | |
| J-2 | Q-79 (R₇=H, R₈=H, R₉=H, R₃=C₂H₅) | CH₃ | H | OCH₃ | OCH₃ | |
| J-2 | Q-79 (R₇=H, R₈=H, R₉=H, R₃=CH₃) | H | 5-OCH₃ | OCH₃ | OCH₃ | |
| J-2 | Q-80 (R₇=H, R₈=H, R₉=H, R₃=CH₃) | H | H | OCH₃ | OCH₃ | |

TABLE 1-continued

| | | | General Formula 1 | | | | |
|---|---|---|---|---|---|---|---|
| J | Q | | R | $R_1$ | X | Y | m.p. (°C.) |
| J-2 | Q-80 ($R_7$=CH$_3$, $R_8$=H, $R_9$=H, $R_3$=CH$_3$) | | H | H | OCF$_2$H | CH$_3$ | |
| J-2 | Q-80 ($R_7$=H, $R_8$=H, $R_9$=CH$_3$, $R_3$=C$_2$H$_5$) | | H | 5-Cl | OCH$_3$ | CH$_3$ | |
| J-2 | Q-81 ($R_7$=H, $R_8$=H, $R_9$=H, $R_3$=CH$_3$) | | H | H | CH$_3$ | OCH$_3$ | |
| J-2 | Q-81 ($R_7$=H, $R_8$=H, $R_9$=H, $R_3$=i-C$_3$H$_7$) | | H | H | CH$_3$ | OCH$_3$ | |
| J-2 | Q-81 ($R_7$=CH$_3$, $R_8$=H, $R_9$=CH$_3$, $R_3$=CH$_3$) | | H | 5-CH$_3$ | OCH$_3$ | OCH$_3$ | |
| J-2 | Q-82 ($R_7$=H, $R_8$=H, $R_9$=H, $R_3$=CH$_3$) | | H | H | OCH$_3$ | OCH$_3$ | |
| J-2 | Q-82 ($R_7$=CH$_3$, $R_8$=H, $R_9$=CH$_3$, $R_3$=H) | | H | H | Cl | OCH$_3$ | |
| J-2 | Q-82 ($R_7$=H, $R_8$=H, $R_9$=C$_2$H$_5$, $R_3$=CH$_3$) | | H | H | CH$_3$ | OCH$_3$ | |
| J-2 | Q-83 ($R_7$=CH$_3$, $R_8$=H, $R_9$=H, $R_{10}$=H) | | CH$_3$ | H | CH$_3$ | OCH$_3$ | |
| J-2 | Q-83 ($R_7$=CH$_3$, $R_8$=CH$_3$, $R_9$=H, $R_{10}$=H) | | H | H | OCH$_3$ | OCH$_3$ | |
| J-2 | Q-84 ($R_7$=H, $R_8$=H, $R_9$=H) | | H | H | OCH$_3$ | OCH$_3$ | |
| J-2 | Q-84 ($R_7$=H, $R_8$=H, $R_9$=CH$_3$) | | H | 5-OCH$_3$ | OCH$_3$ | OCH$_3$ | |
| J-2 | Q-85 ($R_7$=H, $R_8$=H, $R_9$=C$_2$H$_5$, $R_9$=H) | | H | H | OCH$_3$ | OCH$_3$ | |
| J-2 | Q-85 ($R_7$=H, $R_8$=H, $R_9$=H) | | H | H | OCF$_2$H | OCF$_2$H | |
| J-2 | Q-85 ($R_7$=H, $R_8$=H, $R_9$=H) | | H | 5-Cl | OCH$_3$ | OCH$_3$ | |
| J-2 | Q-86 ($R_7$=H, $R_8$=H, $R_9$=C$_2$H$_5$) | | H | H | OCH$_3$ | OCH$_3$ | |
| J-2 | Q-86 ($R_7$=H, $R_8$=H, $R_9$=H) | | H | H | OCH$_3$ | OCH$_3$ | |
| J-2 | Q-86 ($R_7$=CH$_3$, $R_8$=H, $R_9$=H) | | CH$_3$ | 5-OCH$_3$ | OCH$_3$ | OCH$_3$ | |
| J-2 | Q-87 ($R_7$=H, $R_8$=H, $R_9$=C$_2$H$_5$) | | H | H | OCH$_3$ | OCH$_3$ | |
| J-2 | Q-87 ($R_7$=H, $R_8$=H, $R_9$=H) | | H | 5-Cl | OCH$_3$ | CH$_3$ | |
| J-2 | Q-87 ($R_7$=CH$_3$, $R_8$=H, $R_9$=CH$_3$) | | H | H | OCF$_2$H | CH$_3$ | |
| J-2 | Q-88 ($R_7$=H, $R_8$=H, $R_9$=H) | | H | 5-CH$_3$ | OCH$_3$ | OCH$_3$ | |
| J-2 | Q-88 ($R_7$=CH$_3$, $R_8$=H, $R_9$=CH$_3$) | | H | H | CH$_3$ | OCH$_3$ | |
| J-2 | Q-88 ($R_7$=H, $R_8$=H, $R_9$=H) | | H | H | CH$_3$ | OCH$_3$ | |
| J-2 | Q-89 ($R_7$=H, $R_8$=H, $R_9$=H) | | H | H | OCH$_3$ | OCH$_3$ | |
| J-2 | Q-89 ($R_7$=H, $R_8$=CH$_3$, $R_9$=H) | | H | H | Cl | OCH$_3$ | |
| J-2 | Q-90 ($R_7$=H, $R_8$=H, $R_9$=H, $R_3$=CH$_3$) | | CH$_3$ | H | CH$_3$ | OCH$_3$ | |
| J-2 | Q-90 ($R_7$=H, $R_8$=H, $R_9$=H, $R_3$=C$_2$H$_5$) | | H | H | CH$_3$ | OCH$_3$ | |
| J-2 | Q-90 ($R_7$=H, $R_8$=H, $R_9$=CH$_3$, $R_3$=CH$_3$) | | H | H | CH$_3$ | OCH$_3$ | |
| J-2 | Q-91 ($R_7$=H, $R_8$=H, $R_9$=H, $R_3$=CH$_3$) | | H | H | OCH$_3$ | OCH$_3$ | |
| J-2 | Q-91 ($R_7$=CH$_3$, $R_8$=H, $R_9$=H, $R_3$=H) | | H | 5-OCH$_3$ | OCH$_3$ | OCH$_3$ | |
| J-2 | Q-91 ($R_7$=H, $R_8$=H, $R_9$=CH$_3$, $R_3$=CH$_3$) | | H | H | OCH$_3$ | OCH$_3$ | |
| J-2 | Q-92 ($R_7$=H, $R_8$=H, $R_9$=H, $R_{10}$=CH$_3$) | | H | H | OCH$_3$ | OCH$_3$ | |
| J-2 | Q-92 ($R_7$=H, $R_8$=CH$_3$, $R_9$=H, $R_{10}$=H) | | H | 5-Cl | OCH$_3$ | OCH$_3$ | |
| J-2 | Q-93 ($R_7$=H, $R_8$=H, $R_9$=H) | | H | H | OCH$_3$ | OCH$_3$ | |
| J-2 | Q-93 ($R_7$=H, $R_8$=H, $R_9$=H) | | CH$_3$ | H | OCH$_3$ | OCF$_2$H | |
| J-2 | Q-93 ($R_7$=CH$_3$, $R_8$=H, $R_9$=H) | | H | 5-OCH$_3$ | OCH$_3$ | OCH$_3$ | |
| J-2 | Q-94 ($R_7$=CH$_3$, $R_8$=H, $R_9$=H) | | H | H | OCH$_3$ | OCH$_3$ | |
| J-2 | Q-94 ($R_7$=H, $R_8$=H, $R_9$=n-C$_4$H$_9$) | | H | H | OCF$_2$H | OCH$_3$ | |
| J-2 | Q-94 ($R_7$=H, $R_8$=H, $R_9$=H) | | H | H | OCH$_3$ | CH$_3$ | |
| J-2 | Q-95 ($R_7$=H, $R_8$=H, $R_9$=H) | | H | 5-Cl | CH$_3$ | CH$_3$ | |
| J-2 | Q-95 ($R_7$=H, $R_8$=H, $R_9$=CH$_3$) | | H | H | OCH$_3$ | CH$_3$ | |
| J-2 | Q-95 ($R_7$=H, $R_8$=H, $R_9$=s-C$_4$H$_9$) | | H | 5-CH$_3$ | OCH$_3$ | OCH$_3$ | |
| J-2 | Q-96 ($R_7$=H, $R_8$=H, $R_9$=H) | | H | H | OCH$_3$ | OCH$_3$ | |
| J-2 | Q-96 ($R_7$=CH$_3$, $R_8$=H, $R_9$=H) | | H | H | Cl | OCH$_3$ | |
| J-2 | Q-96 ($R_7$=H, $R_8$=H, $R_9$=CH$_3$) | | H | H | CH$_3$ | OCH$_3$ | |
| J-2 | Q-97 ($R_7$=H, $R_8$=H, $R_9$=H) | | H | H | CH$_3$ | OCH$_3$ | |

TABLE 1-continued

| J | Q | R | General Formula 1 R₁ | X | Y | m.p. (°C.) |
|---|---|---|---|---|---|---|
| J-2 | Q-97 (R₇=CH₃, R₈=CH₃, R₉=CH₃) | CH₃ | H | CH₃ | OCH₃ | |
| J-2 | Q-97 (R₇=H, R₈=H, R₉=CH₃) | H | H | OCH₃ | OCH₃ | |
| J-2 | Q-98 (R₇=H, R₈=H, R₉=H) | H | H | OCH₃ | OCH₃ | |
| J-2 | Q-98 (R₇=CH₃, R₈=H, R₉=H) | H | H | OCH₃ | OCH₃ | |
| J-2 | Q-98 (R₇=H, R₈=H, R₉=i-C₃H₇) | H | 5-OCH₃ | OCH₃ | OCH₃ | |
| J-2 | Q-99 (R₇=H, R₈=H, R₉=CH₃, R₃=H) | H | H | OCH₃ | OCH₃ | |
| J-2 | Q-99 (R₇=H, R₈=H, R₉=CH₃, R₃=C₂H₅) | H | H | OCH₃ | OCF₂H | |
| J-2 | Q-100 (R₇=H, R₈=H, R₉=H, R₃=H) | CH₃ | H | OCH₃ | OCH₃ | |
| J-2 | Q-100 (R₇=CH₃, R₈=H, R₉=H, R₃=CH₃) | H | H | OCH₃ | CH₃ | |
| J-2 | Q-100 (R₇=H, R₈=H, R₉=H, R₃=i-C₃H₇) | H | 5-OCH₃ | OCH₃ | OCH₃ | |
| J-2 | Q-101 (R₇=CH₃, R₈=CH₃, R₉=CH₃, R₃=H) | H | H | OCH₃ | CH₃ | |
| J-2 | Q-101 (R₇=H, R₈=H, R₉=H, R₃=H) | H | 5-Cl | OCF₂H | CH₃ | |
| J-2 | Q-102 (R₇=CH₃, R₈=H, R₉=H, R₃=CH₃) | H | H | OCH₃ | OCH₃ | |
| J-2 | Q-102 (R₇=H, R₈=H, R₉=i-C₃H₇, R=CH₃) | H | 5-CH₃ | CH₃ | OCH₃ | |
| J-2 | Q-103 (R₇=H, R₈=H, R₉=H, R₁₀=H) | H | H | CH₃ | OCH₃ | |
| J-2 | Q-103 (R₇=CH₃, R₈=H, R₉=H, R₁₀=CH₃) | H | H | Cl | OCH₃ | |
| J-2 | Q-103 (R₇=H, R₈=H, R₉=H, R₁₀=s-C₄H₉) | H | H | CH₃ | OCH₃ | |
| J-2 | Q-104 (R₇=H, R₈=H, R₉=H, R₂=H) | H | H | CH₃ | OCH₃ | |
| J-2 | Q-104 (R₇=CH₃, R₈=H, R₉=H, R₂=OC₂H₅) | H | H | OCH₃ | OCH₃ | |
| J-2 | Q-104 (R₇=H, R₈=H, R₉=H, R₂=Br) | H | H | OCH₃ | OCH₃ | |
| J-2 | Q-105 (R₇=CH₃, R₈=H, R₉=H, R₂=CH₃) | H | H | OCH₃ | OCH₃ | |
| J-2 | Q-105 (R₇=H, R₈=CH₃, R₉=H, R₂=C₂H₅) | H | 5-OCH₃ | OCH₃ | OCH₃ | |
| J-2 | Q-106 (R₇=CH₃, R₈=H, R₉=H, R₂=CH₃) | H | H | OCH₃ | OCH₃ | |
| J-2 | Q-106 (R₇=Cl, R₈=H, R₉=H, R₂=H) | H | 5-Cl | OCH₃ | OCF₂H | |
| J-2 | Q-107 (R₇=H, R₈=H, R₉=H, R₂=H) | H | H | OCH₃ | OCH₃ | |
| J-2 | Q-107 (R₇=CH₃, R₈=H, R₉=H, R₂=H) | H | 5-OCH₃ | OCH₃ | OCH₃ | |
| J-2 | Q-108 (R₇=H, R₈=H, R₉=H, R₂=CH₃) | H | H | OCH₃ | OCH₃ | |
| J-2 | Q-108 (R₇=CH₃, R₈=H, R₉=H, R₂=H) | H | 5-Cl | OCF₂H | OCH₃ | |
| J-2 | Q-109 (R₇=CH₃, R₈=H, R₉=H) | H | H | CH₃ | CH₃ | |
| J-2 | Q-109 (R₇=H, R₈=H, R₉=CH₃) | H | 5-CH₃ | CH₃ | OCH₃ | |
| J-2 | Q-110 (R₇=CH₃, R₈=H, R₉=H) | H | H | OCH₃ | OCH₃ | |
| J-2 | Q-110 (R₇=H, R₈=CH₃, R₉=H) | H | H | OCH₃ | OCH₃ | |
| J-2 | Q-111 (R₇=H, R₈=H, R₉=H) | CH₃ | H | OCH₃ | OCH₃ | |
| J-2 | Q-111 (R₇=H, R₈=H, R₉=CH₃) | H | 5-OCH₃ | OCH₃ | OCH₃ | |
| J-2 | Q-112 (R₇=CH₃, R₈=H, R₉=H) | H | H | OCH₃ | OCH₃ | |
| J-2 | Q-112 (R₇=H, R₈=CH₃, R₉=H) | H | H | OCH₃ | OCH₃ | |
| J-2 | Q-113 (R₇=H, R₈=H, R₉=H, R₃=i-C₃H₇) | H | 5-OCH₃ | OCH₃ | OCH₃ | |
| J-2 | Q-113 (R₇=C₂H₅, R₈=H, R₉=C₂H₅, R₃=n-C₄H₉) | H | H | OCH₃ | OCF₂H | |
| J-2 | Q-114 (R₇=H, R₈=H, R₉=H, R₃=CH₃) | H | 5-Cl | OCH₃ | OCH₃ | |
| J-2 | Q-114 (R₇=n-C₄H₉, R₈=H, R₉=H, R₃=C₂H₅) | CH₃ | H | OCH₃ | CH₃ | |

TABLE 1-continued

| | | | General Formula 1 | | | |
|---|---|---|---|---|---|---|
| J | Q | R | $R_1$ | X | Y | m.p. (°C.) |
| J-2 | Q-114 ($R_7$=H, $R_8$=$CH_3$, $R_8$=i-$C_3H_7$, $R_3$=H) | H | 5-$OCH_3$ | $OCH_3$ | $OCH_3$ | |
| J-2 | Q-115 ($R_7$=H, $R_8$=H, $R_9$=H, $R_1$=$CH_3$) | H | H | $OCH_3$ | $OCH_3$ | |
| J-2 | Q-115 ($R_7$=i-$C_3H_7$, $R_8$=H, $R_9$=H, $R_3$=$CH_3$) | H | H | $OCF_2H$ | $CH_3$ | |
| J-2 | Q-115 ($R_7$=H, $R_8$=$C_2H_5$, $R_9$=$CH_3$, $R_3$=H) | H | H | $OCH_3$ | $CH_3$ | |
| J-2 | Q-116 ($R_7$=H, $R_8$=H, $R_9$=H, $R_{10}$=H) | H | H | $CH_3$ | $OCH_3$ | |
| J-2 | Q-116 ($R_7$=$CH_3$, $R_8$=H, $R_9$=H, $R_{10}$=$CH_3$) | H | H | $CH_3$ | $OCH_3$ | |
| J-2 | Q-116 ($R_7$=H, $R_8$=H, $R_9$=H, $R_2$=H) | H | 5-$CH_3$ | $OCH_3$ | $OCH_3$ | |
| J-2 | Q-117 ($R_7$=H, $R_8$=H, $R_9$=H, $R_2$=$CH_3$) | H | H | Cl | $OCH_3$ | |
| J-2 | Q-117 ($R_7$=$CH_3$, $R_8$=H, $R_9$=H, $R_2$=H) | H | H | $CH_3$ | $OCH_3$ | |
| J-2 | Q-117 ($R_7$=H, $R_8$=H, $R_9$=H, $R_{10}$=H) | $CH_3$ | H | $CH_3$ | $OCH_3$ | |
| J-2 | Q-118 ($R_7$=$CH_3$, $R_8$=H, $R_9$=H, $R_{10}$=$CH_3$) | H | H | $CH_3$ | $OCH_3$ | |
| J-2 | Q-118 ($R_7$=H, $R_8$=H, $R_9$=H, $R_2$=$CH_3$) | H | H | $OCH_3$ | $OCH_3$ | |
| J-2 | Q-119 ($R_7$=H, $R_8$=H, $R_9$=H, $R_2$=H) | H | H | $OCH_3$ | $OCH_3$ | |
| J-2 | Q-119 ($R_7$=H, $R_8$=$CH_3$, $R_9$=H, $R_2$=$C_2H_5$) | H | H | $OCH_3$ | $OCH_3$ | |
| J-2 | Q-120 ($R_7$=H, $R_8$=H, $R_9$=H, $R_2$=H) | H | 5-$OCH_3$ | $OCH_3$ | $OCH_3$ | |
| J-2 | Q-120 ($R_7$=H, $R_8$=H, $R_9$=$CH_3$, $R_2$=H) | H | H | $OCH_3$ | $OCF_2H$ | |
| J-2 | Q-120 ($R_7$=H, $R_8$=H, $R_9$=H, $R_2$=$C_2H_5$) | H | 5-Cl | $OCH_3$ | $OCH_3$ | |
| J-2 | Q-121 ($R_7$=$CH_3$, $R_8$=$CH_3$, $R_9$=H, $R_2$=H) | H | H | $OCH_3$ | $CH_3$ | |
| J-2 | Q-122 ($R_7$=H, $R_8$=H, $R_9$=H, $R_2$=H) | H | 5-$OCH_3$ | $OCH_3$ | $OCH_3$ | |
| J-2 | Q-122 ($R_7$=H, $R_8$=H, $R_9$=H, $R_2$=$C_2H_5$) | H | H | $OCH_3$ | $OCH_3$ | |
| J-2 | Q-122 ($R_7$=$CH_3$, $R_8$=H, $R_9$=H, $R_2$=H) | H | 5-Cl | $OCF_2H$ | $CH_3$ | |
| J-2 | Q-123 ($R_7$=H, $R_8$=H, $R_9$=H) | H | H | $CH_3$ | $OCH_3$ | |
| J-2 | Q-123 ($R_7$=H, $R_8$=H, $R_9$=$CH_3$) | H | 5-$OCH_3$ | $CH_3$ | $OCH_3$ | |
| J-2 | Q-123 ($R_7$=$CH_3$, $R_8$=H, $R_9$=$CH_3$) | H | H | Cl | $CH_3$ | |
| J-2 | Q-124 ($R_7$=H, $R_8$=H, $R_9$=H) | H | H | $CH_3$ | $OCH_3$ | |
| J-2 | Q-124 ($R_7$=$C_2H_5$, $R_8$=H, $R_9$=$C_2H_5$) | H | H | $OCH_3$ | $OCH_3$ | |
| J-2 | Q-125 ($R_7$=H, $R_8$=H, $R_9$=H) | H | H | $OCH_3$ | $OCH_3$ | |
| J-2 | Q-125 ($R_7$=H, $R_8$=H, $R_9$=n-$C_4H_9$) | H | H | $OCH_3$ | $OCH_3$ | |
| J-2 | Q-126 ($R_7$=H, $R_8$=$CH_3$, $R_9$=H) | H | H | $OCH_3$ | $OCH_3$ | |
| J-2 | Q-126 ($R_7$=H, $R_8$=H, $R_9$=H) | $CH_3$ | H | $OCH_3$ | $OCH_3$ | |
| J-2 | Q-126 ($R_7$=n-$C_3H_7$, $R_8$=H, $R_9$=s-$C_3H_7$) | H | H | $OCH_3$ | $OCH_3$ | |
| J-2 | Q-127 ($R_7$=H, $R_8$=H, $R_9$=H, $R_3$=H) | H | 5-$OCH_3$ | $OCH_3$ | $OCH_3$ | |
| J-2 | Q-127 ($R_7$=H, $R_8$=H, $R_9$=H, $R_3$=$C_2H_5$) | H | H | $OCH_3$ | $OCF_2H$ | |
| J-2 | Q-127 ($R_7$=$CH_3$, $R_8$=H, $R_9$=H, $R_3$=$C_2H_5$) | H | H | $OCH_3$ | $OCH_3$ | |
| J-2 | Q-128 ($R_7$=$CH_3$, $R_8$=H, $R_9$=H, $R_3$=$CH_3$) | H | 5-Cl | $OCH_3$ | $OCH_3$ | |
| J-2 | Q-128 ($R_7$=H, $R_8$=H, $R_9$=H, $R_3$=$C_2H_5$) | H | H | $OCH_3$ | $OCH_3$ | |
| J-2 | Q-128 ($R_7$=$CH_3$, $R_8$=H, $R_9$=$CH_3$, $R_8$=$C_2H_5$) | $CH_3$ | 5-$OCH_3$ | $OCH_3$ | $OCH_3$ | |
| J-2 | Q-129 ($R_7$=H, $R_8$=$CH_3$, $R_9$=H, $R_9$=$CH_3$) | H | H | $OCH_3$ | $CH_3$ | |
| J-2 | Q-129 ($R_7$=H, $R_8$=$CH_3$, $R_9$=H, $R_3$=i-$C_3H_7$) | H | 5-Cl | $OCF_2H$ | $CH_3$ | |
| J-2 | Q-129 ($R_7$=$CH_3$, $R_8$=H, $R_9$=$CH_3$, $R_3$=$CH_3$) | H | H | $OCH_3$ | $OCH_3$ | |
| J-2 | Q-130 ($R_7$=H, $R_8$=H, $R_9$=H, $R_3$=$CH_3$) | H | 5-$CH_3$ | $CH_3$ | $CH_3$ | |
| J-2 | Q-130 ($R_7$=$CH_3$, $R_8$=H, $R_9$=$C_2H_5$, $R_3$=$CH_3$) | H | H | $CH_3$ | $OCH_3$ | |
| J-2 | Q-131 ($R_7$=H, $R_8$=H, $R_9$=H, $R_{10}$=H) | H | H | $OCH_3$ | $OCH_3$ | |
| J-2 | Q-131 ($R_7$=$CH_3$, $R_8$=$CH_3$, $R_9$=H, $R_{10}$=$CH_3$) | H | H | Cl | $OCH_3$ | |

TABLE 1-continued

General Formula 1

| J | Q | | R | $R_1$ | X | Y | m.p. (°C.) |
|---|---|---|---|---|---|---|---|
| J-2 | Q-131 | ($R_7=CH_3, R_8=CH_3, R_9=H, R_{10}=H$) | H | H | $CH_3$ | $OCH_3$ | |
| J-2 | Q-132 | ($R_7=H, R_8=H, R_9=CH_3$) | H | H | $CH_3$ | $OCH_3$ | |
| J-2 | Q-132 | ($R_7=H, R_8=H, R_9=CH_3$) | $CH_3$ | H | $CH_3$ | $OCH_3$ | |
| J-2 | Q-132 | ($R_7=H, R_8=C_2H_5, R_9=H$) | H | H | $OCH_3$ | $OCH_3$ | |
| J-2 | Q-133 | ($R_7=H, R_8=H, R_9=H$) | H | H | $OCH_3$ | $OCH_3$ | |
| J-2 | Q-133 | ($R_7=CH_3, R_8=H, R_9=H$) | H | H | $OCH_3$ | $OCH_3$ | |
| J-2 | Q-133 | ($R_7=H, R_8=H, R_9=C_2H_5$) | H | 5-$OCH_3$ | $OCH_3$ | $OCH_3$ | |
| J-2 | Q-134 | ($R_7=H, R_8=H, R_9=H$) | H | H | $OCH_3$ | $OCH_3$ | |
| J-2 | Q-134 | ($R_7=CH_3, R_8=H, R_9=H$) | H | H | $OCH_3$ | $OCH_3$ | |
| J-2 | Q-134 | ($R_7=H, R_8=H, R_9=C_2H_5$) | H | 5-Cl | $OCH_3$ | $OCF_2H$ | |
| J-2 | Q-135 | ($R_7=H, R_8=H, R_9=H$) | $CH_3$ | H | $OCH_3$ | $OCH_3$ | |
| J-2 | Q-135 | ($R_7=CH_3, R_8=H, R_9=H$) | H | 5-$OCH_3$ | $OCH_3$ | $OCH_3$ | |
| J-2 | Q-136 | ($R_7=H, R_8=H, R_9=H$) | H | H | $OCH_3$ | $OCH_3$ | |
| J-2 | Q-136 | ($R_7=H, R_8=H, R_9=CH_3$) | H | 5-Cl | $OCH_3$ | $OCH_3$ | |
| J-2 | Q-136 | ($R_7=H, R_8=CH_3, R_9=C_2H_5$) | H | H | $OCF_2H$ | $CH_3$ | |
| J-2 | Q-137 | ($R_7=H, R_8=H, R_9=H$) | H | 5-$OCH_3$ | $OCH_3$ | $CH_3$ | |
| J-2 | Q-137 | ($R_7=CH_3, R_8=H, R_9=H$) | H | 5-$CH_3$ | $CH_3$ | $CH_3$ | |
| J-2 | Q-137 | ($R_7=H, R_8=H, R_9=CH_3$) | H | H | $CH_3$ | $OCH_3$ | |
| J-2 | Q-138 | ($R_7=H, R_8=H, R_9=H$) | H | H | $OCH_3$ | $OCH_3$ | |
| J-2 | Q-138 | ($R_7=CH_3, R_8=H, R_9=CH_3$) | H | H | $CH_3$ | $OCH_3$ | |
| J-2 | Q-139 | ($R_7=CH_3, R_8=CH_3, R_9=H$) | H | H | Cl | $OCH_3$ | |
| J-2 | Q-139 | ($R_7=CH_3, R_8=H, R_9=H$) | $CH_3$ | H | $CH_3$ | $OCH_3$ | |
| J-2 | Q-140 | ($R_7=H, R_8=H, R_9=H, R_3=CH_3$) | H | H | $CH_3$ | $OCH_3$ | |
| J-2 | Q-140 | ($R_7=H, R_8=H, R_9=CH_3, R_3=H$) | H | H | $CH_3$ | $OCH_3$ | |
| J-2 | Q-140 | ($R_7=H, R_8=CH_3, R_9=H, R_3=C_2H_5$) | H | H | $OCH_3$ | $OCH_3$ | |
| J-2 | Q-141 | ($R_7=H, R_8=H, R_9=CH_3, R_3=CH_3$) | H | H | $OCH_3$ | $OCH_3$ | |
| J-2 | Q-141 | ($R_7=H, R_8=H, R_9=H, R_3=CH_3$) | H | 5-$OCH_3$ | $OCH_3$ | $OCH_3$ | |
| J-2 | Q-141 | ($R_7=H, R_8=H, R_9=H, R_3=H$) | H | H | $OCH_3$ | $OCH_3$ | |
| J-2 | Q-142 | ($R_7=H, R_8=H, R_9=H, R_{10}=H$) | H | H | $OCH_3$ | $OCF_2H$ | |
| J-2 | Q-142 | ($R_7=CH_3, R_8=H, R_9=H, R_{10}=H$) | H | 5-Cl | $OCF_2H$ | $OCH_3$ | |
| J-2 | Q-142 | ($R_7=H, R_8=H, R_9=H, R_{10}=CH_3$) | H | H | $OCH_3$ | $OCH_3$ | |
| J-2 | Q-143 | ($R_7=CH_3, R_8=H, R_9=H, R_3=CH_3$) | H | 5-$OCH_3$ | Cl | $CH_3$ | |
| J-2 | Q-143 | ($R_7=H, R_8=H, R_9=H, R_3=H$) | H | H | $CH_3$ | $CH_3$ | |
| J-2 | Q-143 | ($R_7=H, R_8=CH_3, R_9=H, R_3=CH_3$) | H | 5-Cl | $CH_3$ | $CH_3$ | |
| J-2 | Q-144 | ($R_7=H, R_8=H, R_9=CH_3, R_3=CH_3$) | H | H | $CH_3$ | $OCH_3$ | |
| J-2 | Q-144 | ($R_7=H, R_8=C_2H_5, R_9=H, R_3=CH_3$) | H | 5-$CH_3$ | $CH_3$ | $OCH_3$ | |
| J-2 | Q-145 | ($R_7=H, R_8=H, R_9=H$) | H | H | $OCH_3$ | $OCH_3$ | |
| J-2 | Q-145 | ($R_7=CH_3, R_8=H, R_9=CH_3$) | H | H | $OCH_3$ | $OCH_3$ | |
| J-2 | Q-146 | ($R_7=H, R_8=H, R_9=H$) | H | 5-$OCH_3$ | $OCH_3$ | $OCH_3$ | |
| J-2 | Q-146 | ($R_7=CH_3, R_8=H, R_9=H$) | H | 5-Cl | $OCH_3$ | $OCH_3$ | |
| J-2 | Q-146 | ($R_7=H, R_8=H, R_9=n-C_4H_9$) | H | H | $OCH_3$ | $OCH_3$ | |
| J-2 | Q-147 | ($R_7=H, R_8=H, R_9=H$) | H | H | $CH_3$ | $OCH_3$ | |
| J-2 | Q-147 | ($R_7=CH_3, R_8=H, R_9=H$) | H | H | $CH_3$ | $OCH_3$ | |
| J-2 | Q-148 | ($R_7=H, R_8=H, R_9=n-C_4H_9$) | H | H | $OCH_3$ | $OCH_3$ | |
| J-2 | Q-148 | ($R_7=H, R_8=H, R_9=H$) | H | H | $OCH_3$ | $OCH_3$ | |
| J-2 | Q-148 | ($R_7=H, R_8=H, R_9=CH_3$) | H | H | $CH_3$ | $OCF_2H$ | |

TABLE 1-continued

General Formula 1

| J | Q | R | R₁ | X | Y | m.p. (°C.) |
|---|---|---|----|---|---|-----------|
| J-2 | Q-148 (R₇=CH₃, R₈=H, R₉=H) | H | 5-Cl | OCH₃ | OCH₃ | |
| J-2 | Q-149 (R₇=H, R₈=H, R₉=H) | H | H | OCH₃ | OCH₃ | |
| J-2 | Q-149 (R₇=H, R₈=H, R₉=CH₃) | CH₃ | H | OCH₃ | OCH₃ | |
| J-2 | Q-149 (R₇=CH₃, R₈=H, R₉=H) | H | 5-OCH₃ | OCH₃ | OCH₃ | |
| J-2 | Q-150 (R₇=H, R₈=H, R₉=H) | H | H | OCF₂H | OCH₃ | |
| J-2 | Q-150 (R₇=CH₃, R₈=H, R₉=H) | H | 5-Cl | OCH₃ | CH₃ | |
| J-2 | Q-150 (R₇=H, R₈=CH₃, R₉=CH₃) | H | H | CH₃ | CH₃ | |
| J-2 | Q-151 (R₇=CH₃, R₈=H, R₉=H) | H | H | CH₃ | OCH₃ | |
| J-2 | Q-151 (R₇=CH₃, R₈=CH₃, R₉=H) | H | 5-CH₃ | OCH₃ | OCH₃ | |
| J-2 | Q-152 (R₇=H, R₈=H, R₉=H) | H | H | Cl | OCH₃ | |
| J-2 | Q-152 (R₇=C₂H₅, R₈=CH₃, R₉=H) | H | H | CH₃ | OCH₃ | |
| J-2 | Q-152 (R₇=CH₃, R₈=H, R₉=H, R₉=H) | H | H | CH₃ | OCH₃ | |
| J-2 | Q-153 (R₇=H, R₈=H, R₉=H, R₁₁=CH₃) | H | H | CH₃ | OCH₃ | |
| J-2 | Q-153 (R₇=CH₃, R₈=H, R₉=H, R₁₁=CH₃) | CH₃ | H | OCH₃ | OCH₃ | |
| J-2 | Q-153 (R₇=H, R₈=H, R₉=H, R₁₁=CH₃) | H | H | OCH₃ | OCH₃ | |
| J-2 | Q-154 (R₇=CH₃, R₈=H, R₉=H, R₁₁=CH₃) | H | H | OCH₃ | OCH₃ | |
| J-2 | Q-154 (R₇=CH₃, R₈=H, R₉=H) | H | 5-OCH₃ | OCH₃ | OCH₃ | |
| J-2 | Q-155 (R₇=H, R₈=CH₃, R₉=CH₃) | H | H | OCH₃ | OCH₃ | |
| J-2 | Q-155 (R₇=CH₃, R₈=CH₃, R₉=H) | H | H | OCH₃ | OCF₂H | |
| J-2 | Q-155 (R₇=H, R₈=H, R₉=H) | H | 5-Cl | OCH₃ | OCH₃ | |
| J-2 | Q-156 (R₇=C₂H₅, R₈=H, R₉=H) | H | H | OCH₃ | OCH₃ | |
| J-2 | Q-156 (R₇=CH₃, R₈=CH₃, R₉=H) | CH₃ | 5-OCH₃ | OCH₃ | OCH₃ | |
| J-2 | Q-157 (R₇=H, R₈=H, R₉=H, R₁₀=H) | H | H | OCH₃ | OCH₃ | |
| J-2 | Q-157 (R₇=CH₃, R₈=H, R₉=H, R₁₀=H) | H | 5-Cl | OCF₂H | CH₃ | |
| J-2 | Q-157 (R₇=H, R₈=H, R₉=H, R₁₀=CH₃) | H | H | OCH₃ | CH₃ | |
| J-2 | Q-158 (R₇=H, R₈=H, R₉=H) | H | H | CH₃ | CH₃ | |
| J-2 | Q-158 (R₇=H, R₈=CH₃, R₉=CH₃) | H | 5-CH₃ | CH₃ | OCH₃ | |
| J-2 | Q-158 (R₇=CH₃, R₈=H, R₉=H) | H | H | OCH₃ | OCH₃ | |
| J-2 | Q-159 (R₇=H, R₈=H, R₉=H) | H | H | Cl | OCH₃ | |
| J-2 | Q-159 (R₇=CH₃, R₈=H, R₉=H, R₁₁=CH₃) | H | H | CH₃ | OCH₃ | |
| J-2 | Q-160 (R₇=H, R₈=H, R₉=H, R₁₁=CH₃) | H | H | CH₃ | OCH₃ | |
| J-2 | Q-160 (R₇=CH₃, R₈=H, R₉=H, R₁₁=i-C₃H₇) | H | H | CH₃ | OCH₃ | |
| J-2 | Q-161 (R₇=H, R₈=H, R₉=H, R₁₁=CH₃) | H | H | OCH₃ | OCH₃ | |
| J-2 | Q-161 (R₇=H, R₈=H, R₉=CH₃, R₁₁=CH₃) | H | 5-OCH₃ | OCH₃ | OCH₃ | |
| J-2 | Q-162 (R₇=H, R₈=H, R₉=H, R₁₀=H) | H | H | OCH₃ | OCH₃ | |
| J-2 | Q-162 (R₇=CH₃, R₈=H, R₉=H, R₁₀=H) | H | 5-Cl | OCH₃ | OCF₂H | |
| J-2 | Q-163 (R₂=H, R₈=H, R₉=H, R₁₀=H) | H | H | OCH₃ | OCH₃ | |
| J-2 | Q-164 (R₇=H) | H | H | OCH₃ | OCH₃ | |
| J-2 | Q-165 (R₃=H, R₇=H) | H | H | OCH₃ | OCH₃ | |
| J-2 | Q-166 (R₃=H, R₇=H) | H | H | OCH₃ | OCF₂H | |
| J-2 | Q-167 (R₇=H, R₈=H, R₉=H, R₁₀=H) | H | H | OCH₃ | OCH₃ | |
| J-2 | Q-167 (R₇=H, R₈=H, R₉=H, R₁₀=H) | H | H | CH₃ | CH₃ | |
| J-3 | Q-1 (R₇=H, R₈=H) | H | H | CH₃ | CH₃ | 204–205 |
| J-3 | Q-1 (R₇=H, R₈=H) | H | H | OCH₃ | CH₃ | 224–225(d) |

TABLE 1-continued

General Formula 1

| J | Q | R | R₁ | X | Y | m.p. (°C.) |
|---|---|---|----|---|---|------------|
| J-3 | Q-1 (R₇=H, R₈=H) | H | H | OCH₃ | OCH₃ | |
| J-3 | Q-1 (R₇=H, R₈=H) | H | 5-CH₃ | OCH₃ | OCH₃ | |
| J-3 | Q-1 (R₇=H, R₈=H) | H | 5-OCH₃ | OCH₃ | OCH₃ | |
| J-3 | Q-1 (R₇=H, R₈=H) | H | 6-OCH₂CH₂Br | OCH₃ | OCH₃ | |
| J-3 | Q-1 (R₇=H, R₈=H) | H | 2-CH₂F | OCH₃ | OCH₃ | |
| J-3 | Q-1 (R₇=H, R₈=H) | H | 2-SCH₃ | OCH₃ | OCH₃ | |
| J-3 | Q-1 (R₇=H, R₈=H) | H | 2-SCH₂F | OCH₃ | OCH₃ | |
| J-3 | Q-1 (R₇=H, R₈=H) | H | 2-NHCH₃ | OCH₃ | OCH₃ | |
| J-3 | Q-1 (R₇=H, R₈=H) | H | 2-Cl | OCH₃ | OCH₃ | |
| J-3 | Q-1 (R₇=H, R₈=H) | H | 2-NO₂ | OCH₃ | OCH₃ | |
| J-3 | Q-1 (R₇=H, R₈=H) | H | 2-OCF₂H | OCH₃ | OCH₃ | |
| J-3 | Q-1 (R₇=H, R₈=H) | H | H | OCH₃ | CH₂CH₃ | |
| J-3 | Q-1 (R₇=H, R₈=H) | H | H | OCH₃ | OCH₂CH₃ | |
| J-3 | Q-1 (R₇=H, R₈=H) | H | H | OCF₂H | OCH₃ | |
| J-3 | Q-1 (R₇=H, R₈=H) | H | H | OCH₂CF₃ | OCH₃ | |
| J-3 | Q-1 (R₇=H, R₈=H) | H | H | CF₃ | OCH₃ | |
| J-3 | Q-1 (R₇=H, R₈=H) | H | H | SCH₃ | OCH₃ | |
| J-3 | Q-1 (R₇=H, R₈=H) | H | H | SCHF₂ | OCH₃ | |
| J-3 | Q-1 (R₇=H, R₈=H) | H | H | Cl | OCH₃ | |
| J-3 | Q-1 (R₇=H, R₈=H) | H | H | OCH₃ | CH₂OCH₃ | |
| J-3 | Q-1 (R₇=H, R₈=H) | H | H | OCH₃ | NH₂ | |
| J-3 | Q-1 (R₇=H, R₈=H) | H | H | OCH₃ | NHCH₃ | |
| J-3 | Q-1 (R₇=H, R₈=H) | H | H | H | OCH₃ | |
| J-3 | Q-1 (R₇=H, R₈=H) | H | H | OCH₃ | OCH₂C≡CH | |
| J-3 | Q-1 (R₇=H, R₈=H) | H | H | OCH₃ | CH₂S(CH₂)₃CH₃ | |
| J-3 | Q-1 (R₇=H, R₈=H) | H | H | OCH₃ | cyclopropyl | |
| J-3 | Q-1 (R₇=H, R₈=H) | H | H | OCH₃ | C≡CH | |
| J-3 | Q-1 (R₇=H, R₈=H) | H | H | OCH₃ | —CH(OCH₃)₂ | |
| J-3 | Q-2 (R₇=H, R₈=H) | H | H | OCH₃ | OCH₃ | |
| J-3 | Q-3 (R₇=H, R₈=H) | H | H | OCH₃ | OCH₃ | |
| J-3 | Q-4 (R₇=H, R₈=H, R₃=CH₃) | H | H | OCH₃ | OCH₃ | |
| J-3 | Q-5 (R₇=H, R₈=H, R₃=H) | H | H | OCH₃ | OCH₃ | |
| J-3 | Q-6 (R₇=CH₃, R₈=H, R₃=CH₃) | H | H | CH₃ | OCH₃ | |
| J-3 | Q-7 (R₇=H, R₈=H, R₉=H) | H | H | OCH₃ | OCH₃ | |
| J-3 | Q-8 (R₇=H, R₈=C₂H₅, R₉=H) | H | H | OCH₃ | OCH₃ | |
| J-3 | Q-9 (R₇=H, R₈=H, R₂=H) | H | H | OCH₃ | OCH₃ | |
| J-3 | Q-10 (R₇=H, R₈=H, R₂=H) | H | H | OCH₃ | OCH₃ | |
| J-3 | Q-11 (R₇=H, R₈=H) | H | H | OCH₃ | OCH₃ | |
| J-3 | Q-12 (R=H, R₈=H) | H | H | OCH₃ | OCH₃ | |
| J-3 | Q-13 (R₇=H, R₈=H, R₃=H) | H | H | CH₃ | OCH₃ | |
| J-3 | Q-14 (R₇=H, R₈=H, R₃=CH₃) | H | H | OCH₃ | OCH₃ | |
| J-3 | Q-15 (R₇=CH, R₈=H, R₃=H) | H | H | CH₃ | OCH₃ | |
| J-3 | Q-16 (R₇=H, R₈=H, R₉=H) | H | H | CH₃ | OCH₃ | |
| J-3 | Q-17 (R₇=H, R₈=H, R₂=H) | H | H | OCH₃ | OCH₃ | |
| J-3 | Q-18 (R₇=H, R₈=H, R₂=H) | H | H | OCH₃ | OCH₃ | |
| J-3 | Q-19 (R₇=H, R₈=H, R₂=H) | H | H | CH₃ | OCH₃ | |
| J-3 | Q-20 (R₇=H, R₈=H) | H | H | OCH₃ | OCH₃ | |
| J-3 | Q-21 (R₇=H, R₈=H) | H | H | CH₃ | OCH₃ | |
| J-3 | Q-22 (R₇=H, R₈=H, R₃=H) | H | H | OCH₃ | OCH₃ | |
| J-3 | Q-23 (R₇=H, R₈=H, R₃=H) | H | H | OCH₃ | OCH₃ | |

TABLE 1-continued

General Formula 1

| J | Q | R | $R_1$ | X | Y | m.p. (°C.) |
|---|---|---|---|---|---|---|
| J-3 | Q-24 ($R_7$=H, $R_8$=H, $R_3$=CH$_3$) | H | H | OCH$_3$ | OCH$_3$ | |
| J-3 | Q-25 ($R_7$=H, $R_8$=H, $R_9$=H) | H | H | CH$_3$ | OCH$_3$ | |
| J-3 | Q-26 ($R_7$=H, $R_8$=H) | H | H | OCH$_3$ | OCH$_3$ | |
| J-3 | Q-27 ($R_7$=H, $R_8$=H) | H | H | CH$_3$ | OCH$_3$ | |
| J-3 | Q-28 ($R_7$=H, $R_8$=H) | H | H | OCH$_3$ | OCH$_3$ | |
| J-3 | Q-29 ($R_7$=H, $R_8$=H) | H | H | OCH$_3$ | OCH$_3$ | |
| J-3 | Q-30 ($R_7$=H, $R_8$=H) | H | H | OCH$_3$ | OCH$_3$ | |
| J-3 | Q-31 ($R_7$=H, $R_8$=H) | H | H | CH$_3$ | OCH$_3$ | |
| J-3 | Q-32 ($R_7$=H, $R_8$=H, $R_3$=H) | H | H | OCH$_3$ | OCH$_3$ | |
| J-3 | Q-33 ($R_7$=H, $R_8$=H, $R_8$=CH$_3$) | H | H | CH$_3$ | OCH$_3$ | |
| J-3 | Q-34 ($R_7$=H, $R_8$=H, $R_3$=H) | H | H | OCH$_3$ | OCH$_3$ | |
| J-3 | Q-35 ($R_7$=H, $R_8$=H, $R_3$=H) | H | H | OCH$_3$ | OCH$_3$ | |
| J-3 | Q-36 ($R_7$=H, $R_8$=H, $R_2$=H) | H | H | OCH$_3$ | OCH$_3$ | |
| J-3 | Q-37 ($R_7$=H, $R_8$=H, $R_2$=H) | H | H | OCH$_3$ | OCH$_3$ | |
| J-3 | Q-38 ($R_7$=H, $R_8$=H, $R_2$=OCF$_2$H) | H | H | CH$_3$ | OCH$_3$ | |
| J-3 | Q-39 ($R_7$=H, $R_8$=H, $R_9$=H ) | H | H | OCH$_3$ | OCH$_3$ | |
| J-3 | Q-40 ($R_7$=H, $R_8$=H) | H | H | OCH$_3$ | OCH$_3$ | |
| J-3 | Q-41 ($R_7$=H, $R_8$=H) | H | H | CH$_3$ | OCH$_3$ | |
| J-3 | Q-42 ($R_7$=H, $R_8$=H, $R_3$=H) | H | H | OCH$_3$ | OCH$_3$ | |
| J-3 | Q-43 ($R_7$=H, $R_8$=H, $R_3$=CH$_3$) | H | H | OCH$_3$ | OCH$_3$ | |
| J-3 | Q-44 ($R_7$=H, $R_8$=H, $R_3$=H) | H | H | CH$_3$ | OCH$_3$ | |
| J-3 | Q-45 ($R_7$=H, $R_8$=H, $R_9$=H) | H | H | OCH$_3$ | OCH$_3$ | |
| J-3 | Q-46 ($R_7$=H, $R_8$=H, $R_2$=H) | H | H | OCH$_3$ | OCH$_3$ | |
| J-3 | Q-47 ($R_7$=H, $R_8$=H, $R_{10}$=H) | H | H | CH$_3$ | OCH$_3$ | |
| J-3 | Q-48 ($R_7$=H, $R_8$=H, $R_2$=H) | H | H | OCH$_3$ | OCH$_3$ | |
| J-3 | Q-49 ($R_7$=H, $R_8$=H, $R_2$=H) | H | H | CH$_3$ | OCH$_3$ | |
| J-3 | Q-50 ($R_7$=H, $R_8$=H, $R_2$=H) | H | H | OCH$_3$ | OCH$_3$ | |
| J-3 | Q-51 ($R_7$=H, $R_8$=H, $R_9$=H) | H | H | OCH$_3$ | OCH$_3$ | |
| J-3 | Q-52 ($R_7$=H, $R_8$=H, $R_9$=H) | H | H | OCH$_3$ | OCH$_3$ | |
| J-3 | Q-53 ($R_7$=H, $R_8$=H, $R_9$=H) | H | H | CH$_3$ | OCH$_3$ | |
| J-3 | Q-54 ($R_7$=H, $R_8$=H, $R_9$=H, $R_3$=H) | H | H | OCH$_3$ | OCH$_3$ | |
| J-3 | Q-55 ($R_7$=H, $R_8$=H, $R_9$=H, $R_3$=C$_2$H$_5$) | H | H | CH$_3$ | OCH$_3$ | |
| J-3 | Q-56 ($R_7$=H, $R_8$=H, $R_9$=H, $R_3$=CH$_3$) | H | H | CH$_3$ | OCH$_3$ | |
| J-3 | Q-57 ($R_7$=H, $R_8$=H, $R_9$=H, $R_3$=i-C$_3$H$_7$) | H | H | OCH$_3$ | OCH$_3$ | |
| J-3 | Q-58 ($R_7$=H, $R_8$=H, $R_9$=H, $R_3$=H) | H | H | CH$_3$ | OCH$_3$ | |
| J-3 | Q-59 ($R_7$=H, $R_8$=H, $R_9$=H, $R_2$=H) | H | H | OCH$_3$ | OCH$_3$ | |
| J-3 | Q-60 ($R_7$=H, $R_8$=H, $R_9$=H, $R_{10}$=H) | H | H | OCH$_3$ | OCH$_3$ | |
| J-3 | Q-61 ($R_7$=H, $R_8$=H, $R_9$=H, $R_2$=H) | H | H | CH$_3$ | OCH$_3$ | |
| J-3 | Q-62 ($R_7$=H, $R_8$=H, $R_9$=H, $R_2$=H) | H | H | OCH$_3$ | OCH$_3$ | |
| J-3 | Q-63 ($R_7$=H, $R_8$=H, $R_9$=H) | H | H | CH$_3$ | OCH$_3$ | |
| J-3 | Q-64 ($R_7$=H, $R_8$=H, $R_9$=H) | H | H | OCH$_3$ | OCH$_3$ | |
| J-3 | Q-65 ($R_7$=H, $R_8$=H, $R_9$=H) | H | H | OCH$_3$ | OCH$_3$ | |
| J-3 | Q-66 ($R_7$=H, $R_8$=H, $R_9$=H) | H | H | OCH$_3$ | OCH$_3$ | |
| J-3 | Q-67 ($R_7$=H, $R_8$=H, $R_9$=H, $R_3$=H) | H | H | CH$_3$ | OCH$_3$ | |
| J-3 | Q-68 ($R_7$=H, $R_8$=H, $R_9$=H, $R_3$=CH$_3$) | H | H | OCH$_3$ | OCH$_3$ | |
| J-3 | Q-69 ($R_7$=H, $R_8$=H, $R_9$=H, $R_3$=CH$_3$) | H | H | OCH$_3$ | OCH$_3$ | |
| J-3 | Q-70 ($R_7$=H, $R_8$=H, $R_9$=H, $R_3$=CH$_3$) | H | H | OCH$_3$ | OCH$_3$ | |
| J-3 | Q-71 ($R_7$=H, $R_8$=H, $R_9$=H, $R_{10}$=H) | H | H | OCH$_3$ | OCH$_3$ | |
| J-3 | Q-72 ($R_7$=H, $R_8$=H, $R_9$=H, $R_2$=H) | H | H | OCH$_3$ | OCF$_2$H | |
| J-3 | Q-73 ($R_7$=H, $R_8$=H, $R_9$=H, $R_2$=H) | H | H | OCH$_3$ | OCH$_3$ | |
| J-3 | Q-74 ($R_7$=H, $R_8$=H, $R_9$=H, $R_2$=H) | H | H | CH$_3$ | OCH$_3$ | |

TABLE 1-continued

General Formula 1

| J | Q | R | R₁ | X | Y | m.p. (°C.) |
|---|---|---|----|---|---|------------|
| J-3 | Q-75 (R₇=H, R₈=H, R₉=H) | H | H | OCH₃ | OCH₃ | |
| J-3 | Q-76 (R₇=H, R₈=H, R₉=H) | H | H | CH₃ | OCH₃ | |
| J-3 | Q-77 (R₇=H, R₈=H, R₉=H) | H | H | OCH₃ | OCH₃ | |
| J-3 | Q-78 (R₇=H, R₈=H, R₉=H) | H | H | OCH₃ | OCH₃ | |
| J-3 | Q-79 (R₇=H, R₈=H, R₉=H, R₃=H) | H | H | OCH₃ | OCH₃ | |
| J-3 | Q-80 (R₇=H, R₈=H, R₉=H, R₃=CH₃) | H | H | OCH₃ | OCH₃ | |
| J-3 | Q-81 (R₇=H, R₈=H, R₉=H, R₃=CH₃) | H | H | CH₃ | OCH₃ | |
| J-3 | Q-82 (R₇=H, R₈=H, R₉=H, R₃=CH₃) | H | H | OCH₃ | OCH₃ | |
| J-3 | Q-83 (R₇=H, R₈=H, R₉=H, R₁₀=H) | H | H | OCH₃ | OCH₃ | |
| J-3 | Q-84 (R₇=H, R₈=H, R₉=H) | H | H | CH₃ | OCH₃ | |
| J-3 | Q-85 (R₇=H, R₈=H, R₉=H) | H | H | OCH₃ | OCH₃ | |
| J-3 | Q-86 (R₇=H, R₈=H, R₉=H) | H | H | OCH₃ | OCH₃ | |
| J-3 | Q-87 (R₇=H, R₈=H, R₉=H) | H | H | OCH₃ | OCH₃ | |
| J-3 | Q-88 (R₇=H, R₈=H, R₉=H) | H | H | CH₃ | OCH₃ | |
| J-3 | Q-89 (R₇=H, R₈=H, R₉=H) | H | H | OCH₃ | OCH₃ | |
| J-3 | Q-90 (R₇=H, R₈=H, R₉=H, R₃=CH₃) | H | H | CH₃ | OCH₃ | |
| J-3 | Q-91 (R₇=H, R₈=H, R₉=H, R₃=CH₃) | H | H | OCH₃ | OCH₃ | |
| J-3 | Q-92 (R₇=H, R₈=H, R₉=H, R₃=H) | H | H | OCH₃ | OCH₃ | |
| J-3 | Q-93 (R₇=H, R₈=H, R₉=H, R₁₀=H) | H | H | OCH₃ | OCH₃ | |
| J-3 | Q-94 (R₇=H, R₈=H, R₉=H) | H | H | CH₃ | OCH₃ | |
| J-3 | Q-95 (R₇=H, R₈=H, R₉=H) | H | H | OCH₃ | OCH₃ | |
| J-3 | Q-96 (R₇=H, R₈=H, R₉=H) | H | H | OCH₃ | OCH₃ | |
| J-3 | Q-97 (R₇=H, R₈=H, R₉=H) | H | H | OCH₃ | OCH₃ | |
| J-3 | Q-98 (R₇=H, R₈=H, R₉=H) | H | H | CH₃ | OCH₃ | |
| J-3 | Q-99 (R₇=H, R₈=H, R₉=H, R₃=H) | H | H | OCH₃ | OCH₃ | |
| J-3 | Q-100 (R₇=H, R₈=H, R₉=H, R₃=C₂H₅) | H | H | OCH₃ | OCH₃ | |
| J-3 | Q-101 (R₇=H, R₈=H, R₉=H, R₃=i-C₂H₅) | H | H | OCH₃ | OCH₃ | |
| J-3 | Q-102 (R₇=H, R₈=H, R₉=H, R₃=H) | H | H | CH₃ | OCH₃ | |
| J-3 | Q-103 (R₇=H, R₈=H, R₉=H, R₁₀=H) | H | H | OCH₃ | OCH₃ | |
| J-3 | Q-104 (R₇=H, R₈=H, R₉=H, R₂=H) | H | H | OCH₃ | OCH₃ | |
| J-3 | Q-105 (R₇=H, R₈=H, R₉=H, R₂=H) | H | H | OCH₃ | OCH₃ | |
| J-3 | Q-106 (R₇=H, R₈=H, R₉=H, R₂=H) | H | H | OCH₃ | OCH₃ | |
| J-3 | Q-107 (R₇=H, R₈=H, R₉=H, R₂=H) | H | H | CH₃ | OCH₃ | |
| J-3 | Q-108 (R₇=H, R₈=H, R₉=H, R₂=H) | H | H | OCH₃ | OCH₃ | |
| J-3 | Q-109 (R₇=H, R₈=H, R₉=H) | H | H | OCH₃ | OCH₃ | |
| J-3 | Q-110 (R₇=H, R₈=H, R₉=H) | H | H | OCH₃ | OCH₃ | |
| J-3 | Q-111 (R₇=H, R₈=H, R₉=H) | H | H | CH₃ | OCH₃ | |
| J-3 | Q-112 (R₇=H, R₈=H, R₉=H) | H | H | OCH₃ | OCH₃ | |
| J-3 | Q-113 (R₇=H, R₈=H, R₉=H, R₃=CH₃) | H | H | OCH₃ | OCH₃ | |
| J-3 | Q-114 (R₇=H, R₈=H, R₉=H, R₃=CH₃) | H | H | OCH₃ | OCH₃ | |
| J-3 | Q-115 (R₇=H, R₈=H, R₉=H, R₃=CH₃) | H | H | CH₃ | OCH₃ | |
| J-3 | Q-116 (R₇=H, R₈=H, R₉=H, R₁₀=H) | H | H | OCH₃ | OCH₃ | |
| J-3 | Q-117 (R₇=H, R₈=H, R₉=H, R₂=H) | H | H | OCH₃ | OCH₃ | |
| J-3 | Q-118 (R₇=H, R₈=H, R₉=H, R₁₀=H) | H | H | OCH₃ | OCH₃ | |
| J-3 | Q-119 (R₇=H, R₈=H, R₉=H, R₂=H) | H | H | CH₃ | OCH₃ | |
| J-3 | Q-120 (R₇=H, R₈=H, R₉=H, R₂=H) | H | H | OCH₃ | OCH₃ | |
| J-3 | Q-121 (R₇=H, R₈=H, R₉=H, R₂=H) | H | H | OCH₃ | OCH₃ | |
| J-3 | Q-122 (R₇=H, R₈=H, R₉=H, R₂=H) | H | H | OCH₃ | OCH₃ | |
| J-3 | Q-123 (R₇=H, R₈=H, R₉=H) | H | H | CH₃ | OCH₃ | |
| J-3 | Q-124 (R₇=H, R₈=H, R₉=H) | H | H | OCH₃ | OCH₃ | |
| J-3 | Q-125 (R₇=H, R₈=H, R₉=H) | H | H | CH₃ | OCH₃ | |

TABLE 1-continued

General Formula 1

| Q | J | R | R₁ | X | Y | m.p. (°C.) |
|---|---|---|---|---|---|---|
| Q-126 (R₇=H, R₈=H, R₉=H) | J-3 | H | H | OCH₃ | OCH₃ | |
| Q-127 (R₇=H, R₈=H, R₉=H, R₃=H) | J-3 | H | H | OCH₃ | OCH₃ | |
| Q-128 (R₇=H, R₈=H, R₉=H, R₃=CH₃) | J-3 | H | H | OCH₃ | OCH₃ | |
| Q-129 (R₇=H, R₈=H, R₉=H, R₃=CH₃) | J-3 | H | H | OCH₃ | OCH₃ | |
| Q-130 (R₇=H, R₈=H, R₉=H, R₃=CH₃) | J-3 | H | H | CH₃ | OCH₃ | |
| Q-131 (R₇=H, R₈=H, R₉=H, R₁₀=H) | J-3 | H | H | OCH₃ | OCH₃ | |
| Q-132 (R₇=H, R₈=H, R₉=H) | J-3 | H | H | OCH₃ | OCH₃ | |
| Q-133 (R₇=H, R₈=H, R₉=H) | J-3 | H | H | OCH₃ | OCH₃ | |
| Q-134 (R₇=H, R₈=H, R₉=H) | J-3 | H | H | OCH₃ | OCH₃ | |
| Q-135 (R₇=H, R₈=H, R₉=H) | J-3 | H | H | OCH₃ | OCH₃ | |
| Q-136 (R₇=H, R₈=H, R₉=H) | J-3 | H | H | CH₃ | OCH₃ | |
| Q-137 (R₇=H, R₈=H, R₉=H) | J-3 | H | H | OCH₃ | OCH₃ | |
| Q-138 (R₇=H, R₈=H, R₉=H) | J-3 | H | H | CH₃ | OCH₃ | |
| Q-139 (R₇=H, R₈=H, R₉=H) | J-3 | H | H | OCH₃ | OCH₃ | |
| Q-140 (R₇=H, R₈=H, R₉=H, R₃=CH₃) | J-3 | H | H | OCH₃ | OCH₃ | |
| Q-141 (R₇=H, R₈=H, R₉=H, R₃=CH₃) | J-3 | H | H | OCH₃ | OCH₃ | |
| Q-142 (R₇=H, R₈=H, R₉=H, R₁₀=H) | J-3 | H | H | OCH₃ | OCH₃ | |
| Q-143 (R₇=H, R₈=H, R₉=H, R₃=CH₃) | J-3 | H | H | OCH₃ | OCH₃ | |
| Q-144 (R₇=H, R₈=H, R₉=H, R₃=CH₃) | J-3 | H | H | CH₃ | OCH₃ | |
| Q-145 (R₇=H, R₈=H, R₉=H) | J-3 | H | H | OCH₃ | OCH₃ | |
| Q-146 (R₇=H, R₈=H, R₉=H) | J-3 | H | H | CH₃ | OCH₃ | |
| Q-147 (R₇=H, R₈=H, R₉=H) | J-3 | H | H | OCH₃ | OCH₃ | |
| Q-148 (R₇=H, R₈=H, R₉=H) | J-3 | H | H | OCH₃ | OCH₃ | |
| Q-149 (R₇=H, R₈=H, R₉=H) | J-3 | H | H | OCH₃ | OCH₃ | |
| Q-150 (R₇=H, R₈=H, R₉=H) | J-3 | H | H | OCH₃ | OCH₃ | |
| Q-151 (R₇=H, R₈=H, R₉=H) | J-3 | H | H | CH₃ | OCH₃ | |
| Q-152 (R₇=H, R₈=H, R₉=H, R₁₁=CH₃) | J-3 | H | H | OCH₃ | OCH₃ | |
| Q-153 (R₇=H, R₈=H, R₉=H, R₁₁=CH₃) | J-3 | H | H | OCH₃ | OCH₃ | |
| Q-154 (R₇=H, R₈=H, R₉=H) | J-3 | H | H | OCH₃ | OCH₃ | |
| Q-155 (R₇=H, R₈=H, R₉=H) | J-3 | H | H | OCH₃ | OCH₃ | |
| Q-156 (R₇=H, R₈=H, R₉=H, R₁₀=H) | J-3 | H | H | OCH₃ | OCH₃ | |
| Q-157 (R₇=H, R₈=H, R₉=H, R₁₀=H) | J-3 | H | H | CH₃ | OCH₃ | |
| Q-158 (R₇=H, R₈=H, R₉=H) | J-3 | H | H | CH₃ | OCH₃ | |
| Q-159 (R₇=H, R₈=H, R₉=H) | J-3 | H | H | CH₃ | OCH₃ | |
| Q-160 (R₇=H, R₈=H, R₉=H, R₁₁=CH₃) | J-3 | H | H | OCH₃ | OCH₃ | |
| Q-161 (R₇=H, R₈=H, R₉=H, R₁₁=CH₃) | J-3 | H | H | OCH₃ | OCH₃ | |
| Q-162 (R₇=H, R₈=H, R₉=H, R₁₀=H) | J-3 | H | H | OCH₃ | OCH₃ | |
| Q-1 (R₇=H, R₈=H) | J-1* | H | H | OCH₃ | CH₃ | |
| Q-1 (R₇=H, R₈=H) | J-1* | H | H | OCH₃ | OCH₃ | |
| Q-1 (R₇=H, R₈=H) | J-2* | H | H | OCH₃ | OCH₃ | |
| Q-167 (R₇=H, R₈=H, R₉=H, R₁₀=H) | J-2* | H | H | OCH₃ | OCH₃ | |
| Q-167 (R₇=H, R₈=H, R₉=H, R₁₀=H) | J-3 | H | H | OCH | CH | |

TABLE 2

General Formula 2

| J | Q | R | R₁ | X | Y | m.p. (°C.) |
|---|---|---|----|---|---|-----------|
| J-1 | Q-1 (R₇=H, R₈=H) | H | H | CH₃ | CH₃ | |
| J-1 | Q-1 (R₇=H, R₈=H) | H | H | OCH₃ | CH₃ | |
| J-1 | Q-1 (R₇=H, R₈=H) | H | H | OCH₃ | OCH₃ | |
| J-1 | Q-1 (R₇=H, R₈=H) | H | 5-CH₃ | OCH₃ | OCH₃ | |
| J-1 | Q-1 (R₇=H, R₈=H) | H | 5-OCH₃ | OCH₃ | OCH₃ | |
| J-1 | Q-1 (R₇=H, R₈=H) | H | 6-OCH₂CH₂Br | OCH₃ | OCH₃ | |
| J-1 | Q-1 (R₇=H, R₈=H) | H | 5-CH₂F | OCH₃ | OCH₃ | |
| J-1 | Q-1 (R₇=H, R₈=H) | H | 5-SCH₃ | OCH₃ | OCH₃ | |
| J-1 | Q-1 (R₇=H, R₈=H) | H | 5-SCH₂F | OCH₃ | OCH₃ | |
| J-1 | Q-1 (R₇=H, R₈=H) | H | 5-NHCH₃ | OCH₃ | OCH₃ | |
| J-1 | Q-1 (R₇=H, R₈=H) | H | 5-Cl | OCH₃ | OCH₃ | |
| J-1 | Q-1 (R₇=H, R₈=H) | H | 4-NO₂ | OCH₃ | OCH₃ | |
| J-1 | Q-1 (R₇=H, R₈=H) | H | 5-CF₃ | OCH₃ | OCH₃ | |
| J-1 | Q-1 (R₇=H, R₈=H) | H | H | OCH₃ | CH₂CH₃ | |
| J-1 | Q-1 (R₇=H, R₈=H) | H | H | OCH₃ | OCH₂CH₃ | |
| J-1 | Q-1 (R₇=H, R₈=H) | H | H | OCH₂CF₃ | OCH₃ | |
| J-1 | Q-1 (R₇=H, R₈=H) | H | H | CF₃ | OCH₃ | |
| J-1 | Q-1 (R₇=H, R₈=H) | H | H | SCH₃ | OCH₃ | |
| J-1 | Q-1 (R₇=H, R₈=H) | H | H | SCHF₂ | OCH₃ | |
| J-1 | Q-1 (R₇=H, R₈=H) | H | H | OCH₃ | CH₂OCH₃ | |
| J-1 | Q-1 (R₇=H, R₈=H) | H | H | OCH₃ | NH₂ | |
| J-1 | Q-1 (R₇=H, R₈=H) | H | H | OCH₃ | NHCH₃ | |
| J-1 | Q-1 (R₇=H, R₈=H) | H | H | H | OCH₃ | |
| J-1 | Q-1 (R₇=H, R₈=H) | H | H | OCH₃ | OCH₂C≡CH | |
| J-1 | Q-1 (R₇=H, R₈=H) | H | H | OCH₃ | CH₂S(CH₂)₃CH₃ | |
| J-1 | Q-1 (R₇=H, R₈=H) | H | H | OCH₃ | cyclopropyl | |
| J-1 | Q-1 (R₇=H, R₈=H) | H | H | OCH₃ | C≡CH | |
| J-1 | Q-1 (R₇=H, R₈=H) | H | H | OCH₃ | —CH(OCH₃)₂ | |
| J-1 | Q-2 (R₇=H, R₈=H) | H | H | OCH₃ | OCH₃ | |
| J-1 | Q-3 (R₇=H, R₈=H) | H | H | OCH₃ | OCH₃ | |
| J-1 | Q-4 (R₇=H, R₈=H, R₃=CH₃) | H | H | OCH₃ | OCH₃ | |
| J-1 | Q-5 (R₇—H, R₈=H, R₃=H) | H | H | CH₃ | OCH₃ | |
| J-1 | Q-6 (R₇=CH₃, R₈=H, R₃=CH₃) | H | H | CH₃ | OCH₃ | |
| J-1 | Q-7 (R₇=H, R₈=H, R₉=H) | H | H | OCH₃ | OCH₃ | |
| J-1 | Q-7 (R₇=H, R₈=C₂H₅, R₉=H) | H | H | OCH₃ | OCH₃ | |
| J-1 | Q-8 (R₇=H, R₈=H, R₂=H) | H | H | OCH₃ | OCH₃ | |
| J-1 | Q-9 (R₇=H, R₈=H, R₂=H) | H | H | OCH₃ | OCH₃ | |
| J-1 | Q-10 (R₇=H, R₈=H) | H | H | CH₃ | OCH₃ | |
| J-1 | Q-11 (R₇=H, R₈=H) | H | H | OCH₃ | OCH₃ | |
| J-1 | Q-12 (R₇=H, R₈=H) | H | H | CH₃ | OCH₃ | |
| J-1 | Q-13 (R₇=H, R₈=H, R₃=H) | H | H | CH₃ | OCH₃ | |
| J-1 | Q-14 (R₇=H, R₈=H, R₃=CH₃) | H | H | OCH₃ | OCH₃ | |
| J-1 | Q-15 (R₇=CH, R₈=H, R₃=H) | H | H | OCH₃ | OCH₃ | |
| J-1 | Q-16 (R₇=H, R₈=H, R₉=H) | H | H | OCH₃ | OCH₃ | |
| J-1 | Q-17 (R₇=H, R₈=H, R₂=H) | H | H | OCH₃ | OCH₃ | |
| J-1 | Q-18 (R₇=H, R₈=H, R₂=H) | H | H | CH₃ | OCH₃ | |
| J-1 | Q-19 (R₇=H, R₈=H) | H | H | CH₃ | OCH₃ | |
| J-1 | Q-20 (R₇=H, R₈=H) | H | H | CH₃ | OCH₃ | |
| J-1 | Q-21 (R₇=H, R₈=H) | H | H | OCH₃ | OCH₃ | |
| J-1 | Q-22 (R₇=H, R₈=H, R₃=H) | H | H | OCH₃ | OCH₃ | |
| J-1 | Q-23 (R₇=H, R₈=H, R₃=H) | H | H | OCH₃ | OCH₃ | |

TABLE 2-continued

| | | | General Formula 2 | | | |
|---|---|---|---|---|---|---|
| J | Q | R | $R_1$ | X | Y | m.p. (°C.) |
| J-1 | Q-24 ($R_7$=H, $R_8$=H, $R_3$=CH$_3$) | H | H | OCH$_3$ | OCH$_3$ | |
| J-1 | Q-25 ($R_7$=H, $R_8$=H, $R_9$=H) | H | H | CH$_3$ | OCH$_3$ | |
| J-1 | Q-26 ($R_7$=H, $R_8$=H) | H | H | OCH$_3$ | OCH$_3$ | |
| J-1 | Q-27 ($R_7$=H, $R_8$=H) | H | H | CH$_3$ | OCH$_3$ | |
| J-1 | Q-28 ($R_7$=H, $R_8$=H) | H | H | OCH$_3$ | OCH$_3$ | |
| J-1 | Q-29 ($R_7$=H, $R_8$=H) | H | H | OCH$_3$ | OCH$_3$ | |
| J-1 | Q-30 ($R_7$=H, $R_8$=H) | H | H | OCH$_3$ | OCH$_3$ | |
| J-1 | Q-31 ($R_7$=H, $R_8$=H) | H | H | CH$_3$ | OCH$_3$ | |
| J-1 | Q-32 ($R_7$=H, $R_8$=H, $R_3$=H) | H | H | OCH$_3$ | OCH$_3$ | |
| J-1 | Q-33 ($R_7$=H, $R_8$=H, $R_8$=CH$_3$) | H | H | CH$_3$ | OCH$_3$ | |
| J-1 | Q-34 ($R_7$=H, $R_8$=H, $R_3$=H) | H | H | OCH$_3$ | OCH$_3$ | |
| J-1 | Q-35 ($R_7$=H, $R_8$=H, $R_9$=H) | H | H | OCH$_3$ | OCH$_3$ | |
| J-1 | Q-36 ($R_7$=H, $R_8$=H, $R_2$=H) | H | H | OCH$_3$ | OCH$_3$ | |
| J-1 | Q-37 ($R_7$=H, $R_8$=H, $R_2$=H) | H | H | CH$_3$ | OCH$_3$ | |
| J-1 | Q-38 ($R_7$=H, $R_8$=H, $R_2$=OCF$_2$H) | H | H | OCH$_3$ | OCH$_3$ | |
| J-1 | Q-39 ($R_7$=H, $R_8$=H, $R_9$=H) | H | H | OCH$_3$ | OCH$_3$ | |
| J-1 | Q-40 ($R_7$=H, $R_8$=H) | H | H | CH$_3$ | OCH$_3$ | |
| J-1 | Q-41 ($R_7$=H, $R_8$=H) | H | H | OCH$_3$ | OCH$_3$ | |
| J-1 | Q-42 ($R_7$=H, $R_8$=H) | H | H | CH$_3$ | OCH$_3$ | |
| J-1 | Q-43 ($R_7$=H, $R_8$=H, $R_3$=H) | H | H | OCH$_3$ | OCH$_3$ | |
| J-1 | Q-44 ($R_7$=H, $R_8$=H, $R_3$=CH$_3$) | H | H | CH$_3$ | OCH$_3$ | |
| J-1 | Q-45 ($R_7$=H, $R_8$=H, $R_3$=H) | H | H | OCH$_3$ | OCH$_3$ | |
| J-1 | Q-46 ($R_7$=H, $R_8$=H, $R_9$=H) | H | H | OCH$_3$ | OCH$_3$ | |
| J-1 | Q-47 ($R_7$=H, $R_8$=H, $R_2$=H) | H | H | OCH$_3$ | OCH$_3$ | |
| J-1 | Q-48 ($R_7$=H, $R_8$=H, $R_2$=H) | H | H | CH$_3$ | OCH$_3$ | |
| J-1 | Q-49 ($R_7$=H, $R_8$=H, $R_2$=H) | H | H | OCH$_3$ | OCH$_3$ | |
| J-1 | Q-50 ($R_7$=H, $R_8$=H, $R_9$=H) | H | H | OCH$_3$ | OCH$_3$ | |
| J-1 | Q-51 ($R_7$=H, $R_8$=H, $R_2$=H) | H | H | CH$_3$ | OCH$_3$ | |
| J-1 | Q-52 ($R_7$=H, $R_8$=H, $R_9$=H) | H | H | OCH$_3$ | OCH$_3$ | |
| J-1 | Q-53 ($R_7$=H, $R_8$=H) | H | H | OCH$_3$ | OCH$_3$ | |
| J-1 | Q-54 ($R_7$=H, $R_8$=H, $R_9$=H, $R_3$=H) | H | H | CH$_3$ | OCH$_3$ | |
| J-1 | Q-55 ($R_7$=H, $R_8$=H, $R_9$=H, $R_3$=C$_2$H$_5$) | H | H | CH$_3$ | OCH$_3$ | |
| J-1 | Q-56 ($R_7$=H, $R_8$=H, $R_9$=H, $R_3$=i-C$_3$H$_7$) | H | H | CH$_3$ | OCH$_3$ | |
| J-1 | Q-57 ($R_7$=H, $R_8$=H, $R_9$=H, $R_3$=H) | H | H | OCH$_3$ | OCH$_3$ | |
| J-1 | Q-58 ($R_7$=H, $R_8$=H, $R_9$=H, $R_{10}$=H) | H | H | OCH$_3$ | OCH$_3$ | |
| J-1 | Q-59 ($R_7$=H, $R_8$=H, $R_9$=H, $R_2$=H) | H | H | CH$_3$ | OCH$_3$ | |
| J-1 | Q-60 ($R_7$=H, $R_8$=H, $R_9$=H, $R_2$=H) | H | H | OCH$_3$ | OCH$_3$ | |
| J-1 | Q-61 ($R_7$=H, $R_8$=H, $R_9$=H, $R_2$=H) | H | H | OCH$_3$ | OCH$_3$ | |
| J-1 | Q-62 ($R_7$=H, $R_8$=H, $R_9$=H, $R_2$=H) | H | H | CH$_3$ | OCH$_3$ | |
| J-1 | Q-63 ($R_7$=H, $R_8$=H, $R_9$=H) | H | H | OCH$_3$ | OCH$_3$ | |
| J-1 | Q-64 ($R_7$=H, $R_8$=H, $R_9$=H) | H | H | OCH$_3$ | OCH$_3$ | |
| J-1 | Q-65 ($R_7$=H, $R_8$=H, $R_9$=H) | H | H | CH$_3$ | OCH$_3$ | |
| J-1 | Q-66 ($R_7$=H, $R_8$=H, $R_9$=H) | H | H | OCH$_3$ | OCH$_3$ | |
| J-1 | Q-67 ($R_7$=H, $R_8$=H, $R_9$=H, $R_3$=H) | H | H | OCH$_3$ | OCH$_3$ | |
| J-1 | Q-68 ($R_7$=H, $R_8$=H, $R_9$=H, $R_3$=CH$_3$) | H | H | CH$_3$ | OCH$_3$ | |
| J-1 | Q-69 ($R_7$=H, $R_8$=H, $R_9$=H, $R_3$=CH$_3$) | H | H | OCH$_3$ | OCH$_3$ | |
| J-1 | Q-70 ($R_7$=H, $R_8$=H, $R_9$=H, $R_3$=CH$_3$) | H | H | OCH$_3$ | OCH$_3$ | |
| J-1 | Q-72 ($R_7$=H, $R_8$=H, $R_9$=H, $R_2$=H) | H | H | OCH$_3$ | OCH$_3$ | |
| J-1 | Q-73 ($R_7$=H, $R_8$=H, $R_9$=H, $R_2$=H) | H | H | OCH$_3$ | OCH$_3$ | |
| J-1 | Q-74 ($R_7$=H, $R_8$=H, $R_9$=H) | H | H | CH$_3$ | OCH$_3$ | |
| J-1 | Q-75 ($R_7$=H, $R_8$=H, $R_9$=H) | H | H | OCH$_3$ | OCH$_3$ | |

TABLE 2-continued

General Formula 2

| J | Q | R | R₁ | X | Y | m.p. (°C.) |
|---|---|---|----|---|---|------------|
| J-1 | Q-76 (R₇=H, R₈=H, R₉=H) | H | H | CH₃ | OCH₃ | |
| J-1 | Q-77 (R₇=H, R₈=H, R₉=H) | H | H | OCH₃ | OCH₃ | |
| J-1 | Q-78 (R₇=H, R₈=H, R₉=H, R₃=H) | H | H | OCH₃ | OCH₃ | |
| J-1 | Q-79 (R₇=H, R₈=H, R₉=H, R₃=CH₃) | H | H | OCH₃ | OCH₃ | |
| J-1 | Q-80 (R₇=H, R₈=H, R₉=H, R₃=CH₃) | H | H | CH₃ | OCH₃ | |
| J-1 | Q-81 (R₇=H, R₈=H, R₉=H, R₃=CH₃) | H | H | OCH₃ | OCH₃ | |
| J-1 | Q-82 (R₇=H, R₈=H, R₉=H, R₃=CH₃) | H | H | OCH₃ | OCH₃ | |
| J-1 | Q-83 (R₇=H, R₈=H, R₉=H, R₁₀=H) | H | H | CH₃ | OCH₃ | |
| J-1 | Q-84 (R₇=H, R₈=H, R₉=H) | H | H | OCH₃ | OCH₃ | |
| J-1 | Q-85 (R₇=H, R₈=H, R₉=H) | H | H | OCH₃ | OCH₃ | |
| J-1 | Q-86 (R₇=H, R₈=H, R₉=H) | H | H | OCH₃ | OCH₃ | |
| J-1 | Q-87 (R₇=H, R₈=H, R₉=H) | H | H | CH₃ | OCH₃ | |
| J-1 | Q-88 (R₇=H, R₈=H, R₉=H) | H | H | OCH₃ | OCH₃ | |
| J-1 | Q-89 (R₇=H, R₈=H, R₉=H) | H | H | OCH₃ | OCH₃ | |
| J-1 | Q-90 (R₇=H, R₈=H, R₉=H, R₃=CH₃) | H | H | OCH₃ | OCH₃ | |
| J-1 | Q-91 (R₇=H, R₈=H, R₉=H, R₃=CH₃) | H | H | CH₃ | OCH₃ | |
| J-1 | Q-92 (R₇=H, R₈=H, R₉=H, R₁₀=H) | H | H | OCH₃ | OCH₃ | |
| J-1 | Q-93 (R₇=H, R₈=H, R₉=H) | H | H | OCH₃ | OCH₃ | |
| J-1 | Q-94 (R₇=H, R₈=H, R₉=H) | H | H | CH₃ | OCH₃ | |
| J-1 | Q-95 (R₇=H, R₈=H, R₉=H) | H | H | OCH₃ | OCH₃ | |
| J-1 | Q-96 (R₇=H, R₈=H, R₉=H) | H | H | OCH₃ | OCH₃ | |
| J-1 | Q-97 (R₇=H, R₈=H, R₉=H) | H | H | OCH₃ | OCH₃ | |
| J-1 | Q-98 (R₇=H, R₈=H, R₉=H) | H | H | CH₃ | OCH₃ | |
| J-1 | Q-99 (R₇=H, R₈=H, R₉=H, R₃=H) | H | H | OCH₃ | OCH₃ | |
| J-1 | Q-100 (R₇=H, R₈=H, R₉=H, R₃=C₂H₅) | H | H | OCH₃ | OCH₃ | |
| J-1 | Q-101 (R₇=H, R₈=H, R₉=H, R₃=i-C₂H₅) | H | H | OCH₃ | OCH₃ | |
| J-1 | Q-102 (R₇=H, R₈=H, R₉=H, R₃=H) | H | H | CH₃ | OCH₃ | |
| J-1 | Q-103 (R₇=H, R₈=H, R₉=H, R₁₀=H) | H | H | OCH₃ | OCH₃ | |
| J-1 | Q-104 (R₇=H, R₈=H, R₉=H, R₂=H) | H | H | CH₃ | OCH₃ | |
| J-1 | Q-105 (R₇=H, R₈=H, R₉=H, R₂=H) | H | H | OCH₃ | OCH₃ | |
| J-1 | Q-106 (R₇=H, R₈=H, R₉=H, R₂=H) | H | H | OCH₃ | OCH₃ | |
| J-1 | Q-107 (R₇=H, R₈=H, R₉=H, R₂=H) | H | H | OCH₃ | OCH₃ | |
| J-1 | Q-108 (R₇=H, R₈=H, R₉=H, R₂=H) | H | H | CH₃ | OCH₃ | |
| J-1 | Q-109 (R₇=H, R₈=H, R₉=H) | H | H | OCH₃ | OCH₃ | |
| J-1 | Q-110 (R₇=H, R₈=H, R₉=H) | H | H | OCH₃ | OCH₃ | |
| J-1 | Q-111 (R₇=H, R₈=H, R₉=H) | H | H | OCH₃ | OCH₃ | |
| J-1 | Q-112 (R₇=H, R₈=H, R₉=H) | H | H | CH₃ | OCH₃ | |
| J-1 | Q-113 (R₇=H, R₈=H, R₉=H, R₃=CH₃) | H | H | OCH₃ | OCH₃ | |
| J-1 | Q-114 (R₇=H, R₈=H, R₉=H, R₃=CH₃) | H | H | OCH₃ | OCH₃ | |
| J-1 | Q-115 (R₇=H, R₈=H, R₉=H, R₃=CH₃) | H | H | OCH₃ | OCH₃ | |
| J-1 | Q-116 (R₇=H, R₈=H, R₉=H, R₁₀=H) | H | H | CH₃ | OCH₃ | |
| J-1 | Q-117 (R₇=H, R₈=H, R₉=H, R₂=H) | H | H | OCH₃ | OCH₃ | |
| J-1 | Q-118 (R₇=H, R₈=H, R₉=H, R₁₀=H) | H | H | OCH₃ | OCH₃ | |
| J-1 | Q-119 (R₇=H, R₈=H, R₉=H, R₂=H) | H | H | OCH₃ | OCH₃ | |
| J-1 | Q-120 (R₇=H, R₈=H, R₉=H, R₂=H) | H | H | CH₃ | OCH₃ | |
| J-1 | Q-121 (R₇=H, R₈=H, R₉=H, R₂=H) | H | H | OCH₃ | OCH₃ | |
| J-1 | Q-122 (R₇=H, R₈=H, R₉=H, R₂=H) | H | H | OCH₃ | OCH₃ | |
| J-1 | Q-123 (R₇=H, R₈=H, R₉=H, R₂=H) | H | H | OCH₃ | OCH₃ | |
| J-1 | Q-124 (R₇=H, R₈=H, R₉=H) | H | H | CH₃ | OCH₃ | |
| J-1 | Q-125 (R₇=H, R₈=H, R₉=H) | H | H | OCH₃ | OCH₃ | |
| J-1 | Q-126 (R₇=H, R₈=H, R₉=H) | H | H | OCH₃ | OCH₃ | |

TABLE 2-continued

General Formula 2

| J | Q | R | R₁ | X | Y | m.p. (°C.) |
|---|---|---|----|---|---|-----------|
| J-1 | Q-127 (R₇=H, R₈=H, R₉=H, R₃=H) | H | H | OCH₃ | OCH₃ | |
| J-1 | Q-128 (R₇=H, R₈=H, R₉=H, R₃=CH₃) | H | H | OCH₃ | OCH₃ | |
| J-1 | Q-129 (R₇=H, R₈=H, R₉=H, R₃=CH₃) | H | H | OCH₃ | OCH₃ | |
| J-1 | Q-130 (R₇=H, R₈=H, R₉=H, R₃=CH₃) | H | H | CH₃ | OCH₃ | |
| J-1 | Q-131 (R₇=H, R₈=H, R₉=H, R₁₀=H) | H | H | OCH₃ | OCH₃ | |
| J-1 | Q-132 (R₇=H, R₈=H, R₉=H) | H | H | CH₃ | OCH₃ | |
| J-1 | Q-133 (R₇=H, R₈=H, R₉=H) | H | H | OCH₃ | OCH₃ | |
| J-1 | Q-134 (R₇=H, R₈=H, R₉=H) | H | H | OCH₃ | OCH₃ | |
| J-1 | Q-135 (R₇=H, R₈=H, R₉=H) | H | H | OCH₃ | OCH₃ | |
| J-1 | Q-136 (R₇=H, R₈=H, R₉=H) | H | H | OCH₃ | OCH₃ | |
| J-1 | Q-137 (R₇=H, R₈=H, R₉=H) | H | H | CH₃ | OCH₃ | |
| J-1 | Q-138 (R₇=H, R₈=H, R₉=H) | H | H | OCH₃ | OCH₃ | |
| J-1 | Q-139 (R₇=H, R₈=H, R₉=H) | H | H | CH₃ | OCH₃ | |
| J-1 | Q-140 (R₇=H, R₈=H, R₉=H, R₃=CH₃) | H | H | OCH₃ | OCH₃ | |
| J-1 | Q-141 (R₇=H, R₈=H, R₉=H, R₃=CH₃) | H | H | OCH₃ | OCH₃ | |
| J-1 | Q-142 (R₇=H, R₈=H, R₉=H, R₁₀=H) | H | H | OCH₃ | OCH₃ | |
| J-1 | Q-143 (R₇=H, R₈=H, R₉=H, R₃=CH₃) | H | H | CH₃ | OCH₃ | |
| J-1 | Q-144 (R₇=H, R₈=H, R₉=H, R₃=CH₃) | H | H | OCH₃ | OCH₃ | |
| J-1 | Q-145 (R₇=H, R₈=H, R₉=H) | H | H | OCH₃ | OCH₃ | |
| J-1 | Q-146 (R₇=H, R₈=H, R₉=H) | H | H | CH₃ | OCH₃ | |
| J-1 | Q-147 (R₇=H, R₈=H, R₉=H) | H | H | OCH₃ | OCH₃ | |
| J-1 | Q-148 (R₇=H, R₈=H, R₉=H) | H | H | OCH₃ | OCH₃ | |
| J-1 | Q-149 (R₇=H, R₈=H, R₉=H) | H | H | OCH₃ | OCH₃ | |
| J-1 | Q-150 (R₇=H, R₈=H, R₉=H) | H | H | OCH₃ | OCH₃ | |
| J-1 | Q-151 (R₇=H, R₈=H, R₉=H) | H | H | CH₃ | OCH₃ | |
| J-1 | Q-152 (R₇=H, R₈=H, R₉=H) | H | H | OCH₃ | OCH₃ | |
| J-1 | Q-153 (R₇=H, R₈=H, R₉=H, R₁₁=CH₃) | H | H | CH₃ | OCH₃ | |
| J-1 | Q-154 (R₇=H, R₈=H, R₉=H, R₁₁=CH₃) | H | H | OCH₃ | OCH₃ | |
| J-1 | Q-155 (R₇=H, R₈=H, R₉=H) | H | H | OCH₃ | OCH₃ | |
| J-1 | Q-156 (R₇=H, R₈=H, R₉=H) | H | H | OCH₃ | OCH₃ | |
| J-1 | Q-157 (R₇=H, R₈=H, R₉=H, R₁₀=H) | H | H | CH₃ | OCH₃ | |
| J-1 | Q-158 (R₇=H, R₈=H, R₉=H) | H | H | OCH₃ | OCH₃ | |
| J-1 | Q-159 (R₇=H, R₈=H, R₉=H) | H | H | CH₃ | OCH₃ | |
| J-1 | Q-160 (R₇=H, R₈=H, R₉=H, R₁₁=CH₃) | H | H | OCH₃ | OCH₃ | |
| J-1 | Q-161 (R₇=H, R₈=H, R₉=H, R₁₁=CH₃) | H | H | OCH₃ | OCH₃ | |
| J-1 | Q-162 (R₇=H, R₈=H, R₉=H, R₁₀=H) | H | H | OCH₃ | OCH₃ | |
| J-1 | Q-163 (R₂=H, R₇=H, R₈=H, R₉=H) | H | H | OCH₃ | OCH₃ | |
| J-1 | Q-164 (R₇=H) | H | H | OCH₃ | OCH₃ | |
| J-1 | Q-165 (R₃=H, R₇=H) | H | H | OCH₃ | OCH₃ | |
| J-1 | Q-166 (R₃=H, R₇=H) | H | H | OCH₃ | OCH₃ | |
| J-2 | Q-1 (R₇=H, R₈=H) | H | 5-SCH₃ | OCH₃ | OCH₃ | |
| J-2 | Q-1 (R₇=H, R₈=H) | H | 5-SOCH₃ | OCH₃ | OCH₃ | |
| J-2 | Q-1 (R₇=H, R₈=H) | H | 5-SO₂CH₃ | OCH₃ | OCH₃ | |
| J-2 | Q-1 (R₇=H, R₈=H) | H | 5-CO₂CH₃ | OCH₃ | OCH₃ | |
| J-2 | Q-1 (R₇=H, R₈=H) | H | 4-SO₂N(CH₃)₂ | OCH₃ | OCH₃ | |
| J-2 | Q-1 (R₇=H, R₈=H) | H | 5-NO₂ | OCH₃ | OCH₃ | |
| J-2 | Q-1 (R₇=H, R₈=H) | H | 5-Cl | OCH₃ | OCH₃ | |
| J-2 | Q-1 (R₇=H, R₈=H) | H | 4-NO₂ | OCH₃ | OCH₃ | |
| J-2 | Q-1 (R₇=H, R₈=H) | H | 6-Cl | OCH₃ | OCH₃ | |
| J-2 | Q-1 (R₇=H, R₈=H) | H | 6-COOCH₂ | OCH₃ | OCH₃ | |
| J-2 | Q-1 (R₇=H, R₈=H) | H | 6-NO₂ | OCH₃ | OCH₃ | |

TABLE 2-continued

General Formula 2

| J | Q | R | R₁ | X | Y | m.p. (°C.) |
|---|---|---|----|---|---|---|
| J-2 | Q-1 (R₇=H, R₈=H) | H | 4-SO₂CH₃ | OCH₃ | OCH₃ | |
| J-2 | Q-1 (R₇=H, R₈=H) | H | 6-OCH₃ | OCH₃ | OCH₃ | |
| J-2 | Q-1 (R₇=H, R₈=H) | H | 5-OCH₃ | OCH₃ | OCH₃ | |
| J-2 | Q-1 (R₇=H, R₈=H) | H | H | CH₃ | CH₃ | |
| J-2 | Q-1 (R₇=H, R₈=H) | H | H | OCH₃ | CH₃ | |
| J-2 | Q-1 (R₇=H, R₈=H) | CH₃ | H | OCH₃ | OCH₃ | |
| J-2 | Q-1 (R₇=H, R₈=H) | CH₃ | H | OCH₃ | CH₃ | |
| J-2 | Q-1 (R₇=H, R₈=H) | H | 5-CH₃ | OCH₃ | OCH₃ | |
| J-2 | Q-1 (R₇=H, R₈=H) | H | 6-CH₂CH₃ | OCH₃ | OCH₃ | |
| J-2 | Q-1 (R₇=H, R₈=H) | H | 5-CH(CH₃)₂ | OCH₃ | OCH₃ | |
| J-2 | Q-1 (R₇=H, R₈=H) | H | 5-OCH₃ | OCH₃ | OCH₃ | |
| J-2 | Q-1 (R₇=H, R₈=H) | H | 5-OCH₂CH₃ | OCH₃ | OCH₃ | |
| J-2 | Q-1 (R₇=H, R₈=H) | H | 5-OCH(CH₃)₂ | OCH₃ | OCH₃ | |
| J-2 | Q-1 (R₇=H, R₈=H) | H | 5-OCF₂H | OCH₃ | OCH₃ | |
| J-2 | Q-1 (R₇=H, R₈=H) | H | 6-OCH₂CH₂Br | OCH₃ | OCH₃ | |
| J-2 | Q-1 (R₇=H, R₈=H) | H | 5-OCH(CH₃)(CH₂Cl) | OCH₃ | OCH₃ | |
| J-2 | Q-1 (R₇=H, R₈=H) | H | 5-CH₂F | OCH₃ | OCH₃ | |
| J-2 | Q-1 (R₇=H, R₈=H) | H | 5-CH₂CH₂Br | OCH₃ | OCH₃ | |
| J-2 | Q-1 (R₇=H, R₈=H) | H | 5-CH(CH₃)CH₂Cl) | OCH₃ | OCH₃ | |
| J-2 | Q-1 (R₇=H, R₈=H) | H | 6-SCH₂CH₃ | OCH₃ | OCH₃ | |
| J-2 | Q-1 (R₇=H, R₈=H) | H | 5-SCH(CH₃)₂ | OCH₃ | OCH₃ | |
| J-2 | Q-1 (R₇=H, R₈=H) | H | 5-SCH₂F | OCH₃ | OCH₃ | |
| J-2 | Q-1 (R₇=H, R₈=H) | H | 5-SCH₂CH₂Br | OCH₃ | OCH₃ | |
| J-2 | Q-1 (R₇=H, R₈=H) | H | 5-SCH(CH₃)(CH₂Cl) | OCH₃ | OCH₃ | |
| J-2 | Q-1 (R₇=H, R₈=H) | H | 4-NH₂ | OCH₃ | OCH₃ | |
| J-2 | Q-1 (R₇=H, R₈=H) | H | 5-NHCH₃ | OCH₃ | OCH₃ | |
| J-2 | Q-1 (R₇=H, R₈=H) | H | 6-NHCH₂CH₃ | OCH₃ | OCH₃ | |
| J-2 | Q-1 (R₇=H, R₈=H) | H | 5-NHCH(CH₃)₂ | OCH₃ | OCH₃ | |
| J-2 | Q-1 (R₇=H, R₈=H) | H | 4-N(CH₃)₂ | OCH₃ | OCH₃ | |
| J-2 | Q-1 (R₇=H, R₈=H) | H | 6-N(CH₃)(CH₂CH₃) | OCH₃ | OCH₃ | |
| J-2 | Q-1 (R₇=H, R₈=H) | H | 5-N(CH₃)(CH(CH₃)₂) | OCH₃ | OCH₃ | |
| J-2 | Q-1 (R₇=H, R₈=H) | H | 5-Cl | OCH₃ | OCH₃ | |
| J-2 | Q-1 (R₇=H, R₈=H) | H | 5-Br | OCH₃ | OCH₃ | |
| J-2 | Q-1 (R₇=H, R₈=H) | H | 4-F | OCH₃ | OCH₃ | |
| J-2 | Q-1 (R₇=H, R₈=H) | H | 5-CF₃ | OCH₃ | OCH₃ | |
| J-2 | Q-1 (R₇=H, R₈=H) | H | 5-OCF₂H | OCH₃ | OCH₃ | |
| J-2 | Q-1 (R₇=H, R₈=H) | H | H | OCH₃ | CH₂CH₃ | |
| J-2 | Q-1 (R₇=H, R₈=H) | H | H | OCH₃ | CH(CH₃)₂ | |
| J-2 | Q-1 (R₇=H, R₈=H) | H | H | OCH₃ | (CH₂)₃CH₃ | |
| J-2 | Q-1 (R₇=H, R₈=H) | H | H | OCH₃ | OCH₂CH₃ | |
| J-2 | Q-1 (R₇=H, R₈=H) | H | H | OCH₃ | OCH(CH₃)₂ | |
| J-2 | Q-1 (R₇=H, R₈=H) | H | H | OCH₃ | O(CH₂)₃CH₃ | |
| J-2 | Q-1 (R₇=H, R₈=H) | H | H | OCH₂CH₂F | OCH₃ | |
| J-2 | Q-1 (R₇=H, R₈=H) | H | H | OCH₂CHF₂ | OCH₃ | |
| J-2 | Q-1 (R₇=H, R₈=H) | H | H | OCH₂CF₃ | OCH₃ | |
| J-2 | Q-1 (R₇=H, R₈=H) | H | H | OCH(CH₃)(CH₂Cl) | OCH₃ | |
| J-2 | Q-1 (R₇=H, R₈=H) | H | H | O(CH₂)₃CH₂Br | OCH₃ | |
| J-2 | Q-1 (R₇=H, R₈=H) | H | H | CH₂F | OCH₃ | |
| J-2 | Q-1 (R₇=H, R₈=H) | H | H | CH₂Cl | OCH₃ | |
| J-2 | Q-1 (R₇=H, R₈=H) | H | H | CH₂Br | OCH₃ | |

TABLE 2-continued

General Formula 2

| J | Q | R | R₁ | X | Y | m.p. (°C.) |
|---|---|---|----|---|---|------------|
| J-2 | Q-1 (R₇=H, R₈=H) | H | H | CF₃ | OCH₃ | |
| J-2 | Q-1 (R₇=H, R₈=H) | H | H | CH₂CH₂Br | OCH₃ | |
| J-2 | Q-1 (R₇=H, R₈=H) | H | H | CH(CH₃)(CH₂Cl) | OCH₃ | |
| J-2 | Q-1 (R₇=H, R₈=H) | H | H | (CH₂)₃CH₂I | OCH₃ | |
| J-2 | Q-1 (R₇=H, R₈=H) | H | H | SCH₃ | OCH₃ | |
| J-2 | Q-1 (R₇=H, R₈=H) | H | H | SCH₂CH₃ | OCH₃ | |
| J-2 | Q-1 (R₇=H, R₈=H) | H | H | SCH(CH₃)₂ | OCH₃ | |
| J-2 | Q-1 (R₇=H, R₈=H) | H | H | S(CH₂)₃CH₃ | OCH₃ | |
| J-2 | Q-1 (R₇=H, R₈=H) | H | H | SCHF₂ | OCH₃ | |
| J-2 | Q-1 (R₇=H, R₈=H) | H | H | SCH₂CH₂Br | OCH₃ | |
| J-2 | Q-1 (R₇=H, R₈=H) | H | H | SCH(CH₃)(CH₂Cl) | OCH₃ | |
| J-2 | Q-1 (R₇=H, R₈=H) | H | H | S(CH₂)₃CH₂F | OCH₃ | |
| J-2 | Q-1 (R₇=H, R₈=H) | H | H | OCH₃ | CH₂OCH₃ | |
| J-2 | Q-1 (R₇=H, R₈=H) | H | H | OCH₃ | CH₂CH₂OCH(CH₃)₂ | |
| J-2 | Q-1 (R₇=H, R₈=H) | H | H | OCH₃ | CH(CH₃)(CH₂OCH₃) | |
| J-2 | Q-1 (R₇=H, R₈=H) | H | H | OCH₃ | (CH₂)₄CH₂OCH₂CH₃ | |
| J-2 | Q-1 (R₇=H, R₈=H) | H | H | OCH₂O(CH₂)₃CH₃ | OCH₃ | |
| J-2 | Q-1 (R₇=H, R₈=H) | H | H | OCH₂CH₂OCH(CH₃)₂ | OCH₃ | |
| J-2 | Q-1 (R₇=H, R₈=H) | H | H | OCH(CH₃)(CH₂OCH₃) | OCH₃ | |
| J-2 | Q-1 (R₇=H, R₈=H) | H | H | O(CH₂)₄CH₂OCH₂CH₃ | OCH₃ | |
| J-2 | Q-1 (R₇=H, R₈=H) | H | H | OCH₃ | NH₂ | |
| J-2 | Q-1 (R₇=H, R₈=H) | H | H | OCH₃ | NHCH₃ | |
| J-2 | Q-1 (R₇=H, R₈=H) | H | H | OCH₃ | NHCH₂CH₃ | |
| J-2 | Q-1 (R₇=H, R₈=H) | H | H | OCH₃ | NHCH(CH₃)₂ | |
| J-2 | Q-1 (R₇=H, R₈=H) | H | H | OCH₃ | N(CH₃)₂ | |
| J-2 | Q-1 (R₇=H, R₈=H) | H | H | OCH₃ | N(CH₃)(CH₂CH₃) | |
| J-2 | Q-1 (R₇=H, R₈=H) | H | H | OCH₃ | N(CH₃)(CH(CH₃)₂) | |
| J-2 | Q-1 (R₇=H, R₈=H) | H | H | OCH₃ | (CH₂)₄CH₂OCH₂CH₃ | |
| J-2 | Q-1 (R₇=H, R₈=H) | H | H | H | OCH₃ | |
| J-2 | Q-1 (R₇=H, R₈=H) | H | H | OCH₃ | OCH₂CH=CH₂ | |
| J-2 | Q-1 (R₇=H, R₈=H) | H | H | OCH₃ | OCH₂C(CH₃)=CH₂ | |
| J-2 | Q-1 (R₇=H, R₈=H) | H | H | OCH₃ | OCH₂C≡CH | |
| J-2 | Q-1 (R₇=H, R₈=H) | H | H | OCH₃ | OCH₂C≡CCH₃ | |
| J-2 | Q-1 (R₇=H, R₈=H) | H | H | OCH₃ | CH₂S(CH₂)₃CH₃ | |
| J-2 | Q-1 (R₇=H, R₈=H) | H | H | OCH₃ | CH₂CH₂SCH(CH₃)₂ | |
| J-2 | Q-1 (R₇=H, R₈=H) | H | H | OCH₃ | CH(CH₃)(CH₂SCH₃) | |
| J-2 | Q-1 (R₇=H, R₈=H) | H | H | OCH₃ | (CH₂)₄CH₂SCH₂CH₃ | |
| J-2 | Q-1 (R₇=H, R₈=H) | H | H | OCH₃ | cyclopropyl | |
| J-2 | Q-1 (R₇=H, R₈=H) | H | H | OCH₃ | 2-methylcyclopropyl | |
| J-2 | Q-1 (R₇=H, R₈=H) | H | H | OCH₃ | cyclopentyl | |
| J-2 | Q-1 (R₇=H, R₈=H) | H | H | OCH₃ | C≡CH | |
| J-2 | Q-1 (R₇=H, R₈=H) | H | H | OCH₃ | C≡CCH₃ | |
| J-2 | Q-1 (R₇=H, R₈=H) | H | H | OCH₃ | —CHO | |
| J-2 | Q-1 (R₇=H, R₈=H) | H | H | OCH₃ | —COCH₃ | |
| J-2 | Q-1 (R₇=H, R₈=H) | H | H | OCH₃ | —CH(OCH₃)₂ | |
| J-2 | Q-1 (R₇=H, R₈=H) | H | H | OCH₃ | —CH(SCH₃)(OCH₂CH₃) | |
| J-2 | Q-1 (R₇=H, R₈=H) | H | H | OCH₃ | —C(CH₃)₂(SCH₃) | |
| J-2 | Q-1 (R₇=H, R₈=H) | H | H | OCH₃ | —CH(SCH₂CH₃)₂ | |
| J-2 | Q-1 (R₇=H, R₈=H) | H | H | OCH₃ | 1,3-dioxolan-2-yl | |
| J-2 | Q-1 (R₇=H, R₈=H) | H | H | OCH₃ | 2-methyl-1,3-oxa-thiolan-2-yl | |

TABLE 2-continued

General Formula 2

| J | Q | R | $R_1$ | X | Y | m.p. (°C.) |
|---|---|---|---|---|---|---|
| J-2 | Q-1 ($R_7$=H, $R_8$=H) | H | H | $OCH_3$ | 1,3-oxathian-2-yl | |
| J-2 | Q-1 ($R_7$=H, $R_8$=H) | H | H | $OCH_3$ | 2-methyl-1,3-dithian-2-yl | |
| J-2 | Q-1 ($R_7$=H, $R_8$=H) | H | H | | 4-methyl-1,3-dioxolan-2-yl | |
| J-2 | Q-1 ($R_7$=H, $R_8$=H) | H | H | $OCH_3$ | 4-methyl-1,3-oxathiolan-2-yl | |
| J-2 | Q-1 ($R_7$=H, $R_8$=H) | H | H | $OCH_3$ | 2,4-dimethyl-1,3-dithiolan-2-yl | |
| J-2 | Q-1 ($R_7$=H, $R_8$=CH_3) | H | H | $OCH_3$ | $N(OCH_3)(CH_3)$ | |
| J-2 | Q-1 ($R_7$=H, $R_8$=CH_3) | H | H | $OCH_3$ | $OCH_3$ | |
| J-2 | Q-1 ($R_7$=H, $R_8$=CH_3) | H | H | $CH_3$ | $CH_3$ | |
| J-2 | Q-1 ($R_7$=H, $R_8$=CH_3) | H | H | $CH_3$ | $OCH_3$ | |
| J-2 | Q-1 ($R_7$=H, $R_8$=CH_2CH_3) | H | H | $OCH_3$ | $OCH_3$ | |
| J-2 | Q-1 ($R_7$=H, $R_8$=CH(CH_3)_2) | H | H | $OCH_3$ | $OCH_3$ | |
| J-2 | Q-1 ($R_7$=H, $R_8$=(CH_2)_3CH_3) | H | H | $OCH_3$ | $OCH_3$ | |
| J-2 | Q-1 ($R_7$=CH_3, $R_8$=CH_3) | H | H | $OCH_3$ | $OCH_3$ | |
| J-2 | Q-2 ($R_7$=H, $R_8$=H) | $CH_3$ | H | $OCH_3$ | $OCH_3$ | |
| J-2 | Q-2 ($R_7$=H, $R_8$=H) | H | 5-$OCH_3$ | $OCH_3$ | $OCH_3$ | |
| J-2 | Q-2 ($R_7$=H, $R_8$=CH_3) | H | H | $OCH_3$ | $OCH_3$ | |
| J-2 | Q-3 ($R_7$=CH_3, $R_8$=H) | H | 5-Cl | $CH_3$ | $CH_3$ | |
| J-2 | Q-4 ($R_7$=H, $R_8$=H, $R_3$=CH_3) | H | H | $OCH_3$ | $OCH_3$ | |
| J-2 | Q-4 ($R_7$=H, $R_8$=H, $R_3$=C_2H_5) | H | 5-$CH_3$ | $OCH_3$ | $OCH_3$ | |
| J-2 | Q-4 ($R_7$=H, $R_8$=H, $R_3$=i-C_3H_7) | H | H | $CH_3$ | $CH_3$ | |
| J-2 | Q-5 ($R_7$=H, $R_8$=H, $R_3$=H) | H | H | $OCH_3$ | $OCH_3$ | |
| J-2 | Q-5 ($R_7$=H, $R_8$=CH_3, $R_3$=CH_3) | H | H | $OCH_3$ | $OCH_3$ | |
| J-2 | Q-6 ($R_7$=CH_3, $R_8$=H, $R_3$=CH_3) | H | H | $CH_3$ | $OCH_3$ | |
| J-2 | Q-6 ($R_7$—H, $R_8$=H, $R_3$=C_2H_5) | $CH_3$ | H | $OCH_3$ | $OCH_3$ | |
| J-2 | Q-6 ($R_7$=C_2H_5, $R_8$=H, $R_9$=H) | H | H | $CH_3$ | $OCH_3$ | |
| J-2 | Q-7 ($R_7$=H, $R_8$=C_2H_5, $R_9$=H) | H | H | $OCH_3$ | $OCH_3$ | |
| J-2 | Q-7 ($R_7$=i-C_3H_7, $R_8$=H, $R_9$=CH_3) | H | 5-$OCH_3$ | $OCH_3$ | $OCH_3$ | |
| J-2 | Q-8 ($R_7$=H, $R_8$=H, $R_2$=H) | H | H | $OCH_3$ | $OCH_3$ | |
| J-2 | Q-8 ($R_7$=H, $R_8$=H, $R_2$=OCH(CH_3)CH_2CH_3) | H | 5-Cl | $CH_3$ | $OCH_3$ | |
| J-2 | Q-9 ($R_7$=H, $R_8$=H, $R_2$=H) | H | 5-$CH_3$ | $OCH_3$ | $OCH_3$ | |
| J-2 | Q-9 ($R_7$=CH_3, $R_8$=H, $R_2$=CH_3) | $CH_3$ | H | $OCH_3$ | $OCH_3$ | |
| J-2 | Q-9 ($R_7$=H, $R_8$=H, $R_2$=Cl) | H | 5-$OCH_3$ | $OCH_3$ | $OCH_3$ | |
| J-2 | Q-10 ($R_7$=H, $R_8$=H) | H | H | $CH_3$ | $OCH_3$ | |
| J-2 | Q-10 ($R_7$=H, $R_8$=CH_3) | H | 5-Cl | $OCH_3$ | $CH_3$ | |
| J-2 | Q-11 ($R_7$=H, $R_8$=H) | H | H | $CH_3$ | $OCH_3$ | |
| J-2 | Q-11 ($R_7$=n-C_4H_9, $R_8$=H) | H | 5-$CH_3$ | $OCH_3$ | $OCH_3$ | |
| J-2 | Q-11 ($R_7$=CH_3, $R_8$=CH_3) | H | H | $OCH_3$ | $OCH_3$ | |
| J-2 | Q-12 ($R_7$=H, $R_8$=H) | H | H | $CH_3$ | $OCH_3$ | |
| J-2 | Q-12 ($R_7$=H, $R_8$=C_2H_5) | H | 5-$OCH_3$ | $OCH_3$ | $OCH_3$ | |
| J-2 | Q-13 ($R_7$=H, $R_8$=H, $R_3$=H) | $CH_3$ | H | $OCH_3$ | $OCH_3$ | |
| J-2 | Q-13 ($R_7$=H, $R_8$=H, $R_3$=CH_3) | H | 5-Cl | $CH_3$ | $OCH_3$ | |
| J-2 | Q-13 ($R_7$=CH_3, $R_8$=H, $R_3$=CH_3) | H | H | $OCH_3$ | $OCH_3$ | |
| J-2 | Q-14 ($R_7$=H, $R_8$=H, $R_3$=CH_3) | H | 5-$CH_3$ | $OCH_3$ | $OCH_3$ | |
| J-2 | Q-14 ($R_7$=CH_3, $R_8$=H, $R_3$=C_2H_5) | H | H | $OCH_3$ | $OCH_3$ | |
| J-2 | Q-14 ($R_7$=H, $R_8$=CH_3, $R_3$=CH_3) | H | 5-$OCH_3$ | $OCH_3$ | $OCH_3$ | |

TABLE 2-continued

General Formula 2

| | Q | R | R₁ | X | Y | m.p. (°C.) |
|---|---|---|---|---|---|---|
| J-2 | Q-15 (R₇=H, R₈=H, R₃=H) | H | H | OCH₃ | OCH₃ | |
| J-2 | Q-15 (R₇=CH₃, R₈=CH₃, R₃=CH₃) | H | 5-Cl | OCH₃ | OCH₃ | |
| J-2 | Q-16 (R₇=H, R₈=H, R₉=H) | H | H | OCH₃ | OCH₃ | |
| J-2 | Q-16 (R₇=CH₃, R₈=H, R₉=H) | CH₃ | H | OCH₃ | OCH₃ | |
| J-2 | Q-16 (R₇=CH₃, R₈=CH₃, R₉=H) | H | 5-OCH₃ | OCH₃ | OCH₃ | |
| J-2 | Q-17 (R₇=H, R₈=H, R₂=H) | H | H | OCH₃ | OCH₃ | |
| J-2 | Q-17 (R₇=H, R₈=H, R₂=C₂H₅) | H | 5-Cl | CH₃ | CH₃ | |
| J-2 | Q-18 (R₇=H, R₈=OC₂H₅, R₂=H) | H | H | CH₃ | OCH₃ | |
| J-2 | Q-18 (R₇=CH₃, R₈=OCH(CH₃)₂, R₂=CH₃) | H | 5-CH₃ | OCH₃ | OCH₃ | |
| J-2 | Q-19 (R₇=H, R₈=H) | H | H | OCH₃ | OCH₃ | |
| J-2 | Q-19 (R₇=CH₃, R₈=CH₃) | H | H | CH₃ | OCH₃ | |
| J-2 | Q-20 (R₇=H, R₈=H) | CH₃ | H | CH₃ | OCH₃ | |
| J-2 | Q-20 (R₇=CH₃, R₈=CH₃) | H | H | OCH₃ | OCH₃ | |
| J-2 | Q-21 (R₇=H, R₈=H) | H | H | OCH₃ | OCH₃ | |
| J-2 | Q-21 (R₇=CH₃, R₈=CH₃) | H | 5-OCH₃ | OCH₃ | OCH₃ | |
| J-2 | Q-22 (R₇=H, R₈=H, R₃=H) | H | 5-Cl | OCH₃ | OCH₃ | |
| J-2 | Q-22 (R₇=CH₃, R₈=CH₃, R₃=C₂H₅) | H | H | CH₃ | OCH₃ | |
| J-2 | Q-23 (R₇=H, R₈=H, R₃=CH₃) | CH₃ | H | OCH₃ | OCH₃ | |
| J-2 | Q-23 (R₇=CH₃, R₈=H, R₃=n-C₄H₉) | H | 5-OCH₃ | OCH₃ | OCH₃ | |
| J-2 | Q-24 (R₇=H, R₈=CH₃, R₃=CH₃) | H | H | OCH₃ | OCH₃ | |
| J-2 | Q-24 (R₇=H, R₈=CH₃, R₃=i-C₃H₇) | H | 5-Cl | OCH₃ | OCH₃ | |
| J-2 | Q-25 (R₇=H, R₈=H, R₉=H) | H | H | CH₃ | CH₃ | |
| J-2 | Q-25 (R₇=CH₃, R₈=H, R₉=H) | H | 5-CH₃ | CH₃ | OCH₃ | |
| J-2 | Q-25 (R₇=H, R₈=H, R₉=C₂H₅) | H | H | OCH₃ | OCH₃ | |
| J-2 | Q-26 (R₇=H, R₈=H) | H | H | OCH₃ | OCH₃ | |
| J-2 | Q-26 (R₇=CH₃, R₈=CH₃) | CH₃ | H | CH₃ | OCH₃ | |
| J-2 | Q-27 (R₇=H, R₈=H) | H | H | CH₃ | OCH₃ | |
| J-2 | Q-27 (R₇=CH₃, R₈=CH₃) | H | H | OCH₃ | OCH₃ | |
| J-2 | Q-27 (R₇=H, R₈=H) | H | 5-Cl | OCH₃ | OCH₃ | |
| J-2 | Q-28 (R₇=CH₃, R₈=H) | H | H | OCH₃ | OCH₃ | |
| J-2 | Q-28 (R₇=CH₃, R₈=H, R₃=CH₃) | H | 5-OCH₃ | OCH₃ | OCH₃ | |
| J-2 | Q-29 (R₇=H, R₈=CH₃) | H | H | OCH₃ | OCH₃ | |
| J-2 | Q-29 (R₇=CH₃, R₈=CH₃) | H | 5-Cl | OCH₃ | OCH₃ | |
| J-2 | Q-30 (R₇=H, R₈=H) | H | H | OCH₃ | OCH₃ | |
| J-2 | Q-30 (R₇=CH₃, R₈=CH₃) | CH₃ | 5-OCH₃ | OCH₃ | CH₃ | |
| J-2 | Q-30 (R₇=C₂H₅, R₈=H) | H | 5-Cl | OCH₃ | OCH₃ | |
| J-2 | Q-31 (R₇=H, R₈=H) | H | H | CH₃ | CH₃ | |
| J-2 | Q-32 (R₇=H, R₈=n-C₄H₉) | H | 5-CH₃ | CH₃ | OCH₃ | |
| J-2 | Q-32 (R₇=CH₃, R₈=H, R₃=CH₃) | H | H | OCH₃ | OCH₃ | |
| J-2 | Q-32 (R₇=H, R₈=CH₃, R₃=C₂H₅) | H | H | OCH₃ | OCH₃ | |
| J-2 | Q-33 (R₇=H, R₈=H, R₈=CH₃) | H | 5-Cl | CH₃ | CH₃ | |
| J-2 | Q-33 (R₇=C₂H₅, R₈=H, R₃=n-C₄H₉) | CH₃ | H | CH₃ | CH₃ | |
| J-2 | Q-34 (R₇=H, R₈=H, R₃=H) | H | H | CH₃ | CH₃ | |
| J-2 | Q-34 (R₇=i-C₃H₇, R₈=H, R₃=CH₃) | CH₃ | H | CH₃ | OCH₃ | |
| J-2 | Q-34 (R₇=H, R₈=n-C₄H₉, R₃=CH₃) | H | H | OCH₃ | OCH₃ | |

TABLE 2-continued

General Formula 2

| J | Q | R | R₁ | X | Y | m.p. (°C.) |
|---|---|---|----|---|---|------------|
| J-2 | Q-35 (R₇=H, R₈=H, R₉=H) | H | H | OCH₃ | OCH₃ | |
| J-2 | Q-35 (R₇=CH₃, R₈=H, R₉=H) | H | H | OCH₃ | OCH₃ | |
| J-2 | Q-35 (R₇=CH₃, R₈=CH₃, R₉=CH₃) | H | 5-OCH₃ | OCH₃ | OCH₃ | |
| J-2 | Q-36 (R₇=H, R₈=H, R₂=H) | H | H | OCH₃ | OCH₃ | |
| J-2 | Q-36 (R₇=H, R₈=H, R₂=C₂H₅) | H | 5-Cl | OCH₃ | OCH₃ | |
| J-2 | Q-37 (R₇=H, R₈=H, R₂=i-C₃H₇) | CH₃ | H | OCH₃ | OCH₃ | |
| J-2 | Q-37 (R₇=H, R₈=H, R₂=n-C₄H₉) | H | 5-OCH₃ | OCH₃ | OCH₃ | |
| J-2 | Q-38 (R₇=H, R₈=H, R₂=OCF₂H) | H | H | OCH₃ | OCH₃ | |
| J-2 | Q-38 (R₇=H, R₈=H, R₂=Cl) | H | 5-Cl | OCH₃ | OCH₃ | |
| J-2 | Q-39 (R₇=H, R₈=H, R₉=H) | H | H | CH₃ | CH₃ | |
| J-2 | Q-39 (R₇=C₂H₅, R₈=H, R₉=H) | H | H | OCH₃ | OCH₃ | |
| J-2 | Q-39 (R₇=H, R₈=H, R₉=CH₃) | H | 5-CH₃ | OCH₃ | OCH₃ | |
| J-2 | Q-40 (R₇=H, R₈=H) | H | H | CH₃ | OCH₃ | |
| J-2 | Q-41 (R₇=H, R₈=CH₃) | H | H | CH₃ | OCH₃ | |
| J-2 | Q-41 (R₇=H, R₈=H) | H | H | OCH₃ | OCH₃ | |
| J-2 | Q-42 (R₇=CH₃, R₈=CH₃) | CH₃ | H | OCH₃ | OCH₃ | |
| J-2 | Q-42 (R₇=C₂H₅, R₈=C₂H₅) | H | 5-OCH₃ | OCH₃ | OCH₃ | |
| J-2 | Q-43 (R₇=CH₃, R₈=H, R₃=H) | H | 5-Cl | OCH₃ | OCH₃ | |
| J-2 | Q-44 (R₇=CH₃, R₈=H, R₃=CH₃) | H | H | OCH₃ | OCH₃ | |
| J-2 | Q-44 (R₇=CH₃, R₈=H, R₃=C₂H₅) | CH₃ | H | OCH₃ | OCH₃ | |
| J-2 | Q-45 (R₇=H, R₈=CH₃, R₃=CH₃) | H | 5-OCH₃ | OCH₃ | OCH₃ | |
| J-2 | Q-45 (R₇=CH₃, R₈=H, R₃=H) | H | H | OCH₃ | OCH₃ | |
| J-2 | Q-45 (R₇=CH₃, R₈=CH₃, R₃=CH₃) | H | 5-Cl | OCH₃ | OCH₃ | |
| J-2 | Q-46 (R₇=H, R₈=H, R₉=H) | H | H | CH₃ | CH₃ | |
| J-2 | Q-46 (R₇=CH₃, R₈=CH₃, R₉=H) | H | 5-CH₃ | OCH₃ | OCH₃ | |
| J-2 | Q-46 (R₇=CH₃, R₈=CH₃, R₉=H) | H | H | OCH₃ | OCH₃ | |
| J-2 | Q-47 (R₇=H, R₈=H, R₂=C₂H₅) | H | H | OCH₃ | OCH₃ | |
| J-2 | Q-48 (R₇=CH₃, R₈=CH₃, R₂=CH₃) | CH₃ | H | CH₃ | CH₃ | |
| J-2 | Q-48 (R₇=H, R₈=C₂H₅, R₂=C₂H₅) | H | H | OCH₃ | OCH₃ | |
| J-2 | Q-49 (R₇=CH₃, R₈=CH₃, R₂=H) | H | 5-OCH₃ | OCH₃ | OCH₃ | |
| J-2 | Q-49 (R₇=CH₃, R₈=CH₃, R₂=CH₃) | H | H | OCH₃ | OCH₃ | |
| J-2 | Q-50 (R₇=H, R₈=H, R₂=H) | H | 5-Cl | OCH₃ | OCH₃ | |
| J-2 | Q-50 (R₇=CH₃, R₈=CH₃, R₂=CH₃) | H | H | CH₃ | CH₃ | |
| J-2 | Q-51 (R₇=H, R₈=H, R₉=H) | CH₃ | H | OCH₃ | OCH₃ | |
| J-2 | Q-51 (R₇=H, R₈=H, R₉=s-C₄H₉) | H | 5-OCH₃ | OCH₃ | OCH₃ | |
| J-2 | Q-52 (R₇=H, R₈=H, R₉=H) | H | H | OCH₃ | OCH₃ | |
| J-2 | Q-52 (R₇=H, R₈=H, R₉=CH₃) | H | 5-Cl | OCH₃ | OCH₃ | |
| J-2 | Q-53 (R₇=H, R₈=H, R₉=H) | H | H | CH₃ | CH₃ | |
| J-2 | Q-53 (R₇=CH₃, R₈=CH₃, R₉=CH₃) | H | 5-OCH₃ | OCH₃ | OCH₃ | |
| J-2 | Q-54 (R₇=H, R₈=H, R₉=CH₃) | H | H | OCH₃ | OCH₃ | |
| J-2 | Q-54 (R₇=H, R₈=H, R₉=i-C₃H₇) | H | H | CH₃ | OCH₃ | |

TABLE 2-continued

| | | General Formula 2 | | | | | |
|---|---|---|---|---|---|---|---|
| J | Q | | R | $R_1$ | X | Y | m.p. (°C.) |
| J-2 | Q-55 ($R_7$=H, $R_8$=H, $R_9$=H, $R_3$=H) | | H | H | $CH_3$ | $OCH_3$ | |
| J-2 | Q-55 ($R_7$=H, $R_8$=H, $R_9$=$CH_3$, $R_3$=$CH_3$) | | $CH_3$ | H | $CH_3$ | $OCH_3$ | |
| J-2 | Q-55 ($R_7$=H, $R_8$=H, $R_9$=s-$C_4H_9$, $R_3$=H) | | H | H | $OCH_3$ | $OCH_3$ | |
| J-2 | Q-56 ($R_7$=H, $R_8$=H, $R_9$=H, $R_3$=$C_2H_5$) | | H | H | $OCH_3$ | $OCH_3$ | |
| J-2 | Q-56 ($R_7$=$CH_3$, $R_8$=H, $R_9$=H, $R_3$=H) | | H | H | $OCH_3$ | $OCH_3$ | |
| J-2 | Q-56 ($R_7$=H, $R_8$=H, $R_9$=$CH_3$, $R_3$=$CH_3$) | | H | 5-$OCH_3$ | $OCH_3$ | $OCH_3$ | |
| J-2 | Q-57 ($R_7$=H, $R_8$=H, $R_9$=H, $R_3$=i-$C_3H_7$) | | H | H | $OCH_3$ | $OCH_3$ | |
| J-2 | Q-57 ($R_7$=H, $R_8$=H, $R_9$=$CH_3$, $R_3$=$CH_3$) | | H | 5-Cl | $OCH_3$ | $OCH_3$ | |
| J-2 | Q-58 ($R_7$=H, $R_8$=H, $R_9$=H, $R_3$=H) | | H | H | $OCH_3$ | $CH_3$ | |
| J-2 | Q-58 ($R_7$=$CH_3$, $R_8$=H, $R_9$=H, $R_3$=$CH_3$) | | $CH_3$ | H | $OCH_3$ | $OCH_3$ | |
| J-2 | Q-58 ($R_7$=H, $R_8$=H, $R_9$=i-$C_3H_7$, $R_3$=$CH_3$) | | H | 5-$OCH_3$ | $OCH_3$ | $OCH_3$ | |
| J-2 | Q-59 ($R_7$=H, $R_8$=H, $R_9$=H, $R_{10}$=H) | | H | H | $OCH_3$ | $CH_3$ | |
| J-2 | Q-59 ($R_7$=H, $R_8$=H, $R_9$=H, $R_{10}$=s-$C_4H_9$) | | H | 5-Cl | $OCH_3$ | $OCH_3$ | |
| J-2 | Q-60 ($R_7$=H, $R_8$=H, $R_9$=H, $R_2$=H) | | H | H | $OCH_3$ | $OCH_3$ | |
| J-2 | Q-60 ($R_7$=$CH_3$, $R_8$=H, $R_9$=H, $R_2$=O($CH_2$)$_3CH_2$Br) | | H | H | $CH_3$ | $CH_3$ | |
| J-2 | Q-60 ($R_7$=H, $R_8$=H, $R_9$=H, $R_2$=Br) | | H | H | $CH_3$ | $CH_3$ | |
| J-2 | Q-61 ($R_7$=H, $R_8$=H, $R_9$=H, $R_2$=H) | | H | H | $CH_3$ | $CH_3$ | |
| J-2 | Q-61 ($R_7$=H, $R_8$=$CH_3$, $R_9$=H, $R_2$=O($CH_2$)$_3CH_3$) | | H | H | $OCH_3$ | $OCH_3$ | |
| J-2 | Q-62 ($R_7$=$CH_3$, $R_8$=H, $R_9$=H, $R_2$=H) | | $CH_3$ | H | $OCH_3$ | $OCH_3$ | |
| J-2 | Q-62 ($R_7$=Cl, $R_8$=H, $R_9$=H, $R_2$=$CH_3$) | | H | H | $OCH_3$ | $OCH_3$ | |
| J-2 | Q-63 ($R_7$=H, $R_8$=H, $R_9$=H) | | H | H | $OCH_3$ | $OCH_3$ | |
| J-2 | Q-63 ($R_7$=$CH_3$, $R_8$=H, $R_9$=H) | | H | 5-$OCH_3$ | $OCH_3$ | $OCH_3$ | |
| J-2 | Q-64 ($R_7$=H, $R_8$=H, $R_9$=H) | | H | 5-Cl | $OCH_3$ | $OCH_3$ | |
| J-2 | Q-65 ($R_7$=H, $R_8$=H, $R_9$=$C_2H_5$) | | H | H | $OCH_3$ | $OCH_3$ | |
| J-2 | Q-65 ($R_7$=n-$C_4H_9$, $R_8$=H, $R_9$=H) | | H | H | $OCH_3$ | $OCH_3$ | |
| J-2 | Q-65 ($R_7$=H, $R_8$=$CH_3$, $R_9$=i-$C_3H_7$) | | H | H | $OCH_3$ | $CH_3$ | |
| J-2 | Q-66 ($R_7$=H, $R_8$=H, $R_9$=$CH_3$) | | H | H | $OCH_3$ | $OCH_3$ | |
| J-2 | Q-67 ($R_7$=H, $R_8$=H, $R_9$=H, $R_3$=$CH_3$) | | H | 5-$OCH_3$ | $OCH_3$ | $OCH_3$ | |
| J-2 | Q-67 ($R_7$=$CH_3$, $R_8$=H, $R_9$=$CH_3$, $R_3$=$C_2H_5$) | | H | H | $CH_3$ | $CH_3$ | |
| J-2 | Q-68 ($R_7$=H, $R_8$=H, $R_9$=$CH_3$, $R_3$=$CH_3$) | | H | 5-Cl | $OCH_3$ | $OCH_3$ | |
| J-2 | Q-68 ($R_7$=H, $R_8$=H, $R_9$=$C_2H_5$, $R_3$=n-$C_4H_9$) | | H | H | $OCH_3$ | $OCH_3$ | |
| J-2 | Q-69 ($R_7$=H, $R_8$=H, $R_9$=H, $R_3$=$CH_3$) | | H | H | $OCH_3$ | $OCH_3$ | |
| J-2 | Q-69 ($R_7$=n-$C_4H_9$, $R_8$=H, $R_9$=H, $R_3$=$C_2H_5$) | | H | 5-$OCH_3$ | $OCH_3$ | $OCH_3$ | |
| J-2 | Q-69 ($R_7$=H, $R_8$=$CH_3$, $R_9$=i-$C_3H_7$, $R_3$=H) | | H | 5-Cl | $OCH_3$ | $OCH_3$ | |
| J-2 | Q-70 ($R_7$=H, $R_8$=H, $R_9$=H, $R_3$=$CH_3$) | | H | H | $OCH_3$ | $OCH_3$ | |
| J-2 | Q-70 ($R_7$=i-$C_3H_7$, $R_8$=H, $R_9$=H, $R_3$=$CH_3$) | | H | H | $OCH_3$ | $OCH_3$ | |
| J-2 | Q-70 ($R_7$=H, $R_8$=$C_2H_5$, $R_9$=$CH_3$, $R_3$=H) | | H | 5-$OCH_3$ | $OCH_3$ | $OCH_3$ | |
| J-2 | Q-71 ($R_7$=$CH_3$, $R_8$=H, $R_9$=H, $R_{10}$=H) | | H | 5-Cl | $OCH_3$ | $OCH_3$ | |
| J-2 | Q-71 ($R_7$=H, $R_8$=H, $R_9$=H, $R_{10}$=$CH_3$) | | H | 5-$OCH_3$ | $OCH_3$ | $OCH_3$ | |
| J-2 | Q-72 ($R_7$=H, $R_8$=H, $R_9$=H, $R_2$=H) | | H | H | $OCH_3$ | $OCH_3$ | |
| J-2 | Q-72 ($R_7$=H, $R_8$=H, $R_9$=H, $R_2$=$CH_3$) | | H | 5-Cl | $OCH_3$ | $OCH_3$ | |
| J-2 | Q-72 ($R_7$=$CH_3$, $R_8$=H, $R_9$=H, $R_2$=H) | | H | 5-$OCH_3$ | $OCH_3$ | $OCH_3$ | |
| J-2 | Q-73 ($R_7$=H, $R_8$=H, $R_9$=H, $R_2$=H) | | H | H | $CH_3$ | $CH_3$ | |
| J-2 | Q-73 ($R_7$=$CH_3$, $R_8$=H, $R_9$=$CH_3$, $R_2$=H) | | H | 5-Cl | $OCH_3$ | $OCH_3$ | |
| J-2 | Q-74 ($R_7$=H, $R_8$=H, $R_9$=H, $R_2$=H) | | H | H | $CH_3$ | $CH_3$ | |
| J-2 | Q-74 ($R_7$=$CH_3$, $R_8$=H, $R_9$=H, $R_2$=H) | | H | H | $CH_3$ | $OCH_3$ | |

TABLE 2-continued

General Formula 2

| J | Q | R | R₁ | X | Y | m.p. (°C.) |
|---|---|---|---|---|---|---|
| J-2 | Q-74 (R₇=H, R₈=H, R₉=H, R₂=CH₃) | H | 5-CH₃ | OCH₃ | OCH₃ | |
| J-2 | Q-75 (R₇=H, R₈=H, R₉=H) | H | H | OCH₃ | OCH₃ | |
| J-2 | Q-75 (R₇=CH₃, R₈=H, R₉=CH₃) | H | H | CH₃ | OCH₃ | |
| J-2 | Q-76 (R₇=H, R₈=H, R₉=H) | H | H | CH₃ | OCH₃ | |
| J-2 | Q-76 (R₇=H, R₈=H, R₉=CH₃) | CH₃ | H | CH₃ | OCH₃ | |
| J-2 | Q-77 (R₇=C₂H₅, R₈=H, R₉=C₂H₅) | H | H | OCH₃ | OCH₃ | |
| J-2 | Q-77 (R₇=H, R₈=H, R₉=n-C₃H₇) | H | H | OCH₃ | OCH₃ | |
| J-2 | Q-77 (R₇=H, R₈=CH₃, R₉=H) | H | 5-OCH₃ | OCH₃ | OCH₃ | |
| J-2 | Q-78 (R₇=n-C₃H₇, R₈=H, R₉=H) | H | 5-Cl | OCH₃ | OCH₃ | |
| J-2 | Q-79 (R₇=H, R₈=H, R₉=H, R₃=H) | H | H | OCH₃ | OCH₃ | |
| J-2 | Q-79 (R₇=CH₃, R₈=H, R₉=H, R₃=CH₃) | CH₃ | H | OCH₃ | OCH₃ | |
| J-2 | Q-80 (R₇=H, R₈=H, R₉=H, R₃=C₂H₅) | H | 5-OCH₃ | OCH₃ | OCH₃ | |
| J-2 | Q-80 (R₇=H, R₈=H, R₉=CH₃, R₃=CH₃) | H | H | OCH₃ | OCH₃ | |
| J-2 | Q-81 (R₇=H, R₈=H, R₉=H, R₃=C₂H₅) | H | 5-Cl | OCH₃ | OCH₃ | |
| J-2 | Q-81 (R₇=H, R₈=CH₃, R₉=H, R₃=i-C₃H₇) | H | H | CH₃ | CH₃ | |
| J-2 | Q-81 (R₇=CH₃, R₈=H, R₉=CH₃, R₃=CH₃) | H | 5-CH₃ | OCH₃ | OCH₃ | |
| J-2 | Q-82 (R₇=H, R₈=H, R₉=H, R₃=CH₃) | H | H | OCH₃ | OCH₃ | |
| J-2 | Q-82 (R₇=H, R₈=H, R₉=C₂H₅, R₃=CH₃) | H | H | CH₃ | OCH₃ | |
| J-2 | Q-83 (R₇=H, R₈=H, R₉=H, R₁₀=H) | H | H | CH₃ | CH₃ | |
| J-2 | Q-83 (R₇=CH₃, R₈=H, R₉=H, R₁₀=CH₃) | H | H | CH₃ | CH₃ | |
| J-2 | Q-83 (R₇=CH₃, R₈=CH₃, R₉=H, R₁₀=H) | H | H | OCH₃ | OCH₃ | |
| J-2 | Q-84 (R₇=H, R₈=H, R₉=H) | H | H | OCH₃ | OCH₃ | |
| J-2 | Q-84 (R₇=H, R₈=H, R₉=CH₃) | H | H | OCH₃ | OCH₃ | |
| J-2 | Q-84 (R₇=H, R₈=C₂H₅, R₉=H) | H | H | OCH₃ | OCH₃ | |
| J-2 | Q-85 (R₇=H, R₈=H, R₉=H) | H | H | OCH₃ | OCH₃ | |
| J-2 | Q-85 (R₇=CH₃, R₈=H, R₉=CH₃) | H | H | OCH₃ | OCH₃ | |
| J-2 | Q-86 (R₇=H, R₈=H, R₉=H) | H | H | OCH₃ | OCH₃ | |
| J-2 | Q-86 (R₇=CH₃, R₈=H, R₉=H) | H | H | OCH₃ | OCH₃ | |
| J-2 | Q-86 (R₇=H, R₈=H, R₉=C₂H₅) | H | H | CH₃ | CH₃ | |
| J-2 | Q-87 (R₇=H, R₈=H, R₉=H) | H | H | OCH₃ | OCH₃ | |
| J-2 | Q-88 (R₇=CH₃, R₈=H, R₉=H) | H | 5-Cl | CH₃ | CH₃ | |
| J-2 | Q-88 (R₇=H, R₈=H, R₉=H) | H | H | OCH₃ | OCH₃ | |
| J-2 | Q-88 (R₇=H, R₈=H, R₉=CH₃) | H | H | OCH₃ | OCH₃ | |
| J-2 | Q-89 (R₇=H, R₈=CH₃, R₉=H) | H | H | OCH₃ | OCH₃ | |
| J-2 | Q-90 (R₇=CH₃, R₈=H, R₉=H, R₁=CH₃) | H | 5-OCH₃ | CH₃ | CH₃ | |
| J-2 | Q-90 (R₇=H, R₈=H, R₉=H, R₃=C₂H₅) | H | 5-Cl | OCH₃ | OCH₃ | |
| J-2 | Q-90 (R₇=H, R₈=CH₃, R₃=CH₃) | H | 5-CH₃ | CH₃ | OCH₃ | |
| J-2 | Q-91 (R₇=H, R₈=H, R₉=H, R₃=CH₃) | H | H | OCH₃ | OCH₃ | |
| J-2 | Q-91 (R₇=CH₃, R₈=H, R₉=H, R₁=CH₃) | H | H | OCH₃ | OCH₃ | |
| J-2 | Q-91 (R₇=H, R₈=H, R₉=CH₃, R₃=CH₃) | H | 5-OCH₃ | OCH₃ | OCH₃ | |
| J-2 | Q-92 (R₇=H, R₈=CH₃, R₉=H, R₁₀=H) | H | 5-Cl | OCH₃ | OCH₃ | |
| J-2 | Q-93 (R₇=H, R₈=H, R₉=H) | H | H | OCH₃ | OCH₃ | |
| J-2 | Q-93 (R₇=H, R₈=H, R₉=CH₃) | CH₃ | H | OCH₃ | OCH₃ | |
| J-2 | Q-94 (R₇=H, R₈=H, R₉=H) | H | 5-OCH₃ | OCH₃ | OCH₃ | |
| J-2 | Q-94 (R₇=H, R₈=H, R₉=H) | H | H | OCH₃ | OCH₃ | |

TABLE 2-continued

General Formula 2

| J | Q | R | R₁ | X | Y | m.p. (°C.) |
|---|---|---|---|---|---|---|
| J-2 | Q-94 (R₇=H, R₈=H, R₉=n-C₄H₉) | H | 5-Cl | OCH₃ | CH₃ | |
| J-2 | Q-95 (R₇=H, R₈=H, R₉=H) | H | H | CH₃ | OCH₃ | |
| J-2 | Q-95 (R₇=H, R₈=H, R₉=CH₃) | H | H | CH₃ | OCH₃ | |
| J-2 | Q-95 (R₇=H, R₈=H, R₉=s-C₄H₉) | H | 5-CH₃ | OCH₃ | OCH₃ | |
| J-2 | Q-96 (R₇=H, R₈=H, R₉=H) | H | H | OCH₃ | OCH₃ | |
| J-2 | Q-96 (R₇=H, R₈=H, R₉=CH₃) | H | H | CH₃ | OCH₃ | |
| J-2 | Q-97 (R₇=H, R₈=H, R₉=H) | CH₃ | H | CH₃ | OCH₃ | |
| J-2 | Q-97 (R₇=CH₃, R₈=CH₃, R₉=CH₃) | H | H | OCH₃ | OCH₃ | |
| J-2 | Q-97 (R₇=H, R₈=H, R₉=CH₃) | H | H | OCH₃ | OCH₃ | |
| J-2 | Q-98 (R₇=H, R₈=H, R₉=H) | H | H | OCH₃ | OCH₃ | |
| J-2 | Q-98 (R₇=CH₃, R₈=H, R₉=H) | H | 5-OCH₃ | OCH₃ | OCH₃ | |
| J-2 | Q-99 (R₇=H, R₈=H, R₉=i-C₃H₇) | H | H | OCH₃ | OCH₃ | |
| J-2 | Q-99 (R₇=H, R₈=H, R₉=H, R₃=H) | H | 5-Cl | OCH₃ | OCH₃ | |
| J-2 | Q-99 (R₇=H, R₈=H, R₉=s-C₄H₉, R₃=C₂H₅) | H | H | CH₃ | CH₃ | |
| J-2 | Q-100 (R₇=CH₃, R₈=H, R₉=H, R₃=H) | CH₃ | 5-OCH₃ | OCH₃ | OCH₃ | |
| J-2 | Q-100 (R₇=H, R₈=H, R₉=CH₃, R₃=CH₃) | H | H | OCH₃ | OCH₃ | |
| J-2 | Q-101 (R₇=H, R₈=H, R₉=H, R₃=i-C₃H₇) | H | H | CH₃ | CH₃ | |
| J-2 | Q-101 (R₇=H, R₈=H, R₉=CH₃, R₃=CH₃) | H | 5-Cl | OCH₃ | OCH₃ | |
| J-2 | Q-102 (R₇=CH₃, R₈=H, R₉=H, R₃=CH₃) | H | H | CH₃ | OCH₃ | |
| J-2 | Q-102 (R₇=H, R₈=H, R₉=i-C₃H₇,R₃=CH₃) | H | 5-CH₃ | OCH₃ | OCH₃ | |
| J-2 | Q-103 (R₇=H, R₈=H, R₉=H, R₁₀=H) | H | H | OCH₃ | OCH₃ | |
| J-2 | Q-103 (R₇=H, R₈=H, R₉=H, R₁₀=s-C₄H₉) | H | H | CH₃ | OCH₃ | |
| J-2 | Q-104 (R₇=H, R₈=H, R₉=H, R₂=H) | H | H | OCH₃ | OCH₃ | |
| J-2 | Q-104 (R₇=CH₃, R₈=H, R₉=H, R₂=OC₂H₅) | H | H | CH₃ | CH₃ | |
| J-2 | Q-104 (R₇=H, R₈=H, R₉=H, R₂=Br) | H | H | OCH₃ | OCH₃ | |
| J-2 | Q-105 (R₇=H, R₈=H, R₉=H, R₂=H) | H | H | OCH₃ | OCH₃ | |
| J-2 | Q-105 (R₇=CH₃, R₈=H, R₉=H, R₂=CH₃) | H | 5-OCH₃ | OCH₃ | OCH₃ | |
| J-2 | Q-105 (R₇=H, R₈=H, R₉=H, R₂=C₂H₅) | H | H | CH₃ | OCH₃ | |
| J-2 | Q-106 (R₇=H, R₈=CH₃, R₉=H, R₂=H) | H | H | OCH₃ | OCH₃ | |
| J-2 | Q-106 (R₇=Cl, R₈=H, R₉=H, R₂=H) | H | 5-Cl | OCH₃ | OCH₃ | |
| J-2 | Q-107 (R₇=CH₃, R₈=H, R₉=H, R₂=H) | CH₃ | H | OCH₃ | OCH₃ | |
| J-2 | Q-107 (R₇=H, R₈=H, R₉=H, R₂=CH₃) | H | 5-OCH₃ | OCH₃ | OCH₃ | |
| J-2 | Q-108 (R₇=H, R₈=H, R₉=H, R₂=H) | H | 5-Cl | OCH₃ | OCH₃ | |
| J-2 | Q-109 (R₇=H, R₈=H, R₉=H) | H | H | CH₃ | CH₃ | |
| J-2 | Q-109 (R₇=CH₃, R₈=H, R₉=H) | H | H | CH₃ | OCH₃ | |
| J-2 | Q-110 (R₇=H, R₈=H, R₉=H) | H | 5-CH₃ | OCH₃ | OCH₃ | |
| J-2 | Q-110 (R₇=H, R₈=CH₃, R₉=H) | H | H | OCH₃ | OCH₃ | |
| J-2 | Q-111 (R₇=H, R₈=H, R₉=H) | CH₃ | H | CH₃ | CH₃ | |
| J-2 | Q-111 (R₇=CH₃, R₈=H, R₉=CH₃) | H | H | OCH₃ | OCH₃ | |
| J-2 | Q-112 (R₇=H, R₈=H, R₉=H) | H | 5-Cl | OCH₃ | OCH₃ | |
| J-2 | Q-112 (R₇=CH₃, R₈=CH₃, R₉=H) | H | H | OCH₃ | OCH₃ | |
| J-2 | Q-113 (R₇=H, R₈=H, R₉=H, R₃=CH₃) | H | 5-OCH₃ | OCH₃ | OCH₃ | |
| J-2 | Q-113 (R₇=H, R₈=H, R₉=C₂H₅, R₃=n-C₄H₉) | H | 5-Cl | OCH₃ | OCH₃ | |
| J-2 | Q-114 (R₇=H, R₈=H, R₉=H, R₃=CH₃) | H | H | OCH₃ | OCH₃ | |

TABLE 2-continued

General Formula 2

| J | Q | R | $R_1$ | X | Y | m.p. (°C.) |
|---|---|---|---|---|---|---|
| J-2 | Q-114 ($R_7$=n-$C_4H_9$, $R_8$=H, $R_9$=H, $R_3$=$C_2H_5$) | $CH_3$ | H | $OCH_3$ | $CH_3$ | |
| J-2 | Q-114 ($R_7$=H, $R_8$=$CH_3$, $R_8$=i-$C_3H_7$, $R_3$=H) | H | 5-$OCH_3$ | $OCH_3$ | $OCH_3$ | |
| J-2 | Q-115 ($R_7$=H, $R_8$=H, $R_9$=H, $R_3$=$CH_3$) | H | H | $OCH_3$ | $OCH_3$ | |
| J-2 | Q-115 ($R_7$=H, $R_8$=$C_2H_5$, $R_9$=$CH_3$, $R_3$=H) | H | 5-Cl | $OCH_3$ | $CH_3$ | |
| J-2 | Q-116 ($R_7$=H, $R_8$=H, $R_9$=H, $R_{10}$=H) | H | H | $CH_3$ | $OCH_3$ | |
| J-2 | Q-116 ($R_7$=$CH_3$, $R_8$=H, $R_9$=H, $R_{10}$=$CH_3$) | H | H | $CH_3$ | $OCH_3$ | |
| J-2 | Q-117 ($R_7$=$CH_3$, $R_8$=H, $R_9$=H, $R_2$=H) | H | 5-$CH_3$ | $OCH_3$ | $OCH_3$ | |
| J-2 | Q-117 ($R_7$=$CH_3$, $R_8$=H, $R_9$=H, $R_2$=H) | H | H | $CH_3$ | $OCH_3$ | |
| J-2 | Q-118 ($R_7$=H, $R_8$=H, $R_9$=H, $R_{10}$=H) | $CH_3$ | H | $CH_3$ | $OCH_3$ | |
| J-2 | Q-118 ($R_7$=$CH_3$, $R_8$=H, $R_9$=H, $R_{10}$=$CH_3$) | H | H | $OCH$ | $OCH_3$ | |
| J-2 | Q-119 ($R_7$=H, $R_8$=H, $R_9$=H, $R_2$=H) | H | H | $OCH_3$ | $OCH_3$ | |
| J-2 | Q-119 ($R_7$=H, $R_8$=$CH_3$, $R_9$=H, $R_2$=$C_2H_5$) | H | 5-$OCH_3$ | $OCH_3$ | $OCH_3$ | |
| J-2 | Q-120 ($R_7$=H, $R_8$=H, $R_9$=$CH_3$, $R_2$=$CH_3$) | H | H | $OCH_3$ | $OCH_3$ | |
| J-2 | Q-120 ($R_7$=H, $R_8$=H, $R_9$=H, $R_2$=H) | H | 5-Cl | $OCH_3$ | $OCH_3$ | |
| J-2 | Q-121 ($R_7$=H, $R_8$=H, $R_9$=H, $R_2$=$C_2H_5$) | $CH_3$ | H | $OCH_3$ | $CH_3$ | |
| J-2 | Q-121 ($R_7$=$CH_3$, $R_8$=$CH_3$, $R_9$=H, $R_2$=H) | H | 5-$OCH_3$ | $OCH_3$ | $OCH_3$ | |
| J-2 | Q-122 ($R_7$=H, $R_8$=H, $R_9$=H, $R_2$=H) | H | H | $OCH_3$ | $CH_3$ | |
| J-2 | Q-122 ($R_7$=H, $R_8$=H, $R_9$=H, $R_2$=H) | H | 5-Cl | $CH_3$ | $OCH_3$ | |
| J-2 | Q-123 ($R_7$=H, $R_8$=H, $R_9$=H) | H | H | $CH_3$ | $OCH_3$ | |
| J-2 | Q-123 ($R_7$=$CH_3$, $R_8$=H, $R_9$=$CH_3$) | H | H | $OCH_3$ | $OCH_3$ | |
| J-2 | Q-123 ($R_7$=H, $R_8$=H, $R_9$=H) | H | 5-$CH_3$ | $OCH_3$ | $OCH_3$ | |
| J-2 | Q-124 ($R_7$=$C_2H_5$, $R_8$=H, $R_9$=$C_2H_5$) | H | H | $CH_3$ | $OCH_3$ | |
| J-2 | Q-125 ($R_7$=H, $R_8$=H, $R_9$=H) | H | H | $OCH_3$ | $OCH_3$ | |
| J-2 | Q-125 ($R_7$=H, $R_8$=H, $R_9$=n-$C_4H_9$) | $CH_3$ | H | $OCH_3$ | $OCH_3$ | |
| J-2 | Q-125 ($R_7$=H, $R_8$=H, $R_9$=H) | H | 5-$OCH_3$ | $OCH_3$ | $OCH_3$ | |
| J-2 | Q-126 ($R_7$=H, $R_8$=H, $R_9$=H) | H | 5-Cl | $OCH_3$ | $OCH_3$ | |
| J-2 | Q-126 ($R_7$=n-$C_3H_7$, $R_8$=H, $R_9$=s-$C_3H_7$) | H | H | $OCH_3$ | $OCH_3$ | |
| J-2 | Q-127 ($R_7$=$CH_3$, $R_8$=H, $R_9$=H, $R_3$=$C_2H_5$) | H | 5-$OCH_3$ | $OCH_3$ | $OCH_3$ | |
| J-2 | Q-128 ($R_7$=$CH_3$, $R_8$=H, $R_9$=H, $R_3$=$CH_3$) | H | 5-Cl | $CH_3$ | $OCH_3$ | |
| J-2 | Q-128 ($R_7$=$CH_3$, $R_8$=H, $R_9$=$CH_3$, $R_3$=$C_2H_5$) | $CH_3$ | H | $CH_3$ | $OCH_3$ | |
| J-2 | Q-129 ($R_7$=H, $R_8$=H, $R_9$=H, $R_3$=$CH_3$) | H | H | $OCH_3$ | $OCH_3$ | |
| J-2 | Q-129 ($R_7$=$CH_3$, $R_8$=H, $R_9$=$CH_3$, $R_3$=$CH_3$) | H | 5-Cl | $OCH_3$ | $OCH_3$ | |
| J-2 | Q-130 ($R_7$=H, $R_8$=H, $R_9$=H, $R_3$=$CH_3$) | H | 5-$CH_3$ | $CH_3$ | $CH_3$ | |
| J-2 | Q-130 ($R_7$=H, $R_8$=H, $R_9$=$C_2H_5$, $R_3$=$CH_3$) | $CH_3$ | H | $CH_3$ | $OCH_3$ | |
| J-2 | Q-131 ($R_7$=H, $R_8$=H, $R_9$=H, $R_{10}$=H) | H | H | $OCH_3$ | $OCH_3$ | |
| J-2 | Q-131 ($R_7$=H, $R_8$=$CH_3$, $R_9$=H, $R_{10}$=H) | H | H | $CH_3$ | $OCH_3$ | |
| J-2 | Q-132 ($R_7$=H, $R_8$=H, $R_9$=$CH_3$) | $CH_3$ | H | $CH_3$ | $CH_3$ | |
| J-2 | Q-132 ($R_7$=H, $R_8$=$C_2H_5$, $R_9$=H) | H | H | $OCH_3$ | $OCH_3$ | |
| J-2 | Q-133 ($R_7$=$CH_3$, $R_8$=H, $R_9$=H) | H | H | $OCH_3$ | $OCH_3$ | |
| J-2 | Q-133 ($R_7$=H, $R_8$=H, $R_9$=$C_2H_5$) | H | 5-$OCH_3$ | $OCH_3$ | $OCH_3$ | |

TABLE 2-continued

General Formula 2

| J | Q | R | R₁ | X | Y | m.p. (°C.) |
|---|---|---|---|---|---|---|
| J-2 | Q-134 (R₇=H, R₈=H, R₉=H) | H | H | OCH₃ | OCH₃ | |
| J-2 | Q-134 (R₇=H, R₈=H, R₉=C₂H₅) | H | 5-Cl | OCH₃ | OCH₃ | |
| J-2 | Q-135 (R₇=H, R₈=H, R =H) | H | H | OCH₃ | OCH₃ | |
| J-2 | Q-135 (R₇=H, R₈=H, R =CH₃) | CH₃ | H | OCH₃ | OCH₃ | |
| J-2 | Q-135 (R₇=CH₃, R₈=H, R₉=H) | H | 5-OCH₃ | OCH₃ | OCH₃ | |
| J-2 | Q-136 (R₇=H, R₈=H, R₉=H) | H | H | OCH₃ | OCH₃ | |
| J-2 | Q-136 (R₇=H, R₈=CH₃, R₉=C₂H₅) | H | 5-Cl | CH₃ | CH₃ | |
| J-2 | Q-137 (R₇=H, R₈=H, R₉=H) | H | H | OCH₃ | OCH₃ | |
| J-2 | Q-137 (R₇=CH₃, R₈=H, R₉=CH₃) | H | 5-CH₃ | OCH₃ | OCH₃ | |
| J-2 | Q-138 (R₇=H, R₈=H, R₉=H) | H | H | OCH₃ | OCH₃ | |
| J-2 | Q-138 (R₇=H, R₈=H, R₉=CH₃) | H | H | CH₃ | CH₃ | |
| J-2 | Q-139 (R₇=H, R₈=H, R₉=H) | H | H | CH₃ | CH₃ | |
| J-2 | Q-139 (R₇=CH₃, R₈=H, R₉=H) | CH₃ | H | OCH₃ | OCH₃ | |
| J-2 | Q-140 (R₇=H, R₈=H, R₉=H, R₃=CH₃) | H | H | OCH₃ | OCH₃ | |
| J-2 | Q-140 (R₇=H, R₈=H, R₉=CH₃, R₃=H) | H | H | OCH₃ | OCH₃ | |
| J-2 | Q-140 (R₇=CH₃, R₈=H, R₉=H, R₃=C₂H₅) | H | 5-OCH₃ | OCH₃ | OCH₃ | |
| J-2 | Q-141 (R₇=H, R₈=H, R₉=H, R₃=CH₃) | H | H | OCH₃ | OCH₃ | |
| J-2 | Q-141 (R₇=H, R₈=H, R₉=CH₃, R₃=CH₃) | H | 5-Cl | OCH₃ | OCH₃ | |
| J-2 | Q-142 (R₇=CH₃, R₈=H, R₉=H, R₁₀=H) | H | H | OCH₃ | OCH₃ | |
| J-2 | Q-142 (R₇=H, R₈=H, R₉=H, R₁₀=CH₃) | H | 5-OCH₃ | OCH₃ | OCH₃ | |
| J-2 | Q-142 (R₇=CH₃, R₈=H, R₉=H, R₁₀=CH₃) | CH₃ | H | CH₃ | CH₃ | |
| J-2 | Q-143 (R₇=H, R₈=H, R₉=H, R₃=CH₃) | H | 5-Cl | OCH₃ | OCH₃ | |
| J-2 | Q-143 (R₇=CH₃, R₈=H, R₉=CH₃, R₃=CH₃) | H | H | CH₃ | CH₃ | |
| J-2 | Q-144 (R₇=H, R₈=H, R₉=H, R₃=CH₃) | H | H | CH₃ | CH₃ | |
| J-2 | Q-144 (R₇=H, R₈=C₂H₅, R₉=H, R₃=CH₃) | H | 5-CH₃ | OCH₃ | OCH₃ | |
| J-2 | Q-145 (R₇=H, R₈=H, R₉=H) | H | H | CH₃ | CH₃ | |
| J-2 | Q-145 (R₇=CH₃, R₈=H, R₉=H) | H | H | OCH₃ | OCH₃ | |
| J-2 | Q-146 (R₇=H, R₈=H, R₉=H) | H | H | OCH₃ | OCH₃ | |
| J-2 | Q-146 (R₇=CH₃, R₈=H, R₉=n-C₄H₉) | H | 5-OCH₃ | OCH₃ | OCH₃ | |
| J-2 | Q-147 (R₇=H, R₈=H, R₉=H) | H | H | OCH₃ | OCH₃ | |
| J-2 | Q-147 (R₇=CH₃, R₈=H, R₉=n-C₄H₉) | H | 5-Cl | OCH₃ | OCH₃ | |
| J-2 | Q-148 (R₇=H, R₈=H, R₉=H) | H | H | OCH₃ | OCH₃ | |
| J-2 | Q-148 (R₇=CH₃, R₈=H, R₉=H) | H | 5-OCH₃ | OCH₃ | OCH₃ | |
| J-2 | Q-149 (R₇=H, R₈=H, R₉=CH₃) | CH₃ | H | OCH₃ | OCH₃ | |
| J-2 | Q-149 (R₇=CH₃, R₈=H, R₉=H) | H | 5-Cl | OCH₃ | OCH₃ | |
| J-2 | Q-150 (R₇=H, R₈=H, R₉=CH₃) | H | H | OCH₃ | CH₃ | |
| J-2 | Q-151 (R₇=H, R₈=CH₃, R₉=H) | H | 5-CH₃ | OCH₃ | OCH₃ | |
| J-2 | Q-151 (R₇=CH₃, R₈=CH₃, R₉=H) | H | H | CH₃ | OCH₃ | |
| J-2 | Q-152 (R₇=H, R₈=CH₃, R₉=H) | H | H | OCH₃ | OCH₃ | |
| J-2 | Q-153 (R₇=CH₃, R₈=H, R₉=H, R₁₁=CH₃) | CH₃ | H | CH₃ | OCH₃ | |
| J-2 | Q-153 (R₇=H, R₈=H, R₉=H, R₁₁=H) | H | H | CH₃ | OCH₃ | |
| J-2 | Q-153 (R₇=H, R₈=CH₃, R₉=H, R₁₁=CH₃) | H | H | OCH₃ | OCH₃ | |

TABLE 2-continued

General Formula 2

| J | Q | R | R₁ | X | Y | m.p. (°C.) |
|---|---|---|---|---|---|---|
| J-2 | Q-154 (R₇=H, R₈=H, R₉=H, R₁₁=CH₃) | H | H | OCH₃ | OCH₃ | |
| J-2 | Q-154 (R₇=CH₃, R₈=H, R₉=H, R₁₁=H) | H | H | OCH₃ | OCH₃ | |
| J-2 | Q-154 (R₇=H, R₈=CH₃, R₉=CH₃) | H | 5-OCH₃ | OCH₃ | OCH₃ | |
| J-2 | Q-155 (R₇=H, R₈=H, R₉=H) | H | 5-Cl | OCH₃ | OCH₃ | |
| J-2 | Q-156 (R₇=H, R₈=H, R₉=H) | H | H | OCH₃ | OCH₃ | |
| J-2 | Q-156 (R₇=C₂H₅, R₈=H, R₉=H) | CH₃ | H | OCH₃ | OCH₃ | |
| J-2 | Q-156 (R₇=CH₃, R₈=CH₃, R₉=H) | H | H | OCH₃ | OCH₃ | |
| J-2 | Q-157 (R₇=H, R₈=H, R₉=H, R₁₀=H) | H | 5-OCH₃ | OCH₃ | OCH₃ | |
| J-2 | Q-157 (R₇=H, R₈=H, R₉=H, R₁₀=CH₃) | H | 5-Cl | OCH₃ | OCH₃ | |
| J-2 | Q-158 (R₇=H, R₈=H, R₉=H) | H | H | CH₃ | CH₃ | |
| J-2 | Q-158 (R₇=CH₃, R₈=H, R₉=H) | H | H | CH₃ | OCH₃ | |
| J-2 | Q-159 (R₇=H, R₈=H, R₉=CH₃) | H | 5-CH₃ | OCH₃ | OCH₃ | |
| J-2 | Q-159 (R₇=H, R₈=H, R₉=H) | H | H | CH₃ | OCH₃ | |
| J-2 | Q-160 (R₇=H, R₈=H, R₉=H, R₁₁=CH₃) | H | H | CH₃ | CH₃ | |
| J-2 | Q-160 (R₇=H, R₈=CH₃, R₉=H, R₁₁=H) | CH₃ | H | OCH₃ | OCH₃ | |
| J-2 | Q-160 (R₇=CH₃, R₈=H, R₉=H, R₁₁=i-C₃H₇) | H | H | OCH₃ | OCH₃ | |
| J-2 | Q-161 (R₇=CH₃, R₈=H, R₉=H, R₁₁=CH₃) | H | H | OCH₃ | OCH₃ | |
| J-2 | Q-161 (R₇=H, R₈=H, R₉=CH₃, R₁₁=H) | H | H | OCH₃ | OCH₃ | |
| J-2 | Q-162 (R₇=H, R₈=H, R₉=CH₃, R₁₁=CH₃) | H | 5-OCH₃ | OCH₃ | OCH₃ | |
| J-2 | Q-162 (R₇=H, R₈=H, R₉=H, R₁₀=CH₃) | H | 5-Cl | OCH₃ | OCH₃ | |
| J-2 | Q-163 (R₂=H, R₇=H, R₈=H, R₉=H) | H | H | OCH₃ | OCH₃ | |
| J-2 | Q-164 (R₇=H) | H | H | OCH₃ | OCH₃ | |
| J-2 | Q-165 (R₃=H, R₇=H) | H | H | OCH₃ | OCH₃ | |
| J-2 | Q-166 (R₃=H, R₇=H) | H | H | OCH₃ | OCH₃ | |
| J-2 | Q-167 (R₇=H, R₈=H, R₉=H, R₁₀=H) | H | H | OCH₃ | OCH₃ | 210–211 |
| J-2 | Q-167 (R₇=H, R₈=H, R₉=H, R₁₀=H) | H | H | OCH₃ | OCH₃ | 95–100 |
| J-3 | Q-1 (R₇=H, R₈=H) | H | H | OCH₃ | CH₃ | |
| J-3 | Q-1 (R₇=H, R₈=H) | H | H | CH₃ | CH₃ | |
| J-3 | Q-1 (R₇=H, R₈=H) | H | H | CH₃ | CH₃ | |
| J-3 | Q-1 (R₇=H, R₈=H) | H | H | OCH₃ | OCH₂CH₃ | |
| J-3 | Q-1 (R₇=H, R₈=H) | H | H | OCH₃ | OCH₂(CH₃)₂ | |
| J-3 | Q-1 (R₇=H, R₈=H) | H | H | OCH₂CF₃ | OCH₃ | |
| J-3 | Q-1 (R₇=H, R₈=H) | H | H | CF₃ | OCH₃ | |
| J-3 | Q-1 (R₇=H, R₈=H) | H | H | SCH₃ | OCH₃ | |
| J-3 | Q-1 (R₇=H, R₈=H) | H | H | OCH₃ | NHCH₃ | |
| J-3 | Q-1 (R₇=H, R₈=H) | H | H | H | OCH₃ | |
| J-3 | Q-3 (R₇=H, R₈=H) | H | H | OCH₃ | OCH₃ | |
| J-3 | Q-4 (R₇=H, R₈=H, R₃=CH₃) | H | H | CH₃ | OCH₃ | |
| J-3 | Q-5 (R₇=H, R₈=H, R₃=H) | H | H | CH₃ | OCH₃ | |
| J-3 | Q-6 (R₇=CH₃, R₈=H, R₃=CH₃) | H | H | CH₃ | OCH₃ | |
| J-3 | Q-7 (R₇=H, R₈=H, R₉=H) | H | H | OCH₃ | OCH₃ | |
| J-3 | Q-8 (R₇=H, R₈=C₂H₅, R₉=H) | H | H | OCH₃ | OCH₃ | |
| J-3 | Q-9 (R₇=H, R₈=H, R₂=H) | H | H | OCH₃ | OCH₃ | |
| J-3 | Q-10 (R₇=H, R₈=H, R₂=H) | H | H | OCH₃ | OCH₃ | |
| J-3 | Q-11 (R₇=H, R₈=H) | H | H | OCH₃ | OCH₃ | |
| J-3 | Q-12 (R₇=H, R₈=H) | H | H | CH₃ | OCH₃ | |
| J-3 | Q-13 (R₇=H, R₈=H, R₃=H) | H | H | CH₃ | OCH₃ | |

TABLE 2-continued

General Formula 2

| J | Q | R | R₁ | X | Y | m.p. (°C.) |
|---|---|---|----|---|---|------------|
| J-3 | Q-14 (R₇=H, R₈=H, R₃=CH₃) | H | H | OCH₃ | OCH₃ | |
| J-3 | Q-15 (R₇=CH₃, R₈=H, R₃=H) | H | H | OCH₃ | OCH₃ | |
| J-3 | Q-16 (R₇=H, R₈=H, R₉=H) | H | H | OCH₃ | OCH₃ | |
| J-3 | Q-17 (R₇=H, R₈=H, R₂=H) | H | H | OCH₃ | OCH₃ | |
| J-3 | Q-18 (R₇=H, R₈=H, R₂=H) | H | H | CH₃ | OCH₃ | |
| J-3 | Q-19 (R₇=H, R₈=H) | H | H | OCH₃ | OCH₃ | |
| J-3 | Q-20 (R₇=H, R₈=H) | H | H | CH₃ | OCH₃ | |
| J-3 | Q-21 (R₇=H, R₈=H) | H | H | OCH₃ | OCH₃ | |
| J-3 | Q-22 (R₇=H, R₈=H, R₃=H) | H | H | OCH₃ | OCH₃ | |
| J-3 | Q-23 (R₇=H, R₈=H, R₃=H) | H | H | OCH₃ | OCH₃ | |
| J-3 | Q-24 (R₇=H, R₈=H, R₃=CH₃) | H | H | OCH₃ | OCH₃ | |
| J-3 | Q-25 (R₇=H, R₈=H, R₉=H) | H | H | CH₃ | OCH₃ | |
| J-3 | Q-26 (R₇=H, R₈=H) | H | H | CH₃ | OCH₃ | |
| J-3 | Q-27 (R₇=H, R₈=H) | H | H | OCH₃ | OCH₃ | |
| J-3 | Q-28 (R₇=H, R₈=H) | H | H | OCH₃ | OCH₃ | |
| J-3 | Q-29 (R₇=H, R₈=H) | H | H | OCH₃ | OCH₃ | |
| J-3 | Q-30 (R₇=H, R₈=H) | H | H | OCH₃ | OCH₃ | |
| J-3 | Q-31 (R₇=H, R₈=H) | H | H | CH₃ | OCH₃ | |
| J-3 | Q-32 (R₇=H, R₈=H, R₃=H) | H | H | OCH₃ | OCH₃ | |
| J-3 | Q-33 (R₇=H, R₈=H, R₈=CH₃) | H | H | OCH₃ | OCH₃ | |
| J-3 | Q-34 (R₇=H, R₈=H, R₃=H) | H | H | OCH₃ | OCH₃ | |
| J-3 | Q-35 (R₇=H, R₈=H, R₉=H) | H | H | OCH₃ | OCH₃ | |
| J-3 | Q-36 (R₇=H, R₈=H, R₂=H) | H | H | CH₃ | OCH₃ | |
| J-3 | Q-37 (R₇=H, R₈=H, R₂=H) | H | H | CH₃ | OCH₃ | |
| J-3 | Q-38 (R₇=H, R₈=H, R₂=OCF₂H) | H | H | OCH₃ | OCH₃ | |
| J-3 | Q-39 (R₇=H, R₈=H, R₉=H) | H | H | OCH₃ | OCH₃ | |
| J-3 | Q-40 (R₇=H, R₈=H) | H | H | CH₃ | OCH₃ | |
| J-3 | Q-41 (R₇=H, R₈=H) | H | H | OCH₃ | OCH₃ | |
| J-3 | Q-42 (R₇=H, R₈=H) | H | H | OCH₃ | OCH₃ | |
| J-3 | Q-43 (R₇=H, R₈=H, R₃=H) | H | H | CH₃ | OCH₃ | |
| J-3 | Q-44 (R₇=H, R₈=H, R₃=CH₃) | H | H | OCH₃ | OCH₃ | |
| J-3 | Q-45 (R₇=H, R₈=H, R₃=H) | H | H | OCH₃ | OCH₃ | |
| J-3 | Q-46 (R₇=H, R₈=H, R₉=H) | H | H | CH₃ | OCH₃ | |
| J-3 | Q-47 (R₇=H, R₈=H, R₂=H) | H | H | OCH₃ | OCH₃ | |
| J-3 | Q-48 (R₇=H, R₈=H, R₂=H) | H | H | CH₃ | OCH₃ | |
| J-3 | Q-49 (R₇=H, R₈=H, R₂=H) | H | H | OCH₃ | OCH₃ | |
| J-3 | Q-50 (R₇=H, R₈=H, R₉=H) | H | H | OCH₃ | OCH₃ | |
| J-3 | Q-51 (R₇=H, R₈=H, R₂=H) | H | H | OCH₃ | OCH₃ | |
| J-3 | Q-52 (R₇=H, R₈=H, R₉=H) | H | H | OCH₃ | OCH₃ | |
| J-3 | Q-53 (R₇=H, R₈=H, R₉=H) | H | H | CH₃ | OCH₃ | |
| J-3 | Q-54 (R₇=H, R₈=H, R₉=H, R₃=H) | H | H | CH₃ | OCH₃ | |
| J-3 | Q-55 (R₇=H, R₈=H, R₉=H, R₃=C₂H₅) | H | H | CH₃ | OCH₃ | |
| J-3 | Q-56 (R₇=H, R₈=H, R₉=H, R₃=i-C₃H₇) | H | H | OCH₃ | OCH₃ | |
| J-3 | Q-57 (R₇=H, R₈=H, R₉=H, R₃=H) | H | H | OCH₃ | OCH₃ | |
| J-3 | Q-58 (R₇=H, R₈=H, R₉=H, R₁₀=H) | H | H | OCH₃ | OCH₃ | |
| J-3 | Q-59 (R₇=H, R₈=H, R₉=H, R₂=H) | H | H | CH₃ | OCH₃ | |
| J-3 | Q-60 (R₇=H, R₈=H, R₉=H, R₂=H) | H | H | OCH₃ | OCH₃ | |
| J-3 | Q-61 (R₇=H, R₈=H, R₉=H, R₂=H) | H | H | CH₃ | OCH₃ | |
| J-3 | Q-62 (R₇=H, R₈=H, R₉=H, R₂=H) | H | H | CH₃ | OCH₃ | |
| J-3 | Q-63 (R₇=H, R₈=H, R₉=H) | H | H | OCH₃ | OCH₃ | |
| J-3 | Q-64 (R₇=H, R₈=H, R₉=H) | H | H | OCH₃ | OCH₃ | |

TABLE 2-continued

General Formula 2

| J | Q | R | R₁ | X | Y | m.p. (°C.) |
|---|---|---|----|---|---|------------|
| J-3 | Q-65 (R₇=H, R₈=H, R₉=H) | H | H | OCH₃ | OCH₃ | |
| J-3 | Q-66 (R₇=H, R₈=H, R₉=H) | H | H | OCH₃ | OCH₃ | |
| J-3 | Q-67 (R₇=H, R₈=H, R₉=H, R₃=H) | H | H | CH₃ | OCH₃ | |
| J-3 | Q-68 (R₇=H, R₈=H, R₉=H, R₃=CH₃) | H | H | OCH₃ | OCH₃ | |
| J-3 | Q-69 (R₇=H, R₈=H, R₉=H, R₃=CH₃) | H | H | CH₃ | OCH₃ | |
| J-3 | Q-70 (R₇=H, R₈=H, R₉=H, R₃=CH₃) | H | H | OCH₃ | OCH₃ | |
| J-3 | Q-72 (R₇=H, R₈=H, R₉=H, R₂=H) | H | H | OCH₃ | OCH₃ | |
| J-3 | Q-73 (R₇=H, R₈=H, R₉=H, R₂=H) | H | H | CH₃ | OCH₃ | |
| J-3 | Q-74 (R₇=H, R₈=H, R₉=H, R₂=H) | H | H | OCH₃ | OCH₃ | |
| J-3 | Q-75 (R₇=H, R₈=H, R₉=H) | H | H | CH₃ | OCH₃ | |
| J-3 | Q-76 (R₇=H, R₈=H, R₉=H) | H | H | OCH₃ | OCH₃ | |
| J-3 | Q-77 (R₇=H, R₈=H, R₉=H) | H | H | OCH₃ | OCH₃ | |
| J-3 | Q-78 (R₇=H, R₈=H, R₉=H, R₃=H) | H | H | CH₃ | OCH₃ | |
| J-3 | Q-79 (R₇=H, R₈=H, R₉=H, R₃=CH₃) | H | H | OCH₃ | OCH₃ | |
| J-3 | Q-80 (R₇=H, R₈=H, R₉=H, R₃=CH₃) | H | H | CH₃ | OCH₃ | |
| J-3 | Q-81 (R₇=H, R₈=H, R₉=H, R₃=CH₃) | H | H | OCH₃ | OCH₃ | |
| J-3 | Q-82 (R₇=H, R₈=H, R₉=H, R₁₀=H) | H | H | CH₃ | OCH₃ | |
| J-3 | Q-83 (R₇=H, R₈=H, R₉=H, R₁₀=H) | H | H | OCH₃ | OCH₃ | |
| J-3 | Q-84 (R₇=H, R₈=H, R₉=H) | H | H | OCH₃ | OCH₃ | |
| J-3 | Q-85 (R₇=H, R₈=H, R₉=H) | H | H | CH₃ | OCH₃ | |
| J-3 | Q-86 (R₇=H, R₈=H, R₉=H) | H | H | OCH₃ | OCH₃ | |
| J-3 | Q-87 (R₇=H, R₈=H, R₉=H) | H | H | OCH₃ | OCH₃ | |
| J-3 | Q-88 (R₇=H, R₈=H, R₉=H) | H | H | CH₃ | OCH₃ | |
| J-3 | Q-89 (R₇=H, R₈=H, R₉=H) | H | H | OCH₃ | OCH₃ | |
| J-3 | Q-90 (R₇=H, R₈=H, R₉=H, R₃=CH₃) | H | H | CH₃ | OCH₃ | |
| J-3 | Q-91 (R₇=H, R₈=H, R₉=H, R₃=CH₃) | H | H | OCH₃ | OCH₃ | |
| J-3 | Q-92 (R₇=H, R₈=H, R₉=H, R₁₀=H) | H | H | CH₃ | OCH₃ | |
| J-3 | Q-93 (R₇=H, R₈=H, R₉=H) | H | H | OCH₃ | OCH₃ | |
| J-3 | Q-94 (R₇=H, R₈=H, R₉=H, R₂=H) | H | H | CH₃ | OCH₃ | |
| J-3 | Q-95 (R₇=H, R₈=H, R₉=H) | H | H | OCH₃ | OCH₃ | |
| J-3 | Q-96 (R₇=H, R₈=H, R₉=H) | H | H | OCH₃ | OCH₃ | |
| J-3 | Q-97 (R₇=H, R₈=H, R₉=H) | H | H | CH₃ | OCH₃ | |
| J-3 | Q-98 (R₇=H, R₈=H, R₉=H) | H | H | OCH₃ | OCH₃ | |
| J-3 | Q-99 (R₇=H, R₈=H, R₉=H, R₃=H) | H | H | OCH₃ | OCH₃ | |
| J-3 | Q-100 (R₇=H, R₈=H, R₉=H, R₃=C₂H₅) | H | H | OCH₃ | OCH₃ | |
| J-3 | Q-101 (R₇=H, R₈=H, R₉=H, R₃=i-C₂H₅) | H | H | CH₃ | OCH₃ | |
| J-3 | Q-102 (R₇=H, R₈=H, R₉=H, R₃=H) | H | H | OCH₃ | OCH₃ | |
| J-3 | Q-103 (R₇=H, R₈=H, R₉=H, R₁₀=H) | H | H | CH₃ | OCH₃ | |
| J-3 | Q-104 (R₇=H, R₈=H, R₉=H, R₂=H) | H | H | OCH₃ | OCH₃ | |
| J-3 | Q-105 (R₇=H, R₈=H, R₉=H, R₂=H) | H | H | OCH₃ | OCH₃ | |
| J-3 | Q-106 (R₇=H, R₈=H, R₉=H, R₂=H) | H | H | OCH₃ | OCH₃ | |
| J-3 | Q-107 (R₇=H, R₈=H, R₉=H, R₂=H) | H | H | OCH₃ | OCH₃ | |
| J-3 | Q-108 (R₇=H, R₈=H, R₉=H, R₂=H) | H | H | OCH₃ | OCH₃ | |
| J-3 | Q-109 (R₇=H, R₈=H, R₉=H) | H | H | OCH₃ | OCH₃ | |
| J-3 | Q-110 (R₇=H, R₈=H, R₉=H) | H | H | CH₃ | OCH₃ | |
| J-3 | Q-111 (R₇=H, R₈=H, R₉=H) | H | H | CH₃ | OCH₃ | |
| J-3 | Q-112 (R₇=H, R₈=H, R₉=H) | H | H | CH₃ | OCH₃ | |
| J-3 | Q-113 (R₇=H, R₈=H, R₉=H, R₃=CH₃) | H | H | OCH₃ | OCH₃ | |
| J-3 | Q-114 (R₇=H, R₈=H, R₉=H, R₃=CH₃) | H | H | OCH₃ | OCH₃ | |
| J-3 | Q-115 (R₇=H, R₈=H, R₉=H, R₃=CH₃) | H.H | H | OCH₃ | OCH₃ | |
| J-3 | Q-116 (R₇=H, R₈=H, R₉=H, R₁₀=H) | H | H | CH₃ | OCH₃ | |

TABLE 2-continued

General Formula 2

| J | Q | R | R₁ | X | Y | m.p. (°C.) |
|---|---|---|----|---|---|-----------|
| J-3 | Q-117 (R₇=H, R₈=H, R₉=H, R₂=H) | H | H | OCH₃ | OCH₃ | |
| J-3 | Q-118 (R₇=H, R₈=H, R₉=H, R₁₀=H) | H | H | CH₃ | OCH₃ | |
| J-3 | Q-119 (R₇=H, R₈=H, R₉=H, R₂=H) | H | H | OCH₃ | OCH₃ | |
| J-3 | Q-120 (R₇=H, R₈=H, R₉=H, R₂=H) | H | H | OCH₃ | OCH₃ | |
| J-3 | Q-121 (R₇=H, R₈=H, R₉=H, R₂=H) | H | H | OCH₃ | OCH₃ | |
| J-3 | Q-122 (R₇=H, R₈=H, R₉=H, R₂=H) | H | H | OCH₃ | OCH₃ | |
| J-3 | Q-123 (R₇=H, R₈=H, R₉=H.) | H | H | CH₃ | OCH₃ | |
| J-3 | Q-124 (R₇=H, R₈=H, R₉=H.) | H | H | OCH₃ | OCH₃ | |
| J-3 | Q-125 (R₇=H, R₈=H, R₉=H.) | H | H | OCH₃ | OCH₃ | |
| J-3 | Q-126 (R₇=H, R₈=H, R₉=H, R₃=H) | H | H | OCH₃ | OCH₃ | |
| J-3 | Q-127 (R₇=H, R₈=H, R₉=H, R₃=CH₃) | H | H | OCH₃ | OCH₃ | |
| J-3 | Q-128 (R₇=H, R₈=H, R₉=H, R₃=CH₃) | H | H | CH₃ | OCH₃ | |
| J-3 | Q-129 (R₇=H, R₈=H, R₉=H, R₃=CH₃) | H | H | OCH₃ | OCH₃ | |
| J-3 | Q-130 (R₇=H, R₈=H, R₉=H, R₁₀=H) | H | H | OCH₃ | OCH₃ | |
| J-3 | Q-131 (R₇=H, R₈=H, R₉=H.) | H | H | CH₃ | OCH₃ | |
| J-3 | Q-132 (R₇=H, R₈=H, R₉=H.) | H | H | OCH₃ | OCH₃ | |
| J-3 | Q-133 (R₇=H, R₈=H, R₉=H.) | H | H | OCH₃ | OCH₃ | |
| J-3 | Q-134 (R₇=H, R₈=H, R₉=H.) | H | H | OCH₃ | OCH₃ | |
| J-3 | Q-135 (R₇=H, R₈=H, R₉=H.) | H | H | CH₃ | OCH₃ | |
| J-3 | Q-136 (R₇=H, R₈=H, R₉=H.) | H | H | OCH₃ | OCH₃ | |
| J-3 | Q-137 (R₇=H, R₈=H, R₉=H.) | H | H | CH₃ | OCH₃ | |
| J-3 | Q-138 (R₇=H, R₈=H, R₉=H.) | H | H | OCH₃ | OCH₃ | |
| J-3 | Q-139 (R₇=H, R₈=H, R₉=H, R₃=CH₃) | H | H | OCH₃ | OCH₃ | |
| J-3 | Q-140 (R₇=H, R₈=H, R₉=H, R₃=CH₃) | H | H | OCH₃ | OCH₃ | |
| J-3 | Q-141 (R₇=H, R₈=H, R₉=H, R₃=CH₃) | H | H | OCH₃ | OCH₃ | |
| J-3 | Q-142 (R₇=H, R₈=H, R₉=H, R₁₀=H) | H | H | CH₃ | OCH₃ | |
| J-3 | Q-143 (R₇=H, R₈=H, R₉=H, R₃=CH₃) | H | H | OCH₃ | OCH₃ | |
| J-3 | Q-144 (R₇=H, R₈=H, R₉=H, R₃=CH₃) | H | H | OCH₃ | OCH₃ | |
| J-3 | Q-145 (R₇=H, R₈=H, R₉=H.) | H | H | CH₃ | OCH₃ | |
| J-3 | Q-146 (R₇=H, R₈=H, R₉=H.) | H | H | OCH₃ | OCH₃ | |
| J-3 | Q-147 (R₇=H, R₈=H, R₉=H.) | H | H | CH₃ | OCH₃ | |
| J-3 | Q-148 (R₇=H, R₈=H, R₉=H.) | H | H | OCH₃ | OCH₃ | |
| J-3 | Q-149 (R₇=H, R₈=H, R₉=H.) | H | H | OCH₃ | OCH₃ | |
| J-3 | Q-150 (R₇=H, R₈=H, R₉=H.) | H | H | OCH₃ | OCH₃ | |
| J-3 | Q-151 (R₇=H, R₈=H, R₉=H.) | H | H | CH₃ | OCH₃ | |
| J-3 | Q-152 (R₇=H, R₈=H, R₉=H.) | H | H | OCH₃ | OCH₃ | |
| J-3 | Q-153 (R₇=H, R₈=H, R₉=H, R₁₁=CH₃) | H | H | CH₃ | OCH₃ | |
| J-3 | Q-154 (R₇=H, R₈=H, R₉=H, R₁₁=CH₃) | H | H | OCH₃ | OCH₃ | |
| J-3 | Q-155 (R₇=H, R₈=H, R₉=H.) | H | H | OCH₃ | OCH₃ | |
| J-3 | Q-156 (R₇=H, R₈=H, R₉=H.) | H | H | CH₃ | OCH₃ | |
| J-3 | Q-157 (R₇=H, R₈=H, R₉=H, R₁₀=H) | H | H | OCH₃ | OCH₃ | |
| J-3 | Q-158 (R₇=H, R₈=H, R₉=H.) | H | H | CH₃ | OCH₃ | |
| J-3 | Q-159 (R₇=H, R₈=H, R₉=H.) | H | H | OCH₃ | OCH₃ | |
| J-3 | Q-160 (R₇=H, R₈=H, R₉=H, R₁₁=CH₃) | H | H | OCH₃ | OCH₃ | |
| J-3 | Q-161 (R₇=H, R₈=H, R₉=H, R₁₁=CH₃) | H | H | OCH₃ | OCH₃ | |
| J-3 | Q-162 (R₇=H, R₈=H, R₉=H, R₁₀=H) | H | H | OCH₃ | OCH₃ | |
| J-1* | Q-1 (R₇=H, R₈=H) | H | H | OCH₃ | CH₃ | |
| J-1* | Q-1 (R₇=H, R₈=H) | H | H | OCH₃ | OCH₃ | |
| J-2* | Q-1 (R₇=H, R₈=H) | H | H | OCH₃ | OCH₃ | |
| J-3* | Q-167 (R₇=H, R₈=H, R₉=H, R₁₀=H) | H | H | OCH₃ | OCH₃ | |
| J-2* | Q-167 (R₇=H, R₈=H, R₉=H, R₁₀=H) | H | H | OCH | CH | |

TABLE 3

| | | General Formula 3 | | | |
|---|---|---|---|---|---|
| J | Q | | R | R$_1$ | X$_1$ | Y$_1$ |
| J-1 | Q-1 (R$_7$=H, R$_8$=H) | | H | H | CH$_3$ | CH$_2$ |
| J-1 | Q-1 (R$_7$=H, R$_8$=H) | | H | 5-CH$_3$ | CH$_3$ | CH$_2$ |
| J-1 | Q-1 (R$_7$=H, R$_8$=H) | | H | 6-OCH$_2$CH$_2$Br | CH$_3$ | CH$_2$ |
| J-1 | Q-1 (R$_7$=H, R$_8$=H) | | H | 5-CH$_2$F | CH$_3$ | CH$_2$ |
| J-1 | Q-1 (R$_7$=H, R$_8$=H) | | H | 5-SCH$_3$ | CH$_3$ | CH$_2$ |
| J-1 | Q-1 (R$_7$=H, R$_8$=H) | | H | 5-SCH$_2$F | CH$_3$ | CH$_2$ |
| J-1 | Q-1 (R$_7$=H, R$_8$=H) | | H | 5-Cl | CH$_3$ | CH$_2$ |
| J-1 | Q-1 (R$_7$=H, R$_8$=H) | | H | 4-NO$_2$ | CH$_3$ | CH$_2$ |
| J-1 | Q-1 (R$_7$=H, R$_8$=H) | | H | 5-CF$_3$ | CH$_3$ | CH$_2$ |
| J-1 | Q-1 (R$_7$=H, R$_8$=H) | | H | 5-OCH$_3$ | CH$_3$ | O |
| J-1 | Q-1 (R$_7$=H, R$_8$=H) | | H | 5-OCH$_2$F | CH$_3$ | O |
| J-1 | Q-1 (R$_7$=H, R$_8$=H) | | H | 5-CH$_2$F | CH$_3$ | O |
| J-1 | Q-1 (R$_7$=H, R$_8$=H) | | H | 5-SCH$_3$ | CH$_3$ | O |
| J-1 | Q-1 (R$_7$=H, R$_8$=H) | | H | 5-SCH$_2$F | CH$_3$ | O |
| J-1 | Q-1 (R$_7$=H, R$_8$=H) | | H | 5-NHCH$_3$ | CH$_3$ | O |
| J-1 | Q-1 (R$_7$=H, R$_8$=H) | | H | 5-Cl | CH$_3$ | O |
| J-1 | Q-1 (R$_7$=H, R$_8$=H) | | H | 4-NO$_2$ | CH$_3$ | O |
| J-1 | Q-1 (R$_7$=H, R$_8$=H) | | H | 5-CF$_3$ | CH$_3$ | O |
| J-1 | Q-1 (R$_7$=H, R$_8$=H) | | H | H | CH$_3$ | O |
| J-1 | Q-1 (R$_7$=H, R$_8$=H) | | H | H | OCH$_3$ | O |
| J-1 | Q-1 (R$_7$=H, R$_8$=H) | | H | H | OCH$_3$ | CH$_2$ |
| J-1 | Q-37 (R$_7$=H, R$_8$=H, R$_2$=H) | | H | H | CH$_3$ | CH$_2$ |
| J-1 | Q-98 (R$_7$=H, R$_8$=H, R$_9$=H) | | H | H | CH$_3$ | CH$_2$ |
| J-1 | Q-105 (R$_7$=H, R$_8$=H, R$_9$=H, R$_2$=H) | | H | H | CH$_3$ | CH$_2$ |
| J-1 | Q-138 (R$_7$=H, R$_8$=H, R$_9$=H) | | H | H | CH$_3$ | CH$_2$ |
| J-1 | Q-143 (R$_7$=H, R$_8$=H, R$_9$=H, R$_3$=CH$_3$) | | H | H | CH$_3$ | CH$_2$ |
| J-2 | Q-1 (R$_7$=H, R$_8$=H) | | H | 5-SCH$_3$ | CH$_3$ | CH$_2$ |
| J-2 | Q-1 (R$_7$=H, R$_8$=H) | | H | 5-SOCH$_3$ | CH$_3$ | CH$_2$ |
| J-2 | Q-1 (R$_7$=H, R$_8$=H) | | H | 5-CO$_2$CH$_3$ | CH$_3$ | CH$_2$ |
| J-2 | Q-1 (R$_7$=H, R$_8$=H) | | H | 5-SO$_2$N(CH$_3$)$_2$ | CH$_3$ | CH$_2$ |
| J-2 | Q-1 (R$_7$=H, R$_8$=H) | | H | 5-NO$_2$ | CH$_3$ | CH$_2$ |
| J-2 | Q-1 (R$_7$=H, R$_8$=H) | | H | 5-Cl | CH$_3$ | CH$_2$ |
| J-2 | Q-1 (R$_7$=H, R$_8$=H) | | H | 4-NO$_2$ | CH$_3$ | CH$_2$ |
| J-2 | Q-1 (R$_7$=H, R$_8$=H) | | H | 6-Cl | CH$_3$ | CH$_2$ |
| J-2 | Q-1 (R$_7$=H, R$_8$=H) | | H | 6-COOCH$_3$ | CH$_3$ | CH$_2$ |
| J-2 | Q-1 (R$_7$=H, R$_8$=H) | | H | 6-NO$_2$ | CH$_3$ | CH$_2$ |
| J-2 | Q-1 (R$_7$=H, R$_8$=H) | | H | 6-SO$_2$CH$_3$ | CH$_3$ | CH$_2$ |
| J-2 | Q-1 (R$_7$=H, R$_8$=H) | | H | 6-OCH$_3$ | CH$_3$ | CH$_2$ |
| J-2 | Q-1 (R$_7$=H, R$_8$=H) | | H | 5-OCH$_3$ | CH$_3$ | CH$_2$ |
| J-2 | Q-1 (R$_7$=H, R$_8$=H) | | H | H | CH$_3$ | CH$_2$ |
| J-2 | Q-1 (R$_7$=H, R$_8$=H) | | H | H | CH$_3$ | CH$_2$ |
| J-2 | Q-1 (R$_7$=H, R$_8$=H) | | CH$_3$ | H | OCH$_3$ | CH$_2$ |
| J-2 | Q-1 (R$_7$=H, R$_8$=H) | | CH$_3$ | H | OC$_2$H$_5$ | CH$_2$ |
| J-2 | Q-1 (R$_7$=H, R$_8$=H) | | CH$_3$ | H | OCF$_2$H | CH$_2$ |
| J-2 | Q-1 (R$_7$=H, R$_8$=H) | | CH$_3$ | H | CH$_3$ | O |
| J-2 | Q-1 (R$_7$=H, R$_8$=H) | | CH$_3$ | H | OCH$_3$ | O |
| J-2 | Q-1 (R$_7$=H, R$_8$=H) | | CH$_3$ | H | OC$_2$H$_5$ | O |
| J-2 | Q-1 (R$_7$=H, R$_8$=H) | | CH$_3$ | H | OCF$_2$H | O |
| J-2 | Q-1 (R$_7$=H, R$_8$=H) | | H | H | CH$_3$ | CH$_2$ |
| J-2 | Q-1 (R$_7$=H, R$_8$=H) | | H | 5-CH$_3$ | CH$_3$ | CH$_2$ |
| J-2 | Q-1 (R$_7$=H, R$_8$=H) | | H | 6-CH$_2$CH$_3$ | CH$_3$ | CH$_2$ |
| J-2 | Q-1 (R$_7$=H, R$_8$=H) | | H | 5-CH(CH$_3$) | CH$_3$ | CH$_2$ |
| J-2 | Q-1 (R$_7$=H, R$_8$=H) | | H | 5-OCH$_2$CH$_3$ | CH$_3$ | CH$_2$ |
| J-2 | Q-1 (R$_7$=H, R$_8$=H) | | H | 5-OCH$_2$(CH$_3$)$_2$ | CH$_3$ | CH$_2$ |
| J-2 | Q-1 (R$_7$=H, R$_8$=H) | | H | 5-OCH$_2$F | CH$_3$ | CH$_2$ |
| J-2 | Q-1 (R$_7$=H, R$_8$=H) | | H | 6-OCH$_2$CH$_2$Br | CH$_3$ | CH$_2$ |
| J-2 | Q-1 (R$_7$=H, R$_8$=H) | | H | 5-OCH(CH$_3$)(CH$_2$Cl) | CH$_3$ | CH$_2$ |
| J-2 | Q-1 (R$_7$=H, R$_8$=H) | | H | 5-CH$_2$F | CH$_3$ | CH$_2$ |
| J-2 | Q-1 (R$_7$=H, R$_8$=H) | | H | 5-CH$_2$CH$_2$Br | CH$_3$ | CH$_2$ |
| J-2 | Q-1 (R$_7$=H, R$_8$=H) | | H | 5-CH(CH$_3$)(CH$_2$Cl) | CH$_3$ | CH$_2$ |
| J-2 | Q-1 (R$_7$=H, R$_8$=H) | | H | 6-SCH$_2$CH$_3$ | CH$_3$ | CH$_2$ |
| J-2 | Q-1 (R$_7$=H, R$_8$=H) | | H | 5-SCH(CH$_3$)$_2$ | CH$_3$ | CH$_2$ |
| J-2 | Q-1 (R$_7$=H, R$_8$=H) | | H | 5-SCH$_2$F | CH$_3$ | CH$_2$ |
| J-2 | Q-1 (R$_7$=H, R$_8$=H) | | H | 5-SCH$_2$CH$_2$Br | CH$_3$ | CH$_2$ |
| J-2 | Q-1 (R$_7$=H, R$_8$=H) | | H | 5-SCH(CH$_3$)(CH$_2$Cl) | CH$_3$ | CH$_2$ |
| J-2 | Q-1 (R$_7$=H, R$_8$=H) | | H | 4-NH$_2$ | CH$_3$ | CH$_2$ |
| J-2 | Q-1 (R$_7$=H, R$_8$=H) | | H | 5-NHCH$_3$ | CH$_3$ | CH$_2$ |
| J-2 | Q-1 (R$_7$=H, R$_8$=H) | | H | 6-NHCH$_2$CH$_3$ | CH$_3$ | CH$_2$ |
| J-2 | Q-1 (R$_7$=H, R$_8$=H) | | H | 5-NHCH(CH$_3$)$_2$ | CH$_3$ | CH$_2$ |
| J-2 | Q-1 (R$_7$=H, R$_8$=H) | | H | 4-N(CH$_3$)$_2$ | CH$_3$ | CH$_2$ |
| J-2 | Q-1 (R$_7$=H, R$_8$=H) | | H | 6-N(CH$_3$)(CH$_2$CH$_3$) | CH$_3$ | CH$_2$ |
| J-2 | Q-1 (R$_7$=H, R$_8$=H) | | H | 5-N(CH$_3$)(CH(CH$_3$)$_2$) | CH$_3$ | CH$_2$ |
| J-2 | Q-1 (R$_7$=H, R$_8$=H) | | H | 5-Br | CH$_3$ | CH$_2$ |
| J-2 | Q-1 (R$_7$=H, R$_8$=H) | | H | 4-F | CH$_3$ | CH$_2$ |
| J-2 | Q-1 (R$_7$=H, R$_8$=H) | | H | 5-I | CH$_3$ | CH$_2$ |
| J-2 | Q-1 (R$_7$=H, R$_8$=H) | | H | 5-CF$_3$ | CH$_3$ | CH$_2$ |
| J-2 | Q-1 (R$_7$=H, R$_8$=H) | | H | 5-OCF$_2$H | CH$_3$ | CH$_2$ |
| J-2 | Q-1 (R$_7$=H, R$_8$=H) | | H | 5-CH$_3$ | CH$_3$ | O |
| J-2 | Q-1 (R$_7$=H, R$_8$=H) | | H | 6-CH$_2$CH$_3$ | CH$_3$ | O |
| J-2 | Q-1 (R$_7$=H, R$_8$=H) | | H | 5-CH(CH$_3$)$_2$ | CH$_3$ | O |

TABLE 3-continued

General Formula 3

| J | Q | R | $R_1$ | $X_1$ | $Y_1$ |
|---|---|---|---|---|---|
| J-2 | Q-1 ($R_7$=H, $R_8$=H) | H | 5-OCH$_3$ | CH$_3$ | O |
| J-2 | Q-1 ($R_7$=H, $R_8$=H) | H | 5-OC$_2$H$_5$ | CH$_3$ | O |
| J-2 | Q-1 ($R_7$=H, $R_8$=H) | H | 5-OCH(CH$_3$)$_2$ | CH$_3$ | O |
| J-2 | Q-1 ($R_7$=H, $R_8$=H) | H | 5-OCH$_2$F | CH$_3$ | O |
| J-2 | Q-1 ($R_7$=H, $R_8$=H) | H | 6-OCH$_2$CH$_2$Br | CH$_3$ | O |
| J-2 | Q-1 ($R_7$=H, $R_8$=H) | H | 5-OCH(CH$_3$)(CH$_2$Cl) | CH$_3$ | O |
| J-2 | Q-1 ($R_7$=H, $R_8$=H) | H | 5-CH$_2$F | CH$_3$ | O |
| J-2 | Q-1 ($R_7$=H, $R_8$=H) | H | 5-CH$_2$CH$_2$Br | CH$_3$ | O |
| J-2 | Q-1 ($R_7$=H, $R_8$=H) | H | 5-CH(CH$_3$)(CH$_2$Cl) | CH$_3$ | O |
| J-2 | Q-1 ($R_7$=H, $R_8$=H) | H | 5-SCH$_3$ | CH$_3$ | O |
| J-2 | Q-1 ($R_7$=H, $R_8$=H) | H | 6-SCH$_2$CH$_3$ | CH$_3$ | O |
| J-2 | Q-1 ($R_7$=H, $R_8$=H) | H | 5-SCH(CH$_3$)$_2$ | CH$_3$ | O |
| J-2 | Q-1 ($R_7$=H, $R_8$=H) | H | 5-SCH$_2$F | CH$_3$ | O |
| J-2 | Q-1 ($R_7$=H, $R_8$=H) | H | 5-SCH$_2$CH$_2$Br | CH$_3$ | O |
| J-2 | Q-1 ($R_7$=H, $R_8$=H) | H | 5-SCH(CH$_3$)(CH$_2$Cl) | CH$_3$ | O |
| J-2 | Q-1 ($R_7$=H, $R_8$=H) | H | 4-NH$_2$ | CH$_3$ | O |
| J-2 | Q-1 ($R_7$=H, $R_8$=H) | H | 5-NHCH$_3$ | CH$_3$ | O |
| J-2 | Q-1 ($R_7$=H, $R_8$=H) | H | 6-OCH CH BrH | CH$_3$ | O |
| J-2 | Q-1 ($R_7$=H, $R_8$=H) | H | 5-NHCH(CH$_3$)$_2$ | CH$_3$ | O |
| J-2 | Q-1 ($R_7$=H, $R_8$=H) | H | 4-N(CH$_3$)$_2$ | CH$_3$ | O |
| J-2 | Q-1 ($R_7$=H, $R_8$=H) | H | 6-N(CH$_3$)(CH$_2$CH$_3$) | CH$_3$ | O |
| J-2 | Q-1 ($R_7$=H, $R_8$=H) | H | 5-N(CH$_3$)(CH(CH$_3$)$_2$) | CH$_3$ | O |
| J-2 | Q-1 ($R_7$=H, $R_8$=H) | H | 5-Cl | CH$_3$ | O |
| J-2 | Q-1 ($R_7$=H, $R_8$=H) | H | 5-Br | CH$_3$ | O |
| J-2 | Q-1 ($R_7$=H, $R_8$=H) | H | 4-F | CH$_3$ | O |
| J-2 | Q-1 ($R_7$=H, $R_8$=H) | H | 5-I | CH$_3$ | O |
| J-2 | Q-1 ($R_7$=H, $R_8$=H) | H | 4-NO$_2$ | CH$_3$ | O |
| J-2 | Q-1 ($R_7$=H, $R_8$=H) | H | 5-CF$_3$ | CH$_3$ | O |
| J-2 | Q-1 ($R_7$=H, $R_8$=H) | H | 5-OCF$_2$H | OCH$_3$ | O |
| J-2 | Q-1 ($R_7$=H, $R_8$=H) | H | H | CH$_3$ | O |
| J-2 | Q-1 ($R_7$=H, $R_8$=H) | H | H | OCH$_3$ | O |
| J-2 | Q-1 ($R_7$=H, $R_8$=H) | H | H | OC$_2$H$_5$ | O |
| J-2 | Q-1 ($R_7$=H, $R_8$=H) | H | H | OCF$_2$H | O |
| J-2 | Q-1 ($R_7$=H, $R_8$=H) | H | H | OCH$_3$ | CH$_2$ |
| J-2 | Q-1 ($R_7$=H, $R_8$=H) | H | H | OC$_2$H$_5$ | CH$_2$ |
| J-2 | Q-1 ($R_7$=H, $R_8$=H) | H | H | OCF$_2$H | CH$_2$ |
| J-2 | Q-1 ($R_7$=H, $R_8$=CH$_3$) | H | H | CH$_3$ | O |
| J-2 | Q-1 ($R_7$=H, $R_8$=CH$_3$) | H | H | CH$_3$ | CH$_2$ |
| J-2 | Q-1 ($R_7$=H, $R_8$=CH$_2$CH$_3$) | H | H | CH$_3$ | CH$_2$ |
| J-2 | Q-1 ($R_7$=H, $R_8$=CH(CH$_3$)$_2$) | H | H | OCH$_3$ | CH$_2$ |
| J-2 | Q-1 ($R_7$=H, $R_8$=n-C$_4$H$_9$) | H | H | OCH$_3$ | O |
| J-2 | Q-1 ($R_7$=H, $R_8$=CH$_3$) | H | H | OCH$_3$ | O |
| J-2 | Q-37 ($R_7$=H, $R_8$=H, $R_2$=H) | H | H | CH$_3$ | CH$_2$ |
| J-2 | Q-98 ($R_7$=H, $R_8$=H, $R_9$=H) | H | H | CH$_3$ | CH$_2$ |
| J-2 | Q-105 ($R_7$=H, $R_8$=H, $R_9$=H, $R_2$=H) | H | H | CH$_3$ | CH$_2$ |
| J-2 | Q-138 ($R_7$=H, $R_8$=H, $R_9$=H) | H | H | CH$_3$ | CH$_2$ |
| J-2 | Q-143 ($R_7$=H, $R_8$=H, $R_9$=H, $R_3$=H) | H | H | CH$_3$ | O |

TABLE 4

General Formula 4

| J | Q | R | $R_1$ | $X_1$ |
|---|---|---|---|---|
| J-1 | Q-1 ($R_7$=H, $R_8$=H) | H | H | CH$_3$ |
| J-1 | Q-1 ($R_7$=H, $R_8$=H) | H | H | CH$_3$ |
| J-1 | Q-1 ($R_7$=H, $R_8$=H) | H | 5-CH$_3$ | CH$_3$ |
| J-1 | Q-1 ($R_7$=H, $R_8$=H) | H | 5-OCH$_3$ | CH$_3$ |
| J-1 | Q-1 ($R_7$=H, $R_8$=H) | H | 6-OCH$_2$CH$_2$Br | CH$_3$ |
| J-1 | Q-1 ($R_7$=H, $R_8$=H) | H | 5-CH$_2$F | CH$_3$ |
| J-1 | Q-1 ($R_7$=H, $R_8$=H) | H | 5-SCH$_3$ | CH$_3$ |
| J-1 | Q-1 ($R_7$=H, $R_8$=H) | H | 5-SCH$_2$F | CH$_3$ |
| J-1 | Q-1 ($R_7$=H, $R_8$=H) | H | 5-NHCH$_3$ | CH$_3$ |
| J-1 | Q-1 ($R_7$=H, $R_8$=H) | H | 5-Cl | CH$_3$ |
| J-1 | Q-1 ($R_7$=H, $R_8$=H) | H | 4-NO$_2$ | CH$_3$ |
| J-1 | Q-1 ($R_7$=H, $R_8$=H) | H | 5-CF$_3$ | CH$_3$ |
| J-1 | Q-1 ($R_7$=H, $R_8$=H) | H | H | CH$_3$ |
| J-1 | Q-37 ($R_7$=H, $R_8$=H, $R_2$=H) | H | H | CH$_3$ |
| J-1 | Q-98 ($R_7$=H, $R_8$=H, $R_9$=H) | H | H | CH$_3$ |
| J-1 | Q-105 ($R_7$=H, $R_8$=H, $R_9$=H, $R_2$=H) | H | H | CH$_3$ |
| J-1 | Q-138 ($R_7$=H, $R_8$=H, $R_9$=H) | H | H | CH$_3$ |
| J-1 | Q-143 ($R_7$=H, $R_8$=H, $R_9$=H, $R_3$=CH$_3$) | H | H | CH$_3$ |
| J-2 | Q-1 ($R_7$=H, $R_8$=H) | H | 5-SO$_2$N(CH$_3$)$_2$ | CH$_3$ |
| J-2 | Q-1 ($R_7$=H, $R_8$=H) | H | 5-NO$_2$ | CH$_3$ |
| J-2 | Q-1 ($R_7$=H, $R_8$=H) | H | 5-Cl | CH$_3$ |
| J-2 | Q-1 ($R_7$=H, $R_8$=H) | H | 4-NO$_2$ | CH$_3$ |
| J-2 | Q-1 ($R_7$=H, $R_8$=H) | H | 6-Cl | CH$_3$ |
| J-2 | Q-1 ($R_7$=H, $R_8$=H) | H | 6-COOCH$_3$ | CH$_3$ |
| J-2 | Q-1 ($R_7$=H, $R_8$=H) | H | 6-NO$_2$ | CH$_3$ |
| J-2 | Q-1 ($R_7$=H, $R_8$=H) | H | 6-SO$_2$CH$_3$ | CH$_3$ |

TABLE 4-continued

General Formula 4

| J | Q | R | R₁ | X₁ |
|---|---|---|----|-----|
| J-2 | Q-1 (R₇=H, R₈=H) | H | 6-OCH₃ | CH₃ |
| J-2 | Q-1 (R₇=H, R₈=H) | H | 5-OCH₃ | CH₃ |
| J-2 | Q-1 (R₇=H, R₈=H) | H | H | CH₃ |
| J-2 | Q-1 (R₇=H, R₈=H) | H | H | CH₃ |
| J-2 | Q-1 (R₇=H, R₈=H) | CH₃ | H | OCH₃ |
| J-2 | Q-1 (R₇=H, R₈=H) | CH₃ | H | OC₂H₅ |
| J-2 | Q-1 (R₇=H, R₈=H) | CH₃ | H | OCF₂H |
| J-2 | Q-1 (R₇=H, R₈=H) | H | 5-CH₃ | CH₃ |
| J-2 | Q-1 (R₇=H, R₈=H) | H | 6-CH₂CH₃ | CH₃ |
| J-2 | Q-1 (R₇=H, R₈=H) | H | 4-CH(CH₃)₂ | CH₃ |
| J-2 | Q-1 (R₇=H, R₈=H) | H | 5-OCH₂CH₃ | CH₃ |
| J-2 | Q-1 (R₇=H, R₈=H) | H | 4-OCH₂(CH₃)₂ | CH₃ |
| J-2 | Q-1 (R₇=H, R₈=H) | H | 5-OCH₂F | CH₃ |
| J-2 | Q-1 (R₇=H, R₈=H) | H | 6-OCH₂CH₂Br | CH₃ |
| J-2 | Q-1 (R₇=H, R₈=H) | H | 5-OCH(CH₃)(CH₂Cl) | CH₃ |
| J-2 | Q-1 (R₇=H, R₈=H) | H | 5-CH₂F | CH₃ |
| J-2 | Q-1 (R₇=H, R₈=H) | H | 5-CH₂CH₂Br | CH₃ |
| J-2 | Q-1 (R₇=H, R₈=H) | H | 5-CH(CH₃)(CH₂Cl) | CH₃ |
| J-2 | Q-1 (R₇=H, R₈=H) | H | 6-SCH₂CH₃ | CH₃ |
| J-2 | Q-1 (R₇=H, R₈=H) | H | 5-SCH(CH₃)₂ | CH₃ |
| J-2 | Q-1 (R₇=H, R₈=H) | H | 5-SCH₂F | CH₃ |
| J-2 | Q-1 (R₇=H, R₈=H) | H | 5-SCH₂CH₂Br | CH₃ |
| J-2 | Q-1 (R₇=H, R₈=H) | H | 5-SCH(CH₃)(CH₂Cl) | CH₃ |
| J-2 | Q-1 (R₇=H, R₈=H) | H | 4-NH₂ | CH₃ |
| J-2 | Q-1 (R₇=H, R₈=H) | H | 5-NHCH₃ | CH₃ |
| J-2 | Q-1 (R₇=H, R₈=H) | H | 6-NHCH₂CH₃ | CH₃ |
| J-2 | Q-1 (R₇=H, R₈=H) | H | 5-NHCH(CH₃)₂ | CH₃ |
| J-2 | Q-1 (R₇=H, R₈=H) | H | 4-N(CH₃)₂ | CH₃ |
| J-2 | Q-1 (R₇=H, R₈=H) | H | 6-N(CH₃)(CH₂CH₃) | CH₃ |
| J-2 | Q-1 (R₇=H, R₈=H) | H | 5-N(CH₃)(CH(CH₃)₂) | CH₃ |
| J-2 | Q-1 (R₇=H, R₈=H) | H | 5-Br | CH₃ |
| J-2 | Q-1 (R₇=H, R₈=H) | H | 4-F | CH₃ |
| J-2 | Q-1 (R₇=H, R₈=H) | H | 5-I | CH₃ |
| J-2 | Q-1 (R₇=H, R₈=H) | H | 5-CF₃ | CH₃ |
| J-2 | Q-1 (R₇=H, R₈=H) | H | 5-OCF₂H | CH₃ |
| J-2 | Q-1 (R₇=H, R₈=H) | H | H | OCH₃ |
| J-2 | Q-1 (R₇=H, R₈=H) | H | H | OC₂H₅ |
| J-2 | Q-1 (R₇=H, R₈=H) | H | H | OCF₂H |
| J-2 | Q-1 (R₇=H, R₈=CH₃) | H | H | CH₃ |
| J-2 | Q-1 (R₇=H, R₈=CH₂CH₃) | H | H | CH₃ |
| J-2 | Q-1 (R₇=H, R₈=CH(CH₃)₂) | H | H | OCH₃ |
| J-2 | Q-1 (R₇=H, R₈=n-C₄H₉) | H | H | OCH₃ |
| J-2 | Q-1 (R₇=H, R₈CH₃) | H | H | OCH₃ |
| J-2 | Q-37 (R₇=H, R₈=H, R₂=H) | H | H | CH₃ |
| J-2 | Q-98 (R₇=H, R₈=H, R₉=H) | H | H | CH₃ |
| J-2 | Q-105 (R₇=H, R₈=H, R₉=H, R₂=H) | H | H | CH₃ |
| J-2 | Q-138 (R₇=H, R₈=H, R₉=H) | H | H | CH₃ |
| J-2 | Q-143 (R₇=H, R₈=H, R₉=H, R₃=CH₃) | H | H | CH₃ |

TABLE 5

General Formula 5

| J | Q | R | R₁ | X₁ | Y₂ |
|---|---|---|----|-----|-----|
| J-1 | Q-1 (R₇=H, R₈=H) | H | H | CH₃ | CH₃ |
| J-1 | Q-1 (R₇=H, R₈=H) | H | H | CH₃ | H |
| J-1 | Q-1 (R₇=H, R₈=H) | H | H | OCH₃ | CH₃ |
| J-1 | Q-1 (R₇=H, R₈=H) | H | H | OCF₂H | CH₃ |
| J-1 | Q-1 (R₇=H, R₈=H) | H | H | OCH₃ | H |
| J-1 | Q-1 (R₇=H, R₈=H) | H | H | OCF₂H | H |
| J-1 | Q-1 (R₇=H, R₈=H) | H | 5-CH₃ | OCH₃ | H |
| J-1 | Q-1 (R₇=H, R₈=H) | H | 5-OCH₃ | OCH₃ | H |
| J-1 | Q-1 (R₇=H, R₈=H) | H | 6-OCH₂CH₂Br | OCH₃ | H |
| J-1 | Q-1 (R₇=H, R₈=H) | H | 5-CH₂F | OCH₃ | H |
| J-1 | Q-1 (R₇=H, R₈=H) | H | 5-SCH₃ | OCH₃ | H |
| J-1 | Q-1 (R₇=H, R₈=H) | H | 5-SCH₂F | OCH₃ | H |
| J-1 | Q-1 (R₇=H, R₈=H) | H | 5-NHCH₃ | OCH₃ | H |
| J-1 | Q-1 (R₇=H, R₈=H) | H | 5-Cl | OCH₃ | H |
| J-1 | Q-1 (R₇=H, R₈=H) | H | 4-NO₂ | OCH₃ | H |
| J-1 | Q-1 (R₇=H, R₈=H) | H | 5-CF₃ | OCH₃ | H |
| J-1 | Q-37 (R₇=H, R₈=H, R₂=H) | H | H | OCH₃ | H |
| J-1 | Q-105 (R₇=H, R₈=H, R₉=H, R₂=H) | H | H | OCH₃ | H |
| J-1 | Q-138 (R₇=H, R₈=H, R₉=H) | H | H | OCH₃ | H |
| J-1 | Q-143 (R₇=H, R₈=H, R₉=H, R₃=CH₃) | H | H | OCH₃ | H |
| J-2 | Q-1 (R₇=H, R₈=H) | H | 5-SCH₃ | CH₃ | CH₃ |
| J-2 | Q-1 (R₇=H, R₈=H) | H | 5-SOCH₃ | CH₃ | CH₃ |
| J-2 | Q-1 (R₇=H, R₈=H) | H | 5-CO₂CH₃ | CH₃ | CH₃ |
| J-2 | Q-1 (R₇=H, R₈=H) | H | 5-SO₂N(CH₃)₂ | CH₃ | CH₃ |
| J-2 | Q-1 (R₇=H, R₈=H) | H | 5-NO₂ | CH₃ | CH₃ |

TABLE 5-continued

General Formula 5

| J | Q | R | $R_1$ | $X_1$ | $Y_2$ |
|---|---|---|---|---|---|
| J-2 | Q-1 ($R_7$=H, $R_8$=H) | H | 5-Cl | $CH_3$ | $CH_3$ |
| J-2 | Q-1 ($R_7$=H, $R_8$=H) | H | 4-$NO_2$ | $CH_3$ | $CH_3$ |
| J-2 | Q-1 ($R_7$=H, $R_8$=H) | H | 6-Cl | $CH_3$ | $CH_3$ |
| J-2 | Q-1 ($R_7$=H, $R_8$=H) | H | 6-$COOCH_3$ | $CH_3$ | $CH_3$ |
| J-2 | Q-1 ($R_7$=H, $R_8$=H) | H | 6-$NO_2$ | $CH_3$ | $CH_3$ |
| J-2 | Q-1 ($R_7$=H, $R_8$=H) | H | 6-$SO_2CH_3$ | $CH_3$ | $CH_3$ |
| J-2 | Q-1 ($R_7$=H, $R_8$=H) | H | 6-$OCH_3$ | $CH_3$ | $CH_3$ |
| J-2 | Q-1 ($R_7$=H, $R_8$=H) | H | 5-$OCH_3$ | $CH_3$ | $CH_3$ |
| J-2 | Q-1 ($R_7$=H, $R_8$=H) | H | H | $CH_3$ | H |
| J-2 | Q-1 ($R_7$=H, $R_8$=H) | H | H | $OCH_3$ | $CH_3$ |
| J-2 | Q-1 ($R_7$=H, $R_8$=H) | H | H | $OC_2H_5$ | $CH_3$ |
| J-2 | Q-1 ($R_7$=H, $R_8$=H) | H | H | $OCF_2H$ | $CH_3$ |
| J-2 | Q-1 ($R_7$=H, $R_8$=H) | H | H | $OCH_3$ | H |
| J-2 | Q-1 ($R_7$=H, $R_8$=H) | H | H | $OC_2H_5$ | H |
| J-2 | Q-1 ($R_7$=H, $R_8$=H) | H | H | $OCF_2H$ | H |
| J-2 | Q-1 ($R_7$=H, $R_8$=H) | $CH_3$ | H | $CH_3$ | $CH_3$ |
| J-2 | Q-1 ($R_7$=H, $R_8$=H) | $CH_3$ | H | $OCH_3$ | $CH_3$ |
| J-2 | Q-1 ($R_7$=H, $R_8$=H) | $CH_3$ | H | $CH_3$ | H |
| J-2 | Q-1 ($R_7$=H, $R_8$=H) | H | 5-$CH_3$ | $OCH_3$ | H |
| J-2 | Q-1 ($R_7$=H, $R_8$=H) | H | 6-$CH_2CH_3$ | $OCH_3$ | H |
| J-2 | Q-1 ($R_7$=H, $R_8$=H) | H | 5-$CH(CH_3)_2$ | $OCH_3$ | H |
| J-2 | Q-1 ($R_7$=H, $R_8$=H) | H | 5-$OCH_2CH_3$ | $OCH_3$ | H |
| J-2 | Q-1 ($R_7$=H, $R_8$=H) | H | 5-$OCH(CH_3)_2$ | $OCH_3$ | H |
| J-2 | Q-1 ($R_7$=H, $R_8$=H) | H | 5-$OCF_2H$ | $OCH_3$ | H |
| J-2 | Q-1 ($R_7$=H, $R_8$=H) | H | 6-$OCH_2CH_2Br$ | $OCH_3$ | H |
| J-2 | Q-1 ($R_7$=H, $R_8$=H) | H | 6-$OCH(CH_3)(CH_2Cl)$ | $OCH_3$ | H |
| J-2 | Q-1 ($R_7$=H, $R_8$=H) | H | 5-$CH_2F$ | $OCH_3$ | H |
| J-2 | Q-1 ($R_7$=H, $R_8$=H) | H | 5-$CH_2CH_2Br$ | $OCH_3$ | H |
| J-2 | Q-1 ($R_7$=H, $R_8$=H) | H | 5-$CH(CH_3)(CH_2Cl)$ | $OCH_3$ | H |
| J-2 | Q-1 ($R_7$=H, $R_8$=H) | H | 5-$SCH_3$ | $OCH_3$ | H |
| J-2 | Q-1 ($R_7$=H, $R_8$=H) | H | 6-$SCH_2CH_3$ | $OCH_3$ | H |
| J-2 | Q-1 ($R_7$=H, $R_8$=H) | H | 5-$SCH(CH_3)_2$ | $OCH_3$ | H |
| J-2 | Q-1 ($R_7$=H, $R_8$=H) | H | 5-$SCH_2F$ | $OCH_3$ | H |
| J-2 | Q-1 ($R_7$=H, $R_8$=H) | H | 5-$SCH_2CH_2Br$ | $OCH_3$ | H |
| J-2 | Q-1 ($R_7$=H, $R_8$=H) | H | 5-$SCH(CH_3)(CH_2Cl)$ | $OCH_3$ | H |
| J-2 | Q-1 ($R_7$=H, $R_8$=H) | H | 4-$NH_2$ | $OCH_3$ | H |
| J-2 | Q-1 ($R_7$=H, $R_8$=H) | H | 5-$NHCH_3$ | $OCH_3$ | H |
| J-2 | Q-1 ($R_7$=H, $R_8$=H) | H | 6-$NHCH_2CH_3$ | $OCH_3$ | H |
| J-2 | Q-1 ($R_7$=H, $R_8$=H) | H | 5-$NHCH(CH_3)_2$ | $OCH_3$ | H |
| J-2 | Q-1 ($R_7$=H, $R_8$=H) | H | 4-$N(CH_3)_2$ | $OCH_3$ | H |
| J-2 | Q-1 ($R_7$=H, $R_8$=H) | H | 6-$N(CH_3)(CH_2CH_3)$ | $OCH_3$ | H |
| J-2 | Q-1 ($R_7$=H, $R_8$=H) | H | 5-$N(CH_3)(CH(CH_3)_2)$ | $OCH_3$ | H |
| J-2 | Q-1 ($R_7$=H, $R_8$=H) | H | 5-Br | $OCH_3$ | H |
| J-2 | Q-1 ($R_7$=H, $R_8$=H) | H | 4-F | $OCH_3$ | H |
| J-2 | Q-1 ($R_7$=H, $R_8$=H) | H | 5-I | $OCH_3$ | H |
| J-2 | Q-1 ($R_7$=H, $R_8$=H) | H | 5-$CF_3$ | $OCH_3$ | H |
| J-2 | Q-1 ($R_7$=H, $R_8$=H) | H | 5-$OCF_2H$ | $OCH_3$ | H |
| J-2 | Q-1 ($R_7$=H, $R_8$=$CH_3$) | H | H | $OCH_3$ | H |
| J-2 | Q-1 ($R_7$=H, $R_8$=$CH_3$) | H | H | $OCH_3$ | $CH_3$ |
| J-2 | Q-1 ($R_7$=H, $R_8$=$CH_2CH_3$) | H | H | $CH_3$ | H |
| J-2 | Q-1 ($R_7$=H, $R_8$=$CH(CH_3)_2$) | H | H | $CH_3$ | $CH_3$ |
| J-2 | Q-1 ($R_7$=H, $R_8$=n-$C_4H_9$) | H | H | $OCF_2H$ | H |
| J-2 | Q-1 ($R_7$=$CH_3$, $R_8CH_3$) | H | H | $OCH_3$ | H |
| J-2 | Q-37 ($R_7$=H, $R_8$=H, $R_2$=H) | H | H | $OCH_3$ | H |
| J-2 | Q-98 ($R_7$=$CH_3$, $R_8$=H, $R_9$=H) | H | H | $OCH_3$ | H |
| J-2 | Q-105 ($R_7$=H, $R_8$=H, $R_9$=H, $R_2$=H) | H | H | $OCH_3$ | H |
| J-2 | Q-138 ($R_7$=H, $R_8$=H, $R_9$=H) | H | H | $OCH_3$ | H |
| J-2 | Q-143 ($R_7$=H, $R_8$=H, $R_9$=H, $R_3$=H) | H | H | $OCH_3$ | $CH_3$ |

TABLE 6

General Formula 6

| J | Q | R | $R_1$ | $X_2$ | $Y_3$ |
|---|---|---|---|---|---|
| J-1 | Q-1 ($R_7$=H, $R_8$=H) | H | H | $CH_3$ | $CH_3$ |
| J-1 | Q-1 ($R_7$=H, $R_8$=H) | H | H | $OCH_3$ | $CH_3$ |
| J-1 | Q-1 ($R_7$=H, $R_8$=H) | H | H | $SCH_3$ | $CH_3$ |
| J-1 | Q-1 ($R_7$=H, $R_8$=H) | H | H | $CH_3$ | $CH_2CF_3$ |
| J-1 | Q-1 ($R_7$=H, $R_8$=H) | H | H | $OCH_3$ | $CH_2CF_3$ |
| J-1 | Q-1 ($R_7$=H, $R_8$=H) | H | H | $SCH_3$ | $CH_2CF_3$ |
| J-1 | Q-1 ($R_7$=H, $R_8$=H) | H | 5-$OCH_3$ | $OCH_3$ | $CH_3$ |
| J-1 | Q-1 ($R_7$=H, $R_8$=H) | H | 6-$OCH_2CH_2Br$ | $OCH_3$ | $CH_3$ |
| J-1 | Q-1 ($R_7$=H, $R_8$=H) | H | 5-$CH_2F$ | $OCH_3$ | $CH_3$ |
| J-1 | Q-1 ($R_7$=H, $R_8$=H) | H | 5-$SCH_3$ | $OCH_3$ | $CH_3$ |
| J-1 | Q-1 ($R_7$=H, $R_8$=H) | H | 5-$SCH_2F$ | $OCH_3$ | $CH_3$ |
| J-1 | Q-1 ($R_7$=H, $R_8$=H) | H | 5-$NHCH_3$ | $OCH_3$ | $CH_3$ |
| J-1 | Q-1 ($R_7$=H, $R_8$=H) | H | 5-Cl | $OCH_3$ | $CH_3$ |
| J-1 | Q-1 ($R_7$=H, $R_8$=H) | H | 4-$NO_2$ | $OCH_3$ | $CH_3$ |

TABLE 6-continued

General Formula 6

| J | Q | R | $R_1$ | $X_2$ | $Y_3$ |
|---|---|---|---|---|---|
| J-1 | Q-1 ($R_7$=H, $R_8$=H) | H | 5-$CF_3$ | $OCH_3$ | $CH_3$ |
| J-1 | Q-37 ($R_7$=H, $R_8$=H, $R_2$=H) | H | H | $OCH_3$ | $CH_3$ |
| J-1 | Q-98 ($R_7$=H, $R_8$=H, $R_9$=H) | H | H | $OCH_3$ | $CH_3$ |
| J-1 | Q-105 ($R_7$=H, $R_8$=H, $R_9$=H, $R_2$=H) | H | H | $OCH_3$ | $CH_3$ |
| J-1 | Q-138 ($R_7$=H, $R_8$=H, $R_9$=H) | H | H | $OCH_3$ | $CH_3$ |
| J-1 | Q-143 ($R_7$=H, $R_8$=H, $R_9$=H, $R_3$=$CH_3$) | H | H | $OCH_3$ | $CH_3$ |
| J-2 | Q-1 ($R_7$=H, $R_8$=H) | H | 5-$SCH_3$ | $OCH_3$ | $CH_3$ |
| J-2 | Q-1 ($R_7$=H, $R_8$=H) | H | 5-$SOCH_3$ | $OCH_3$ | $CH_3$ |
| J-2 | Q-1 ($R_7$=H, $R_8$=H) | H | 5-$CO_2CH_3$ | $OCH_3$ | $CH_3$ |
| J-2 | Q-1 ($R_7$=H, $R_8$=H) | H | 5-$SO_2N(CH_3)_2$ | $OCH_3$ | $CH_3$ |
| J-2 | Q-1 ($R_7$=H, $R_8$=H) | H | 5-$NO_2$ | $OCH_3$ | $CH_3$ |
| J-2 | Q-1 ($R_7$=H, $R_8$=H) | H | 5-Cl | $OCH_3$ | $CH_3$ |
| J-2 | Q-1 ($R_7$=H, $R_8$=H) | H | 4-$NO_2$ | $OCH_3$ | $CH_3$ |
| J-2 | Q-1 ($R_7$=H, $R_8$=H) | H | 6-Cl | $OCH_3$ | $CH_3$ |
| J-2 | Q-1 ($R_7$=H, $R_8$=H) | H | 6-$COOCH_3$ | $OCH_3$ | $CH_3$ |
| J-2 | Q-1 ($R_7$=H, $R_8$=H) | H | 6-$NO_2$ | $OCH_3$ | $CH_3$ |
| J-2 | Q-1 ($R_7$=H, $R_8$=H) | H | 6-$SO_2CH_3$ | $OCH_3$ | $CH_3$ |
| J-2 | Q-1 ($R_7$=H, $R_8$=H) | H | 6-$OCH_3$ | $OCH_3$ | $CH_3$ |
| J-2 | Q-1 ($R_7$=H, $R_8$=H) | H | 5-$OCH_3$ | $OCH_3$ | $CH_3$ |
| J-2 | Q-1 ($R_7$=H, $R_8$=H) | H | H | $CH_3$ | $CH_3$ |
| J-2 | Q-1 ($R_7$=H, $R_8$=H) | H | H | $OCH_3$ | $CH_3$ |
| J-2 | Q-1 ($R_7$=H, $R_8$=H) | H | H | $SCH_3$ | $CH_3$ |
| J-2 | Q-1 ($R_7$=H, $R_8$=H) | H | H | $CH_3$ | $CH_2CH_3$ |
| J-2 | Q-1 ($R_7$=H, $R_8$=H) | H | H | $OCH_3$ | $CH_2CH_3$ |
| J-2 | Q-1 ($R_7$=H, $R_8$=H) | H | H | $SCH_3$ | $CH_2CH_3$ |
| J-2 | Q-1 ($R_7$=H, $R_8$=H) | H | H | $CH_3$ | $CH_2CF_3$ |
| J-2 | Q-1 ($R_7$=H, $R_8$=H) | H | H | $OCH_3$ | $CH_2CF_3$ |
| J-2 | Q-1 ($R_7$=H, $R_8$=H) | H | H | $SCH_3$ | $CH_2CF_3$ |
| J-2 | Q-1 ($R_7$=H, $R_8$=H) | $CH_3$ | 5-$CH_3$ | $CH_3$ | $CH_3$ |
| J-2 | Q-1 ($R_7$=H, $R_8$=H) | $CH_3$ | 6-$CH_2CH_3$ | $OCH_3$ | $CH_3$ |
| J-2 | Q-1 ($R_7$=H, $R_8$=H) | $CH_3$ | 5-$CH(CH_3)_2$ | $SCH_3$ | $CH_3$ |
| J-2 | Q-1 ($R_7$=H, $R_8$=H) | H | 5-$OCH_3$ | $OCH_3$ | $CH_3$ |
| J-2 | Q-1 ($R_7$=H, $R_8$=H) | H | 5-$OCH_2CH_3$ | $OCH_3$ | $CH_3$ |
| J-2 | Q-1 ($R_7$=H, $R_8$=H) | H | 5-$OCH(CH_3)_2$ | $OCH_3$ | $CH_3$ |
| J-2 | Q-1 ($R_7$=H, $R_8$=H) | H | 5-$OCF_2H$ | $OCH_3$ | $CH_3$ |
| J-2 | Q-1 ($R_7$=H, $R_8$=H) | H | 6-$OCH_2CH_2Br$ | $OCH_3$ | $CH_3$ |
| J-2 | Q-1 ($R_7$=H, $R_8$=H) | H | 6-$OCH(CH_3)(CH_2Cl)$ | $OCH_3$ | $CH_3$ |
| J-2 | Q-1 ($R_7$=H, $R_8$=H) | H | 5-$CH_2F$ | $OCH_3$ | $CH_3$ |
| J-2 | Q-1 ($R_7$=H, $R_8$=H) | H | 5-$CH_2CH_2Br$ | $OCH_3$ | $CH_3$ |
| J-2 | Q-1 ($R_7$=H, $R_8$=H) | H | 5-$CH(CH_3)(CH_2Cl)$ | $OCH_3$ | $CH_3$ |
| J-2 | Q-1 ($R_7$=H, $R_8$=H) | H | 6-$SCH_2CH_3$ | $OCH_3$ | $CH_3$ |
| J-2 | Q-1 ($R_7$=H, $R_8$=H) | H | 5-$SCH(CH_3)_2$ | $OCH_3$ | $CH_3$ |
| J-2 | Q-1 ($R_7$=H, $R_8$=H) | H | 5-$SCH_2F$ | $OCH_3$ | $CH_3$ |
| J-2 | Q-1 ($R_7$=H, $R_8$=H) | H | 5-$SCH_2CH_2Br$ | $OCH_3$ | $CH_3$ |
| J-2 | Q-1 ($R_7$=H, $R_8$=H) | H | 5-$SCH(CH_3)(CH_2Cl)$ | $OCH_3$ | $CH_3$ |
| J-2 | Q-1 ($R_7$=H, $R_8$=H) | H | 4-$NH_2$ | $OCH_3$ | $CH_3$ |
| J-2 | Q-1 ($R_7$=H, $R_8$=H) | H | 5-$NHCH_3$ | $OCH_3$ | $CH_3$ |
| J-2 | Q-1 ($R_7$=H, $R_8$=H) | H | 6-$NHCH_2CH_3$ | $OCH_3$ | $CH_3$ |
| J-2 | Q-1 ($R_7$=H, $R_8$=H) | H | 5-$NHCH(CH_3)_2$ | $OCH_3$ | $CH_3$ |
| J-2 | Q-1 ($R_7$=H, $R_8$=H) | H | 4-$N(CH_3)_2$ | $OCH_3$ | $CH_3$ |
| J-2 | Q-1 ($R_7$=H, $R_8$=H) | H | 6-$N(CH_3)(CH_2CH_3)$ | $OCH_3$ | $CH_3$ |
| J-2 | Q-1 ($R_7$=H, $R_8$=H) | H | 5-$N(CH_3)(CH(CH_3)_2)$ | $OCH_3$ | $CH_3$ |
| J-2 | Q-1 ($R_7$=H, $R_8$=H) | H | 5-Br | $OCH_3$ | $CH_3$ |
| J-2 | Q-1 ($R_7$=H, $R_8$=H) | H | 4-F | $OCH_3$ | $CH_3$ |
| J-2 | Q-1 ($R_7$=H, $R_8$=H) | H | 5-I | $OCH_3$ | $CH_3$ |
| J-2 | Q-1 ($R_7$=H, $R_8$=H) | H | 4-$NO_2$ | $OCH_3$ | $CH_3$ |
| J-2 | Q-1 ($R_7$=H, $R_8$=H) | H | 5-$CF_3$ | $OCH_3$ | $CH_3$ |
| J-2 | Q-1 ($R_7$=H, $R_8$=H) | H | 5-$OCF_2H$ | $OCH_3$ | $CH_3$ |
| J-2 | Q-1 ($R_7$=H, $R_8$=$CH_3$) | H | H | $OCH_3$ | $CH_3$ |
| J-2 | Q-1 ($R_7$=H, $R_8$=$CH_3$) | H | H | $CH_3$ | $CH_2CF_3$ |
| J-2 | Q-1 ($R_7$=H, $R_8$=$CH_2CH_3$) | H | H | $CH_3$ | $CH_3$ |
| J-2 | Q-1 ($R_7$=H, $R_8$=$CH(CH_3)_2$) | H | H | $OCH_3$ | $CH_3$ |
| J-2 | Q-1 ($R_7$=H, $R_8$=n-$C_4H_9$) | H | H | $SCH_3$ | $CH_3$ |
| J-2 | Q-1 ($R_7$=$CH_3$, $R_8$=$CH_3$) | H | H | $OCH_3$ | $CH_3$ |
| J-2 | Q-37 ($R_7$=H, $R_8$=H, $R_2$=H) | H | H | $OCH_3$ | $CH_3$ |
| J-2 | Q-98 ($R_7$=H, $R_8$=H, $R_9$=H) | H | H | $OCH_3$ | $CH_3$ |
| J-2 | Q-105 ($R_7$=H, $R_8$=H, $R_9$=H, $R_2$=H) | H | H | $OCH_3$ | $CH_3$ |
| J-2 | Q-138 ($R_7$=H, $R_8$=H, $R_9$=H) | H | H | $OCH_3$ | $CH_3$ |
| J-2 | Q-143 ($R_7$=H, $R_8$=H, $R_9$=H, $R_3$=H) | H | H | $OCH_3$ | $CH_3$ |

TABLE 7

General Formula 7

| J | Q | R | $R_1$ | $X_3$ |
|---|---|---|---|---|
| J-2 | Q-1 ($R_7$=H, $R_8$=H) | H | H | $CH_3$ |
| J-2 | Q-2 ($R_7$=H, $R_8$=H) | H | H | $OCH_3$ |
| J-2 | Q-3 ($R_7$=H, $R_8$=H) | H | H | $CH_3$ |
| J-2 | Q-4 ($R_7$=H, $R_8$=H, $R_3$=$CH_3$) | H | H | $OCH_3$ |
| J-2 | Q-5 ($R_7$=H, $R_8$=H, $R_3$=H) | H | H | $CH_3$ |
| J-2 | Q-6 ($R_7$=$CH_3$, $R_8$=H, $R_3$=$CH_3$) | H | H | $OCH_3$ |
| J-2 | Q-7 ($R_7$=H, $R_8$=H, $R_9$=H) | H | H | $CH_3$ |
| J-2 | Q-8 ($R_7$=H, $R_8$=H, $R_2$=H) | H | H | $OCH_3$ |

TABLE 7-continued

General Formula 7

| J | Q | R | $R_1$ | $X_3$ |
|---|---|---|---|---|
| J-2 | Q-9 ($R_7$=H, $R_8$=H, $R_2$=H) | H | H | $CH_3$ |
| J-2 | Q-13 ($R_7$=H, $R_8$=H, $R_3$=H) | H | H | $OCH_3$ |
| J-2 | Q-14 ($R_7$=H, $R_8$=H, $R_3$=$CH_3$) | H | H | $CH_3$ |
| J-2 | Q-15 ($R_7$=H, $R_8$=H, $R_3$=H) | H | H | $OCH_3$ |
| J-2 | Q-16 ($R_7$=H, $R_8$=H, $R_9$=H) | H | H | $CH_3$ |
| J-2 | Q-29 ($R_7$=H, $R_8$=H) | H | H | $OCH_3$ |
| J-2 | Q-30 ($R_7$=H, $R_8$=H) | H | H | $CH_3$ |
| J-2 | Q-31 ($R_7$=H, $R_8$=H) | H | H | $OCH_3$ |
| J-2 | Q-32 ($R_7$=H, $R_8$=H, $R_3$=H) | H | H | $CH_3$ |
| J-2 | Q-33 ($R_7$=H, $R_8$=H, $R_8$=$CH_3$) | H | H | $OCH_3$ |
| J-2 | Q-34 ($R_7$=H, $R_8$=H, $R_3$=H) | H | H | $CH_3$ |
| J-2 | Q-35 ($R_7$=H, $R_8$=H, $R_9$=H) | H | H | $OCH_3$ |
| J-2 | Q-36 ($R_7$=H, $R_8$=H, $R_2$=H) | H | H | $CH_3$ |
| J-2 | Q-37 ($R_7$=H, $R_8$=H, $R_2$=H) | H | H | $OCH_3$ |
| J-2 | Q-38 ($R_7$=H, $R_8$=H, $R_2$=$OCF_2H$) | H | H | $CH_3$ |
| J-2 | Q-39 ($R_7$=H, $R_8$=H, $R_9$=H) | H | H | $OCH_3$ |
| J-2 | Q-43 ($R_7$=H, $R_8$=H, $R_3$=H) | H | H | $CH_3$ |
| J-2 | Q-44 ($R_7$=H, $R_8$=H, $R_3$=$CH_3$) | H | H | $OCH_3$ |
| J-2 | Q-45 ($R_7$=H, $R_8$=H, $R_3$=H) | H | H | $CH_3$ |
| J-2 | Q-46 ($R_7$=H, $R_8$=H, $R_9$=H) | H | H | $OCH_3$ |
| J-2 | Q-47 ($R_7$=H, $R_8$=H, $R_2$=H) | H | H | $CH_3$ |
| J-2 | Q-51 ($R_7$=H, $R_8$=H, $R_9$=H) | H | H | $OCH_3$ |
| J-2 | Q-52 ($R_7$=H, $R_8$=H, $R_9$=H) | H | H | $CH_3$ |
| J-2 | Q-53 ($R_7$=H, $R_8$=H, $R_9$=H) | H | H | $OCH_3$ |
| J-2 | Q-54 (R=H, R=H, R=H) | H | H | $CH_3$ |
| J-2 | Q-55 ($R_7$=H, $R_8$=H, $R_9$=H, $R_3$=H) | H | H | $OCH_3$ |
| J-2 | Q-56 ($R_7$=H, $R_8$=H, $R_9$=H, $R_3$=$C_2H_5$) | H | H | $CH_3$ |
| J-2 | Q-57 ($R_7$=H, $R_8$=H, $R_9$=H, $R_3$=i-$C_3H_7$) | H | H | $OCH_3$ |
| J-2 | Q-58 ($R_7$=H, $R_8$=H, $R_9$=H, $R_3$=H) | H | H | $CH_3$ |
| J-2 | Q-59 ($R_7$=H, $R_8$=H, $R_9$=H, $R_{10}$=H) | H | H | $OCH_3$ |
| J-2 | Q-95 ($R_7$=H, $R_8$=H, $R_9$=H) | H | H | $CH_3$ |
| J-2 | Q-96 ($R_7$=H, $R_8$=H, $R_9$=H) | H | H | $OCH_3$ |
| J-2 | Q-97 ($R_7$=H, $R_8$=H, $R_9$=H) | H | H | $CH_3$ |
| J-2 | Q-98 ($R_7$=H, $R_8$=H, $R_9$=H) | H | H | $OCH_3$ |
| J-2 | Q-99 ($R_7$=H, $R_8$=H, $R_9$=H, $R_3$=H) | H | H | $CH_3$ |
| J-2 | Q-100 ($R_7$=H, $R_8$=H, $R_9$=H, $R_3$=$C_2H_5$) | H | H | $OCH_3$ |
| J-2 | Q-101 ($R_7$=H, $R_8$=H, $R_9$=H, $R_3$=i-$C_3H_7$) | H | H | $CH_3$ |
| J-2 | Q-102 ($R_7$=H, $R_8$=H, $R_3$=H) | H | H | $OCH_3$ |
| J-2 | Q-103 ($R_7$=H, $R_8$=H, $R_9$=H, $R_{10}$=H) | H | H | $CH_3$ |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 8

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide, 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 5th Ed., McGraw-Hill, New York, 1973, pp. 8–57ff.

EXAMPLE 5

Wettable Powder

| | |
|---|---|
| N—[(4-methoxy-6-methyltriazin-2-yl)aminocarbonyl]-2-(tetrahydro-2-oxofuran-3-yl)-3-pyridine-sulfonamide | 80% |
| sodium alkylnaphthalenesulfonate | 2% |
| sodium ligninsulfonate | 2% |
| synthetic amorphous silica | 3% |
| Kaolinite | 13% |

The ingredients are blended, hammer-milled until all the solids are essentially under 50 microns, reblended, and packaged.

EXAMPLE 6

Wettable Powder

| | |
|---|---|
| N—[(4-6-dimethoxypyrimidin-2-yl)aminocarbonyl]-2-(tetrahydro-2-oxofuran-3-yl)-3-pyridine-sulfonamide | 50% |
| sodium alkylnaphthalenesulfonate | 2% |
| low viscosity methyl cellulose | 2% |

-continued

| | |
|---|---|
| diatomaceous earth | 46% |

The ingredients are blended, coarsely hammer-milled and then air-milled to produce particles essentially all below 10 microns in diameter. The product is reblended before packaging.

EXAMPLE 7

Granule

| | |
|---|---|
| Wettable Powder of Example 5 | 5% |
| attapulgite granules | 95% |
| (U.S.S. 20–40 mesh; 0.84–0.42 mm) | |

A slurry of wettable powder containing 25% solids is sprayed on the surface of attapulgite granules while tumbling in a double-cone blender. The granules are dried and packaged.

EXAMPLE 8

Extruded Pellet

| | |
|---|---|
| N—[(4-6-methoxy-6-methyltriazin-2-yl)aminocarbonyl]-2-(tetrahydro-2-oxofuran-3-yl)-3-pyridine-sulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cyclinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 9

Oil Suspension

| | |
|---|---|
| N—[(4-methoxy-6-methyltriazin-2-yl)aminocarbonyl]-2-(tetrahydro-2-oxofuran-3-yl)-3-pyridine-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 10

Wettable Powder

| | |
|---|---|
| N—[(4-methoxy-6-methyltriazin-2-yl)aminocarbonyl]-2-(tetrahydro-2-oxofuran-3-yl)-3-pyridinesulfonamide | 20% |
| sodium alkynaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 11

Low Strength Granule

| | |
|---|---|
| N—[(4-6-dimethoxypyrimidin-2-yl)aminocarbonyl]-2-(tetrahydro-2-oxofuran-3-yl)-3-pyridinesulfonamide | 1% |
| N,N—dimethylformamide | 9% |
| attapulgite granules | 90% |
| (U.S.S. 20–4- sieve) | |

The active ingredient is dissolved in the solvent and the solution is sprayed upon dedusted granules in a double cone blender. After spraying of the solution has been completed, the blender is allowed to run for a short period and then the granules are packaged.

EXAMPLE 12

Aqueous Suspension

| | |
|---|---|
| N—[(4-methoxy-6-methyltriazin-2-yl)aminocarbonyl]-2-(tetrahydro-2-oxofuran-3-yl)-3-pyridinesulfonamide | 40% |
| polyacrylic acid thickener | 0.3% |
| dodecylphenol polyethlene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 13

Solution

| | |
|---|---|
| N—[(4-methoxy-6-methyltriazin-2-yl)aminocarbonyl]-2-(tetrahydro-2-oxofuran-3-yl)-3-pyridinesulfon-amide, sodium salt | 5% |
| water | 95% |

The salt is added directly to the water with stirring to produce the solution, which may then be packaged for use.

EXAMPLE 14

Low Strength Granule

| | |
|---|---|
| N—[(4,6-dimethoxypyrimidin-2-yl)aminocarbonyl]-2-(tetrahydro-2-oxofuran-3-yl)-3-pyridinesulfonamide | 0.1% |
| attapulgite granules | 99.9% |
| (U.S.S. 20–40 mesh) | |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 15

Granule

| | |
|---|---|
| N—[(4-methoxy-6-methyltriazin-2-yl)aminocarbonyl]-2-(tetrahydro-2-oxofuran-3-yl)-3-pyridinesulfonamide | 80% |
| a wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 16

High Strength Concentrate

| | |
|---|---|
| N—[(4-methoxy-6-methyltriazin-2-yl)aminocarbonyl]-2-(tetrahydro-2-oxofuran-3-yl)-3-pyridinesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 17

Wettable Powder

| | |
|---|---|
| N—[(4,6-dimethoxypyrimidin-2-yl)aminocarbonyl]-2-(tetrahydro-2-oxofuran-3-yl)-3-pyridinesulfonamide. | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 18

Wettable Powder

| | |
|---|---|
| N—[(4-methoxy-6-methyltriazin-2-yl)aminocarbonyl]-2-(tetrahydro-2-oxofuran-3-yl)-3-pyridinesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 19

Oil Suspension

| | |
|---|---|
| N—[(4-methoxy-6-methyltriazin-2-yl)aminocarbonyl]-2-(tetrahydro-2-oxofuran-3-yl)-3-pyridinesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Utility

Tests results indicate that the compounds of the present invention are highly active preemergent or postemergent herbicides or plant growth regulants. Many of them have utility for broad-spectrum pre- and/or post-emergence weed control in areas where complete control of all vegetation is desired, such as ground fuel storage tanks, ammunition depots, industrial storage areas, parking lots, drive-in theaters, around billboards, highway and railroad structures. Alternatively, some of the compounds may have utility for selective weed control, or may be useful to modify plant growth.

The rates of application for the compounds of the invention are determined by a number of factors, including their use as plant growth modifiers or as herbicides, the crop species involved, the types of weeds to be controlled, weather and climate, formulations, selected mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide, examples of which are those of the triazine, triazole, uracil, urea, amide, diphenylether, carbamate and bipyridylium types. The herbicidal properties of the subject compounds were discovered in a number of greenhouse tests. The test procedures and results follow.

Test A

Seeds of crabgrass (Digitaria sp.), barnyardgrass (*Echinochloa crusgalli*), wild oats (*Avena fatua*), cheatgrass (*Bromus secalinus*), velvetleaf (*Abutilon theophrasti*), morningglory (Ipomoea spp.), cocklebur (*Xanthium pensylvanicum*), sorghum, corn, soybean, sugarbeet, cotton, rice, wheat and purple nutsedge (*Cyperus rotundus*) tubers were planted and treated preemergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to &=complete kill. The accompanying descriptive symbols have the following meanings:

C=chlorosis/necrosis;
B=burn;
D=defoliation;
E=emergence inhibition;
G=growth retardation;
H=formative effects;
U=unusual pigmentation;
X=axillary stimulation;
S=albinism; and
6Y=abscised buds or flowers.

COMPOUNDS

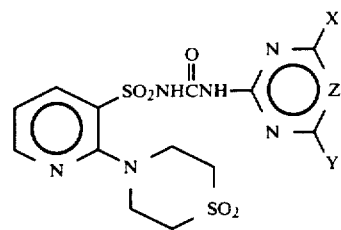

| Compound No. | X | Y | Z |
|---|---|---|---|
| 1 | OCH₃ | OCH₃ | CH |
| 2 | OCH₃ | CH₃ | CH |
| 3 | OCH₃ | OCH₃ | N |
| 4 | OCH₃ | CH₃ | N |

TABLE A

Compound 1

| TYPE TEST | RATE K/HA | MORNING GLORY | COCKLE BUR | VELVET LEAF | NUT SEDGE | CRAB GRASS | BARNYARD GRASS | CHEAT GRASS | WILD OATS |
|---|---|---|---|---|---|---|---|---|---|
| POST | 0.4 | 9C | 4C | 4C | 5C | 4G | 3C | 3C | 0 |
| POST | 0.4 | | 9H | 9H | 9G | | 7H | 9G | |
| POST | 0.05 | 4C | 4C | 3C | 2C | 2G | 5G | 7G | 0 |
| POST | 0.05 | 9G | 8H | 7H | 8G | | | | |
| PRE | 0.4 | 3C | 2C | 3C | 5G | 0 | 2C | 6G | 0 |
| PRE | 0.4 | 8H | | 4H | | | 4G | | |
| PRE | 0.05 | 2C | 1C | 2C | 0 | 0 | 0 | 0 | 0 |
| PRE | 0.05 | 8H | | 5H | | | | | |

| TYPE TEST | RATE K/HA | SICKLE POD | WHEAT | CORN | SOYBEAN | RICE | SORGHUM | SUGARBEET | COTTON |
|---|---|---|---|---|---|---|---|---|---|
| POST | 0.4 | 0 | 0 | 3C | 2C | 2C | 9C | | 3C |
| POST | 0.4 | | | 9G | 5G | 6G | | | 9H |
| POST | 0.05 | 0 | 0 | 2C | 5G | 4G | 4C | — | 4C |
| POST | 0.05 | | | 8G | | | 8H | | 8H |
| PRE | 0.4 | 0 | 3G | 2C | 2C | 2C | 4C | | 5G |
| PRE | 0.4 | | | 2H | 6G | 5G | 8G | | |
| PRE | 0.05 | 0 | 2G | 2G | 2G | 3C | 5G | | 5G |
| PRE | 0.05 | | | | | 3H | | | |

Compound 2

| TYPE TEST | RATE K/HA | MORNING GLORY | COCKLE BUR | VELVET LEAF | NUT SEDGE | CRAB GRASS | BARNYARD GRASS | CHEAT GRASS | WILD OATS |
|---|---|---|---|---|---|---|---|---|---|
| POST | 0.4 | 5C | 5C | 5C | 2C | 3C | 3C | 9C | 0 |
| POST | 0.4 | 9G | 9G | 9H | 9G | 6G | 8H | | |
| POST | 0.05 | 4C | 4C | 4C | 0 | 2G | 7H | 3C | 0 |
| POST | 0.05 | 9H | 9G | 7H | | | | 9G | |
| PRE | 0.4 | 3C | 3C | 3C | 9G | 0 | 3C | 4C | 2C |
| PRE | 0.4 | 8G | 4H | 7H | | | 7H | 9H | 5G |
| PRE | 0.05 | 3C | 2C | 2C | 0 | 0 | 0 | 0 | 0 |
| PRE | 0.05 | 5H | | 5G | | | | | |

| TYPE TEST | RATE K/HA | SICKLE POD | WHEAT | CORN | SOYBEAN | RICE | SORGHUM | SUGARBEET | COTTON |
|---|---|---|---|---|---|---|---|---|---|
| POST | 0.4 | 0 | | 3H | 4C | 3C | 3C | 9C | 5C |
| POST | 0.4 | | | | 8G | 7G | 7H | | 9H |
| POST | 0.05 | 0 | | 1H | 3C | 3G | 1H | 4C | 4C |
| POST | 0.05 | | | | 7H | | | 8G | 8G |
| PRE | 0.4 | 4G | | 3C | 3C | 3C | 3C | 6E | 3C |
| PRE | 0.4 | | | 7H | 5H | 7H | 7H | | 6G |
| PRE | 0.05 | 0 | | 0 | 1H | 0 | 0 | 4C | 4G |
| PRE | 0.05 | | | | | | | 6G | |

Compound 3

| TYPE TEST | RATE K/HA | MORNING GLORY | COCKLE BUR | VELVET LEAF | NUT SEDGE | CRAB GRASS | BARNYARD GRASS | CHEAT GRASS | WILD OATS |
|---|---|---|---|---|---|---|---|---|---|
| POST | 0.4 | 3H | 1H | 0 | 0 | 0 | 5H | 0 | 0 |
| POST | 0.05 | 0 | 0 | 0 | 0 | 0 | 0 | 0 | 0 |
| PRE | 0.4 | 0 | 0 | 0 | 0 | 0 | 0 | 0 | 0 |
| PRE | 0.05 | 0 | 0 | 0 | 0 | 0 | 0 | 0 | 0 |

| TYPE TEST | RATE K/HA | SICKLE POD | WHEAT | CORN | SOYBEAN | RICE | SORGHUM | SUGARBEET | COTTON |
|---|---|---|---|---|---|---|---|---|---|

TABLE A-continued

| POST | 0.4  | 0 | 0 | 1H | 4G | 2G | 4G | 0 |
|------|------|---|---|----|----|----|----|---|
| POST | 0.05 | 0 | 0 | 0  | 0  | 0  | 0  | 0 |
| PRE  | 0.4  | 0 | 0 | 2G | 0  | 0  | 0  | 0 |
| PRE  | 0.05 | 0 | 0 | 0  | 0  | 0  | 0  | 0 |

Compound 4

| TYPE TEST | RATE K/HA | MORNING GLORY | COCKLE BUR | VELVET LEAF | NUT SEDGE | CRAB GRASS | BARNYARD GRASS | CHEAT GRASS | WILD OATS |
|-----------|-----------|---------------|------------|-------------|-----------|------------|----------------|-------------|-----------|
| POST | 0.4  | 2C | 0 | 1C | 0 | 0 | 4H | 2G | 0 |
| POST | 0.05 | 0  | 0 | 0  | 0 | 0 | 0  | 0  | 0 |
| PRE  | 0.4  | 0  | 0 | 0  | 0 | 0 | 0  | 0  | 0 |
| PRE  | 0.05 | 0  | 0 | 0  | 0 | 0 | 0  | 0  | 0 |

| TYPE TEST | RATE K/HA | SICKLE POD | WHEAT | CORN | SOYBEAN | RICE | SORGHUM | SUGARBEET | COTTON |
|-----------|-----------|------------|-------|------|---------|------|---------|-----------|--------|
| POST | 0.4  | 0 | 0 | 0 | 3G | 0 | 3H | 1H | |
| POST | 0.05 | 0 | 0 | 0 | 0  | 0 | 0  | 0  | |
| PRE  | 0.4  | 0 | 0 | 0 | 0  | 0 | 0  | 0  | |
| PRE  | 0.05 | 0 | 0 | 0 | 0  | 0 | 0  | 0  | |

What is claimed is:

1. A compound of the formula:

$$JSO_2NHCNA$$
$$\underset{R}{|}\ \overset{W_1}{\overset{\|}{C}}$$

wherein

J is

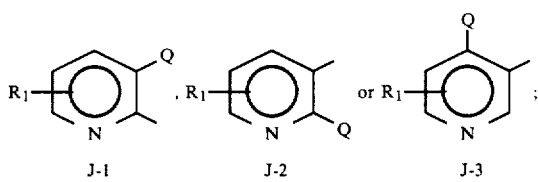

$W_1$ is O or S;

R is H or $CH_3$;

$R_1$ is H, $C_1$-$C_3$ alkyl, $C_1$-$C_3$ haloalkyl, halogen, nitro, $C_1$-$C_3$ alkoxy, $SO_2NR^IR^{II}$, $C_1$-$C_3$ alkylthio, $C_1$-$C_3$ alkylsulfinyl, $C_1$-$C_3$ alkylsulfonyl, $CO_2R^{III}$, $C_1$-$C_3$ haloalkoxy, amino, $C_1$-$C_3$ haloalkylthio, di($C_1$-$C_3$ alkyl)amino, $CH_2CN$, $CH_2OCH_3$ or $CH_2SCH_3$;

$R^I$ is H, $C_1$-$C_4$ alkyl, $C_2$-$C_3$ cyanoalkyl, methoxy or ethoxy;

$R^{II}$ is H, $C_1$-$C_4$ alkyl or $C_3$-$C_4$ alkenyl; or $R^I$ and $R^{II}$ may be taken together as $-(CH_2)_3-$, $-(CH_2)_4-$, $-(CH_2)_5-$ or $-CH_2CH_2OCH_2CH_2-$;

$R^{III}$ is $C_1$-$C_4$ alkyl, $C_3$-$C_4$ alkenyl, $C_3$-$C_4$ alkynyl, $C_2$-$C_4$ haloalkyl, $C_2$-$C_3$ cyanoalkyl, $C_5$-$C_6$ cycloalkyl, $C_4$-$C_7$ cycloalkylalkyl or $C_2$-$C_4$ alkoxyalkyl;

Q is

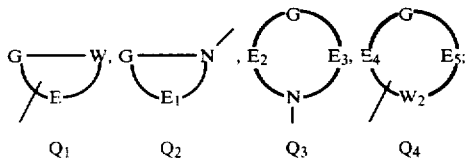

G is $C=O$ or $SO_2$;
W is O, S, $CHR_2$ or $NR_3$;
$W_2$ is O, S, $SO_2$, $CHR_2$ or $NR_3$;
$R_2$ is H, $C_1$-$C_2$ alkyl, Cl, F or Br;

$R_3$ is H, $C_1$-$C_4$ alkyl, $C_1$-$C_4$ haloalkyl, $C_2$-$C_4$ alkoxyalkyl, $C_2$-$C_4$ cyanoalkyl, $C_3$-$C_4$ alkenyl or $C_3$-$C_4$ alkynyl;

E and $E_1$ independently are $C_3$-$C_4$ alkylene, alkenylene or alkenyldienyl;

$E_2$ and $E_4$ independently are $C_1$-$C_2$ alkylene or $C_2$ alkenylene;

$E_3$ and $E_5$ independently are $C_2$-$C_3$ alkylene or alkenylene; and

E, $E_1$, $E_2$, $E_3$, $E_4$ and $E_5$ may optionally be substituted by 1-4 groups selected from $C_1$-$C_4$ alkyl, $C_1$-$C_4$ alkoxy, $C_1$-$C_4$ alkenyl, OH, halogen or $C_1$-$C_4$ haloalkoxy; further, when W is O, $CHR_2$ or $NR_3$, one of the carbon atoms of E may be in the form of a carbonyl group, and when $W_2$ is O, $CHR_2$ or $NR_3$, one of the carbon atoms of $E_4$ or $E_5$ may be in the form of a carbonyl group, provided that said carbonyl groups are not bonded directly to G;

A is

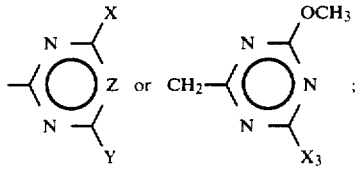

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_1$-$C_4$ haloalkyl, $C_3$-$C_5$ cycloalkyl, $C_2$-$C_4$ alkynyl, $C(O)R_6$,

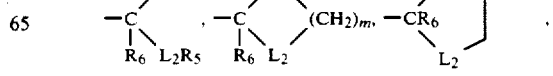

N(OCH$_3$)CH$_3$, C$_2$-C$_5$ alkylsulfinylalkyl, or C$_2$-C$_5$ alkylsulfonylalkyl;

m is 2 or 3;

L$_1$ and L$_2$ are independently O or S;

R$_4$ and R$_5$ are independently C$_1$-C$_2$ alkyl;

R$_6$ is H or CH$_3$;

Z is N; and

X$_3$ is CH$_3$ or OCH$_3$ and their agriculturally suitable salts; provided that (a) when G is SO$_2$, then W is O, CHR$_2$ or NR$_3$;

(b) when E$_2$ and E$_4$ are C$_2$ alkylene or C$_2$ alkenylene, then E$_3$ and E$_5$ are C$_2$ alkylene or alkenylene;

(c) X or Y is other than OCF$_2$H;

(d) when the total number of carbon atoms of X and Y is greater than four, then the number of carbons of R$_1$ is less than or equal to two and the number of carbons of Q is less than or equal to eight; and (e) when W$_1$ is S, then R is H, A is A-1, and Y is CH$_3$, OCH$_3$, OC$_2$H$_5$, CH$_2$OCH$_3$, C$_2$H$_5$, CF$_3$, SCH$_3$, OCH$_2$CH=CH$_2$, OCH$_2$C≡CH, OCH$_2$CH$_2$OCH$_3$, CH(OCH$_3$)$_2$ or

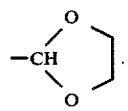

2. Compounds of claim 1 where W$_1$ is O; and R is H.

3. Compounds of claim 2 where

R$_1$ is H, Cl, CH$_3$, OCH$_3$ or N(CH$_3$)$_2$;

X is CH$_3$, OCH$_3$, OCH$_2$CH$_3$, CH$_2$F, OCH$_2$CH$_2$F, OCH$_2$CHF$_2$, OCH$_2$CF$_3$, CF$_3$, CH$_2$Cl or CH$_2$Br; and Y is H, CH$_3$, OCH$_3$, OC$_2$H$_5$, CH$_2$OCH$_3$, NHCH$_3$, N(OCH$_3$)CH$_3$, N(CH$_3$)$_2$, CH$_2$CH$_3$, CF$_3$, SCH$_3$, OCH$_2$CH=CH$_2$, OCH$_2$C≡CH, CH$_2$OCH$_2$CH$_3$, SCF$_2$H, OCH$_2$CH$_2$OCH$_3$, CH$_2$SCH$_3$, C(O)R$_6$,

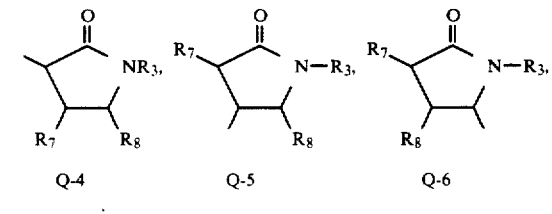

propyl, C≡H or C≡CCH$_3$.

4. Compounds of claim 3 where Q is Q$_1$.
5. Compounds of claim 3 where Q is Q$_2$.
6. Compounds of claim 3 where Q is Q$_3$.
7. Compounds of claim 3 where Q is Q$_4$.
8. Compounds of claim 3 where Q is

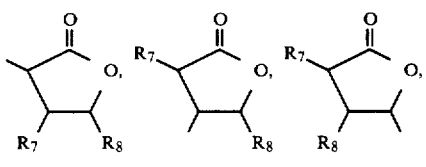

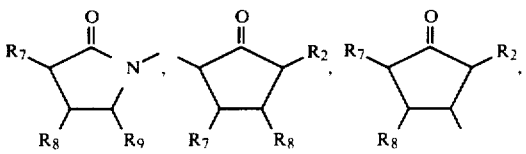

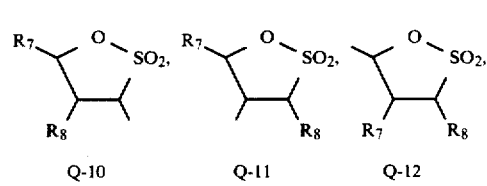

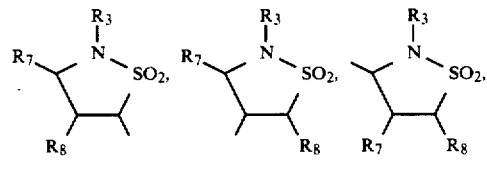

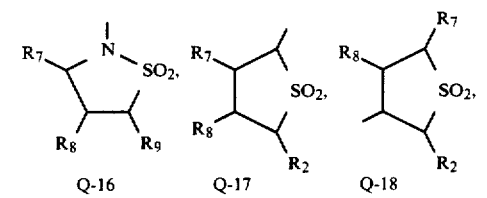

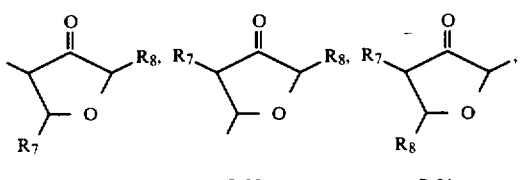

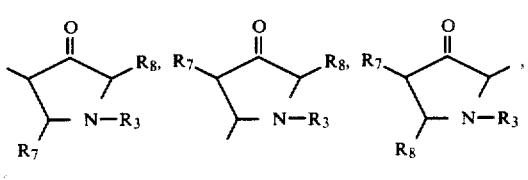

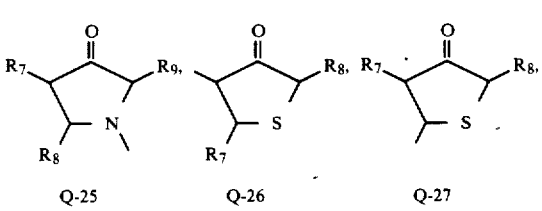

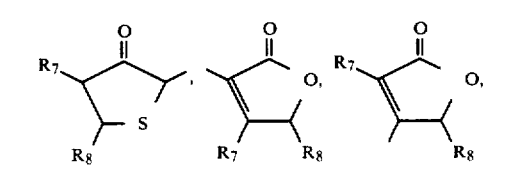

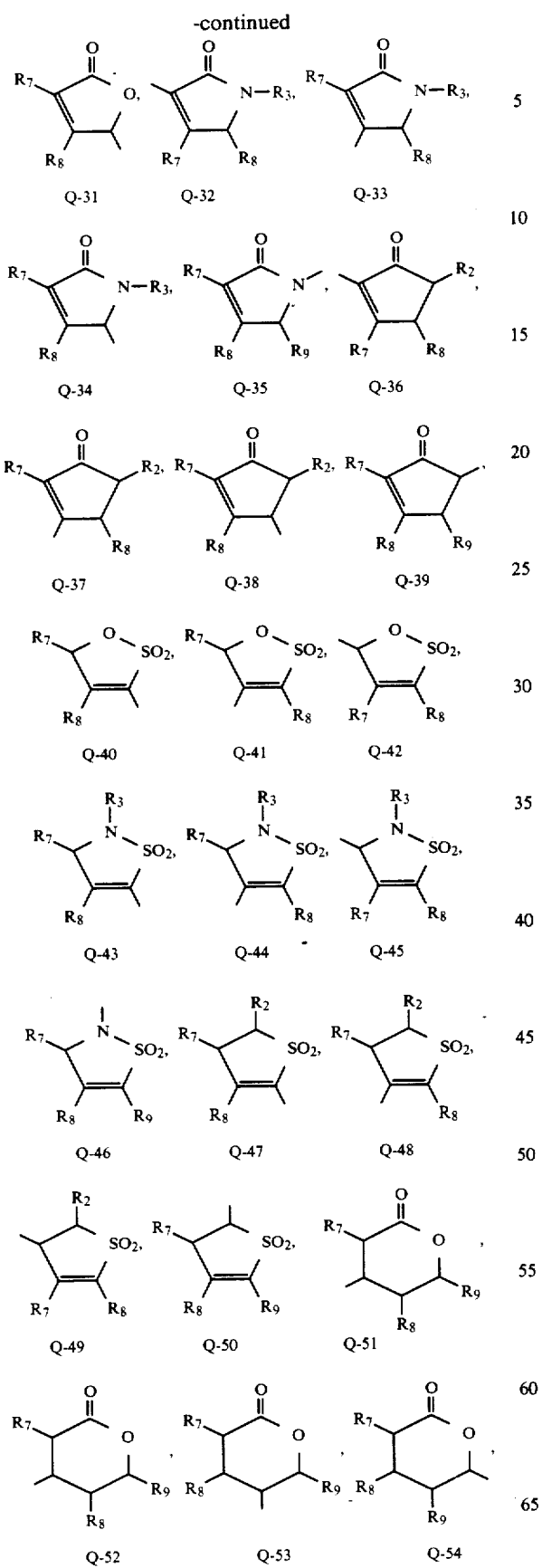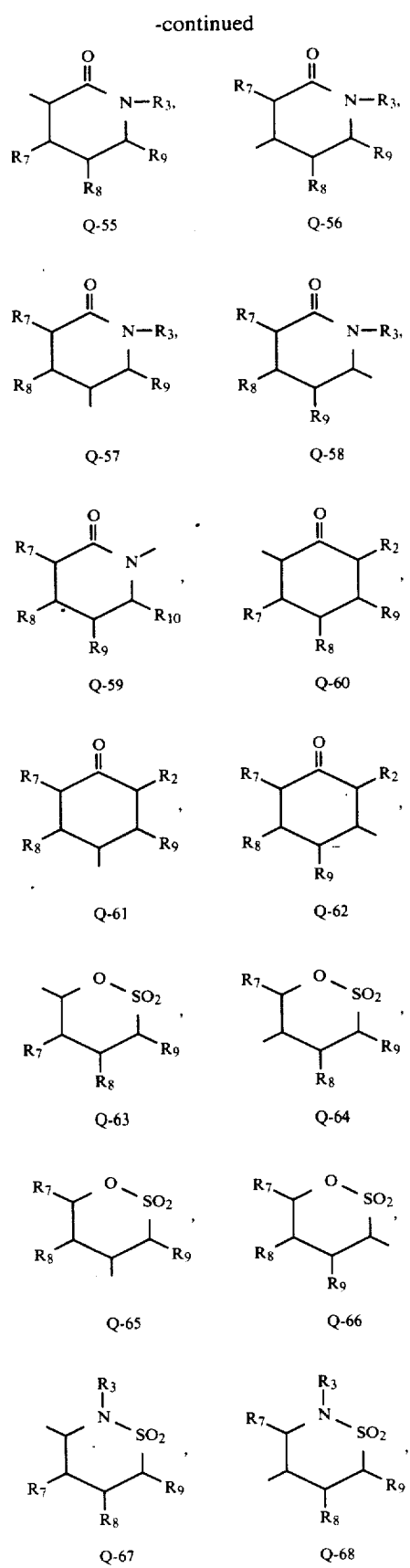

-continued
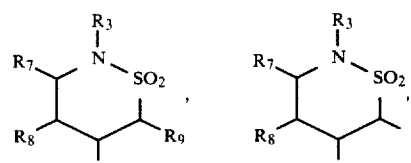
Q-69        Q-70
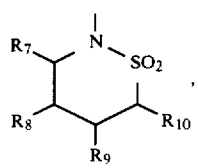
Q-71        Q-72
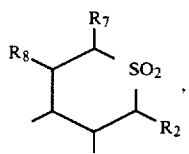
Q-73        Q-74
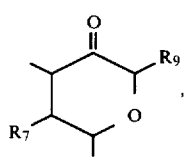
Q-75        Q-76
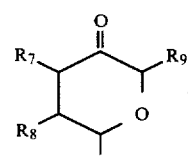
Q-77        Q-78
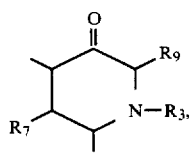
Q-79        Q-80
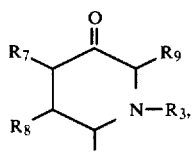
Q-81        Q-82
-continued
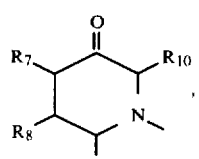
Q-83        Q-84
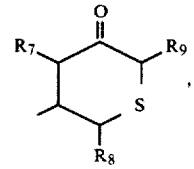
Q-85        Q-86
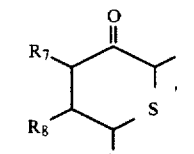
Q-87        Q-88
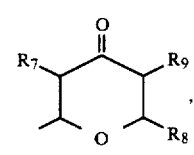
Q-89        Q-90
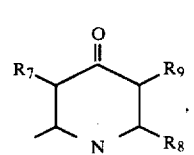
Q-91        Q-92
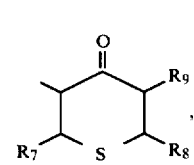
Q-93        Q-94
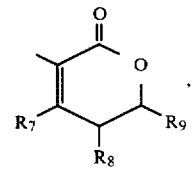
Q-95        Q-96

-continued
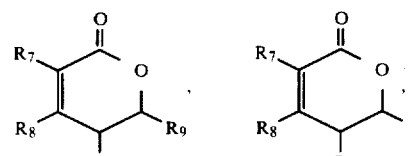 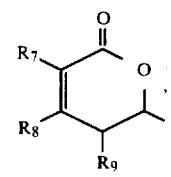
Q-97    Q-98
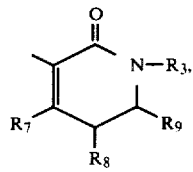 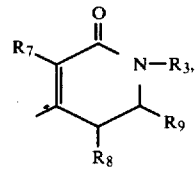
Q-99    Q-100
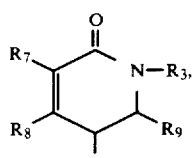 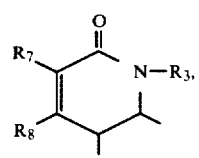
Q-101    Q-102
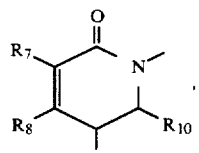 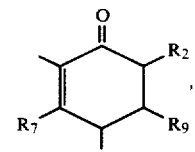
Q-103    Q-104
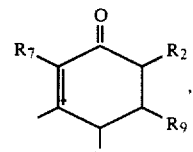 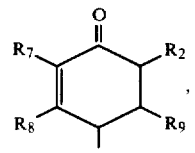
Q-105    Q-106
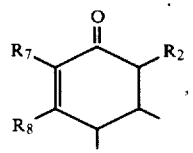 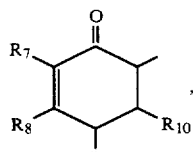
Q-107    Q-108
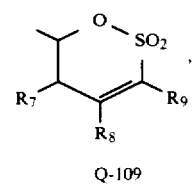 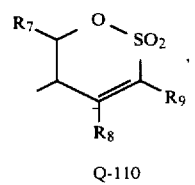
Q-109    Q-110
-continued
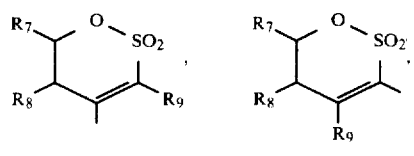 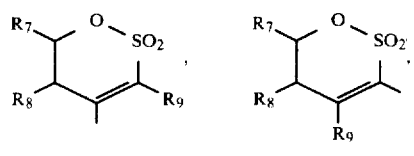
Q-111    Q-112
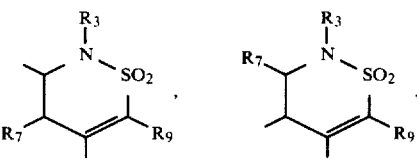 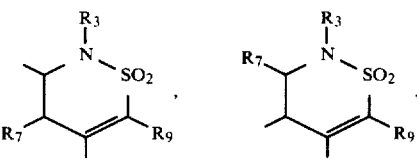
Q-113    Q-114
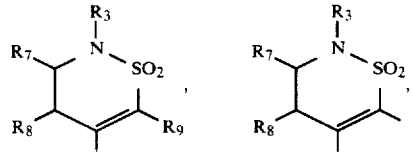 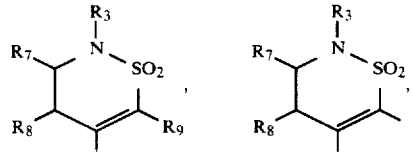
Q-115    Q-116
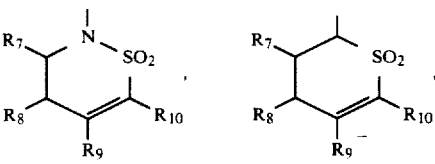 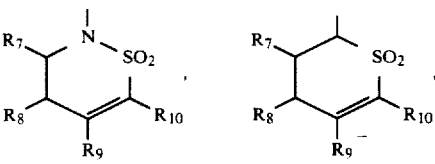
Q-117    Q-118
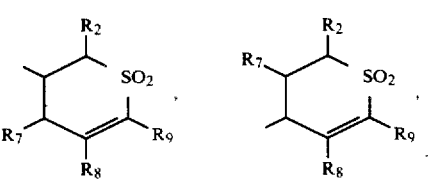 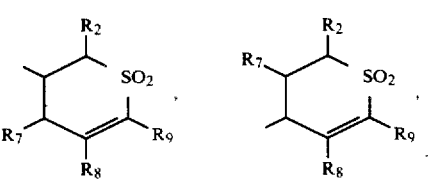
Q-119    Q-120
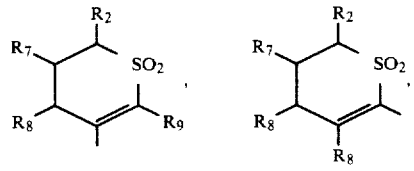 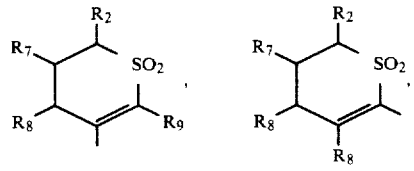
Q-121    Q-122
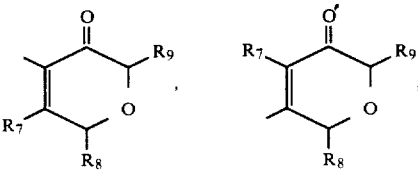 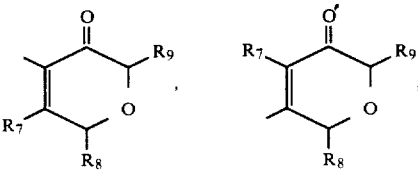
Q-123    Q-124

-continued
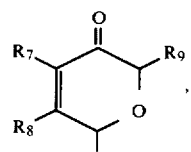
Q-125
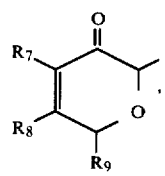
Q-126
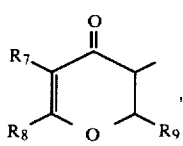
Q-139
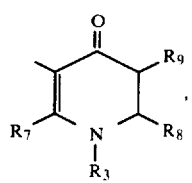
Q-140
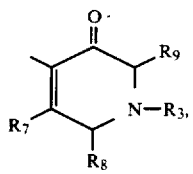
Q-127
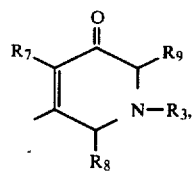
Q-128
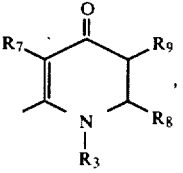
Q-141
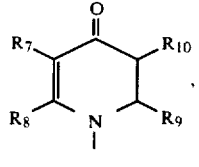
Q-142
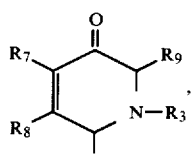
Q-129
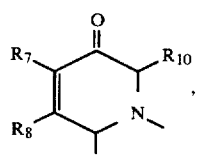
Q-130
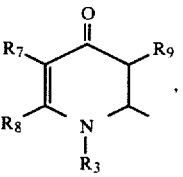
Q-143
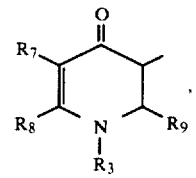
Q-144
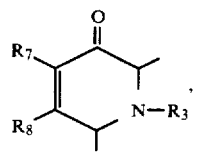
Q-131
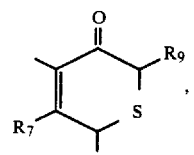
Q-132
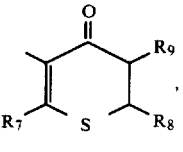
Q-145
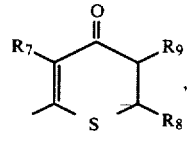
Q-146
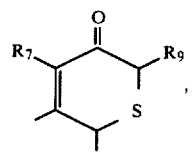
Q-133
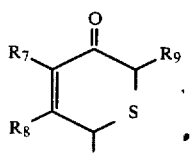
Q-134
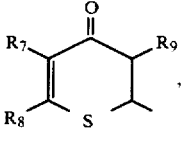
Q-147
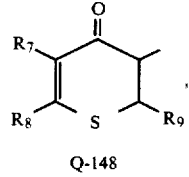
Q-148
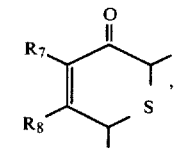
Q-135
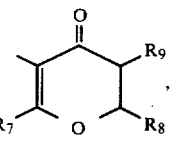
Q-136
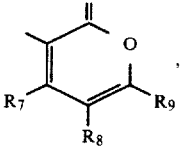
Q-149
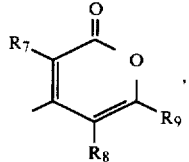
Q-150
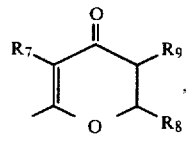
Q-137
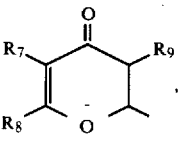
Q-138
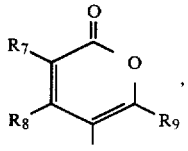
Q-151
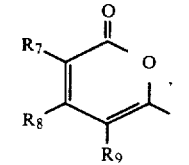
Q-152

-continued

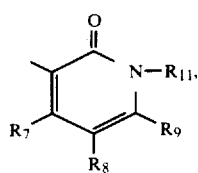
Q-153

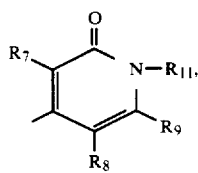
Q-154

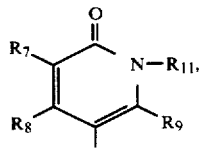
Q-155

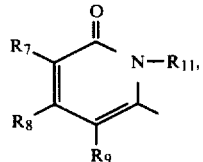
Q-156

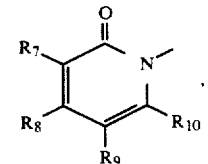
Q-157

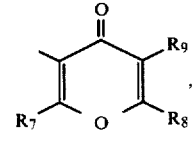
Q-158

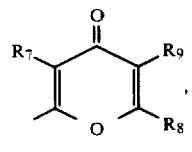
Q-159

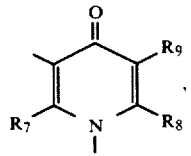
Q-160

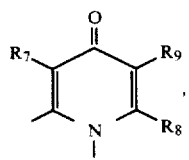
Q-161

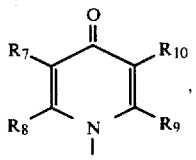
Q-162

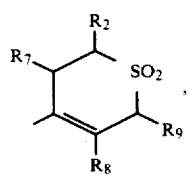
Q-163

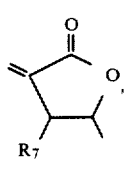
Q-164

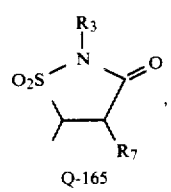
Q-165

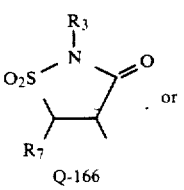
Q-166 or

-continued

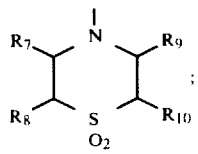
Q-167

$R_7$, $R_8$, $R_9$ and $R_{10}$ are independently H or $CH_3$; and $R_{11}$ is H, $CH_3$ or $CH_2CH_3$.

9. Compounds of claim 8 where J is J-1 or J-2.

10. Compounds of claim 9 where $R_1$ is H; and Y is $CH_3$, $OCH_3$, $C_2H_5$, $OC_2H_5$, $CH_2OCH_3$, $NHCH_3$, $CH(OCH_3)_2$ or cyclopropyl.

11. Compounds of claim 10 where $R_2$ is H or $CH_3$; and $R_3$ is H, $CH_3$ or $C_2H_5$.

12. Compounds of claim 11 where A is A-1; and X is $CH_3$, or $OCH_3$.

13. Compounds of claim 12 where Q is Q-1, Q-2, Q-3, Q-4, Q-7, Q-13, Q-14, Q-17, Q-18, Q-29, Q-37, Q-51, Q-60, Q-105 or Q-167.

14. The compound of claim 1 which is N-[(4-methoxy-6-methyltriazin-2-yl)aminocarbonyl]-2-(tetrahydro-2-oxofuran-3-yl)-3-pyridinesulfonamide.

15. A composition suitable for controlling the growth of undesired vegetation which comprises an effective amount of a compound of claim 1 and at least one of the following: surfactant, solid or liquid diluent.

16. A composition suitable for controlling the growth of undesired vegetation which comprises an effective amount of a compound of claim 2 and at least one of the following: surfactant, solid or liquid diluent.

17. A composition suitable for controlling the growth of undesired vegetation which comprises an effective amount of a compound of claim 3 and at least one of the following: surfactant, solid or liquid diluent.

18. A composition suitable for controlling the growth of undesired vegetation which comprises an effective amount of a compound of claim 4 and at least one of the following: surfactant, solid or liquid diluent.

19. A composition suitable for controlling the growth of undesired vegetation which comprises an effective amount of a compound of claim 5 and at least one of the following: surfactant, solid or liquid diluent.

20. A composition suitable for controlling the growth of undesired vegetation which comprises an effective amount of a compound of claim 6 and at least one of the following: surfactant, solid or liquid diluent.

21. A composition suitable for controlling the growth of undesired vegetation which comprises an effective amount of the compound of claim 7 and at least one of the following: surfactant, solid or liquid diluent.

22. A composition suitable for controlling the growth of undesired vegetation which comprises an effective amount of the compound of claim 8 and at least one of the following: surfactant, solid or liquid diluent.

23. A method for controlling the growth of undesired vegetation which comprises applying to the locus to be protected an effective amount of a compound of claim 1.

24. A method for controlling the growth of undesired vegetation which comprises applying to the locus to be protected an effective amount of a compound of claim 2.

25. A method for controlling the growth of undesired vegetation which comprises applying to the locus to be protected an effective amount of a compound of claim 3.

26. A method for controlling the growth of undesired vegetation which comprises applying to the locus to be protected an effective amount of a compound of claim 4.

27. A method for controlling the growth of undesired vegetation which comprises applying to the locus to be protected an effective amount of a compound of claim 5.

28. A method for controlling the growth of undesired vegetation which comprises applying to the locus to be protected an effective amount of a compound of claim 6.

29. A method for controlling the growth of undesired vegetation which comprises applying to the locus to be protected an effective amount of the compound of claim 7.

30. A method for controlling the growth of undesired vegetation which comprises applying to the locus to be protected an effective amount of the compound of claim 8.

* * * * *

UNITED STATES PATENT AND TRADEMARK OFFICE
CERTIFICATE OF CORRECTION

PATENT NO. : 4,707,179
DATED : November 17, 1987
INVENTOR(S) : Mark E. Thompson

It is certified that error appears in the above-identified patent and that said Letters Patent is hereby corrected as shown below:

In the Specification:

Column 3, line 30:

"$-(CH_2)_2-,$" should read "$-(CH_2)_3-,$".

In the Claims:

Claim 3, Column 205, line 45:

"propyl, C=H or C≡CCH$_3$." should read "cyclopropyl, C≡CH or C≡CCH$_3$."

Signed and Sealed this

Fourteenth Day of June, 1988

Attest:

DONALD J. QUIGG

*Attesting Officer*      *Commissioner of Patents and Trademarks*